US012590148B2

(12) United States Patent
Liu et al.

(10) Patent No.:  US 12,590,148 B2
(45) Date of Patent:     Mar. 31, 2026

(54) METHODS FOR THE SIMULTANEOUS EXPANSION OF MULTIPLE IMMUNE CELL TYPES, RELATED COMPOSITIONS AND USES OF SAME IN CANCER IMMUNOTHERAPY

(71) Applicant: NKARTA, INC., South San Francisco, CA (US)

(72) Inventors: Daofeng Liu, Pleasanton, CA (US); Guangnan Li, Foster City, CA (US); James B. Trager, Albany, CA (US)

(73) Assignee: Nkarta, Inc., South San Francisco, CA (US)

( * ) Notice: Subject to any disclaimer, the term of this patent is extended or adjusted under 35 U.S.C. 154(b) by 1276 days.

(21) Appl. No.: 17/309,209

(22) PCT Filed: Nov. 22, 2019

(86) PCT No.: PCT/US2019/062851
§ 371 (c)(1),
(2) Date: May 6, 2021

(87) PCT Pub. No.: WO2020/112563
PCT Pub. Date: Jun. 4, 2020

(65) Prior Publication Data
US 2022/0047635 A1       Feb. 17, 2022

Related U.S. Application Data

(60) Provisional application No. 62/771,482, filed on Nov. 26, 2018.

(51) Int. Cl.
| | |
|---|---|
| *A61K 40/15* | (2025.01) |
| *A61K 40/11* | (2025.01) |
| *A61K 40/31* | (2025.01) |
| *A61K 40/42* | (2025.01) |
| *A61P 35/00* | (2006.01) |
| *C07K 16/28* | (2006.01) |
| *C12N 5/0783* | (2010.01) |
| *C12N 15/86* | (2006.01) |
| *A61K 39/00* | (2006.01) |

(52) U.S. Cl.
CPC .......... *C07K 16/2803* (2013.01); *A61K 40/11* (2025.01); *A61K 40/15* (2025.01); *A61K 40/31* (2025.01); *A61K 40/4211* (2025.01); *A61P 35/00* (2018.01); *C12N 5/0636* (2013.01); *C12N 5/0638* (2013.01); *C12N 5/0646* (2013.01); *C12N 15/86* (2013.01); *A61K 2039/505* (2013.01); *A61K 2239/38* (2023.05); *A61K 2239/48* (2023.05); *C07K 2317/622* (2013.01); *C07K 2317/76* (2013.01); *C07K 2319/30* (2013.01); *C07K 2319/33* (2013.01); *C12N 2501/2302* (2013.01); *C12N 2501/2312* (2013.01); *C12N 2501/2315* (2013.01); *C12N 2501/2318* (2013.01); *C12N 2501/51*

(2013.01); *C12N 2501/515* (2013.01); *C12N 2501/70* (2013.01); *C12N 2502/30* (2013.01); *C12N 2533/50* (2013.01); *C12N 2740/10043* (2013.01)

(58) Field of Classification Search
None
See application file for complete search history.

(56) References Cited

U.S. PATENT DOCUMENTS

| | | | |
|---|---|---|---|
| 4,650,764 A | 3/1987 | Temin et al. |
| 4,690,915 A | 9/1987 | Rosenberg |
| 4,844,893 A | 7/1989 | Honsik et al. |
| 4,980,289 A | 12/1990 | Temin et al. |
| 5,124,263 A | 6/1992 | Temin et al. |
| 5,359,046 A | 10/1994 | Capon et al. |
| 5,399,346 A | 3/1995 | Anderson et al. |
| 5,415,874 A | 5/1995 | Bender et al. |
| 5,653,977 A | 8/1997 | Saleh |
| 5,674,704 A | 10/1997 | Goodwin et al. |
| 5,686,281 A | 11/1997 | Roberts |
| 5,712,149 A | 1/1998 | Roberts |
| 5,902,733 A | 5/1999 | Hirt et al. |
| 6,103,521 A | 8/2000 | Capon et al. |

(Continued)

FOREIGN PATENT DOCUMENTS

| | | |
|---|---|---|
| CA | 2964785 A1 | 5/2016 |
| CN | 101684456 A | 3/2010 |

(Continued)

OTHER PUBLICATIONS

Bachiller, M. et al., J Immunother Cancer, 2021, vol. 9: 16 pages.*

(Continued)

*Primary Examiner* — Michael D Burkhart

(74) *Attorney, Agent, or Firm* — Knobbe Martens Olson & Bear LLP

(57) ABSTRACT

Several embodiments disclosed herein relate to methods and processes for the co-expansion of multiple types of immune cells, in order to generate a mixed cell population. Some embodiments relate to the use of various stimuli specific to the various subpopulations to achieve expansion of those subpopulations at a particular time in a culturing process in order to generate an expanded population of immune cells having a desired ratio of the various subpopulations. In several embodiments, such mixed cell populations exhibit desirable characteristics, such as cytotoxic effects against tumor cells that enhance the efficacy of cancer immunotherapy.

22 Claims, 35 Drawing Sheets

Specification includes a Sequence Listing.

(56) References Cited

U.S. PATENT DOCUMENTS

| | | | |
|---|---|---|---|
| 6,261,839 | B1 | 7/2001 | Multhoff et al. |
| 6,303,121 | B1 | 10/2001 | Kwon |
| 6,319,494 | B1 | 11/2001 | Capon et al. |
| 6,355,476 | B1 | 3/2002 | Kwon et al. |
| 6,361,998 | B1 | 3/2002 | Bell et al. |
| 6,410,319 | B1 | 6/2002 | Raubitschek et al. |
| 6,464,973 | B1 | 10/2002 | Levitsky et al. |
| 6,797,514 | B2 | 9/2004 | Berenson et al. |
| 7,052,906 | B1 | 5/2006 | Lawson et al. |
| 7,070,995 | B2 | 7/2006 | Jensen |
| 7,390,483 | B2 | 6/2008 | Levitsky et al. |
| 7,435,596 | B2 | 10/2008 | Campana et al. |
| 7,446,179 | B2 | 11/2008 | Jensen et al. |
| 7,446,190 | B2 | 11/2008 | Sadelain et al. |
| 7,735,596 | B2 | 6/2010 | Sasaki et al. |
| 7,740,871 | B2 | 6/2010 | Ambinder et al. |
| 7,763,243 | B2 | 7/2010 | Lum et al. |
| 7,932,055 | B2 | 4/2011 | Spee et al. |
| 7,994,298 | B2 | 8/2011 | Zhang et al. |
| 8,012,469 | B2 | 9/2011 | Levitsky et al. |
| 8,026,097 | B2 | 9/2011 | Campana et al. |
| 8,252,914 | B2 | 8/2012 | Zhang et al. |
| 8,383,096 | B2 | 2/2013 | Ambinder et al. |
| 8,389,282 | B2 | 3/2013 | Sadelain et al. |
| 8,399,645 | B2 | 3/2013 | Campana et al. |
| 8,802,374 | B2 | 8/2014 | Jensen |
| 8,877,182 | B2 | 11/2014 | Alici |
| 8,906,682 | B2 | 12/2014 | June et al. |
| 8,911,993 | B2 | 12/2014 | June et al. |
| 8,916,381 | B1 | 12/2014 | June et al. |
| 8,926,964 | B2 | 1/2015 | Hariri et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,212,229 | B2 | 12/2015 | Schnfeld et al. |
| 9,328,156 | B2 | 5/2016 | June et al. |
| 9,365,641 | B2 | 6/2016 | June et al. |
| 9,447,194 | B2 | 9/2016 | Jensen |
| 9,464,140 | B2 | 10/2016 | June et al. |
| 9,464,274 | B2 | 10/2016 | Hariri et al. |
| 9,481,728 | B2 | 11/2016 | June et al. |
| 9,487,800 | B2 | 11/2016 | Schonfeld et al. |
| 9,499,629 | B2 | 11/2016 | June et al. |
| 9,511,092 | B2 | 12/2016 | Campana et al. |
| 9,518,523 | B2 | 12/2016 | Ikeda et al. |
| 9,540,445 | B2 | 1/2017 | June et al. |
| 9,580,685 | B2 | 2/2017 | Jensen |
| 9,605,049 | B2 | 3/2017 | Campana et al. |
| 9,623,082 | B2 | 4/2017 | Copik et al. |
| 9,629,877 | B2 | 4/2017 | Cooper et al. |
| 9,701,758 | B2 | 7/2017 | Cooper et al. |
| 9,765,342 | B2 | 9/2017 | Kochenderfer |
| 9,834,590 | B2 | 12/2017 | Campana et al. |
| 9,856,322 | B2 | 1/2018 | Campana et al. |
| 10,100,281 | B2 | 10/2018 | Jensen |
| 10,125,193 | B2 | 11/2018 | Cooper et al. |
| 10,428,305 | B2 | 10/2019 | Campana et al. |
| 10,774,311 | B2 | 9/2020 | Campana et al. |
| 10,829,735 | B2 | 11/2020 | Bedoya et al. |
| 11,141,436 | B2 | 10/2021 | Trager et al. |
| 11,154,575 | B2 | 10/2021 | Trager et al. |
| 11,253,547 | B2 | 2/2022 | Trager et al. |
| 11,365,236 | B2 | 6/2022 | Leong et al. |
| 11,560,548 | B2 | 1/2023 | Campana et al. |
| 11,673,937 | B2 | 6/2023 | Campana et al. |
| 11,690,874 | B2 | 7/2023 | Xiao et al. |
| 11,896,616 | B2 | 2/2024 | Kamiya et al. |
| 12,398,187 | B2 | 8/2025 | Trager et al. |
| 2002/0018783 | A1 | 2/2002 | Sadelain et al. |
| 2002/0037282 | A1 | 3/2002 | Levitsky et al. |
| 2003/0147869 | A1 | 8/2003 | Riley et al. |
| 2003/0157713 | A1 | 8/2003 | Ohno et al. |
| 2003/0215427 | A1 | 11/2003 | Jensen |
| 2004/0038886 | A1 | 2/2004 | Finney et al. |
| 2004/0043401 | A1 | 3/2004 | Sadelain et al. |
| 2004/0115216 | A1 | 6/2004 | Schneck et al. |
| 2004/0126363 | A1 | 7/2004 | Jensen et al. |
| 2004/0161433 | A1 | 8/2004 | Teshigawara et al. |
| 2005/0042208 | A1 | 2/2005 | Sagawa et al. |
| 2005/0048549 | A1 | 3/2005 | Cao et al. |
| 2005/0113564 | A1 | 5/2005 | Campana et al. |
| 2005/0127473 | A1 | 6/2005 | Sakagami |
| 2005/0233391 | A1 | 10/2005 | Spies et al. |
| 2005/0255118 | A1 | 11/2005 | Wehner |
| 2006/0057680 | A1 | 3/2006 | Zheng et al. |
| 2006/0093605 | A1 | 5/2006 | Campana et al. |
| 2006/0140922 | A1 | 6/2006 | Levitsky et al. |
| 2006/0233770 | A1 | 10/2006 | Ambinder et al. |
| 2006/0247191 | A1 | 11/2006 | Finney et al. |
| 2006/0257407 | A1 | 11/2006 | Chen et al. |
| 2007/0077241 | A1 | 4/2007 | Spies et al. |
| 2007/0160578 | A1 | 7/2007 | Waldmann et al. |
| 2007/0166327 | A1 | 7/2007 | Cooper et al. |
| 2008/0026413 | A1 | 1/2008 | Savage |
| 2008/0247990 | A1 | 10/2008 | Campbell |
| 2008/0260758 | A1 | 10/2008 | Levitsky et al. |
| 2008/0299137 | A1 | 12/2008 | Svendsen et al. |
| 2009/0011498 | A1 | 1/2009 | Campana et al. |
| 2009/0202501 | A1 | 8/2009 | Zhang et al. |
| 2010/0029749 | A1 | 2/2010 | Zhang et al. |
| 2010/0178276 | A1 | 7/2010 | Sadelain et al. |
| 2010/0272760 | A1 | 10/2010 | Ambinder et al. |
| 2011/0059137 | A1 | 3/2011 | Antonia et al. |
| 2011/0287058 | A1 | 11/2011 | Levitsky et al. |
| 2012/0015434 | A1 | 1/2012 | Campana et al. |
| 2012/0029063 | A1 | 2/2012 | Zhang et al. |
| 2012/0148552 | A1 | 6/2012 | Jensen |
| 2012/0148553 | A1 | 6/2012 | Hariri et al. |
| 2012/0258085 | A1 | 10/2012 | Alici |
| 2012/0282256 | A1 | 11/2012 | Campana et al. |
| 2012/0321666 | A1 | 12/2012 | Cooper et al. |
| 2013/0052158 | A1 | 2/2013 | Van Rhee |
| 2013/0058921 | A1 | 3/2013 | Van Rhee |
| 2013/0071414 | A1 | 3/2013 | Dotti et al. |
| 2013/0121960 | A1 | 5/2013 | Sadelain et al. |
| 2013/0216509 | A1 | 8/2013 | Campana et al. |
| 2013/0251752 | A1 | 9/2013 | Antonia et al. |
| 2013/0266551 | A1 | 10/2013 | Campana et al. |
| 2013/0280221 | A1 | 10/2013 | Schonfeld et al. |
| 2013/0280285 | A1 | 10/2013 | Schoenfeld et al. |
| 2013/0287748 | A1 | 10/2013 | June et al. |
| 2013/0288368 | A1 | 10/2013 | June et al. |
| 2013/0309258 | A1 | 11/2013 | June et al. |
| 2013/0323214 | A1 | 12/2013 | Gottschalk et al. |
| 2014/0023626 | A1 | 1/2014 | Peled et al. |
| 2014/0099309 | A1 | 4/2014 | Powell et al. |
| 2014/0099340 | A1 | 4/2014 | June et al. |
| 2014/0115198 | A1 | 4/2014 | White |
| 2014/0227237 | A1 | 8/2014 | June et al. |
| 2014/0271635 | A1 | 9/2014 | Brogdon et al. |
| 2014/0286934 | A1 | 9/2014 | Blein et al. |
| 2014/0286973 | A1 | 9/2014 | Powell, Jr. |
| 2014/0302608 | A1 | 10/2014 | Dominici et al. |
| 2014/0322183 | A1 | 10/2014 | Milone et al. |
| 2014/0328812 | A1 | 11/2014 | Campana et al. |
| 2014/0341869 | A1 | 11/2014 | Campana et al. |
| 2014/0370017 | A1 | 12/2014 | June et al. |
| 2015/0072425 | A1 | 3/2015 | Hariri et al. |
| 2015/0139943 | A1 | 5/2015 | Campana et al. |
| 2015/0190471 | A1 | 7/2015 | Copik et al. |
| 2015/0218649 | A1 | 8/2015 | Saenger et al. |
| 2015/0224143 | A1 | 8/2015 | Malmberg et al. |
| 2015/0225470 | A1 | 8/2015 | Zhang et al. |
| 2015/0273089 | A1 | 10/2015 | Gray |
| 2015/0306141 | A1 | 10/2015 | Jensen et al. |
| 2015/0329640 | A1 | 11/2015 | Finer |
| 2015/0344844 | A1 | 12/2015 | Better et al. |
| 2015/0368342 | A1 | 12/2015 | Wu et al. |
| 2016/0000828 | A1 | 1/2016 | Campana et al. |
| 2016/0008398 | A1 | 1/2016 | Sadelain et al. |
| 2016/0009784 | A1 | 1/2016 | Campana et al. |
| 2016/0030659 | A1 | 2/2016 | Cheney |
| 2016/0045551 | A1 | 2/2016 | Brentjens et al. |

(56) References Cited

U.S. PATENT DOCUMENTS

| | | |
|---|---|---|
| 2016/0046724 A1 | 2/2016 | Brogdon et al. |
| 2016/0046729 A1 | 2/2016 | Schnfeld et al. |
| 2016/0122766 A1 | 5/2016 | Wucherpfennig et al. |
| 2016/0122782 A1 | 5/2016 | Crisman et al. |
| 2016/0152723 A1 | 6/2016 | Chen et al. |
| 2016/0158285 A1 | 6/2016 | Cooper et al. |
| 2016/0185862 A1 | 6/2016 | Wu et al. |
| 2016/0207989 A1 | 7/2016 | Short |
| 2016/0228547 A1 | 8/2016 | Wagner et al. |
| 2016/0235787 A1 | 8/2016 | June et al. |
| 2016/0250258 A1 | 9/2016 | Delaney et al. |
| 2016/0272718 A1 | 9/2016 | Wang et al. |
| 2016/0289293 A1 | 10/2016 | Pule et al. |
| 2016/0289294 A1 | 10/2016 | Pul et al. |
| 2016/0296562 A1 | 10/2016 | Pule et al. |
| 2016/0326265 A1 | 11/2016 | June et al. |
| 2016/0333108 A1 | 11/2016 | Forman et al. |
| 2016/0377035 A1 | 12/2016 | Osawa et al. |
| 2017/0002322 A1 | 1/2017 | Hariri et al. |
| 2017/0014508 A1 | 1/2017 | Pule et al. |
| 2017/0015975 A1 | 1/2017 | Fu et al. |
| 2017/0016025 A1 | 1/2017 | Poirot et al. |
| 2017/0044227 A1 | 2/2017 | Schnfeld et al. |
| 2017/0049819 A1 | 2/2017 | Friedman et al. |
| 2017/0073423 A1 | 3/2017 | Juillerat et al. |
| 2017/0073638 A1 | 3/2017 | Campana et al. |
| 2017/0081411 A1 | 3/2017 | Engels et al. |
| 2017/0107178 A1 | 4/2017 | Cowley et al. |
| 2017/0107286 A1 | 4/2017 | Kochenderfer |
| 2017/0129967 A1 | 5/2017 | Wels et al. |
| 2017/0137515 A1 | 5/2017 | Chang et al. |
| 2017/0137783 A1 | 5/2017 | Bedoya et al. |
| 2017/0158749 A1 | 6/2017 | Cooper et al. |
| 2017/0183415 A1 | 6/2017 | Brogdon et al. |
| 2017/0226223 A1 | 8/2017 | Williams et al. |
| 2017/0232070 A1 | 8/2017 | Junghans |
| 2017/0239294 A1 | 8/2017 | Thomas-Tikhonenko et al. |
| 2017/0260594 A1 | 9/2017 | Molinero et al. |
| 2017/0281766 A1 | 10/2017 | Wiltzius |
| 2017/0283482 A1 | 10/2017 | Campana et al. |
| 2017/0283775 A1 | 10/2017 | June et al. |
| 2017/0296678 A1 | 10/2017 | Frost et al. |
| 2017/0319659 A1 | 11/2017 | Copik et al. |
| 2017/0333481 A1 | 11/2017 | Jantz et al. |
| 2017/0334968 A1 | 11/2017 | Cooper et al. |
| 2017/0355957 A1 | 12/2017 | Biondi et al. |
| 2018/0002397 A1 | 1/2018 | Shah et al. |
| 2018/0002435 A1 | 1/2018 | Sasu et al. |
| 2018/0008638 A1 | 1/2018 | Campana et al. |
| 2018/0022828 A1 | 1/2018 | Schnfeld et al. |
| 2018/0028633 A1 | 2/2018 | Chen |
| 2018/0044391 A1 | 2/2018 | Gundram et al. |
| 2018/0044404 A1 | 2/2018 | Oda et al. |
| 2018/0044417 A1 | 2/2018 | Pule et al. |
| 2018/0051292 A1 | 2/2018 | Kochenderfer |
| 2018/0057563 A1 | 3/2018 | Campana et al. |
| 2018/0057609 A1 | 3/2018 | June et al. |
| 2018/0057795 A1 | 3/2018 | Childs et al. |
| 2018/0086831 A1 | 3/2018 | Pule et al. |
| 2018/0086846 A1 | 3/2018 | Wiltzius et al. |
| 2018/0104278 A1 | 4/2018 | Zhang et al. |
| 2018/0117146 A1 | 5/2018 | Yu et al. |
| 2018/0118845 A1 | 5/2018 | Campana et al. |
| 2018/0125889 A1 | 5/2018 | Leek et al. |
| 2018/0133296 A1 | 5/2018 | Barrett et al. |
| 2018/0134765 A1 | 5/2018 | Landgraf et al. |
| 2018/0134787 A1 | 5/2018 | Liu et al. |
| 2018/0135015 A1 | 5/2018 | Campana et al. |
| 2018/0153977 A1 | 6/2018 | Wu et al. |
| 2018/0186878 A1 | 7/2018 | Rosenthal |
| 2018/0187149 A1 | 7/2018 | Ma et al. |
| 2018/0200298 A1 | 7/2018 | Jensen et al. |
| 2018/0244748 A1 | 8/2018 | Gill et al. |
| 2018/0258391 A1 | 9/2018 | June et al. |
| 2018/0312580 A1 | 11/2018 | Chen et al. |
| 2018/0312588 A1 | 11/2018 | Wiltzius et al. |
| 2018/0319862 A1 | 11/2018 | Thompson et al. |
| 2018/0325955 A1 | 11/2018 | Terrett et al. |
| 2018/0353544 A1 | 12/2018 | Rezvani et al. |
| 2019/0000881 A1 | 1/2019 | Sadelain et al. |
| 2019/0038733 A1 | 2/2019 | Campana et al. |
| 2019/0046571 A1 | 2/2019 | Campana et al. |
| 2019/0290693 A1 | 9/2019 | Qi et al. |
| 2019/0336533 A1 | 11/2019 | Hwang et al. |
| 2019/0338011 A1 | 11/2019 | Zhang et al. |
| 2019/0343801 A1 | 11/2019 | Barda-Saad |
| 2019/0376037 A1 | 12/2019 | Campana et al. |
| 2019/0381104 A1 | 12/2019 | Delaney et al. |
| 2020/0016208 A1 | 1/2020 | Kamiya et al. |
| 2020/0123217 A1 | 4/2020 | Zhang et al. |
| 2020/0131244 A1 | 4/2020 | Leong et al. |
| 2020/0246382 A1 | 8/2020 | Perez et al. |
| 2020/0255803 A1 | 8/2020 | Zhang et al. |
| 2020/0390816 A1 | 12/2020 | Kerbauy et al. |
| 2020/0407686 A1 | 12/2020 | Campana et al. |
| 2021/0017248 A1 | 1/2021 | Bluestone et al. |
| 2021/0017271 A1 | 1/2021 | Tan et al. |
| 2021/0046115 A1 | 2/2021 | Seow et al. |
| 2021/0054409 A1 | 2/2021 | Zhu et al. |
| 2021/0060073 A1 | 3/2021 | Trager et al. |
| 2021/0070856 A1 | 3/2021 | Trager et al. |
| 2021/0070857 A1 | 3/2021 | Trager et al. |
| 2021/0077527 A1 | 3/2021 | Lee |
| 2021/0139914 A1 | 5/2021 | Wucherpfennig et al. |
| 2021/0284752 A1 | 9/2021 | Brogdon et al. |
| 2021/0324388 A1 | 10/2021 | Vinanica et al. |
| 2022/0072041 A1 | 3/2022 | Cooper et al. |
| 2022/0073585 A1 | 3/2022 | Fehniger et al. |
| 2022/0119544 A1 | 4/2022 | Elliott et al. |
| 2022/0233590 A1 | 7/2022 | Trager et al. |
| 2022/0259563 A1 | 8/2022 | Hariri et al. |
| 2022/0411754 A1 | 12/2022 | Trager et al. |
| 2023/0002471 A1 | 1/2023 | Leong et al. |
| 2023/0004622 A1 | 1/2023 | Ekron |
| 2023/0190814 A1 | 6/2023 | Ramsborg et al. |
| 2023/0220343 A1 | 7/2023 | Campana et al. |
| 2023/0265390 A1 | 8/2023 | Trager et al. |
| 2023/0295296 A1 | 9/2023 | Bedoya et al. |
| 2023/0346838 A1 | 11/2023 | Pul et al. |
| 2024/0025962 A1 | 1/2024 | Orentas et al. |
| 2024/0092862 A1 | 3/2024 | Campana et al. |
| 2025/0049845 A1 | 2/2025 | Copik et al. |
| 2025/0296970 A1 | 9/2025 | Trager et al. |
| 2025/0339528 A1 | 11/2025 | Trager et al. |

FOREIGN PATENT DOCUMENTS

| | | |
|---|---|---|
| CN | 102268405 A | 12/2011 |
| CN | 102924596 A | 2/2013 |
| CN | 103113470 A | 5/2013 |
| CN | 105838677 A | 8/2016 |
| CN | 105985931 A | 10/2016 |
| CN | 106085958 A | 11/2016 |
| CN | 106459914 A | 2/2017 |
| CN | 107109363 A | 8/2017 |
| CN | 107206100 A | 9/2017 |
| CN | 107567461 A | 1/2018 |
| CN | 107709548 A | 2/2018 |
| CN | 107827990 A | 3/2018 |
| CN | 110623979 A | 12/2019 |
| CN | 112143707 A | 12/2020 |
| EP | 0830599 A1 | 3/1998 |
| EP | 0952213 A2 | 10/1999 |
| EP | 1036327 A2 | 9/2000 |
| EP | 1053301 A1 | 11/2000 |
| EP | 1231262 A1 | 8/2002 |
| EP | 1233058 A1 | 8/2002 |
| EP | 1306427 A1 | 5/2003 |
| EP | 1645291 A1 | 4/2006 |
| EP | 1820017 A2 | 8/2007 |
| EP | 2141997 A1 | 1/2010 |
| EP | 2411507 A1 | 2/2012 |
| EP | 2493485 A1 | 9/2012 |
| EP | 2493486 A1 | 9/2012 |

(56) References Cited

FOREIGN PATENT DOCUMENTS

| | | | |
|----|------------------|------|---------|
| EP | 2537416 | A1 | 12/2012 |
| EP | 2593542 | A1 | 5/2013 |
| EP | 2614077 | A1 | 7/2013 |
| EP | 2614151 | A1 | 7/2013 |
| EP | 2756521 | A2 | 7/2014 |
| EP | 2856876 | A1 | 4/2015 |
| EP | 2866834 | A1 | 5/2015 |
| EP | 2893003 | A1 | 7/2015 |
| EP | 2903637 | A1 | 8/2015 |
| EP | 2904106 | A2 | 8/2015 |
| EP | 2948544 | A1 | 12/2015 |
| EP | 2956175 | A1 | 12/2015 |
| EP | 2961831 | A1 | 1/2016 |
| EP | 2964753 | A1 | 1/2016 |
| EP | 2968492 | A1 | 1/2016 |
| EP | 2968601 | A1 | 1/2016 |
| EP | 2970426 | A2 | 1/2016 |
| EP | 2986636 | A1 | 2/2016 |
| EP | 2593540 | A1 | 3/2016 |
| EP | 3008173 | A2 | 4/2016 |
| EP | 3012268 | A1 | 4/2016 |
| EP | 3057986 | A1 | 8/2016 |
| EP | 3063175 | A2 | 9/2016 |
| EP | 3071221 | A1 | 9/2016 |
| EP | 3071222 | A1 | 9/2016 |
| EP | 3071223 | A1 | 9/2016 |
| EP | 3083671 | A1 | 10/2016 |
| EP | 3083691 | A2 | 10/2016 |
| EP | 3094653 | A1 | 11/2016 |
| EP | 3105318 | A1 | 12/2016 |
| EP | 3105335 | A1 | 12/2016 |
| EP | 3115373 | A1 | 1/2017 |
| EP | 3115573 | A1 | 1/2017 |
| EP | 3119425 | A1 | 1/2017 |
| EP | 3126380 | A1 | 2/2017 |
| EP | 3134432 | A2 | 3/2017 |
| EP | 3180359 | A1 | 6/2017 |
| EP | 2649086 | B1 | 7/2017 |
| EP | 3189132 | A1 | 7/2017 |
| EP | 3214091 | A1 | 9/2017 |
| EP | 3567049 | A2 | 11/2019 |
| JP | 2016-514462 | A | 5/2016 |
| JP | 2017-112982 | A | 6/2017 |
| JP | 2017-515506 | A | 6/2017 |
| JP | 2018-516592 | A | 6/2018 |
| KR | 10-2015-0132850 | A | 11/2015 |
| WO | 95/07358 | A1 | 3/1995 |
| WO | 96/23814 | A1 | 8/1996 |
| WO | 96/24671 | A1 | 8/1996 |
| WO | 96/41163 | A1 | 12/1996 |
| WO | 97/23613 | A2 | 7/1997 |
| WO | 98/26061 | A2 | 6/1998 |
| WO | 99/00494 | A2 | 1/1999 |
| WO | 99/06557 | A2 | 2/1999 |
| WO | 99/28748 | A2 | 6/1999 |
| WO | 99/38954 | A1 | 8/1999 |
| WO | 99/57268 | A1 | 11/1999 |
| WO | 00/14257 | A1 | 3/2000 |
| WO | 00/23573 | A2 | 4/2000 |
| WO | 01/29191 | A1 | 4/2001 |
| WO | 01/38494 | A1 | 5/2001 |
| WO | 02/10350 | A1 | 2/2002 |
| WO | 02/33101 | A1 | 4/2002 |
| WO | 02/77029 | A2 | 10/2002 |
| WO | 03/89616 | A2 | 10/2003 |
| WO | 2004/027036 | A2 | 4/2004 |
| WO | 2004/039840 | A1 | 5/2004 |
| WO | 2004/091657 | A2 | 10/2004 |
| WO | 2005/000890 | A1 | 1/2005 |
| WO | 2005/044996 | A2 | 5/2005 |
| WO | 2005/118788 | A2 | 12/2005 |
| WO | 2006/036445 | A2 | 4/2006 |
| WO | 2006/052534 | A2 | 5/2006 |
| WO | 2006/061626 | A2 | 6/2006 |
| WO | 2006/089133 | A2 | 8/2006 |
| WO | 2006/093605 | A1 | 9/2006 |
| WO | 2006/121852 | A2 | 11/2006 |
| WO | 2007/046006 | A2 | 4/2007 |
| WO | 2008/121420 | A1 | 10/2008 |
| WO | 2009/091826 | A2 | 7/2009 |
| WO | 2009/117566 | A1 | 9/2009 |
| WO | 2010/071836 | A1 | 6/2010 |
| WO | 2010/095031 | A2 | 8/2010 |
| WO | 2010/110734 | A1 | 9/2010 |
| WO | 2011/020047 | A1 | 2/2011 |
| WO | 2011/053321 | A1 | 5/2011 |
| WO | 2011/053322 | A1 | 5/2011 |
| WO | 2011/069019 | A2 | 6/2011 |
| WO | 2011/080740 | A1 | 7/2011 |
| WO | 2011/150976 | A1 | 12/2011 |
| WO | 2012/009422 | A1 | 1/2012 |
| WO | 2012/031744 | A1 | 3/2012 |
| WO | 2012/040323 | A2 | 3/2012 |
| WO | 2012/071411 | A2 | 5/2012 |
| WO | 2012/079000 | A1 | 6/2012 |
| WO | 2012/136231 | A1 | 10/2012 |
| WO | 2013/040371 | A2 | 3/2013 |
| WO | 2013/040557 | A2 | 3/2013 |
| WO | 2013/043196 | A1 | 3/2013 |
| WO | 2013/123720 | A1 | 8/2013 |
| WO | 2013/123726 | A1 | 8/2013 |
| WO | 2013/126720 | A2 | 8/2013 |
| WO | 2013/126726 | A1 | 8/2013 |
| WO | 2013/138244 | A2 | 9/2013 |
| WO | 2014/005072 | A1 | 1/2014 |
| WO | 2014/011993 | A2 | 1/2014 |
| WO | 2014/037422 | A1 | 3/2014 |
| WO | 2014/055413 | A2 | 4/2014 |
| WO | 2014/055442 | A2 | 4/2014 |
| WO | 2014/055657 | A1 | 4/2014 |
| WO | 2014/055668 | A1 | 4/2014 |
| WO | 2014/099671 | A1 | 6/2014 |
| WO | 2014/117121 | A1 | 7/2014 |
| WO | 2014/127261 | A1 | 8/2014 |
| WO | 2014/134165 | A1 | 9/2014 |
| WO | 2014/138704 | A1 | 9/2014 |
| WO | 2014/145252 | A2 | 9/2014 |
| WO | 2014/153270 | A1 | 9/2014 |
| WO | 2014/164554 | A1 | 10/2014 |
| WO | 2014/172584 | A1 | 10/2014 |
| WO | 2014/186469 | A2 | 11/2014 |
| WO | 2014/201021 | A2 | 12/2014 |
| WO | 2015/058018 | A1 | 4/2015 |
| WO | 2015/066551 | A2 | 5/2015 |
| WO | 2015/075468 | A1 | 5/2015 |
| WO | 2015/075469 | A1 | 5/2015 |
| WO | 2015/075470 | A1 | 5/2015 |
| WO | 2015/092024 | A2 | 6/2015 |
| WO | 2015/095895 | A1 | 6/2015 |
| WO | 2015/105522 | A1 | 7/2015 |
| WO | 2015/120421 | A1 | 8/2015 |
| WO | 2015/123642 | A1 | 8/2015 |
| WO | 2015/142314 | A1 | 9/2015 |
| WO | 2015/142661 | A1 | 9/2015 |
| WO | 2015/150771 | A1 | 10/2015 |
| WO | 2015/154012 | A1 | 10/2015 |
| WO | 2015/164759 | A2 | 10/2015 |
| WO | 2015/174928 | A1 | 11/2015 |
| WO | 2015/187528 | A1 | 12/2015 |
| WO | 2015/188119 | A1 | 12/2015 |
| WO | 2015/193411 | A1 | 12/2015 |
| WO | 2016/011210 | A2 | 1/2016 |
| WO | 2016/013849 | A1 | 1/2016 |
| WO | 2016/025880 | A1 | 2/2016 |
| WO | 2016/030691 | A1 | 3/2016 |
| WO | 2016/033331 | A1 | 3/2016 |
| WO | 2016/033690 | A1 | 3/2016 |
| WO | 2016/040441 | A1 | 3/2016 |
| WO | 2016/042041 | A1 | 3/2016 |
| WO | 2016/042461 | A1 | 3/2016 |
| WO | 2016/061574 | A1 | 4/2016 |
| WO | 2016/069607 | A1 | 5/2016 |
| WO | 2016/073602 | A2 | 5/2016 |
| WO | 2016/073629 | A1 | 5/2016 |

(56) References Cited

FOREIGN PATENT DOCUMENTS

| | | | |
|---|---|---|---|
| WO | 2016/073755 | A2 | 5/2016 |
| WO | 2016/075612 | A1 | 5/2016 |
| WO | 2016/090034 | A2 | 6/2016 |
| WO | 2016/100985 | A2 | 6/2016 |
| WO | 2016/109410 | A2 | 7/2016 |
| WO | 2016/109661 | A1 | 7/2016 |
| WO | 2016/109668 | A1 | 7/2016 |
| WO | 2016/115482 | A1 | 7/2016 |
| WO | 2016/118857 | A1 | 7/2016 |
| WO | 2016/123122 | A1 | 8/2016 |
| WO | 2016/123333 | A1 | 8/2016 |
| WO | 2016/124765 | A1 | 8/2016 |
| WO | 2016/124930 | A1 | 8/2016 |
| WO | 2016/126213 | A1 | 8/2016 |
| WO | 2016/126608 | A1 | 8/2016 |
| WO | 2016/139487 | A1 | 9/2016 |
| WO | 2016/141357 | A1 | 9/2016 |
| WO | 2016/142314 | A1 | 9/2016 |
| WO | 2016/149254 | A1 | 9/2016 |
| WO | 2016/151315 | A1 | 9/2016 |
| WO | 2016/154055 | A1 | 9/2016 |
| WO | 2016/154585 | A1 | 9/2016 |
| WO | 2016/168595 | A1 | 10/2016 |
| WO | 2016/172537 | A1 | 10/2016 |
| WO | 2016/172583 | A1 | 10/2016 |
| WO | 2016/174405 | A1 | 11/2016 |
| WO | 2016/174406 | A1 | 11/2016 |
| WO | 2016/174407 | A1 | 11/2016 |
| WO | 2016/174408 | A1 | 11/2016 |
| WO | 2016/174409 | A1 | 11/2016 |
| WO | 2016/174461 | A1 | 11/2016 |
| WO | 2016/174652 | A1 | 11/2016 |
| WO | 2016/179684 | A1 | 11/2016 |
| WO | 2016/191587 | A1 | 12/2016 |
| WO | 2016/191755 | A1 | 12/2016 |
| WO | 2016/196388 | A1 | 12/2016 |
| WO | 2016/197108 | A1 | 12/2016 |
| WO | 2016/201304 | A1 | 12/2016 |
| WO | WO 2016/201300 | A1 | 12/2016 |
| WO | WO 2016/210293 | | 12/2016 |
| WO | 2017/004150 | A1 | 1/2017 |
| WO | 2017/011804 | A1 | 1/2017 |
| WO | 2017/021701 | A1 | 2/2017 |
| WO | 2017/023859 | A1 | 2/2017 |
| WO | 2017/024131 | A1 | 2/2017 |
| WO | 2017/025038 | A1 | 2/2017 |
| WO | 2017/027325 | A1 | 2/2017 |
| WO | 2017/028374 | A1 | 2/2017 |
| WO | 2017/029511 | A1 | 2/2017 |
| WO | 2017/032777 | A1 | 3/2017 |
| WO | 2017/034615 | A1 | 3/2017 |
| WO | 2017/037083 | A1 | 3/2017 |
| WO | 2017/041749 | A1 | 3/2017 |
| WO | 2017/049166 | A1 | 3/2017 |
| WO | 2017/058752 | A1 | 4/2017 |
| WO | 2017/058753 | A1 | 4/2017 |
| WO | 2017/058850 | A1 | 4/2017 |
| WO | 2017/062820 | A1 | 4/2017 |
| WO | 2017/062952 | A1 | 4/2017 |
| WO | 2017/069958 | A2 | 4/2017 |
| WO | 2017/079673 | A1 | 5/2017 |
| WO | 2017/079694 | A2 | 5/2017 |
| WO | 2017/079705 | A1 | 5/2017 |
| WO | 2017/079881 | A1 | 5/2017 |
| WO | 2017/093969 | A1 | 6/2017 |
| WO | 2017/096329 | A1 | 6/2017 |
| WO | 2017/100176 | A1 | 6/2017 |
| WO | 2017/127729 | A1 | 7/2017 |
| WO | 2017/127755 | A1 | 7/2017 |
| WO | 2017/172952 | A1 | 10/2017 |
| WO | 2017/172981 | A2 | 10/2017 |
| WO | 2017/182643 | A1 | 10/2017 |
| WO | 2017/192440 | A1 | 11/2017 |
| WO | 2017/214207 | A2 | 12/2017 |
| WO | 2017/222593 | A1 | 12/2017 |
| WO | 2018/013918 | A2 | 1/2018 |
| WO | 2018/022646 | A1 | 2/2018 |
| WO | 2018/023025 | A1 | 2/2018 |
| WO | 2018/026819 | A2 | 2/2018 |
| WO | 2018/049248 | A1 | 3/2018 |
| WO | 2018/075807 | A1 | 4/2018 |
| WO | 2018/089476 | A1 | 5/2018 |
| WO | 2018/103503 | A1 | 6/2018 |
| WO | 2018/106732 | A1 | 6/2018 |
| WO | 2018/124766 | A2 | 7/2018 |
| WO | 2018/136762 | A1 | 7/2018 |
| WO | 2018/161017 | A1 | 9/2018 |
| WO | 2018/170458 | A1 | 9/2018 |
| WO | 2018/170506 | A1 | 9/2018 |
| WO | 2018/182511 | A1 | 10/2018 |
| WO | 2018/183385 | A1 | 10/2018 |
| WO | 2018/195175 | A1 | 10/2018 |
| WO | 2019/062817 | A1 | 4/2019 |
| WO | 2019/075395 | A1 | 4/2019 |
| WO | 2019/077037 | A1 | 4/2019 |
| WO | 2019/081591 | A1 | 5/2019 |
| WO | 2019/112347 | A2 | 6/2019 |
| WO | 2019/118885 | A1 | 6/2019 |
| WO | 2019/126574 | A1 | 6/2019 |
| WO | 2019/129002 | A1 | 7/2019 |
| WO | 2019/129220 | A1 | 7/2019 |
| WO | 2019/133793 | A1 | 7/2019 |
| WO | 2019/155286 | A2 | 8/2019 |
| WO | 2019/155288 | A1 | 8/2019 |
| WO | 2019/165121 | A1 | 8/2019 |
| WO | 2019/193476 | A1 | 10/2019 |
| WO | 2019/217253 | A1 | 11/2019 |
| WO | 2020/044239 | A1 | 3/2020 |
| WO | 2020/055862 | A1 | 3/2020 |
| WO | 2020/077356 | A1 | 4/2020 |
| WO | 2020/083282 | A1 | 4/2020 |
| WO | 2020/112563 | A1 | 6/2020 |
| WO | 2020/180882 | A1 | 9/2020 |
| WO | 2020/181221 | A1 | 9/2020 |
| WO | 2020/190737 | A1 | 9/2020 |
| WO | 2020/210232 | A1 | 10/2020 |
| WO | 2020/223327 | A1 | 11/2020 |
| WO | 2020/224606 | A1 | 11/2020 |
| WO | 2020/233589 | A1 | 11/2020 |
| WO | 2020/247392 | A1 | 12/2020 |
| WO | 2021/009694 | A1 | 1/2021 |
| WO | 2021/021907 | A1 | 2/2021 |
| WO | 2021/061832 | A1 | 4/2021 |
| WO | 2021/173471 | A1 | 9/2021 |
| WO | 2021/205173 | A1 | 10/2021 |
| WO | 2022/012683 | A1 | 1/2022 |
| WO | 2022/036224 | A1 | 2/2022 |
| WO | 2022/051749 | A1 | 3/2022 |
| WO | 2022/120107 | A1 | 6/2022 |
| WO | 2022/133057 | A1 | 6/2022 |
| WO | 2022/216811 | A2 | 10/2022 |
| WO | 2022/216963 | A1 | 10/2022 |
| WO | 2022/226522 | A1 | 10/2022 |
| WO | 2023/003809 | A1 | 1/2023 |
| WO | 2023/122337 | A1 | 6/2023 |
| WO | 2023/164256 | A2 | 8/2023 |
| WO | 2023/228093 | A1 | 11/2023 |
| WO | 2023/240042 | A1 | 12/2023 |
| WO | 2023/240064 | A1 | 12/2023 |

OTHER PUBLICATIONS

Baek, Hee-Jo, et al. "Ex vivo expansion of natural killer cells using cryopreserved irradiated feeder cells." Anticancer Research 33.5(2013): 2011-2019. (Year: 2013).

European Examination ,re EP 202848600.1, dated Dec. 12, 2024.

International Preliminary Report on Patentability, re PCT Application No. PCT/US2019/062851, dated Jun. 10, 2021.

International Preliminary Report on Patentability, re PCT Application No. PCT/US2023/077336, dated May 1, 2025.

Lemar H et al: "KIR haplotype can inform donor selection production of allogeneic memory-like CAR NK cells for clinical applica-

(56) References Cited

OTHER PUBLICATIONS tion", Journal For Immunotherapy Of Cancer, vol. 9, No. Suppl. 2, Nov. 10, 2021, p. A137.

Porrata, L. et al., "Infusion of NKp30/KIR2DL2 Natural Killer Cell Ratio and Survival Post-Autologous Stem Cell Transplantation in Lymphomas", Blood, vol. 132, No. Suppl. 1, Nov. 29, 2018, 3 pages.

Wu, Yang, Zhigang Tian, and Haiming Wei. "Developmental and functional control of natural killer cells by cytokines." Frontiers in immunology 8 (2017): 930. (Year: 2017).

Cho, D. et al., "Expansion and activation of natural killer cells for cancer immunotherapy," The Korean Journal of Laboratory Medicine, 29(2): 89-96 (2009).

Choi, B. D. et al., Chimeric antigen receptor T-cell immunotherapy for glioblastoma: practical insights for neurosurgeons, Neurosurg Focus, 44(6):E1 3, 1-6 (2018).

Choi, et al., "Donor-Derived natural Killer Cells Infused after Human Leukocyte Antigen-Haploidentical Hematopoietic Cell Transplantation" A Dose-Escalation Study Biol Blood Marrow Transplant 20, 696-704 (2014).

Chung, et al., "American College of Rheumatology/Vasculitis Foundation guideline for the management of antineutrophil cytoplasmic antibody-associated vasculitis," Arthritis & Rheumatology. Aug. 2021; 73(8):1366-83.

Ciurea, et al., "Phase 1 clinical trial using mbIL21 ex vivo-expanded donor-derived NK cells after haploidentical transplantation" Blood, (Oct. 19, 2017) vol. 130, No. 16, pp. 1857-1868 Oct. 19, 2017.

Clarke et al., "Folding studies of immunoglobulin-like beta-sandwich proteins suggest that they share a common folding pathway," Structure, 7(9):1145-1153, Sep. 15, 1999.

ClinicalTrials.gov, "A Multi-Center Study Evaluating KTE-C19 in Pediatric and Adolescent Subjects With Relapsed/Refractory B-precursor Acute Lymphoblastic Leukemia (ZUMA-4)," available at https://clinicaltrials.gov/show/NCT02625480, NCT02625480 (Retrieved from the Internet on Jun. 21, 2016).

ClinicalTrials.gov, "A Phase 1-2 Multi-Center Study Evaluating KTE-C19 in Subjects With Refractory Aggressive Non-Hodgkin Lymphoma (ZUMA-1) (ZUMA-1)," available at https://clinicaltrials.gov/show/NCT02348216, NCT02348216 (Retrieved from the Internet on Jun. 21, 2016).

ClinicalTrials.gov, "A Study Evaluating KTE-C19 in Adult Subjects With Relapsed/Refractory B-precursor Acute Lymphoblastic Leukemia (r/r ALL) (ZUMA-3) (ZUMA-3)," available at https://clinicaltrials.gov/show/NCT02614066, NCT02614066 (Retrieved from the Internet on Jun. 21, 2016).

ClinicalTrials.gov, "Anti-CD19 White Blood Cells for Children and Young Adults With B Cell Leukemia or Lymphoma," available at https://clinicaltrials.gov/show/NCT01593696, NCT01593696.

ClinicalTrials.gov, "CAR T Cell Receptor Immunotherapy for Patients With B-cell Lymphoma," available at https://clinicaltrials.gov/show/NCT00924326, NCT00924326 (Retrieved from the Internet on Jun. 21, 2016).

ClinicalTrials.gov, "CD 19 CAR T Cells for B Cell Malignancies After Allogeneic Transplant," available at https://clinicaltrials.gov/show/NCT01475058, NCT01475058 (Retrieved from the Internet on Jun. 21, 2016).

ClinicalTrials.gov, "CD 19+ CAR T Cells for Lymphoid Malignancies," available at https://clinicaltrials.gov/show/NCT02529813, NCT02529813 (Retrieved from the Internet on Jun. 21, 2016).

ClinicalTrials.gov, "CD19 Chimeric Receptor Expressing T Lymphocytes In B-Cell Non Hodgkin's Lymphoma, ALL & CLL (CRETI-NH)," available at https://clinicaltrials.gov/show/NCT00586391, NCT00586391.

ClinicalTrials.gov, "Consolidation Therapy With Autologous T Cells Genetically Targeted to the B Cell Specific Antigen CD19 in Patients With Chronic Lymphocytic Leukemia Following Upfront Chemotherapy With Pentostatin, Cyclophosphamide and Rituximab," available at https://clinicaltrials.Qov/show/NCT01416974, NCT01416974.

ClinicalTrials.gov, "Genetically Engineered Lymphocyte Therapy in Treating Patients With B-Cell Leukemia or Lymphoma That is Resistant or Refractory to Chemotherapy," available at https://clinicaltrials.gov/show/NCT01029366, NCT01029366.

ClinicalTrials.gov, "High Dose Therapy and Autologous Stem Cell Transplantation Followed by Infusion of Chimeric Antigen Receptor (CAR) Modified T-Cells Directed Against CD19+ B-Cells for Relapsed and Refractory Aggressive B Cell Non-Hodgkin Lymphoma," available at https://clinicaltrials.Qov/show/NCT01840566, NCT01840566.

ClinicalTrials.gov, "In Vitro Expanded Allogeneic Epstein-Barr Virus Specific C11otoxic T- Lymphocyles (EBV-CTLs) Genetically Targeted to the CD19 Antigen in B-cell Malignancies," available at https://clinicaltrials.gov/show/NCT01430390, NCT01430390 (Retrieved from the Internet on Jun. 21, 2016).

ClinicalTrials.gov, "Precursor B Cell Acute Lymphoblastic Leukemia (B-ALL) Treated With Autologous T Cells Genetically Targeted to the B Cell Specific Antigen CD19," available at https://clinicaltrials.gov/show/NCT01044069, NCT01044069.

ClinicalTrials.gov, "Study Evaluating the Efficacy and Safety of JCAR015 in Adult B-cell Acute Lymphoblastic Leukemia (B-ALL) (Rocket)," available at https://clinicaltrials.gov/show/NCT02535364, NCT02535364.

ClinicalTrials.gov, "T Cells Expressing a Fully-human AntiCD19 Chimeric Antigen Receptor for Treating B-cell Malignancies," available at https://clinicaltrials.gov/show/NCT02659943, NCT02659943.

ClinicalTrials.gov, "T-Lymphocytes Genetically Targeted to the B-Cell Specific Antigen CD19 in Pediatric and Young Adult Patients With Relapsed B-Cell Acute Lymphoblastic Leukemia," available at https://clinicaltrials.gov/show/NCT01860937, NCT01860937(Retrieved from the Internet on Jun. 21, 2016).

ClinicalTrials.gov, "Treatment of Relapsed or Chemotherapy Refractory Chronic Lymphocytic Leukemia or Indolent B Cell Lymphoma Using Autologous T Cells Genetically Targeted to the B Cell Specific Antigen CD 19", Available at: https://clinicaltrials.gov/show/NCT00466531, NCT00466531(Retrieved from the Internet on Jun. 21, 2016).

Cochran et aL, "Receptor clustering and transmembrane signaling in T cells," Trends Biochem Sci., 26(5):304-310, May 2001.

Collins ct al., "Donor leukocyte infusions in 140 patients with relapsed malignancy after allogeneic bone marrow transplantation," J Clin Oncol, Feb. 1997, 15(2): 433-44.

Collins et al., "Donor leukocyte infusions in acute lymphocytic leukemia," Bone Marrow Transplantation, 2000, 26: 511-516.

Colman, "Effects of amino acid sequence changes on antibody-antigen interactions" Research in Immunology 145:33-36 (1994).

Comi, et al., "The role of B cells in Multiple Sclerosis and related disorders" Ann Neural. 89(1), Jan. 13-23, 2021.

Complaint in *Trustees of the University of Pennsylvania* v. *St. Jude Children's Research Hospital* in the U.S. District Court for the Eastern District of Pennsylvania, dated Mar. 22, 2013.

Contreras, et al., "Sequential Therapies for Proliferative Lupus Nephritis" The New England Journal of Medicine vol. 350, No. 10, 971-980, Mar. 4, 2004.

Cooley S. et al., "Donor selection for natural killer cell receptor genes leads to superior survival after unrelated transplantation for acute myelogenous leukemia", Blood (2010), vol. 116, No. 14, pp. 2411-2419.

Cooper et al., "T-Cell Clones can be Rendered Specific for CD 1 9: Toward the Selective Augmentation Of the Graft-Versus-B Lineage Leukemia Effect," Blood, 2003, pp. 1637-1644, vol. 101.

Cooper et al., "The epidemiology of autoimmune diseases" Elsevier Autoimmunity Reviews (2003) vol. 2, No. 3, pp. 119-125.

Cooper et al., "In vivo evidence for a dependence on interleukin 15 for Survival of natural killer cells"; Blood 100: 3633-3638 (2002).

Cordoba, S. P. et al., "The large ectodomains of CD45 and CD148 regulate their segregation from and inhibition of ligated T-cell receptor," Blood, The Journal of the American Society of Hematology, V. 121, N. 21, p. 4295-4302, c. 4301 (2013).

(56) References Cited

OTHER PUBLICATIONS

Cruz et al., "Infusion of donor-derived CD 19-redirected virus-specific T cells for B-cell malignancies relapsed after allogeneic stem cell transplant: a phase 1 study," Blood 122(17):2965-2973 (2013).

Culpepper, D. J. et al., "Systematic mutation and thermodynamic analysis of central tyrosine pairs in polyspecific NKG2D receptor interactions," Molecular Immunology, V. 48, N. 4, p. 516-523, c. 521-522 (2011).

Curti, A. et al., "Successful transfer of alloreactive haploidentical KIR ligand-mismatched natural killer cells after Infusion in elderly high risk acute myeloid leukemia patients" Blood (2011) vol. 118, No. 12, pp. 3273-3279.

Daikeler, et al., "Allogeneic Hematopoietics SCT for patients with autoimmune diseases", Bone Marrow Transplantation, (2009) vol. 44, No. 1, pp. 27-33. doi: 10.1038/bmt.2008.424.

Dalakas MC. Role of Complement, Anti-Complement Therapeutics, and Other Targeted Immunotherapies in Myasthenia Gravis. Expert Rev Clin Immunol. 2022; 18(7):691-701. doi: 10. 1080/1744666X. 2022.2082946.

Dalal, A.-R. et al., Third-Generation Human Epidermal Growth Factor Receptor 2 Chimeric Antigen Receptor Expression on Human T Cells Improves with Two-Signal Activation, Human Gene Therapy, 845-852 (2018) (Abstract).

Damle et al., "Differential regulatory signals delivered by antibody binding to the CD28 (Tp44) molecule during the activation of human T lymphocytes," J Immunol., 140(6):1753-1761, Mar. 15, 1988.

Darcy, P.K., et al., "Expression in cytotoxic T lymphocytes of a single-chain anti- carcinoembryonic antigen antibody. Redirected Fas ligand-mediated lysis of colon carcinoma," Eur. J. Immunol. 28: 1663-1672 (1998).

Davidson, et al., "Renal remission status and long-term renal survival in patients with lupus nephritis: a retrospective cohort analysis" J Rheumatol, 45(5): 671-677, May 2018.

Davila, M.L., et al., "Efficacy and Toxicity Management of 19-28z CAR T Cell Therapy in B Cell Acute Lymphoblastic Leukemia," Science Translat. Med. 6(24) (2014).

De Felipe, P., "Polycistronic Viral Vectors," Current Gene Therapy, V. 2, N. 3, p. 355-378, c. 360 (2002).

De La Chapelle, A. et al., "Truncated erythropoietin receptor causes dominantly inherited benign human erythroc) tosis," Proc Natl Acad Sci USA., vol. 90, No. 10, pp. 4495-4499 (May 1993).

De Silva, et al., "Haemopoietic stem cell transplantation in Systemic lupus erythematosus: a systematic review", Allergy Asthma Clin Immunol, 15:59 (2019).

Debenedette et al., "Role of 4-1BB ligand in costimulation of T lymphocyte growth and its upregulation on M12 B lymphomas by cAMP," J Exp Med, Mar. 1995, 181(3): 985-992.

Debenedette, MA, et al.. "Costimulatin ofCD28-T Lymphocytes by 4-1 BB Ligand," J. Jmmzmol., 1997, pp. 551-559, vol. 158.

Declaration in Support of Trustees of the University of Pennsylvania's Motion for Summary Judgment for Invalidity of Patent in Suit in Trustees of the University of Pennsylvania v. St. Jude Children's Research Hospital in the US District Court for the Eastern District of Pennsylvania, dated Nov. 15, 2013. (Lit Doc. 24).

Delahaye, N. F. et al., "Alternatively spliced NKp30 isoforms affect the prognosis of gastrointestinal stromal tumors" Nature Medicine (2011) vol. 17, No. 6, pp. 700-708.

Denman et al. Membrane-Bound IL-21 Promotes Sustained Ex Vivo Proliferation of Human Natural Killer Cells. PLos One. Jan. 2012 | vol. 7 | Issue 1 | e30264 (Year: 2012).

Dickinson, et al., "First in Human Data of NKX019, an Allogeneic CAR NK for the treatment of Relapsed/Refractory (R/R) B-cell Malignancies", Hematological Oncology. (2023), vol. 41, pp. 526-527. https://doi.org/10.1002/hon.3164 389.

Diefenbach et al., "Selective associations with signaling proteins determine stimulatory versus costimulatory activity of NKG2D," Nature Publishing Group, vol. 3, No. 12, pp. 1142-1149, (Dec. 2002).

Doglio, et al., "New insights in systemic lupus erythematosus: From regulatory T cells to CAR-T cell strategies", Review article J Allergy Clin Immunol, vol. 150, No. 6, pp. 1289-1301 Dec. 2022.

Dotti ct al., "Design and Development of Therapies using Chimeric Antigen Receptor-Expressing T cells," Immunol Rev., 257(1), 35 pages, Jan. 2014.

Doubrovian, et al., "Evasion from NK Cell Immunity by MHC Class I Chain-Related Molecules Expressing Colon Adenocarcinoma," Journal ofImmunology, vol. 171, pp. 6891-6899, (2003).

Dowell, A. C., "Studies of Human T cell Costimulation: Potential for the Immunotherapy of Cancer," A thesis submitted to The University of Birmingham for the degree of Doctor of Philosophy, Cruk Institute for Cancer Studies, 2010.

Dubois et al., "IL-15Ra recycles and presents IL-15 In trans to neighboring cells," Immunity, Nov. 2002, 17(5): 537-47.

Dubois, S. et al., "Preassociation of IL-15 with IL-15R alpha-lgG1-Fc Enhances Its Activity on Proliferation of NK and CD8+/CD44high T Cells and Its Antitumor Action" The Journal of Immunology (2008) vol. 180, pp. 2099-2106.

Dudley, M.E., et al., "Adoptive Transfer of Cloned Melanoma-Reactive T Lymphocytes for the Treatment of Patients with Metastatic Melanoma," J. Immunother. 24: 363-373 (2001).

Eagle, et al., "ULBP6/RAET1L is an additional human NKG2D ligand," 2009, Eur. J_ Immunol. 39: 3207-16.

Eisuke D. et al., "Synergistic effect of IL-2, IL-12 and IL-18 on the activation of ex vivo-expanded human V[gamma]9V [delta]2 T cells", J Osaka Dent Univ, Apr. 1, 2018, pp. 51-57.

Ellebrecht, et al., "Reengineering chimeric antigen receptor T cells for targeted therapy of autoimmune disease" Immunotherapy, vol. 353, Issue 6295, pp. 179-184, Jul. 8, 2016.

Ellis et al., "Interactions of CD80 and CD86 with CD28 and CTLA4," J Immunol., 156(8):2700-2709, Apr. 15, 1996.

Eshhar et al., "Specific activation and targeting of cytotoxic lymphocytes through chimeric single chains consisting of antibody-binding domains and the y or ( subunits of the inmunoglobulin and T-cell receptors," Proc. Natl. Acad. Sci. USA, 1993, 90:720-724.

Eshhar, Z, et al , "Functional Expression of Chimeric Receptor Genes in Human T Cells," J. Immunol. Methods, 2001, 248(1-2):67-76.

Eshhar, Z., "Tumor-specific T-bodies: towards clinical application," Cancer Immunol. Immunother. 45: 131-136 (1997).

Extended European Search Report and Written Opinion dated Dec. 10, 2020 for International Application No. PCT/SG2018/050138, entitled "Stimulatory Cell Lines for Ex Vivo Expansion and Activation of Natural Killer Cells".

Eyguem et al., "Targeting a CAR to the TRAC locus with CRISPR/Cas9 enchances tumour rejction" Nature, 2017, 543 (7643): 113-117.

Fagan, E.A., and Eddleston, A.L.W.F., "Immunotherapy for cancer: the use oflymphokine activated killer (LAK) cells," Gut 28: 113-116 (1987).

Fang, F., et al., "NK cell-based immunotherapy for cancer", Seminars in Immunology, vol. 31, Jun. 2017, pp. 37-54.

Fanouriakis, et al., "2019 Update of the Joint European League Against Rheumatism and European Renal Association—European Dialysis and Transplant Association (EULAR/ERA-EDTA) recommendations for the manaaement of lupus nephritis", Ann Rheum Dis, 79:713-723, 2020.

Fanouriakis, et al., "Update on the diagnosis and management of systemic lupus erythematosus", Ann Rheum Dis. 80:14-25, 2021.

Farag et al., "Natural killer cell receptors: new biology and insights into the Graft-versus-leukemia effect," Blood, 2002, 100(6):1935-1947.

Fasano et al., "Hydroxychloroquine daily dose, hydroxychloroquine blood levels and the risk of flares in patients with systemic lupus erythematosus" Immunology and Inflammation, Lupus Science & Medicine, 2023, vol. 10, No. 1, e000841. doi: 10.1136/lupus-2022-000841.

Fava, et al., "Systemic Lupus Erythematosus Diagnosis and Clinical management" J Autoimmun. 96: 1-13, Jan. 2019.

Fehniger and Caligiuri, "Interleukin 15: biology and relevance to human disease," Blood, Jan. 2001, 97(1): 14-32.

(56) References Cited

OTHER PUBLICATIONS

Fehniger TA, et al., "Ontogeny and expansion of human natural killer cells: clinical implications", Int Rev Immunol. Jun. 2001; 20(3-4):503-534.

Ferlazzo, G. et al., "Distinct roles of IL-12 and IL-15 in human natural killer cell activation by dendritic cells from secondary lymphoid organs," PNAS, 101(47): 16606-16611 (2004).

Fernandez-Messina et al., "Human NKG2D-ligands: cell biology strategies ensure immune recognition," Frontiers in Immunology, vol. 3, Article 299, 9 Pages, (Sep. 2012).

Ferris, R. L. et al., "Tumor Antigen-Targeted, Monoclonal Antibody-Based Immunotherapy: Clinical Response, Cellular Immunity and Immunoescape" Journal of Clinical Oncology (2010) vol. 28, No. 28, pp. 4390-4399.

Fikri al., "Cloning, sequencing, and cell surface expression pattern of bovine immunoreceptor NKG2D and adaptor molecules DAP10 and DAP12," Immunogenetics 59(8): 653-9. (2017).

Finney et al., "Chimeric receptors providing both primary and costimulatory signaling in T cells from a single gene product," J Immunol. Sep. 15, 1998;161(6):2791-2797.

Foon et al., "Clinical and immune responses in advanced melanoma patients immunized with an anti-idiotype antibody mimicking disialoganglioside GD2," J Clin Oncol., 18(2):376-384, Jan. 2000.

Freshney, Animal Cell Culture, Cancer Research Campaign, Dept. of Oncology, University of Glasgow, 1986, 248 pages [Table of Contents Only].

Fujisaki et al., "Expansion of Highly Cytotoxic Human Natural Killer Cells for Cancer Cell Therapy", Cancer Res. (2009), vol. 59, pp. 4010-4017.

Fujisaki, H. et al., "Replicative potential of human natural killer cells" British Journal of Haematology (2009) vol. 145, pp. 606-613.

Fundamental Immunology, Third Edition, Chs. 1, 13 and 32, Paul, W.E., ed., pp. 1-20, 467-504, 1143-1178, Raven Press, New York (1993).

Furie, et al., "B-cell depletion with obinutuzumab for the treatment of proliferative lupus nephritis: a randomised, double-blind placebo-controlled trial" Ann Rheum Dis 81:100-107 (2022).

Furie, et al., "Two-Year, Randomized, Controlled Trial of Belimumab in Lupus Nephritis" The New England Journal of Medicine, 383:12, pp. 1117-1128, Sep. 17, 2020.

Gacerez, A et al., "How Chimeric Antigen Receptor Design Affects Adoptive T Cell Therapy," Journal of Cellular Physiology, vol. 231, No. 12, pp. 2590-2598 (Jun. 2, 2016).

Galustian C. et al., MP84-07A tale of tails—A novel approach to immunotherapy of prostate cancer. J Ural., May 10, 2016, vol. 195, No. 4S, pp. e1092.

Gardner, R., et al., "Acquisition of a CD19 negative myeloid phenotype allows immune escape of MLL-rearranged B-ALL from CD19 CAR-T cell therapy," Blood (forthcoming 2016).

Garrity et al. "The activating NKG2D receptor assembles in the membrane with two signaling dimers into a hexameric structure", 2005, Proc. Natl. Acad. Sci. USA. 102:7641-7646.

Mackensen, et al., "Anti-CD19 CAR T cell therapy for refractory systemic lupus erythematosus" nature medicine, (2022) vol. 28, No. 10, pp. 2124-2132. doi: 10.1038/s41591-022-02017-5.

Maher J, et al., "Human T-lymphocyte cytotoxicity and proliferation directed by a single chimeric TCRzeta/CD28 receptor", Nat Biotechnol. Jan. 2002; 20(1):70-75.

Maloney, D.G., "Newer Treatments for Non-Hodgkin's Lymphoma: Monoclonal Antibodies," Oncology 12(10): 63-76 (1998).

Manabe et al., "Interleukin-4 induces programmed cell death (apoptosis) in cases of high-risk acute lymphoblastic leukemia," Blood, Apr. 1994, 83(7): 1731-1737.

Mann et al., "Construction of a retrovirus packaging mutant and its use to produce helper-free defective retrovirus," Cell, May 1983, 33(1): 153-159.

Manzke et al., "Immunotherapeutic strategies in neuroblastoma: antitumoral activity of deglycosylated Ricin A conjugated anti-GD2 antibodies and anti-CD3xanti-GD2 bispecific antibodies," Med Pediatr Oncol., 36(1):185-189, Jan. 2001.

Manzke et al., "Locoregional treatment of low-grade B-cell lymphoma with CD3xCD19 bispecific antibodies and CD28 costimulation. I. Clinical phase I evaluation," Int J Cancer., 91(4):508-515, Feb. 15, 2001.

Manzke et al., "Locoregional treatment of low-grade B-cell lymphoma with CD3xCD19 bispecific antibodies and CD28 costimulation. II. Assessment of cellular immune responses," Int J Cancer., 91(4):516-522, Feb. 15, 2001.

Marcais et al. "The metabolic checkpoint kinase mTOR is essential for interleukin-15 signaling during NK cell development and activation," Nat Immunol., Aug. 2014; 15(8); 749-757, 24 pages.

Marcus, et al., "Recognition of tumors by the innate immune system and natural killer cells", Adv. Immunol. 122:91-128 (2014).

Marincola, F.M., et al., "Escape of Human Solid Tumors from T-Cell Recognition: Molecular Mechanisms and Functional Significance," Adv. Immunol. 74: 181-273 (2000).

Markowitz et al., "A safe packaging line for gene transfer: separating viral genes on two different plasmids," J Virol, Apr. 1988, 62(4): 1120-1124.

Marktel et al., "Immunologic potential of donor lymphocytes expressing a suicide gene for early immune reconstitution after hematopoietic T-cell-depleted stem cell transplantation," Blood, Feb. 2003, 101(4): 1290-1298.

Marrack et al. "Autoimmune disease: why and where it occurs". Nature Medicine, (2001) vol. 7, No. 8, pp. 899-905. doi: 10.1038/90935.

Marston, et al., "B cells in the pathogenesis and treatment of rheumatoid arthritis" Curr Opin Rheumatol. 22(3): 307-315, May 2010.

Martinet O., et al., "T cell activation with systemic agonistic antibody versus local 4-1 BB ligand gene delivery combined with interleukin-12 eradicate liver metastases of breast cancer," Gene Ther. Jun. 2002; 9(12):786-792.

Maude et al., "Chimeric antigen receptor T cells for sustained remissions in leukemia," N Engl J Med., 371 (16):1507-1517, Oct. 16, 2014.

Maus MV, et al., "Ex vivo expansion of polyclonal and antigen-specific cytotoxic T lymphocytes by artificial APCs expressing ligands for the T-cell receptor, CD28 and 4-1BB", Nat BiotechnoL Feb. 2002; 20(2): 143-148.

May KF, JR et al., "Anti-4-1 BB monoclonal antibody enhances rejection oflarge tumor burden by promoting survival but not clonal expansion of tumor-specific CDS+ T cells," Cancer Res. 2002, 62(12):3459-3465.

McHugh, et al., "CAR T cells drive out B cells in SLE" Systemic Lupus Erythematosus, Research Highlights, Nature Reviews, Rheumatology, vol. 15, pp. 249, May 2019.

McLaughlin et al., "Adoptive T-cell therapies for refractory/relapsed leukemia and lymphoma: current strategies and recent advances," Ther Adv Hematol., 6(6):295-307, Dec. 2015.

Melero et al., "Monoclonal antibodies against the 4-IBB T-cell activation molecule eradicate established tumors," Nat. Med., 1997, 3(6): 682-685.

Memorandum Consolidating the Actions in Trustees of the *University of Pennsylvania* v. *St. Jude Children's Research Hospital* in the US District Court for the Eastern District of Pennsylvania, dated Nov. 13, 2013. (Lit. Doc. 20).

Merino-Vico, et al., "B Lineage Cells in ANCA-Associated Vasculitis" International Journal of Molecular Sciences, 23, 387, in 18 pages (2022).

Merkel, et al., "Overview of and approach to the vasculitides in adults" UpToDate, Oct. 2, 2023 in 17 pages.

Merrill, et al., "Anifrolumab effects on rash and arthritis: impact of the type I interferon gene signature in the phase lib MUSE study in patients with systemic lupus erythematosus", Lupus Science & Medicine, in 7 pages (2018).

Mihara et al., "Development and functional characterization of human bone marrow mesenchymal cells immortalized by enforced expression of telomerase," Br J Haematol, Mar. 2003, 120(5): 846-849.

(56)         References Cited

OTHER PUBLICATIONS

Miller et al. Successful adoptive transfer and in vivo expansion of human haploidentical NK cells in patients with cancer. Blood. (2005) vol. 105, No. 8, pp. 3051-3057. doi: 10.1182/blood-2004-07-2974.

Miller et al., "Role of monocyles in the expansion of human activated natural killer cells," Blood, Nov. 1992, 80(9): 2221-2229.

Miller, J. S. et al., "Therapeutic applications: natural killer cells in the clinic" Hematology (2013) pp. 247-253.

Milone MC, et al., "Chimeric receptors containing CD137 signal transduction domains mediate enhanced survival of T cells and increased anti leukemic efficacy in vivo", Mol Ther. Apr. 21, 2009; 17(8):1453-1464.

Minamoto, S. et al., "Acquired Erythopoietin Responsiveness of Interleukin-2-dependent T lymphocytes Retrovirally Transduced with Genes Encoding Chimeric Erythropoietin/Interleukin-2 Receptors," Blood, vol. 86, No. 6, pp. 2281-2287 (1995).

Mishra, A. et al., "Aberrant Overexpression of IL-15 Initiates Large Granular Lymphocyte Leukemia through Chromosomal Instability and DNA Hypermethylalion" Cancer Cell (2012) vol. 22, pp. 645-655.

Mogi et al., "Tumour rejection by gene transfer of 4-IBB ligand and into a CD80(+) murine squamous cell carcinoma and the requirements of co-stimulatory molecules on tumour and host cells," Immunology, Dec. 2000, 101(4):541-7.

Mohammed, S. et al., "Improving Chimeric Antigen Receptor-Modified T Cell Function by Reversing the Immunosuppressive Tumor Microenvironment of Pancreatic Cancer," Mol. Ther. 4, vol. 25, No. 1, pp. 249-258 (2017).

Mok, et al., "Con: Cyclophosphamide for the treatment of lupus nephritis" Nephrol Dial Transplant, 31: 1053-1057 (2016).

Mondino and Jenkins, "Surface proteins involved in T cell costimulation," J Leukoc Biol, Jun. 1994, 55(6): 805-15.

Mora, "Dinutuximab for the treatment of pediatric patients with high-risk neuroblastoma," Expert Rev Clin Pharmacol., 9(5):647-653, Epub Mar. 21, 2016.

Morandi, B. et al., "NK cells provide helper signal for CD8+ T cells by inducing the expression of membrane-bound IL-15 on DCs" Int. Immunology (2009) vol. 21, No. 5, pp. 599-606.

Moretta L, et a., "Unravelling natural killer cell function: triggering and inhibitory human NK receptors," EMBO J., 2004, 23(2):255-259.

Morgan, et al., "Distinct Effects of Dexamethasone on Human Natural Killer Cell Responses Dependent on Cytokines", frontiers in immunology, vol. 8, Article 432, in 15 pages, Apr. 13, 2017.

Morgan, R.A. et al., Recognition of Glioma Stem Cells by Genetically Modified T Cells Targeting EGFRvlll and Development of Adoptive Cell Therapy for Glioma, Human Gene Therapy, 23(10), 1043-1053 (2012).

Morisot, N., Wadsworth S., Davis T., et al. (2020). Preclinical evaluation of NKX019, a CD19-targeting CAR NK cell. J Immunother Cancer 8:A140.

Moritz and Groner "A spacer region between the single chain antibody- and the CD3 chain domain of chimeric T cell receptor components is required for efficient ligand binding and signaling activity," Gene Tuer. Oct. 1995; 2(8):539-546.

Moritz, D., et al., "Cylotoxic T lymphocyles with a grafted recognition specificity for ERBB2-expressing tumor cells," Proc. Natl. Acad. Sci. USA 91:4318-4322 (1994).

Mortier, E. et al., "IL-15Ralpha chaperones IL-15 to stable dendrilic cell membrane complexes that activate NK cells trans presentation" JEM (2008), pp. 1213-1225.

Morvan, et al., "NK cells and cancer: you can teach innate cells new tricks", Nature Reviews Cancer, vol. 16, in 13 pages, Jan. 2016.

St. Jude Children's Research Hospital's Answer and Counterclaims in *Trustees of the University of Pennsylvania* v. *St. Jude Children's Research Hospital* in the U.S. District Court for the Eastern District of Pennsylvania, dated Jun. 27, 2013. (Doc 17).

St. Jude Children's Research Hospital's Motion in *Trustees of the University of Pennsylvania* v. *St. Jude Children's Research Hospital* in the U.S. District Court for the Eastern District of Pennsylvania, dated Dec. 3, 2013. (Doc. 31).

St. Jude Children's Research Hospital's Opposition to Trustees of the University of Pennsylvania's Motion to Dismiss Willful Infringement Allegations of Counterclaim in *Trustees of the University of Pennsylvania* v. *St. Jude Children's Research Hospital* in the U.S. District Court for the Eastern District of Pennsylvania, dated Aug. 8, 2013. (Doc. 19).

Stamper et al., "Crystal structure of the B7-1/CTLA-4 complex that inhibits human immune responses," Nature, 410(6828):608-611, Mar. 29, 2001.

Steel et al., "Interleukin-15 biology and its therapeutic implications in cancer," Trends Pharmacol. Sci. 33(1) :35-41, Jan. 2012.

Stein, P.H., et al., "The Cytoplasmic Domain of CD28 is both Necessary and Sufficient for Costimulation of Interleukin-2 Secretion and Association with Phosphatidylinositol 3'-Kinase," Mol. Cell. Biol. 14: 3392-3402 (1994).

Stong RC, et al., "Human acute leukemia cell line with the t(4;11) chromosomal rearrangement exhibits B lineage and monocytic characteristics," Blood, 1985,65:21-31.

Suerth et al., "Efficient Generation of Gene-Modified Human Natural Killer Cells via Alpharetroviral Vectors," J. Mol. Med. 94:83-93, 2016, published online 25 Au. 2015.

Sullivan, L.C. et al., "The Heterodimenc Assembly of the CD94-NKG2 Receptor Family and Implications for Human Leukocyte Antigen-E Recognition," Immunity, 27(6): 900-911 (Dec. 2007).

Sun, J ., et al., "Early transduction produces highly functional chimeric antigen receptor-modified virus-specific T-cells with central memory markers: a Production Assistant for Cell Therapy (PACT) translational application," J. Immunother. Cancer (2015).

Sundstrom and Nilsson, "Establishment and characterization of a human histiocy lic lymphoma cell line (U-937)," Int J Cancer, May 1976, 17(5): 565-577.

Sureth et al. Efficient generation of gene-modified human natural killer cells via alpharetroviral vectors, J. Mol. Med. 94:83-93, 2016., published online Aug. 25, 2015.

Sussman et al., "Protein Data Bank (PDB): database of three-dimensional structural information of biological macromolecules," Acta Crystallogr D Biol Crystallogr., 54(Pt 6 Pt 1):1078-1084, Nov. 1, 1998.

Szmania, "Ex vivo-expanded natural killer cells demonstrate robust proliferation in vivo in high-risk relapsed multiple myeloma patients," J Immunother.38(1):24-36. 2015doi: 10.1097/CJI.0000000000000059.

Tacke et al., "CD28-mediated induction of proliferation in resting T cells in vitro and in vivo without engagement of the T cell receptor: evidence for functionally distinct forms of CD28," Eur J Immunol., 27(1):239-247, Jan. 1997.

Tagaya, Y. et al., "IL-15: A Pleiotropic Cytokine with Diverse Receptor/Signaling Pathways Whose Expression Is Controlled at Multiple Levels" Immunity (1996) vol. 4, pp. 329-336.

The human protein atlas, [retrieved from: https://www.proteinatlas.org/ENSG00000177455-CD19/pathology], accessed Jun. 27, 2019, 3 pages.

Themeli et al., "Generation of tumor-targeted human T lympocytes from Induced pluripotent stem cells for cancer therapy", Nat Biotechnol., Oct. 2013; 31(10): 928-933.

Thomas et al., "Monoclonal antibody therapy with rituximab for acute lymphoblastic leukemia," Hematol Oncol Clin North Am., 23(5):949-971, Oct. 2009.

Topp, M.S., et al., "Universal chimeric immunoreceptors for targeting B-cell malignancies with engineered CTL: combining CD 19-specific TCR zeta signaling with engineered CD28-mediated co-stimulation," Mol. Ther. 3(5)(part 2 of 2): S21 (2001).

Trinchieri et al., "Response of resting human peripheral blood natural killer cells to interleukin 2," J Exp Med, Oct. 1984, 160(4): 1147-1169.

Trompeter et al., "Rapid and highly efficient gene transfer into natural killer cells by nucelofection," J Immunol Methods, Mar. 2003, 274(1-2): 245-256.

Trustees of the University of Pennsylvania's Answer to Defendant's Counterclaims in *Trustees of the University of Pennsylvania* v. *St.*

(56) References Cited

OTHER PUBLICATIONS

*Jude Children's Research Hospital* in the U.S. District Court for the Eastern District of Pennsylvania, dated Nov. 29, 2013. (Doc. 28).

Trustees of the University of Pennsylvania's Answer to Juno Therapeutics, Inc.'s Counterclaim in *Trustees of the University of Pennsylvania* v. *St. Jude Children's Research Hospital* in the U.S. District Court for the Eastern District of Pennsylvania, dated Jan. 13, 2014. (Doc. 56).

Trustees of the University of Pennsylvania's Brief in Support of Motion for Summary Judgment for Invalidity of Patent in Suit in *Trustees of the University of Pennsylvania* v. *St. Jude Children's Research Hospital* in the U.S. District Court for the Eastern District of Pennsylvania, dated Nov. 15, 2013. (Doc. 23).

Trustees of the University of Pennsylvania's Motion for Summary Judgment for Invalidity of Patent in Suit in *Trustees of the University of Pennsylvania* v. *St. Jude Children's Research Hospital* in the U.S. District Court for the Eastern District of Pennsylvania, dated Nov. 15, 2013.

Trustees of the University of Pennsylvania's Motion to Dismiss in *Trustees of the University of Pennsylvania* v. *St. Jude Children's Research Hospital* in the U.S. District Court for the Eastern District of Pennsylvania, dated Jul. 22, 2013. (Doc. 18).

Tsukamoto, K. er al., "Juxtacrine function of interleukin-15/interleukin-15 receptor system in tumour derived human B-cell lines," Clinical and Experimental Immunology, 146(3): 559-566 (2006).

Tunnicliffe, et al., "Immunosuppressive treatment for proliferative lupus nephritis," Cochrane Database Syst Rev. 2018; 6(6): CD002922. Published Jun. 29, 2018. doi:10.1002/14651858.CD002922.pub4.

Turaj, et al. "Augmentation of CD134 (OX40)-dependent NK anti-tumour activity is dependent on antibody cross-linking" Scientific Reports, (2018) 8, 2278.

Turtle, "Therapy of B Cell Malignancies with CD19-Specific Chimeric Antigen Receptor Modified T Cells of Defined Subset Composition," Blood 124(21): 384, 6 pages, 2014.

Turtle, C.J., et al., Abstract, "A Phase I/II Clinical Trial of Immunotherapy for CD19+ B Cell Malignancies With Defined Composition of CD4+ and CD8+ Central Memory T Cells Lentivirally Engineered to Express a CD19-Specific Chimeric Antigen Receptor" Mol. Ther., 2014, 22(Supp. 1):296.

Turtle, et al., "Durable molecular remissions in chronic lymphocytic leukemia treated with CD19-specific chimeric antigen receptor-modified T cells after failure of ibrutinib," J Clin Oncol.35(26):3010-3020, (2017). https://doi: 10.1200/JCO.2017.72.8519.

U.S. Appl. No. 11/074,525, filed Mar. 8, 2005, U.S. Pat. No. 7,435,596, Oct. 14, 2008, Campana et al.

U.S. Appl. No. 12/206,204, filed Sep. 8, 2008, U.S. Pat. No. 8,026,097, Sep. 27, 2011, Campana et al.

U.S. Appl. No. 13/548,148, filed Jul. 12, 2012, U.S. Pat. No. 8,399,645, Mar. 19, 2013, Campana et al.

U.S. Appl. No. 14/301,122, filed Jun. 10, 2014, U.S. Pat. No. 9,605,049, Mar. 28, 2017, Campana et al.

U.S. Appl. No. 14/303,331, filed Jun. 12, 2014, U.S. Pat. No. 9,856,322, Jan. 2, 2018, Campana et al.

U.S. Appl. No. 14/872,947, filed Oct. 1, 2015, U.S. Pat. No. 9,834,590, Dec. 5, 2017, Campana et al.

U.S. Appl. No. 15/470,678, filed Mar. 27, 2017, 2017-0283482, Oct. 5, 2017, Campana et al.

U.S. Appl. No. 15/837,715, filed Dec. 11, 2017, Campana et al.

U.S. Appl. No. 60/383,872*, filed May 28, 2002, Sadelain et al.

Uday K. O. et al., "Distinct Signaling By Chimeric Antigen Receptors (CARs) Containing CD28 Signaling Domain Versus 4-IBB In Primary Human T Cells", Blood, American Society of Hematology, vol. 122, No. 21, Nov. 15, 2013, 1 page abstract.

Union Hospital Achieved Breakthrough in Systemic Lupus Erythematosus Treatment with CAR-T Therapy, Union Hospita, Tongji Medical College, Huazhong University of Science and Technology, https://www.whuh.com/en/info/1007/1823.htm, in 4 pages, May 31, 2023.

Upshaw et al., "NKG2D-Mediated Signaling Requires a DAP10-Bound Grb2-Vav1 Intermediate and Phosphatidylinositol-3-kinase in Human Natural Killer Cells", Nat. Immunol. (2006), vol. 7, pp. 524-532.

Vajdos, et al. "Comprehensive Functional Maps of the Antigen-binding Site of an Anti-ErbB2 Antibody Obtained with Shotgun Scanning Mutagenesis" J. Mol. Biol. (Jul. 5, 2002) 320, 415-428.

Venna and Stock, "Management of adult acute lymphoblastic leukemia: moving tmvard a risk-adapted approach," Curr Opin Oncol, Jan. 2001, 13(1): 14-20.

Verdonck et al., "Donor leukocyte infusions for recurrent hematologic malignancies after allogeneic bone marrow transplantation: impact of infused and residual donor T cells," Bone Marrmv Transplant, Dec. 1998, 22(11):1057-1063.

Vinanica, N., et al., "Specific stimulation of T lymphocytes with erythropoietin for adoptive immunotherapy", Blood, 135(9): 668-679 (Feb. 27, 2020).

Vinay OS, et al., "Role of 4-1 BB in immune responses", Semin Immunol. Dec. 1998; 10(6):481-489.

Viola, "The amplification of TCR signaling by dynamic membrane microdomains," Trends Immunol., 22(6):322-327, Jun. 2001.

Vivier, E. et al., "Innate or Adaptive Immunity? The Example of Natural Killer Cells" Science (2011) vol. 331, pp. 44-49.

Vohra et al., Use of Stimulatory Cells in Conjunction with IL-12 and IL-18 augments NK cell expansion and transduction, drives a memory phenotype, and improve in vitro and in vivo CAR NK Activity, Journal for ImmunoTherapy of Cancer, vol. 7, Supplement 1: P194, 2019.

Vohra, et al., Stimulatory cells plus IL-12 and IL-18 augments KN cell expansion, transduction, memory phenotype, and in vitro and in vivo CAR NK cytotoxicity & persistence, SITC, Nov. 2019.

Voss et al., "Targeting p53, hdm2, and CD19: vaccination and immunologic strategies," Bone Marrow Transplant., 25 Suppl 2:S43-S45, May 2000.

Vujanovic, L. et al., "Virally infected and matured human dendritic cells activate natural killer cells via cooperative activity of plasma membrane-bound TNF and IL-15" Blood (2010) vol. 116, No. 4, pp. 575-583.

Waldmann, T.A. et al., "Safety (toxicity), pharmacokinetics, immunogenicity, and impact on elements of the normal immune system of recombinant human IL-15 in rhesus macaques," Blood, 117(18): 4787-4795 (2011).

Walter et al., "Reconstitution of cellular immunity against cytomegalovirus in recipients of allogeneic bone marrow by transfer of T-cell clones from the donor," N Engl J Med, Oct. 1995, 333(16): 1038-1044.

Wang et al., "Human NK cells maintain licensing status and are subject to killer immunoglobulin-like receptor (KIR) and KIR-ligand inhibition following ex vivo expansion," Cancer Immunol Immunother, 65:1047-1059, 2016.

Wang, et al., "Phase I Studies of central-memory-derived CD19 CAR T cell therapy following autologous HSCT in patients with B-Cell NHL," Blood (forthcoming 2016).

Warrens AN, et al., "Splicing by overlap extension by PCR using asymmetric amplification: an improved technique for the generation of hybrid proteins of immunological interest," Gene 20;186: 29-35 (1997).

Watowich et al., "The Erythropoietin Receptor: Molecular Structure and Hematopoietic Signaling Pathways," J. Investig Med. 2011, 59(7): 1067-1072.

Weijtens, M.E.M., et al., "Functional balance between T cell chimeric receptor density and tumor associated antigen density: CTL mediated cytolysis and lymphokine production," Gene Ther. 7: 35-42 (2000).

Weissman et al., "Molecular cloning and chromosomal localization of the human T-cell receptor-chain: Distinction from the molecular CD3 complex," PNAS USA, 1988, 85:9709-9713.

Westwood, J.A., et al., "Adoptive transfer of T cells modified with a humanized chimeric receptor gene inhibits growth of Lewis-Y expressing tumors in mice," PNAS 102(52): 19051-19056 (2005).

WHO, "WHO Classification of Tumours of Haematopoietic and Lymphoid Tissues," International Agency for Research on Cancer (IARC), 4th Edition, 40 pages, 2008.

(56)     References Cited

OTHER PUBLICATIONS

Wilcox et al., "Signaling through NK cell-associated CD137 promotes both helper function for CD8+ cytolytic T cells and responsiveness to IL-2 but not cytolytic activity," J. Immunol., Oct. 2002, 169(8):4230-6.

Wilkie, S. et al., "Selective Expansion of Chimeric Antigen Receptor-targeted T-cells with Potent Effector Function Using Interleukin-4," J Biol Chem., vol. 285, No. 33, pp. 25538-25544 (2010).

Willimsky, G. and Blankenstein, T., "Sporadic immunogenic tumours avoid destruction by inducing T-cell tolerance," Nature 437: 141-146 (2005).

Wittnebel, S. et al., "Membrane-Bound Interleukin (IL)-15 on Renal Tumor Cells Rescues Natural Killer Cells from IL-2 Starvation-Induced Apoptosis" Cancer Research (2007) vol. 67, No. 12, pp. 5594-5599.

Wu and Lanier, "Natural killer cells and cancer," Adv Cancer Res, 2003, 90: 127-156.

Wu, J. et al., "An Activating Immunoreceptor Complex Formed by NKG2D and DAP10" Science (1999) vol. 285, pp. 730-732.

Wyss-Coray, T., et al., "The B7 adhesion molecule is expressed on activated human T cells: functional involvement in T-T cell interactions," Eur. J. ImmunoL., 23: 2175-2180 (1993).

Xu, Y., et al., "Closely related T-memory stem cells correlate with in vivo expansion of CAR.CD19-T cells and are preserved by IL-7 and IL-15," Blood 123(24):3750-3759 (2014).

Yan et al., "Murine CD8 lymphocyte expansion in vitro by artificial antigen-presenting cells expressing CD137L (4-1 BBL) is superior to CD28, and CD137L expressed on neuroblastoma expands CD8 tumour-reactive effector cells in vivo," Immunology, 2004, 112(1):105-116.

Ye et al. "Effects of target cell overexpression of IL-15, 4-1 BBL and IL-18 1-102 combine with IL-2 on NK cell activation and cytotoxicity during ex vivo expansion" Chin J Cancer Biother, Oct. 31, 2014, vol. 21, No. 5, pp. 537-542.

Ye et al., "Gene therapy for cancer using single-chain Fv fragments specific for 4-IBB," Nat Med, Apr. 2002, 8(4): 343-348.

Yeoh et al., "Classification, subtype discovery, and prediction of outcome in pediatric acute lymphoblastic leukemia by gene expression profiling," Cancer Cell, Mar. 2002, 1(2): 133-143.

Yim, D. et al., "Molecular Cloning and Characterization of Pig Immunoreceptor DAP10 and NKG2D" Immunogenetics (2001) vol. 53, pp. 243-249.

Yoshida et al., "A novel adenovims expressing human 4-1BB ligand enhances antitumor immunity," Cancer Immunol Immunother, Feb. 2003, 52(2): 97-106.

Zanoni, I. et al., "IL-15 cis presentation is required for optimal NK cell activation in lipopolysaccharide-mediated inflammatory conditions," Cell Reports, 4: 1235-1249 (2013).

Zeis et al., "Allogeneic MHC-Mismatched Activated Natural Killer Cells Administered After Bone Marrow Transplantation Provide a Strong Graft-Versus-Leukemia Effect in Mice," BrJ Haematol, 1997, 96:757-761.

Zhang at al., Chimeric NKG2D-Modified T Cells Inhibit Systemic T-Cell Lymphoma Growth in a Manner Involving Multiple Cytokines and Cytotoxic Pathways, Cancer Res (2007), vol. 67, pp. 11029-11036.

Zhang et al, "Generation of Antitumor Responses by Genetic Modification of Primary Human T Cells with a chimeric NKG2D Receptor", Cancer Res (2006), vol. 66, No. 11, pp. 5927-5933.

Zhang et al., "Mouse Tumor Vasculature Expresses NKG2D Ligands and Can Be Targeted by Chimeric NKG2D-Modified T Cells", J Immunol (2013), vol. 190, pp. 2455-2463.

Zhang et al. Chimeric NK-receptor-bearing T cells mediate antitumor immunotherapy, Sep. 1, 2005, Blood Journal 106 (5): 1544-1551.

Zhang et al., "Improving Adoptive T Cell Therapy by Targeting and Controlling IL-12 Expression to the Tumor Environment," The American Society of Gene & Cell Therapy Molecular Therapy, vol. 19, No. 4, 751-759, 2011.

Zhang et al., Characterization of interleukin-15 gene-modified human natural killer cells: implications for adoptive cellular immunotherapy, Haematologica, 89: 338-347, Jan. 2004. (Year: 2004).

Zhao, et al., "A Herceptin-Based Chimeric Antigen Receptor with Modified Signaling Domains Leads to Enhanced Survival of Transduced T Lymphocytes and Antitumor Activity", The Journal of Immunology, 2009; 183:5563-5574.

Zhou et al., "Effects of RNA Interference on CD70 in dendritic cells of patients with immune thrombocvtooenia" Blood. Dec. 2, 2016; 128(22): 1373. (Abstract Only) in two pages.

Israeli, R.S., et al., "Expression of the Prostate-specific Membrane Antigen," Cancer Res., 1994, 54:1807-1811.

Ito et al., "Hyperdiploid acute lymphoblastic leukemia with 51 to 65 chromosomes: a distinct biological entity with a marked propensity to undergo apoptosis," Blood, Jan. 1999, 93(1): 315-20.

Jacobson, et al., "Epidemiology and Estimated Population Burden of Selected Autoimmune Diseases in the United States" Clinical Immunology and Immunopathology, vol. 84, No. 3, pp. 223-243, Sep. 1997.

Jagasia, et at. "National Institutes of Health Consensus Development Project on Criteria for Clinical Trials in Chronic Graft-versus-Host Disease: 1. The 2014 Diagnosis and Staging Working Group Report" Biol Blood marrow Transp author manuscript 21(3): 389-401, Mar. 2015.

Jayne, et al., "Phase 11 randomised trial of type I interferon inhibitor anifrolumab in patients with active lupus nephritis" Ann Rheum Dis.:496-506 (2022).

Jena et al., "Redirecting T-cell specificity by introducing a tumor-specific chimeric antigen receptor," Blood, 2010, 116 (7):1035-1044.

Jenkins et al , "Inhibition of antigen-specific proliferation of type 1 murine T cell clones after stimulation with immobilized anti-CD3 monoclonal antibody," J Immunol., 144(1):16-22, Jan. 1, 1990.

Jennette, et al., "B-Cell Mediated Pathogenesis of ANCA-Mediated Vasculitis" Semin Immunopathol., 36(3): 327-338, May 2014.

Jensen, M., et al., "CD20 is a molecular target for scFvFc: receptor redirected T cells: implications for cellular immunotherapy of CD20+ malignancy," Biol. Blood and Marrow Transplantation 4: 75-83 (1998).

Jensen, M.C. et al., "Anti-transgene Rejection Responses Contribute to Attenuated Persistence of Adoptively Transferred CD20/CD19-Specific Chimeric Antigen Receptor Redirected T Cells in Humans," Biol. Blood Marrow Transplant 16: 1245-1256 (2010).

Jiang et al., "Functional characterization of interleukin-15 gene transduction into the human natural killer cell line N KL," Cytother. 10(3):265-274, 2008.

Jiang et al., "Role of IL-2 in cancer immunotherapy," (2016, Oncoimmunology, vol. 5(6), pp. 1-10). (Year: 2016).

Jiang, W. et al., "hIL-15 gene-modified human natural killer cells (NKL-IL15) augments the anti-human hepatocellular carcinoma effect in vivo," Immunobiology, 219: 547-553 (Mar. 12, 2014).

Jin, et al., "CAR-T cell therapy: new hope for systemic lupus erythematosus patients", Cellular & Molecular Immunology 18:2581-2582 (2021).

Jin, et al., "Therapeutic efficacy of anti-CD19 CAR-T cells in a mouse model of systemic lupus erythematosus" Cellular & Molecular Immunology, 18:1896-1903 (2021).

Johnson and Jenkins, "The role of anergy in peripheral T cell unresponsiveness," Life Sci, 1994, 55(23): 1767-1780.

June et al. CART cell immunotherapy for human cancer. Science. (2018) vol. 359, No. 6382, pp. 1361-1365. doi: 10.1126/science. aar6711.

June et al., "The B7 and CD28 receptor families," Immunol Today, Jul. 1994, 15(7): 321-331.

Juno Therapeutics, Inc.'s Answer to Amended Complaint in Trustees of the University of Pennsylvania v. St. Jude Children's Research Hospital in the U.S. District Court for the Eastern District of Pennsylvania, dated Dec. 20, 2013. (Lit Doc. 50).

Kabalak et al., "Association of an NKG2D gene variant with systemic lupus erythematosus in two populations," Human Immunology, vol. 71, pp. 74-78, 2010.

(56)         References Cited

OTHER PUBLICATIONS

Kaiser, B.K. et al., "Structural basis for NKG2A/CD94 Recognition of HLA-E," Proc Nat'l Acad Sci USA, 105(18): 6696-6701 (Apr. 2008).

Kalos et al., "T Cells vvith Chimeric Antigen Receptors Have Potent Antitumor Effects and Can Establish Memory in Patients with Advanced Leukemia," Sci Transl Med. Aug. 10, 2011;3(95):95ra73.

Kansal, et al., "Sustained B cell depletion by CD19-targeted CAR T cells is a highly effective treatment for murine lupus" Science Translational Medicine, (2019) vol. 11, No. 482. eaav1648. doi:10.1126/scitranslmed.aav1648.

Kariv, I., ct al., "Analysis of the Site of Interaction of CD28 with Its Counter-Receptors CD80 and CD86 and Correlation with Function," J. of Immunol. 157: 29-38 (1996).

Kawamata, et al., "Activation of OX40 Signal Transduction Pathways Leads to Tumor Necrosis Factor Receptor- associated Factor (TRAF) 2- and TRAF5-mediated NF-kB Activation" The Journal of Biological Chemistry, 1998, vol. 273, No. 10, 5808-5814.

KDIGO 2021 Clinical Practice Guideline for the Management of Glomerular Diseases, Kidney International, 100:S1-S276, (2021).

Kershaw, M.H., et al., "A Phase I Study on Adoptive Immunotherapy Using Gene-Modified T Cells for Ovarian Cancer," Clin. Cancer Res. 12: 6106-6115 (2006).

Kilgour, et al., "Advancements in CAR-NK therapy: lessons to be learned from CAR-T therapy", frontiers in Immunology, in 10 pages, May 2, 2023.

Kim Y J, et al., "Novel T cell antigen 4-1 BB associates with the protein tyrosine kinase p56 I ckl", J Immunol. Aug. 1, 1993; 151(3): 1255-1262.

King et al., "CAR NK Cell Therapy for T Follicular Helper Cells" Cell Press Open Access, Cell Reports Medicine, in two pages, Apr. 21, 2020.

Kitaya, K. et al., "IL-15 expression at human endometrium and decidua," Biology of Reproduction, 63(3): 683-687 (2000).

Kitaya, K. et al., "Regulatory role of membrane-bound form interleukin-15 on human uterine microvascular endothelial cells in circulating CD16(-) natural killer cell extravasation into human endometrium," Bioloav of Reproduction, 89(3): 70 (2013).

Kitching, et al., "ANCA-associated vasculitis", Nature Reviews Disease primers, 6, 71, (2020).

Kite Pharma Inc.'s Reply to Patent Owner'S Response to the Petition re: 1PR2015-01719, 35 pages, Aug. 4, 2016.

Klein E, et al., "Properties of the K562 cell line, derived from a patient with chronic myeloid leukemia", Int J Cancer. Oct. 15, 1976; 18(4 ):421-431.

Klingemann HG, et al., "Ex vivo expansion of natural killer cells for clinical applications", Cylotherapy. 2004; 6 (1 ):15-22.

Kobayashi et al., "Role of trans-cellular IL-15 presentation in the activation ofNK cell-mediated killing, which leads to enhanced tumor immunosurveillance," Blood, Jan. 2005, 105(2): 721-727.

Kober, J., et al. "The capacity of the TNF family members 4-1BBL, OX40L, CD70, GITRL, CD30L and LIGHT to costimulate human T cells," Eur J Immuno, vol. 38, No. 10, pp. 2678-2688 (Oct. 28, 2008).

Kochenderfer, J .N., et al., "B-cell depletion and remissions of malignancy along With cytokine-associated toxicity in a clinical trial of anti-CD19 chimeric-antigen-receptor-transduced T cells," Blood 119(12):2709-2720 (2012).

Kochenderfer, J.N. et al. "Construction and Preclinical Evaluation of an Anti-CD19 Chimeric Antigen Receptor," J. Immunother. 32(7):689-702 (2009).

Kochenderfer, J.N., "Eradication of B-lineage and regression of lymphoma in a patient treated with autologous T cells genetically engineered to recognize CD19," Blood, 2010, 116(20), 4099-4102.

Kochenderfer, J.N., et al. "Chemotherapy-Refractory Diffuse Large B-Cell Lymphoma and Indolent B-Cell Malignancies Can be Effectively Treated With Autologous T Cells Expressing an Anti-CD19 Chimeric Antigen Receptor," J. Clin. Oneal. (2014).

Kochenderfer, J.N., et al. "Donor-derived CD19-targeted T cells cause regression of malignancy persisting after allogeneic hematopoietic stem cell transplantation," Blood 122(25): 4129-4139 (2013).

Koeffler and Golde, "Acute myelogenous leukemia: a human cell line responsive to colony-stimulating activity," Science, Jun. 1978, 200(4337): 1153-1154.

Koehler et al. "Engineered T Cells for the Adoptive Therapy of B-Cell Chronic Lymphocytic Leukaemia," Advances in Hematology, vol. 2012, Article ID 595060, 13 pages; doi:10.1155/2012/595060.

Kohn et al. "CARs on track in the clinic," Mar. 2011, Molecular Therapy: The Journal of the American Society of Gene Therapy, 19:432-438.

Koka, R. et al., "Cutting edge: murine dendritic cells require IL-15R a to prime NK cells," J Immunol., 173(6): 3594-3598 (2004).

Kolb HJ, et al., "Graft-versus-leukemia effect of donor lymphocyte transfusions in marrow grafted patients," Blood, 1995, 6:2041-2050.

Gauthier, et al., "High IL-15 Serum Concentrations are Associated with Response to CD19 CAR T-Cell Therapy and Robust In Vivo CAR T-Cell Kinetics", Blood, 136:supp 1:37, in 4 pages, Nov. 5, 2020.

Geiger and Jyothi, "Development and application for receptor-modified T lymphocytes for adoptive immunotherapy," Transfus Med Rev, Jan. 2001, 15(1): 21-34.

Geiger et al., "Integrated src kinase and costimulatory activity enhances signal transduction through single-chain chimeric receptors in T lymphocytes", Blood. Oct. 15, 2001; 98(8):2364-2371.

GenBank Accession No. AF072844.1, "*Homo sapiens* membrane protein DAP10 (DAP10) mRNA, complete cds", Aug. 4, 1999.

GenBank Accession No. NM 007360 GI:15221123, *Homo sapiens* killer cell lectin like receptor K1 (KLRK1), mRNA, dated May 29, 2017, 4 pages.

GenBank Accession No. NM_0 1 1612 GI: 6755830, Mus musculus tumor necrosis factor receptor superfamily, member 9 (Tnfrsf9), mRNA, dated Oct. 26, 2004, 8 pages.

GenBank Accession No. NM_000734 GI: 27886640, *Homo sapiens* CD8 antigen, alpha polypeptide (TiT3 complex) (CD3Z), transcript variant 2, mRNA, dated Oct. 27, 2004, 6 pages.

GenBank Accession No. NM_000734 GI: 37595563, *Homo sapiens* CD3Z antigen, s polypeptide (TiT3 complex) (CD3Z), transcript variant 2, mRNA, dated Oct. 27, 2004, 6 pages.

GenBank Accession No. NM_001768 GI: 27886640, *Homo sapiens* CD8 antigen, a polypeptide (p32) (CD8A), transcript variant 1, mRNA, dated Oct. 27, 2004, 5 pages.

GenBank Accession No. NM_007360.3, "*Homo sapiens* killer cell lectin like receptor K1 (KLRK1), mRNA", Sequence D 315221123, Jan. 12, 2013.

GenBank Accession No. NM_172175.2, *Homo sapiens* interleukin 15 (IL15), transcript variant 2, mRNA, dated Feb. 12, 2011, 4 pages.

Germain et al., "T-cell signaling: the importance of receptor clustering," Curr Biol., 7(10): R640-R644, Oct. 1, 1997.

Ghobadi, et al., "Updated Phase 1 Results from ZUMA-1: A Phase 1-2 Multicenter StudyEvaluating the Safety and Efficacy of KTE-C19 (Anti-CD 19 CAR T Cells) in Subjects With Refractory Aggressive Non-Hodgkin Lymphoma," Slides accompanying oral presentation at the American Association for Cancer Research Annual Meeting, New Orleans, Louisiana 2016.

Ghorashian, S., et al., "CD 19 chimeric antigen receptor T cell therapy for haematological mali nancies," Br. J. Haematol. 169:463-478 2015).

Giebel, S. et al., "Survival advantage with KIR ligand incompatibility in hematopoietic stem cell transplantation from unrelated donors" Blood (2003) vol. 102, No. 3, pp. 814-819.

Gill. S., et al., "Chimeric antigen receptor T cell therapy: 25 vears in tire making," Blood Rev. (2015), 30 (3): 157-167.

Gillet et al., Selectable Markers for Gene Therapy, Chapter 26 of Gene and Cell Therapy: Therapeutic Mechanisms and Strategies, 3rd Ed. N .S. Templeton Ed, (CRC Press:Bpca Ratpm. FL), pp. 555 and 558, 2009.

Ginald, L., et al., "Levels of expression of CD19 and CD20 in chronic B cell leukaemias," J. Clin. Pathol. 51: 364-369 (1998).

(56)                    References Cited

OTHER PUBLICATIONS

Giuliani, M. et al., "Generation of a novel regulatory NK cell subset from peripheral blood CD34+ progenitors promoted by membrane-bound IL-15," PLos One, 3(5): e2241 (2008).

Goklemez, et al., "Long-term follow-up after lymphodepleting autologous haematopoietic cell transplantation for treatment-resistant systemic lupus erythematosus" Rheumatology, 61:3317-3328 (2022).

Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neop lasia, 1999, 1(2): 123-127.

Goodier and Londei, "CD28 is not directly involved in the response of human CD3-CD56+ natural killer cells to lipopolysaccharide: a role for T cells," Immunology, Apr. 2004, 111(4): 384-90.

Goodwin et al., "Molecular cloning of a ligand for the inducible T cell gene 4-1 BB: a member of an emerging family of cytokines with homology to tumor necrosis factor", Eur J Immunol. Oct. 1993; 23(10):263 1-2641.

Gordon, P.A., Winer, J. B., Hoogendijk, J. E., & Choy, E. H. (2012). Immunosuppressant and immunomodulatory treatment for dermatomyositis and polymyositis. Cochrane Database Syst Rev, 2012(8), Cd003643. https://doi.ora/10.1002/14651858.CD003643. oub4.

Grabstein et al., "Cloning of a T cell growth factor that interacts with the ß chain of the interleukin-2 receptor," Comparitive Study, Science, May 13, 1994; 264(5161):965-8.

Granit, et al., "Safety and clinical activity of autologous RNA chimeric antigen receptor T-cell therapy in myasthenia gravis (MG-001): a prospective, multicentre, open-label, non-randomised phase 1 b/2a study", Lancet Neurol. 22:578-90 (2023).

Grauer et al., "Identification, Purification, and Subcellular Localization of Prostate-specific Membrane Antigen PSM' Protein in the LNCaP Prostatic Carcinoma Cell Line," Cancer Res., 58: 4787-4789 (1998).

Greene et al., "Covalent dimerization of CD28/CTLA-4 and oligomerization of CD80/CD86 regulate T cell costimulatory interactions," J Biol Chem., 271(43):26762-26771, Oct. 25, 1996.

Greenfield, E.A., et al., "CD28/B7 Costimulation: A Review," Crit. Rev. Immunol. 18: 389-418 (1998).

Greenwald et al., "The B7 Family Revisited," Annu. Rev. ImmunoL, 2005, 23: 515-548.

Grillo-Lopez, "Rituximab: An Insider's Historical Perspective," Seminars in Oncology 27(6 Suppl 12): 9-16 (2012).

Grootscholten, et al., Discontinuation of immunosuppression in proliferative lupus nephritis: is it possible? Nephrol Dial Transplant 21:1465-1469 (2006).

Gross and Eshhar "Endowing T cells with antibody specificity using chimeric T cell receptors," FASEB J. Dec. 1992;6(15):3370-3378.

Grupp et al., "Chimeric antigen receptor-modified T cells for acute lymphoid leukemia," N Engl J Med. Apr. 18, 2013; 368 (16):1509-1518.

Hahn et al. American College of Rheumatology guidelines for screening, treatment and management of lupus nephritis. Arthritis Care Res (Hoboken), (2012), vol. 64, No. 6, pp. 797-808. doi: 10.1002/acr.21664.

Handgretinger, R., et al., "A phase I study of neuroblastoma with the anti-ganglioside GD2 antibody 14.G2a," Cancer Immunol. Immunother. 35: 199-204 (1992).

Hara et al., "NKG2D gene polymorphisms are associated with disease control of chronic myeloid leukemia by dasatinib," Int. J. Hematol., 9 pages, Aug. 9, 2017.

Harada H, et al., "Selective expansion of human natural killer cells from peripheral blood mononuclear cells by the cell line, HFWT", Jpn J Cancer Res. Mar. 2002; 93(3):313-319.

Harada, H., et al., "A Wilms Tumor Cell Line, HFWT, can Greatly Stimulate Proliferation of CD56+ Human Natural Killer Cells and their Novel Precursors in Blood Mononuclear Cells," Exp. Hematology, 2004, pp. 614-621, vol. 32.

Harding et al., "CD28-mediated signalling co-stimulates murine T cells and prevents induction of anergy in T-cell clones," Nature, 356(6370):607-609, Apr. 16, 1992.

Harmon et al., "Dexamethasone induces irreversible G1 arrest and death of a human lymphoid cell line," J Cell Physiol, Feb. 1979, 98(2): 267-278.

Harris et al. International, multi-center standardization of acute graft-versus-host disease clinical data collection: a report from the MAGIC consortium. Biol Blood Marrow Transplant. (2016); vol. 22, No. 1, pp. 4-10. doi: 10.1016/j.bbmt.2015.09.001.

Hasan, A.N., "Soluble and membrane-bound interleukin (IL)-15 Ra/IL-15 complexesmediate proliferation of high-avidity central memory CD81T cells foradoptive immunotherapy of cancer and infections," Clinical and Experimental Immunology, 186: 249-265, 2016.

Hay et al. Kinetics and biomarkers of severe cytokine release syndrome after CD19 chimeric antigen receptor-modified T-cell therapy. Blood. (2017), vol. 130, No. 21, pp. 2295-2306. doi: 10.1182/blood- 2017-06-793141.

Hayashi, T. et al., "Identification of the NKG2D Haplotypes Associated with Natural Cytotoxic Activity of Peripheral Blood Lymphocytes and Cancer Immunosurveillance", Cancer Research (2006) vol. 66, No. 01, pp. 563-570.

Haynes NM, et al., "Single-chain antigen recognition receptors that costimulate potent rejection of established experimental tumors", Blood, Nov. 2002 I; 100(9):3155-3163.

Haynes, N.M., et al., "Redirecting Mouse CTL Against Colon Carcinoma: Superior Signaling Efficacy of Single-Chain Variable Domain Chimeras Containing TCR- vs Fc£RI-y," J. Immunol. 166: 182-187 (2001).

He et al. "Dilemma of immunosuppression and infection risk in systemic lupus erythematosus." Rheumatology (Oxford). 2022; vol. 62, Suppl 1, pp i22-i29. doi:10.1093/rheumatology/keac678.

Kowalik, C.M., "CD28 Costimulation Provided through a CD19-Specific Chimeric Antigen Receptor Enhances In vivo Persistence and Antitumor Efficacy of Adoptively Transferred T Cells," Cancer Research 66: 10995-11004 (2006).

Krampera et al., "Bone marrow mesenchymal stem cells inhibit the respnose of nai:Ve and memory antigen-specific T cells to their cognate peptide," Blood, May 2003, 101(9): 3722-9.

Krause et al., "Antigen-dependent CD28 Signaling Selectively Enhances Survival and Proliferation in Genetically Modified Activated Human Primary T Lymphocytes," J. Exp. Med., 1998, 188(4): 619-626.

Kretschmann, et al., "Successful Generation of CD19 Chimeric Antigen Receptor T Cells from Patients with Advanced Systemic Lupus Erythematosus" Transplantation and Cellular Therapy 29:27-33 (2023).

Krug, C., et al., "Stability and activity of MCSP-specific chimeric antigen receptors (CARs) depend on the scFv antigen-binding domain and the protein backbone," Cancer Immunol. Immunother. 64:1623-1635 (2015).

Kumar B. B. et al., "Natural Killer Cells Expanded and Preactivated Exhibit Enhanced Antitumor Activity against Different Tumor Cells in Vitro", Asian Pacific Journal of Cancer Prevention, vol. 21, No. 6, Jun. 6, 2020, pp. 1595-1605.

Kuo et al., "Efficient gene transfer into primary murine lymphocytes obviating the need for drug selection," Blood, Aug. 1993, 82(3): 845-52.

Kurokawa, M. and S. Kombluth, "Caspascs and kinascs in a death grip," Cell, 138(5): 838-854 (2009).

Kussie P.H., et al., "A single engineered amino acid substitution changes antibody fine specificity", J Immunol, Jan. 1994, 152(1), pp. 146-152.

Kwon B, et al., "cDNA sequences of two inducible T-cell genes", Proc Natl Acad Sci U SA., Mar. 1986; 86(6):1963-1967.

Kymriah, Highlights of Prescribing Information, in 31 pages (2017).

Labonte, M.L et al., "Molecular Determinants Regulating the Pairing of NKG2 Molecules with CD94 for Cell Surface Heterodimer Expression," J Immunol, 172(11): 6902-6912 (May 2004).

(56) References Cited

OTHER PUBLICATIONS

Lafreniere, R., et al.. , "Successful Immunotherapy of Murine Experimental Hepatic Metastases with Lymphokine-activated Killer Cells and Recombinant Interleukin 2," Cancer Res. 45: 3735-3741 (1985).

Lamers, C.H.J., et al., "Treatment of Metastatic Renal Cell Carcinoma With Autologous T- Lymphocytes Genetically Retargeted Against Carbonic Anhydrase IX: First Clinical Experience," J. Clin. Oncol. 24: e20-e22 (2006).

Lang et al., "Absence of B7.1-CD28/CTLA-4-mediated co-stimulation in human NK cells," Eur. J. Immunol, Mar. 1998, 28: 780-786.

Langer et al., "Comparative Evaluation of Peripheral Blood T Cells and Resultant Engineered Anti-CD19 CAR T-Cell Products From Patients With Relapsed/Refractory Non-Hodgkin Lymphoma (NHL)," Poster session presented at the American Association for Cancer Research Annual Meeting, New Orleans, Louisiana.

Lanier, Lewis L., "NK Cell Recognition," Annual Review of Immunology, vol. 23, No. 1, pp. 225-274 (2005).

Lanjewar et al. Long-term immunosuppression and multiple transplants predispose systemic lupus erythematosus patients with cytopenias to hematologic malignancies. Medicine (Baltimore). 2021;100(21):e25985. doi:10.1097/MD.0000000000025985.

Lanzavecchia et al., "Antigen decoding by T lymphocytes: from synapses to fate determination," Nat Immunol., 2(6):487-492, Jun. 2001.

Lapteva, N. et al., "Large-scale ex vivo expansion and characterization of natural killer cells for clinical applications," Cytotherapy, 14(9): 1131-1143 (2012).

Lauwerys, et al., "Synergistic Proliferation And Activation Of Natural Killer Cells By Interleukin 12 And Interleukin 18", Cytokine, vol. 11, No. 11, Nov. 1, 1999, pp. 822-830.

Leandro, "Rituximab—The First Twenty Years", Centre for Rheumatology, Division of Medicine, University College London, in 15 pages, (2021).

Lee et al., "T cells expressing CD19 chimeric antigen receptors for acute lymphoblastic leukaemia in children and young adults: a phase 1 dose-escalation trial," Lancet 385:517-528 (2015).

Lee, et al., "ASTCT Consensus Grading for Cytokine Release Syndrome and Neurologic Toxicity Associated with Immune Effector Cells" Biol Blood Marrow Transplant 25: 625-638 (2019).

Lehner at al. "Redirecting T Cells to Ewing's Sarcoma family of Tumors by a Chimeric NKG2D Receptor Expressed by Lentiviral Transduction or Mrna Transfection", 2012, PloS. One 7:e31210.

Leitner et al., "T cell stimulator cells, an efficient and versatile cellular system to assess the role of costimulatory ligands in the activation of human T cells," Journal of Immunological Methods, 362, 131-141, 2010.

Leung et al., "Determinants of antileukemia effects of allogneic NK cells," J Immunol, Jan. 2004, 172(1): 644-50.

Li et al., "Costimulation by CD48 and B7-1 induces immunity against poorly immunogenic tumors," J Exp Med, Feb. 1996, 183(2): 639-644.

Li et al., "Human iPSC-Derived Natural Killer Cells Engineered with Chimeric Antigen Receptors Enhance Anti-tumor Activity," Cell Stem Cell 23, 1-12, Aug. 2, 2018.

Li et al., "Polarization Effects of 4-1BB during CD28 Costimulation in Generating Tumor- reactive T Cells for Cancer Immunotherapy," Cancer Research, vol. 63, pp. 2546-2552, May 15, 2003.

Li Q. et al., Bifacial effects of engineering tumour cell-derived exosomes on human natural killer cells. Experimental Cell Research, Dec. 19, 2017, vol. 363, No. 2, pp. 141-150.

Liao, W. et al. ., "Interleukin-2 at the crossroads of effector responses, tolerance, and immunotherapy." Immunity, 38(1): 13-25 (2013).

Liebowitz et al., "Costimulatory approaches to adoptive immunotherapy," Curr Opin Oncol, Nov. 1998, 10(6): 533-41.

Lima, et al., "Interleukin-6 Neutralization by Antibodies Immobilized at the Surface of Polymeric Nanoparticles as a Therapeutic Strategy for Arthritic Diseases," ACS Appl. Mater. Interfaces 2018, 10, 13839-13850.

Linsley and Ledbetter, "The role of CD28 receptor during T cell responses to antigen," Annu Rev Immunol, 1993, 191-212.

Liu, E. et al., "GMP-Compliant Universal Antigen Presenting Cells (Uapc) Promote the Metabolic Fitness and Antitumor Activity of Armored Cord Blood CAR-NK Cells", frontiers in Immunology, Feb. 26, 2021, vol. 12, Article 626098, 14 pages.

Liu, E. et al., "Use of CAR-Transduced Natural Killer Cells in CD19-Positive Lymphoid Tumors", N. Engl .J. Med., vol. 382, No. 6, Feb. 6, 2020, pp. 545-553.

Liu, H., et al., "Monoclonal Antibodies to the Extracellular Domain of Prostate-specific Membrane Antigen Also React with Tumor Vascular Endothelium," Cancer Res. 57: 3629-3634 (1997).

Liu, L, et al. "Novel CD4-Based Bispecific Chimeric Antigen Receptor Designed for Enhanced Anti-HIV Potency and Absence of HIV Entry Receptor Activity," J. Viral. 89(13):6685-6694 (2015).

Lode et al., "Targeted cytokines for cancer immunotherapy," Immunol Res., 21(2-3):279-288, (2000).

Lopez-Requena et al., "Gangliosides, Ab1 and Ab2 antibodies III. The idiotype of anti-ganglioside mAb P3 is immtmogenic in a T cell-dependent manner," Mol Immunol, 2007, 44(11):2915-2922.

Lopez-Requena et al., "Gangliosides, Ab1 and Ab2 antibodies IV, Dominance of VH domain in the induction of anti-idiotypic antibodies by Jene gun immunization," Mol Immunol. Apr. 2007;44(11):3070-3075. Epub Mar. 2, 2007.

Lozzio C.B. and Lozzio, B.B.; "Human chronic myelogeneous leukemia cell-line with positive Philadelphia chromosome"; Blood 45:321-334 (1975).

Lozzio et al., "Properties and Usefulness of the Original K-562 Human Myelogenous Leukemia Cell Line," Leukemia Research, vol. 3, No. 6, pp. 363-370, 1979.

Lugli, E. et al., "Transient and persistent effects of IL-15 on lymphocyte homeostasis in nonhuman primates" Blood vol. 116, No. 17, pp. 3238-3248.

Lundberg, et al., "Classification of myositis" Nature Reviews, Rheumatology, vol. 14, pp. 269-278, May 2018.

Lupkynis, "Highlights of Prescribing Information" in 24 pages, (2021).

Ma et al., "Chapter 15: Genetically engineered T cells as adoptive immunotherapy of cancer," Cancer Chemotherapy and Biological Response Modifiers Annual 20, Ch. 15, 315-341, Giaccone.

Mosakowska, Magdalena, et al. "Assessment of the correlation of commonly used laboratory tests with clinical activity, renal involvement and treatment of systemic small-vessel vasculitis with the presence of ANCA antibodies." BMC nephrology 22.1 (2021): 290.

Motion to Intervene filed by Juno Therapeutics, Inc. in *Trustees of the University of Pennsylvania v. St. Jude Children's Research Hospital* in the U.S. District Court for the Eastern District of Pennsylvania, dated Dec. 13, 2013. (Doc. 24).

Murad, et al. "Manufacturing development and clinical production of NKG2D Chimeric Antigen Receptor-expressing T cells for autologous adoptive cell therapy" Cytotherapy, Jul. 2018; 20(7): 952-963.

Musso, T et al., "Human monocytes constitutively express membrane-bound, biologically active, and interferon-gamma-upregulated interleukin-15," Blood, 93(10): 3531-3539 (1999).

Nadler et al., "B4, a human B lymphocyle-associated antigen expressed on normal, mitogen-activated, and malignant B lymphocytes," J Immunol, Jul. 1983, 131(1): 244-250.

Nagashima et al., "Stable transduction of the interleukin-2 gene into human natural killer cell lines and their phenotypic and functional characterization in vitro and in vivo," Blood, May 1998, 91(10): 3850-3861.

Nakamura et al., "Chimeric anti-ganglioside GM2 antibody with antitumor activity," Cancer Res. Mar. 15, 1994; 54(6): 1511-6.

Nayyar G. et al., "Overcoming Resistance to Natural Killer Cell Based Immunotherapies for Solid Tumors", Frontiers in Oncology, vol. 9, Feb. 11, 2019, XP055700879.

(56)　　　　　References Cited

OTHER PUBLICATIONS

NCBI Reference Sequence NM_ 198053, "*Homo sapiens* CD247 molecule (CD247), transcript variant 1, mRNA", Jan. 20, 2008, 11 pages total.

NCBI Reference Sequence NM_ 198053, "*Homo sapiens* CD247 molecule (CD247), transcript variant 1, mRNA", Feb. 20, 2021, 9 pages total.

NCBI Reference Sequence NM_007360.2, "*Homo sapiens* killer cell lectin-like receptor subfamily K, member 1 (KLRK1 ), mRNA", Dec. 5, 2010, 10 pages total.

NCI Thesaurus, Bicistronic chimeric antigen receptor vector, Retrieved online from: <URL:https://ncit.nci.nih.gov/ncitbrowser/pages/home.jsf;jsessionid= 12BOF7AF7 I E9A4035C38B5E4F6C055B0>, Retrieved on: Jan. 21, 2021, 2021.

Neepalu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Society of Hematology Annual Meeting, Orlando, Florida (Dec. 5-8, 2015).

Neeplapu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Society of Hematology Annual Meeting, Orlando, Florida (Dec. 5-8, 2015).

Negrini, S. et al., "Membrane-bound IL-15 stimulation of peripheral blood natural killer progenitors leads to the generation of an adherent subset co-expressing dendritic cells and natural killer functional markers," Haematologica, 96(5): 762-766 (2011).

Nishigaki et al., "Prevalence and growth characteristics of malignant stem cells in B-lineage acute lymphoblastic leukemia," Blood, May 1997, 89(10): 3735-3744.

NKARTA Power Point Presentation "Next Generation Natural Killer Cells Engineered to Beat Cancer", Dec. 5, 2022, available at https://ir.nkartatx.com/static-files/9cb11d46-a4aa-49a3-baca-dc1a36e5aa60.

NKARTA Therapeutics, "Press Release: NKARTA Announces updated Clinical Data on Anti-CD19 Allogeneic Car-NK Cell Therapy NKX019 for patients with relapsed or Refractory Non-Hodgkin Lymphoma" (2022) available at https://ir.nkartatx.com/news-releases/news-release-details/nkarta- announces-updated-clinical-data-anti-cdl9-allogeneic-car.

Novartis Pharmaceuticals Corp.'s Motion to Intervene in *Trustees of the University of Pennsylvania* v. *St. Jude Children's Research Hospital* in the U.S. District Court for the Eastern District of Pennsylvania, dated Jan. 22, 2014. (Doc. 57).

Nunes et al., "The role of p21ras in CD28 signal transduction: triggering of CD28 With antibodies, but not the ligand B7-1, activates p21ras," J Exp Med, 180(3): 1067-1076, Sep. 1, 1994.

Oelke M, et al., "Ex vivo induction and expansion of antigen-specific cytotoxic T cells by HLA-1g-coated artificial antigen-presenting cells," Nat Med., 2003, 9(5):619-624.

Office Action in U.S. Appl. No. 10/981,352, dated Nov. 29, 2006.

Office Action in U.S. Appl. No. 13/548,148, dated Aug. 9, 2012.

Office Action in U.S. Appl. No. 13/548,148, dated Oct. 11, 2012.

Office Action in U.S. Appl. No. 11/074,525, dated Jan. 3, 2008.

Office Action of U.S. Appl. No. 10/981,352, dated Jan. 4, 2007.

Office Action of U.S. Appl. No. 10/981,352, dated Jan. 4, 2008.

Office Action of U.S. Appl. No. 10/981,352, dated Jun. 7, 2007.

Office Action of U.S. Appl. No. 10/981,352, dated Mar. 14, 2007.

Office Action of U.S. Appl. No. 11/074,525, dated Mar. 23, 2007.

Office Action of U.S. Appl. No. 11/074,525, dated Sep. 18, 2007.

Olsen, S. et al., "Crystal Structure of the Inteleukin-15-Interleukin-15 Receptor alpha complex" The Journal for Biological Chemistry (2007) vol. 282, No. 51, pp. 37191-37204.

Order in *Trustees of the University of Pennsylvania* v. *St. Jude Children's Research Hospital* in the U.S. District Court for the Eastern District of Pennsylvania, dated Nov. 13, 2013.

Order in *Trustees of the University of Pennsylvania* v. *St. Jude Children's Research Hospital* in the U.S. District Court for the Eastern District of Pennsylvania, dated Nov. 18, 2013. (Doc. 21).

Order in *Trustees of the University of Pennsylvania* v. *St. Jude Children's Research Hospital* in the U.S. District Court for the Eastern District of Pennsylvania, dated Nov. 18, 2013. (Doc. 26).

Order in *Trustees of the University of Pennsylvania* v. *St. Jude Children's Research Hospital* in the U.S. District Court for the Eastern District of Pennsylvania, dated Nov. 22, 2013. (Doc. 27).

Oyer et al., "Natural killer cells stimulated with PM21 particles expand and biodistribute in vivo: Clinical implications for cancer treatment," Cytotherapy, 18: 653-663, 2016.

Ozkaynak, M.F. et al., "Phase I Study of Chimeric Human/Murine Anti-Ganglioside GD2 Monoclonal Antibody (chl4.18) With Granulocyte-Macrophage Colony-Stimulating Factor in Children With Nueroblastoma Immediately After Hematopoietic Stem-Cell Transplantation: A Children's Cancer Group Study," J. Clinical Oncol. 18: 4077-4085 (2000).

Pakula, A. A. et al., "Genetic analysis of protein stability and function," Annual Review of Genetics, V. 23, N. 1, p. 289-310, c. 305-306 (1989).

Palmer SC, Tunnicliffe DJ, Singh-Grewal D, et al. Induction and Maintenance Immunosuppression Treatment of Proliferative Lupus Nephritis: A Network Meta-analysis of Randomized Trials. Am J Kidney Dis. 2017; 70(3):324-336. doi:10.1053/i.aikd.2016.12.008.

Parihar, et al., "NK cells expressing a chimeric activating receptor eliminate MDSCs and rescue impaired CAR-T cell activity against solid tumors", cancerimmunolres.aacrjournals.org, Jan. 19, 2019, in 47 pages.

Park et al. "CD19-targeted CART-cell therapeutics for hematologic malignancies: interpreting clinical outcomes to date", Blood, Jun. 30, 2016, 157(26): 3312-3320 (See Abstract).

Park et al. "Complex regulation of human NKG2D-DAP10 cell surface expression: opposing roles of the Ye cytokines and TGF-B1", 2011, Blood 118:3019-3027.

Park et al., "CD19-Targeted 19-28z CAR Modified Autologous T Cells Induce High Rates of Complete Remission and Durable Responses in Adult Patients with Relapsed, Refractory B-Cell ALL," Abstract presented at the American Society of Hematology Annual Meeting, San Francisco, California, available at https://ash.confex.com/ash/2014/webprogram/Paper76573.html.

Park, J.H., and Brentjens, R J., "Are All Chimeric Antigen Receptors Created Equal?" J. Clin. Oncol. 33:651-653 (2015).

Park, J.H., et al., Abstract, "682 Implications of Minimal Residual Disease Negative Complete Remission (MRD-CR) and Allogeneic Stem Cell Transplant on Safety and Clinical Outcome of CD19-Targeted 19-28z CAR Modified T cells in Adult Patients with Relapsed, Refractory B-Cell ALL," Am. Soc'v Hematol., available at https://ash.confex.com/ash/2015/weboroaram/Paoer86688.html.

Parkhurst, M. R., et al., "Adoptive Transfer of Autologous Natural Killer Cells Leads to High Levels of Circulating Natural Killer Cells but Does Not Mediate Tumor Regression", Clinical Cancer Research (2011), vol. 17, No. 19, pp. 6287-6297.

Sadelain et al., "The promise and potential pitfalls of chimeric antigen receptors," Curr Opin Immunol., 2009, 21 (2):215-223.

Sadelain, M. et al., "The Basic Principles of Chimeric Antigen Receptor Design," Cancer Discovery, vol. 3, No. 4, pp. 388-398 (Apr. 1, 2013).

Sadelain, M., "CAR Therapy: the CD19 Paradigm," J. Clin. Investigation 125: 3392-3400 (2015).

Sahm et al., "Expression of IL-15 in N K cells results in rapid enrichment and selective cytotoxicity of gene-modified effectors that carry a tumor-specific antigen receptor," Cancer hunol. Immunother., 61 (9): 1451-1461, Feb. 2012.

Salih et al., "Cutting Edge: Down-Regulation of MICA on Human Tumors by Proteolytic Shedding", J. Immunol. (2002), vol. 169, pp. 4098-4102.

Salomon and Bluestone, "Complexities of CD28/B7: CTLA-4 costimulatory pathways in autoimmunity and transplantation," Annu Rev Immunol, 2001, 19: 225-252.

Sambrook et al., "Molecular Cloning: A Laboratory Manual," (1989) [Table of Contents and Preface Only].

(56)          References Cited

OTHER PUBLICATIONS

Sankhla, S.K. et al., "Adoptive immunotherapy using lymphokineactivated killer (LAK) cells and interleukin-2 for recurrent malignant primary brain tumors," J Neurooncol. 27: 133-140 (1995).

Santegoets S. J. et al., IL-21 promotes the expansion of CD27+ CD28+tumor infiltrating lymphocytes with high cytotoxic potential and low collateral expansion of regulatory T cells. Journal of Translational Medicine, Feb. 12, 2013, vol. 11, No. 37, pp. e1-10.

Santomasso B, Bachler C, Westin J, f-1ezvanl K, Shpail EJ. The Other Side of CAFI T-Ceii Therapy: Cytokine Release Syndrome, Neurologic Toxicity, and Financial Burden. Am Soc Ciin Oneal Educ Book. 2019; 39:433-444. doi:10.1200/EDBK 238691.

Sattler, S. et al., "Evolution of the C-Type Lectin-Like Receptor Genes od the DECTIN-1 Cluster in the NK Gene Complex," The Scientific World Journal, vol. 2012, 2011.

Savoldo, B., et al., "CD28 costimulation improves expansion and persistence of chimeric antigen receptor modified T cells in lymphoma patients," J. Clin. Invest. 121(5):1822-1826 (2011).

Schirrmann, et al. "Human natural killer cell line modified with a chimeric immunoglobulin T-cell receptor gene leads to tumor growth inhibition in vivo" Cancer Gene Therapy (2002) 9, 390-398.

Schlums, H. et al., "Cytomegalovirus Infection Drives Adaptive Epigenetic Diversification of NK Cells with Altered Signaling and Effector Function", Immunity Author manuscript, Mar. 17, 2015, 42(3), 443-456, in 28 pages.

Schmaltz et al., "T cells require TRAIL for optimal graft-versus-tumor activity," Nat Med, Dec. 2002, 8(12): 1433-7.

Schneider et al., "Characterization of EBV-genome negative "null" and "T" cell lines derived from children with acute lymphoblastic leukemia and leukemic transformed non-Hodgkin lymphoma," Int J Cancer, May 1977, 19(5): 621-626.

Schroers et al., "Gene transfer into human T lymphocytes and natural killer cells by Ad5/F35 chimeric adenoviral vectors," Exp Hematol, Jun. 2004, 32(6): 536-46.

Schulz, G., et al., "Detection of Ganglioside GD2 in Tumor Tissues and Sera of Neuroblastoma Patients," Cancer Research 44: 5914-5920 (1984).

Schumacher, "T-cell-receptor gene therapy," Nat Rev Immunol, Jul. 2002, 2(7): 512-519.

Schwartz et al., "Structural basis for co-stimulation by the human CTLA-4/B7-2 complex," Nature, 410(6828):604-608, Mar. 29, 2001.

Schwarz et al., "ILA, the human 4-1BB homologue, is inducible in lymphoid and other cell lineages," Blood, Feb. 1995, 85(4): 1043-1052.

Scott, A. M. et al., "Antibody therapy of cancer" Nature Reviews (2012) vol. 12, pp. 278-287.

Search Report and Written Opinion for Singapore Application No. 11201908337V, titled, "Stimulatory cell lines for ex vivo expansion and activation of natural killer cells," Date Completed: Nov. 25, 2020.

Seif et al., "The role of JAK-STAT signaling pathway and its regulators in the fate of T helper cells" Cell Communication and Signaling (2017) 15:23.

Sentman, C. L. et al., "NK Cell Receptors as Tools in Cancer Immunotherapy" Advances in Cancer Research (2006) pp. 249-292.

Sentman, C. L., et al., "NKG2D CARs as Cell Therapy for Cancer", The Cancer Journal (2014), vol. 20, No. 2, pp. 156-159.

Sentman, et al., "NK Cell Receptors as Tools in Cancer Immunotherapy," Department of Microbiology and Immunology, Dartmouth Medical School, Lebanon, New Hampshire 03756, 2006.

Shanghai Hospital, "Shanghai Changhai Hospital is the first to realize the treatment of systemic lupus erythematosus with CAR-NK", Cell & Gene Therapy, Jan. 5, 2024, in 9 pages.

Sheard, M. A et al., "Membrane-bound TRAIL Supplements Natural Killer Cell Cytoxicity Against Neuroblastoma Cells" J. Immunother. (2013) vol. 36, No. 5, pp. 319-329.

Shimabukuro-Vornhagen A, Godel P, Subklewe M, et al. Cytokine release syndrome. J Immunother Cancer. 2018; 6 (1):56. doi:10.1186/s40425-018--0343-9.

Shimasaki et al., "A Clinically Adaptable Method to Enhance the Cytotoxicity of Natural Killer Cells Against B-cell Malignancies", Cytotherapy (2012), vol. 14, pp. 830-840.

Shook et al., "Refinitiv Streetevents Edited Transcript NKTX.OQ-Nkarta Inc NKX101 Clinical Update Conference Call" Jun. 27, 2023, in 16 pages.

Shook et al., "Natural Killer Cell Engineering for Cellular Therapy of Cancer," National Institutes of Health, Tissue Antigens, vol. 78, No. 6, pp. 409-415, Dec. 2011.

Shuford WW, et al., "4-1 BB costimulatory signals preferentially induce Cds+ T cell proliferation and lead to the amplification in vivo of cytotoxic T cell responses", J Exp Med. Jul. 7, 1997; 186(1):47-55.

Shum et al., "Conservation and Variation in Human and Common Chimpanzee CD($ and NKG2 Genes," The American Association of Immunologists, The Journal of Immunology, pp. 240-252, Downloaded on Jun. 18, 2017.

Sica G, Chen L. Modulation of the immune response through 4-1 BB. In: Habib N, ed. Cancer gene therapy: past achievements and future challenges. New York: Kluwer Academic/Plenum Publishers; 355-362 (2000) [Book].

Slavik et al., "CD28/CTLA-4 and CD80/CD86 families: signaling and function," Immunol Res., 19(1):1-24, 1999.

Slavin et al., "Allogeneic cell therapy with donor peripheral blood cells and recombinant human interleukin-2 to treat leukemia relapse after allogeneic bone marrow transplantation," Blood, Mar. 1996, 87(6): 2195-204.

Sloan Kettering Institute for Cancer Research'a Patent Owner Response re: IPR2015-01719, 86 pages, May 5, 2016.

Sloan Kettering Institute for Cancer Research's Patent Owner Preliminary Response re: IPR2015-01719, 68 pages, dated Nov. 25, 2015.

Sneller, M.C. et al., "IL-15 administered by continuous infusion to rhesus macaques induces massive expansion of CD8+ T effector memory population in peripheral blood," Blood, 118(26): 6845-6848 (2011).

Sokolic et al., "A Selectable Bicistronic Retroviral Vector Corrects the Molecular Defect in a Cell Line Derived from a Patient with Leukocyte Adhesion Deficiency," Biol. Blood Marrow Transpl. 12(2) Suppl 1: 20-21, Feb. 2006.

Somanchi, S.S. et al., "Expansion, purification, and functional assessment of human peripheral blood NK cells," Journal of Visualized Experiments, 48A: 2540 (2011).

Song et al., "Chimeric NKG2D CAR-Expressing T Cell-Mediated Attack of Human Ovarian Cancer is Enhanced by Histone Deacetylase Inhibition," Human Gene Therapy, vol. 24, pp. 295-305, Mar. 2013.

Song, D.G et al., "In vivo persistence, tumor localization and anti-tumor activity of CAR engineered T cells is enhanced by costimulatory signaling through CD137 (4-1 BB)" Cancer Res. (2011) vol. 71, No. 13, pp. 4617-4627.

Spear al., "Collaboration of Chimeric Antigen Receptor (CAR)-expressing T Cells for Optimal Elimination of Established Ovarian Tumors", Oncolmmunology (2013), vol. 2, No. 4, pp. e23564-1-e23564-12.

Spear et al., 2013, NKG2D CAR T-Cell Therapy Inhibits the Growth of NKG2D Ligand Heterogeneous Tumors, Immunology and Cell Biology 91: 435-440.

Spear et al., "Chimeric Antigen Receptor T Cells Shape Myeloid Cell Function within the Tumor Microenvironment through IFN-y and GM-CSF," The Journal of Immunology, pp. 6389-6399, 2014.

Srinivasan et al., "A retro-inverso peptide mimic of CD28 encompassing the MYPPPY motif adopts a polyproline type II helix and inhibits encephalitogenic T cells in vitro," J Immunol., 167(1):578-585, Jul. 1, 2001.

Srivannaboon et al., "Interleukin-4 variant (BAY 36-1677) selectively induces apoptosis in acute lymphoblastic leukemia cells," Blood, Feb. 2001, 97(3): 752-758.

Besser, M.J., et al., "Adoptive Transfer of Tumor-Infiltrating Lymphocytes in Patients with Metastatic Melanoma: Intent-to-Treat Analysis and Efficacy after Failure to Prior Immunotherapies," Clin. Cancer Res. 19: 4792-4800 (2013).

Better et al., "Manufacturing and Characterization of KTE-C19 in a Multicenter Trial of Subjects with Refractory Aggressive Non-

(56) References Cited

OTHER PUBLICATIONS

Hodgkin Lymphoma (NHL) (ZUMA-1)," Poster session presented at the American Association for Cancer Research Annual Meeting, New Orleans, Louisiana (2016).

Beziat, V. et al., "NK cell responses to cytomegalovirus infection lead to stable imprints in the human KIR repertoire and involve activating KIRs", blood, Apr. 4, 2013, 121(14), 2678-2688.

Billadeau D.D. et al., "NKG2D-DAP10 triggers human NK cell-mediated killing via a Syk-independent regulatory pathway", Nature Immunology (2003), vol. 4, No. 6, pp. 557-564.

Bischof et al., "Autonomous induction of proliferation, JNK and NF-alphaB activation in primary resting T cells by mobilized CD28," Eur J Immunol., 30(3):876-882, Mar. 2000.

Borchers et al. The geoepidemiology of systemic lupus erythematosus. Autoimmun Rev. 2010;9(5): A277-A287. doi:10.1016/j.autrev.2009.12.008.

Bork et al., "The immunoglobulin fold. Structural classification, sequence patterns and common core," J Mol Biol., 242 (4):309-320, Sep. 30, 1994.

Boyman, O et al., "The role of interleukin-2 during homeostasis and activation of the immune system" Nature Reviews (2012) vol. 12, pp. 180-190.

Brand, L.J. et al., "Abstract LB-185: A PSMA-directed natural killer cell approach for prostate cancer immunotherapy," Cancer Research, 77(13 Supplement): Abstract No. LB-185, 1-4 (Jul. 2017).

Brentjens et al., "Eradication of Systemic B-Cell Tumors by Genetically Targeted Human T Lymphocytes Co-Stimulated B Cd80 and Interleukin-15," Nature Medicine, 2003, 9: 279-286.

Brentjens, R.J., et al., "CD 19-Targeted T Cells Rapidly Induce Molecular Remissions in Adults with Chemotherapy-Refractory Acute Lymphoblastic Leukemia," Sci. Trans. Med. 5: 1-9 (2013).

Brentjens, R.J., et al., "Safety and persistence of adoptively transferred autologous CD19-targeted T cells in patients with relapsed or chemotherapy refractory B-cell leukemias," Blood 119(18): 4817-4828 (2011).

Breyanzi, Highlights of Prescribing Information, in 11 pages (2021).

Bridgeman J. S. et al., The Optimal Antigen Response of Chimeric Antigen Receptors Harboring the CD3 Transmembrane Domain Is Dependent upon incorporation of the Receptor into the Endogenous TCR/CD3 Complex. J Immunol., May 17, 2010, vol. 184, No. 12, pp. 6938-3949.

Bridgeman, J.S., et al., "Building Better Chimeric Antigen Receptors for Adoptive T Cell Therapy," Current Gene Therapy 10: 77-90 (2010).

Bridgeman, J.S., et al., "The Optimal Antigen Response of Chimeric Antigen Receptors Harboring the CD3 Transmembrane Domain Is Dependent upon Incorporation of the Receptor into the Endogenous TCR/CD3 ComDlex" The Journal of Immunoloav, Oct. 15, 2019, in 13 Daaes.

Brocker et al., "New simplified molecular design for functional T cell receptor," Eur J Immunol., 23(7): 1435-1439, Jul. 1993.

Bromley et al., "The immunological synapse and CD28-CD80 interactions," Nat Immunol., 2(12): 1159-1166, Dec. 2001.

Bronte, V., and Mocellin, S., "Suppressive Influences in the Immune Response to Cancer," J. Immunother . 32: 1-11 (2009).

Brown et al. "Tolerance to Single, but Not Multiple, Amino Acid Replacements in Antibody VH CDR2" The Journal of Immunology (May 1, 1996) 156, 3285-3291.

Budagian, V. et al., "IL-15/IL-15 receptor biology: A guided tour through an expanding universe," Cytokine & Growth Factor Reviews, 17(4): 259-280 (2006).

Bukczynski et al., "Costimulation of Human CD28-T Cells by 4-1BB Ligand," Eur. J. Immunol., 2003, 33: 446-454.

Burkett et al., "Coordinate expression and trans presentation of interleukin (IL<)-15 supports natural killer cell and memory CD8+T Cell Homeostasis," J. Exp. Med, 2004, 200:825-834.

Butler et al. Effect of minimal lymphodepletion prior to ACT with TBI 1301, NY-ESO-1 specific gene-engineered TCR-T cells, on clinical responses and Crs. J Clin Oncol 2019; 37:15_suppl 2537-2537 doi: 10.1200/JO.2019.37.15suppl.2537.

Cabaletta, "Corporate Presentation", Mar. 2023, in 23 pages.

Cabaletta, "IND application cleared within 6 months of in-licensing CABA-201 Binder" Mar. 31, 2023, in 7 pages.

Calabrese, et al., "IL-6 biology: implications for clinical targeting in rheumatic disease," S. Nat. Rev. Rheumatol, 10, 720-727 (2014); published online Aug. 19, 2014 (corrected online Sep. 19, 2014).

Caligiuri et al., "Immunotherapeutic approaches for hematologic malignancies," Hematology Am Soc Hematol Educ Program, 2004, 37-53.

Campana et al., "Immunophenotyping of Leukemia," Journal of Immunol Methods, 2000, 243: 59-75.

Caratelli et al., "FCy Chimeric Receptor-Engineered T Cells: Methodology, Advantages, Limitations, and Clinical Relevance," Front Immunol., vol. 8, Article 457 , 8 pages (Apr. 27, 2017).

Cardoso AA, et al. Pre-B acute lymphoblastic leukemia cells may induce T-cell anergy to alloantigen. Blood 88:41-48 (1996).

Carlsten et al., "Genetic manipulation of NK cells for cancer immunotherapy: techniques and clinical implications," Frontiers in Immunology, vol. 6, Article 266, Jun. 2015.

Carr AS, et al. A Systematic Review of Population Based Epidemiological Studies in Myasthenia Gravis. BMC Neural. 2010; 10:46. Published Jun. 18, 2010. doi:10.1186/1471-2377-10-46.

Carson et al., "A potential rold for Interleukin-15 in the regulation of human natural killer cell survival," J. Clin. Invest., 1997, 99(5): 937-943.

Carter, P., et al. ., "Identification and validation of cell surface antigens for antibody targeting in oncology," Endocrine-Related Cancer 11: 659-687 (2004).

Cecele J. Denman, et al., "Membrane-Bound IL-21 Promotes Sustained Ex Vivo Proliferation of Human Natural Killer Cells" Plos One, www.plosone.org, Jan. 18, 2012, vol. 7, in 13 pages.

Ceribelli, et al., "The Immune Response and the Pathogenesis of Idiopathic Inflammatory Myositis: a Critical Review," Clin Rev Allergy Immunol, 52(1), 58-70. (2017). https://doi.ora/10.1007/s12016-016-8527-x.

Cesano, A., et al. "Reversal of Acute Myelogenous Leukemia in Humanized SCID Mice Using a Novel Adoptive Transfer Approach," J. Clin. Invest. 94: 1076-1084 (1994).

Chambers, C.A., "The expanding world of co-stimulation: the two-signal model revisited," TRENDS in Immunol., 2001, 22(4):217-223.

Champlin R. "T-cell depletion to prevent graft-versus-host disease after bone marrow transplantation," Hematol Oncol Clin North Am. Jun. 1990;4(3):687-698.

Chang et al., "Five Different Anti-Prostate-specific Membrane Antigen (PSMA) Antibodies Confirm PSIVIA Expression in Tumor-associated Neovasculature," Cancer Res., 59: 3192-3198 (1999).

Chang et al., "A Chimeric Receptor with NKG2D Specificity Enhances Natural Killer Cell Activation and Killing of Tumor Cells", Cancer Res. (2013), vol. 73, No. 6, pp. 1777-1786.

Chao, D. T. et al., "BCL-2 Family: Regulators of Cell Death", Annu. Rev. Immunol. (1998), vol. 16, pp. 395-419.

Chen et al., B cell targeting in CART cell therapy: Side effect or driver of CART cell function? Sci Transl Med. 2022;14(650):eabn3353. doi: 10.1126/scitranslmed.abn3353.

Chen, et al., "Regulatory effects of dexamethasone on NK and T cell immunity" Inflammopharmacology, 26:1331-1338 (2018).

Chen, et al., "Value of a complete or Partial Remission in severe Lupus Nephritis", Clin J Am Soc Nephrol 3:46-53, 2008.

Cheresh et al., "Disialoganghosidcs GD2 and GD3 Arc Involved in the Attachment of Human Melanoma and Neuroblastoma Cells to Extracellular Matrix Proteins," J Cell Biol. 1986, 102(3):688-696.

Chertova, E. et al., "Characterization and favorable in vivo properties of heterodimeric soluble IL-15.IL-15Ralpha cytokine compared to IL-15 monomer," J Biol Chem., 288(25): 18093-18103 (2013).

Cheung et al., "Anti-Idiotypic Antibody Facilitates scFv Chimeric Immune Receptor-Gene Transduction and Clonal Expansion of Human Lymphocytes for Tumor Therapy," Hybridoma and Hybridomics, 2003, 24(4): 209-218.

Chiorean and Miller, "The biology of natural killer cells and implications for therapy of human disease," J Hematother Stem Cell Res, Aug. 2001, 10(4): 451-463.

(56) References Cited

OTHER PUBLICATIONS

AASEQ1_05172022_135256_pep_vs AASEQ2_05172022_135256_pep_align_4-1BBL (Year: 2022).

Abakushina, E.V., "Immunotherapy With Natural Killer Cells In The Treatment Of Cancer," Russian Journal of Immunology, vol. 10, No. 2, pp. 131-142 (2016) (Abstract only).

Abken et al., "Chimeric T-cell receptors: highly specific tools to target cytotoxic T-lymphocytes to tumour cells," Cancer Treat Rev., 23(2):97-112, Mar. 1997.

Abken, H. et al., "Antigen-specific T-cell activation independently of the MHC: chimeric antigen receptor-redirected T cells," Frontiers in Immunology, V. 4, Article 371, c. 4 (2013).

Abken, H., et al., "Tuning tumor-specific T-cell activation: a matter of costimulation?" Trends in Immunol. 23: 240-245 (2002).

Aggarwal, et al., "Trial of Intravenous Immune Globulin in Dermatomyositis" The New England Journal of Medicine, 387; 14, 1264-1278, Oct. 6, 2022.

Aguera-Gonzalez et ah, "Palmitoylation of MICA, a ligand forNKG2D, mediates its recruitment to membrane microdomains and promotes its shedding," Eur. J. Immunol. vol. 41, pp. 3667-3676 (2011).

Alderson et al., "Molecular and Biological Characterization of Human 4-1BB and its Ligand," Eur. J. Immunol., 1994, 24: 2219-2227.

Alignment I L-18 (Year: 2022).

Allison and Lanier, "Structure, function, and serology of the T-cell antigen receptor complex," Annu Rev Immunol, 1987, 5:503-40.

Almaani, et al., "Glomerular Disease, Update on Lupus Nephritis" The Clinical Journal of the American Society of Nephrology, vol. 12, pp. 825-835, May 2017.

Amended Complaint in *Trustees of the University of Pennsylvania v. St. Jude Children's Research Hospital* in the U.S. District Court for the Eastern District of Pennsylvania, dated Jun. 10, 2013. (Doc. 15).

Anfosi, N. et al., "Human NK Cell Education by Inhibitory Receptors for MHC Class I" Immunity 25, 331-342, Aug. 2006.

Ang S.O. et al, "Avoiding the need for clinical-grade OKT3: ex vivo expansion of T cells using artificial antigen presenting cells genetically modified to crosslink CD3." Biology of Blood and Marrow Transplantation, Jan. 9, 2012, vol. 18, No. 2, pp. S258.

Annenkov et al. "Engineering mouse T lymphocytes specific to type II collagen by transduction with a chimeric receptor consisting of a single chain Fv and TCR zeta," Gene Therapy 7: 714-722 (2000).

Antony, G.K. et al., "Interleukin 2 in Cancer Therapy" Current Medicinal Chemistry (2010) vol. 17, pp. 3297-3302.

Aoudjit and Vuori, "Integrin Signaling in Cancer Cell Survival and Chemoresistance," Chemotherapy Research and Practice, 2012(Article ID 283181), 1-16, 2012.

Appel, et al., "Mycophenolate Mofetil versus Cyclophosphamide for Induction Treatment of Lupus Nephritis" Journal of the American Society of Nephrology, vol. 20, 1103.1112 (2009).

Appelbaum, "Haematopoietic cell transplantation as immunotherapy," Nature, 2001, 411(6835): 385-389.

Arbuckle, et al., "Development of Autoantibodies before the Clinical Onset of Systemic Lupus Erythematosus" The New England Journal of Medicine, 349; 16, 1526-1533, Oct. 16, 2003.

Arch et al., "4-1BB and Ox40 Are Members of a Tumor Necrosis Factor (TNF)-Nerve Growth Factor Receptor Subfamily That Bind TNF Receptor-Associated Factors and Activate Nuclear Factor Kb" Molecular and Cellular Biology, Jan. 1998, p. 558-565.

Arora, et al., "Expert Perspective: An Approach to Refractory Lupus Nephritis" Arthritis Rheumatol. 74(6): 915-926, Jun. 2022.

Aruffo, A., and Seed, B., "Molecular cloning of a CD28 cDNA by a high-efficiency COS cell expression system," Proc. Natl. Acad. Sci., 1987, 84:8573-8577.

ATCC (American Type Culture Collection) [online], "ATCC No. CCL-243," Designation K-562, 1975.

Azuma, M, et al., "Functional Expression of B7/BB1 on Activated T Lymphocytes," J. Exp. Med. 177: 845-850 (1993).

Bachier, et al., A Phase 1 Study of NKX101, an Allogeneic CAR Natural Killer (NK) Cell Therapy, in Subjects with Relapsed-Refractory (R/R) Acute Myeloid Leukemia (AML) or Higher-Risk Myelodysplastic Syndrome (MDS), bood journal, vol. 136, Issue Supplement 1, in 7 pages, Nov. 5, 2020.

Baek, H. et al., "Ex Vivo Expansion of Natural Killer Cells Using Cryopreserved Irradiated Feeder Cells" Anticancer Research (2013) vol. 33, pp. 2011-2019.

Bajema, et al., "Revision of the International Society of Nephrology/Renal Pathology Society classification for lupus nephritis: clarification of definitions, and modified National Institutes of Health activity and chronicity indices" Kidney International, 93, 789-796, Feb. 16, 2018.

Bakr et al., "Induction Immunosuppressive Therapy in Kidney Transplantation"Experimental and Clinical Transplantation, Suppl 1: 60-69, (2014).

Barber et al., "Treatment of Multiple Myeloma with Adoptively Transferred Chimeric NKG2D Receptor-Expressing T Cells", Gene Therapy (2011), vol. 18, pp. 509-516.

Barber et al., 2008, Immunotherapy with Chimeric NKG2D Receptors Leads to Long-Term Tumor-Free Survival and Development of Host Antitumor Immunity in Murine Ovarian Cancer, J Immunol 180: 72-78.

Barber et al. "Chimeric NKG2D Receptor-Bearing T Cells as Immunotherapy for Ovarian Cancer Research" Cancer Research, (2007) vol. 67, No. 10, pp. 5003-5008.

Barber et al. "Chimeric NKG2D Receptor-Expressing T Cells as an immunotherapy for multiple myeloma" Experimental Hematology., (2008) vol. 36, pp. 1318:1328.

Barber et al., "Chimeric NKG2D Expressing T Cells Eliminate Immunosuppression and Activate Immunity within the Ovarian Tumor Microenvironment," J. Immunol, vol. 183, pp. 6939-6947 (2009).

Barber et al., "Chimeric NKG2D T Cells Require Both T Cell- and Host-Derived Cytokine Secretion and Perforin Expression to Increase Tumor Antigen Presentation and Systemic Immunity," J. Immunol, vol. 183, pp. 2365-2372 (2009).

Barber, et al., "Global epidemiology of systemic lupus erythematosus" Nature Reviews, Rheumatology, vol. 17, 515-532, Sep. 2021.

Barrett, D.M., et al., "Chimeric Antigen Receptor Therapy for Cancer," Annu Rev. Med. 65: 333-347 (2014).

Bartholomew et al., "Mesenchymal stem cells suppress lymphocyte proliferation in vitro and prolong skin graft survival in vivo," Exp Hematol, Jan. 2002, 30(1): 42-48.

Baum et al., "Side effects of retroviral gene transfer into hematopoietic stem cells," Blood, Mar. 2003, 101(6): 2099-2114.

Bedouelle, et al. "Diversity and junction residues as hotspots of binding energy in an antibody neutralizing the dengue virus" the FEBS Journal, (Jan. 2006) 273, 34-46.

Bejcek et al., "Development and Characterization of Three Recombinant Single Chain Antibody Fragments (scFvs) Directed against the CD19 Antigen," Cancer Res., 1995, 55:2346-2351.

Benlysta product insert, Revised Jul. 2017, in 48 pages.

Benyamine et al. (2018). Natural Killer Cells Exhibit a Peculiar Phenotypic Profile in Systemic Sclerosis and Are Potent Inducers of Endothelial Microparticles Release. Front Immunol, 9, 1665. https://doi.ora/10.3389/fimmu.2018.01665.

Berger, C. et al., "Safety and immunologic effects of IL-15 administration in nonhuman primates," Blood, 114(12): 2417-2426 (2009).

Bergmann, et al., "Treatment of a patient with severe systemic sclerosis (SSc) using CD19-targeted CAR T cells" Ann Rheum Dis., vol. 82, No. 8, pp. 1117-1120, Aug. 2023.

Bernatsky, et al., "Mortality in Systemic Lupus Erythematosus", Arthritis & Rheumatism, vol. 54, No. 8, pp. 2550-2557, Aug. 2006.

Bertsias et al. EULAR recommendations for the management of systemic lupus erythematosus. Report of a Task Force of the EULAR Standing Committee for International Clinical Studies Including Therapeutics. Ann Rheum Dis. 2008;67(2):195-205. doi:10.1136/ard.2007.070367.

Bertsias et al. Joint European League Against Rheumatism and European Renal Association—European Dialysis and Transplant Association (EULAR/ERA-EDTA) recommendations for the management of adult and paediatric lupus nephritis. Ann Rheum Dis. 2012; 71(11):1771-1782. doi: 10.1136/annrheumdis-2012-201940.

(56)        References Cited

OTHER PUBLICATIONS

Heuser, C., et al., "T-cell activation by recombinant immunorecep-tors: Impact of the intracellular signalling domain on the stability of receptor expression and antigen-specific activation of grafted T cells," Gene Therapy 10: 1408-1419 (2003).

Hill, et al., Durable preservation of antiviral antibodies after CD19-directed chimeric antigen receptor T-cell immunotherapy, Blood Advances, (2019) vol. 3, No. 22, pp. 3590-3601.

Hirayama, et al., Toxicities of CD19 CAR-T cell immunotherapy, Wiley, Am J Hematol., 94:S42-S49, 2019.

Hirayama, et al., "The response to lymphodepletion impacts PFS in patients with aggressive non- Hodgkin lymphoma treated with CD19 CART cells", Immunobiology and Immunotherapy, blood, (2019) vol. 133, No. 17, pp. 1876-1887. doi: 10.1182/blood-2018-11-887067.

Ho E.L. et al., "Murine Nkg2d and Cd94 are clustered within the natural killer complex and are expressed independently in natural killer cells," Proc. Natl. Acad. Sci. USA, vol. 95, DD. 6320-6325, May 1998.

Hoffmann, S.C. et al. "2B4 Engagement Mediates Rapid LFA-1 and Actin-Dependent NK Cell Adhesion to Tumor Cells as Measured by Single Cell Force Spectroscopy," J. Immunol, 186(5): 2757-2764 (Jan. 2011).

Holbrook, et al., "Direct Suppression of Natural Killer Activity in Human Peripheral Blood Leukocyte Cultures by Glucocorticoids and its Modulation by Interferon", cancer Research, 43, 4019-4025, Sep. 1983.

Hollyman, D , et al., "Manufacturing Validation of Biologically Functional T Cells Targeted to CD19 Antigen for Autologous Adoptive T cell Therapy," J. Immunother. 32: 169-180 (2009).

Hombach , et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule", J Immunol., Dec. 1, 2001; 167(11 ):6123-6131.

Hombach et al., "T-Cell Activation by Recombinant Receptors: CD28 Costimulation Is Required for Interleukin 2 Secretion and Receptor-mediated T-Cell Proliferation but Does Not Affect Receptor-mediated Target Cell Lysis," Cancer Res., Mar. 1, 2001, 61:1976-1982.

Hombach et al., "Costimulation by chimeric antigen receptors revisited the T cell antitumor response benefits from combined CD28-OX40 signalling," Int. J. Cane. 129:2935-2944 (2011).

Hombach et al., "The recombinant T cell receptor strategy: insights into structure and function of recombinant immunoreceptors on the Ivay towards an optimal receptor design for cellular immunotherapy," Curr Gene Ther. 2002 2(2):211-226.

Hombach, A., et al., "Adoptive immunotherapy with genetically engineered T cells: modification of the IgG1 Fe 'spacer' domain in the extracellular moiety of chimeric antigen receptors avoids 'offtarget' activation and unintended initiation of an innate immune response," Gene Therapy 17: 1206-1213 (2010).

Hombach, A., et al., "T cell activation by recombinant Fc£RI y-chain immune receptors: an extracellular spacer domain impairs antigendependent T cell activation but not antigen recognition," Gene Therapy 7: 1067-1075 (2000).

Horng et al., "NKG2D signaling is coupled to the interleukin 15 receptor signaling pathway," Nature Immunology, vol. 8, No. 12, pp. 1345-1352, Dec. 2007.

Hsu, C. er al., "Cytokine-independent growth and clonal expansion of a primary human CD8+ T-cell Clone following retroviral transduc-tion with the IL-15 gene," Blood, 109(12): 5168-5177 (2007).

Hsu, K. C. et al., "Improved outcome in HLA-identical sibling hematopoietic stem-cell transplantation for acute myelogenous leu-kemia predicted by KIR and HLA genotypes" Blood (2005) vol. 105, No. 12, pp. 4878-4884.

https ://www.proteinatlas.org/ENSG00000177455-CD19/pathology, accessed Jun. 27, 2019.

Huang, et al. "Abstract A207: Utilizing human OX40 knock-in mice (HuGEMM™) to assess antitumor efficacy of OX40-agonistic anti-bodies" Molecular Cancer Therapeutics, (Jan. 1, 2018) vol. 17, Issue 1 Supplement in 4 pages.

Huntington et al. "Interleukin 15-mediated survival of natural killer cells is determined by interactions among Bim, Noxa and Mcl-1," Nat. Immunol. Aug. 2007; 8(8): 856-863.

Hurtado et al., "Potential role of 4-IBB in T cell activation. Comparison with the costimulatory molecule CD28," J Immunol, Oct. 1995, 155(7): 3360-3367.

Hurton et al., "Tethered IL-15 augments antitumor activity and promotes a stem-cell memory subset in tumor-specific T cells," Proc. Natl. Acad. Sci, USA, 113(48):E7788-E7797 (Nov. 2016).

Ignacio et al, "Monoclonal antibodies against the 4-1BB T-cell activation molecule eradicate established tumors," Nature Med., 1997, 3:682-685.

Illei et al., "Combination therapy with pulses of Cyc and methylprednisolone improves long-term renal outcome without increasing toxicity in patients with lupus nephritis", Evidence-Based Rheumatology, pp. 287-288, (2001).

Imai C et al. "Genetic modification of primary natural killer cells overcomes inhibitory signals and induces specific killing of leuke-mic cells," Blood. 2005; 106:376-383.

Imai, C., et al., "Chimeric receptors with 4-1BB signaling capacity provoke potent cytotoxicity against acute lymphoblastic leukemia", Leukemia. Feb. 12, 2004; 18(4):676-684.

Imai C, et al., "T-cell immunotherapy for B-lineage acute lymphoblastic leukemia using chimeric antigen receptors that deliver 4-1 BB-mediated costimulatory signals", Blood. Nov. 16, 2003; 102(11):66a-67a.

Imai et al. "Genetic modification of T cells for cancer therapy", Journal of Biological Regulators and Homeostatic Agents, 18 (1): p. 62-71; Jan. 2004; (abstract only).

Imai, C., et al., "A novel method for propagating primary natural killer (NK) cells allows highly efficient expression of anti-CD19 chimeric receptors and generation of powerful cytotoxicity against NK-resistant acute lymphoblastic leukemia cells", Abtract #306, Blood 104 (Nov. 16, 2004).

Imamura M et al. Autonomous growth and increased cytotoxicity of natural killer cells expressing membrane-bound interleukin-15. Blood (2014) 124 (7): 1081-1088) (Year: 2014).

Inaguma et al., "Expression of neural cell adhesion molecule L1 (CD171) in neuroectodermal and other tumors. An immunohistochemi-cal study of 5155 tumors and critical evaluation of CD171 prog-nostic value in gastrointestinal stromal tumors," Oncotarge., 7(34):55276-55289, Jul. 11, 2016.

International Preliminary Report on Patentability for Int'l Applica-tion No. PCT/IB2019/000181, titled: Activating Chimeric Recep-tors and Uses Thereof in Natural Killer Cell Immunotherapy, Dated: Aug. 11, 2020.

International Preliminary Report on Patentability, re PCT Applica-tion No. PCT/SG2018/050138, dated Oct. 10, 2019.

International Preliminary Report on Patentability, re PCT Applica-tion No. PCT/US2020/020824, dated Sep. 16, 2021.

International Preliminary Report on Patentability, re PCT Applica-tion No. PCT/US2020/044033, dated Feb. 10, 2022.

International Preliminary Report on Patentability, re PCT Applica-tion No. PCT/US2021/071330, dated Mar. 16, 2023.

International Preliminary Report on Patentability, re PCT Applica-tion No. PCT/US2022/074164, dated Feb. 8, 2024.

International Search Report and Written Opinion for International Application No. PCT/US21/71330, mailed Feb. 15, 2022, in 20 pages.

International Search Report and Written Opinion, re PCT Applica-tion No. PCT/US2024/013779, dated May 10, 2024.

International Search Report and Written Opinion, re PCT Applica-tion No. PCT/SG2018/050138, dated Jul. 4, 2018.

International Search Report and Written Opinion, re PCT Applica-tion No. PCT/US2020/020824, dated Jul. 30, 2020.

International Search Report and Written Opinion, re PCT Applica-tion No. PCT/US2020/044033, dated Dec. 18, 2020.

International Search Report and Written Opinion, re PCT Applica-tion No. PCT/US2022/074164, dated Oct. 18, 2022.

(56)             References Cited

OTHER PUBLICATIONS

International Search Report and Written Opinion, re PCT Application No. PCT/US2023/069403, dated Jan. 4, 2024.

International Search Report and Written Opinion, re PCT Application No. PCT/US2023/077336, dated Apr. 12, 2024.

Isenberg, David et al., "Influence of race/ethnicity on response to lupus nephritis treatment: the ALMS study" Rheumatology, (2010) vol. 49, pp. 128-140. doi: 10.1093/rheumatology/kep346.

Ishii, H et al., "Monocytes enhance cell proliferation and LMP1 expression of nasal natural killer/T-cell lymphoma cells by cell contact-dependent interaction through membrane-bound IL-15," International Journal of Cancer, 130: 48-58 (2012).

Ishiwata I, et al., "Carcinoembryonic proteins produced by Wilms' tumor cells in vitro and in vivo," Exp Pathol. 1991; 41(1):1-9.

International Search Report and Written Opinion for International Application No. PCT/US2019/062851, mailed Apr. 1, 2020 in 25 pages.

Patel, S.D., et al., "Impact of chimeric immune receptor extracellular protein domains on T cell function," Gene Therapy 6: 412-419 (1999).

Paul, W.E., Fundamental Immunology, Third Edition, Chs. 1, 13 and 32 (pp. 1-20, 467- 504, and 1143-1178), Raven Press, New York (1993).

Pavlova, et al., "Adoptitive immunotherapy with genetically engineered T lymphocytes modified to express chimeric antigen receptors" Onkogematologiia, 2017, vol. 12, No. 1, pp. 17-32 (see annotation).

Peach, R.J. et al., "Complementarity Determining Region 1 (CDR1)- and CDR3-analogous Regions in CTLA-4 and CD28 Determine the Binding to B7-1," J. Exp. Med. 180: 2049-2058 (1994).

Perussia et al., "Preferential proliferation of natural killer cells among peripheral blood mononuclear cells cocultured with B lymphoblastoid cell lines," Nat Immun Cell Growth Regul, 1987, 6(4): 171-88.

Petition for Inter Partes Review of U.S. Pat. No. 7,446,190 Under 35 U.S.C. ?? 311-319 and 37 C.F.R, ?? 42.1-.80,42.100-.123, 64 pages, Aug. 13, 2015.

Poirot, et al., "Multiplex Genome-Edited T-cell Manufacturing Platform for Off-the_Shelf" Adoptive T-cell Immunotherapies, Cancer Research, Jul. 16, 2015, 3853-3864.

Pollok et al., "Regulation of 4-1BB expression by cell-cell interactions and the cytokines, interleukin-2 and interleukin-4," Eur J Imnunol, Feb. 1995, 25(2): 488-494.

Pollok KE, et al., "Inducible T cell antigen 4-1 BB Analysis of expression and function," J Immunol., 1993, 150(3):771-781.

Porter and Antin, "The graft-versus-leukemia of allogeneic cell therapy," Annu Rev Med, 1999, 50: 369-86.

Porter DL et al., "Chimeric Antigen Receptor-Modified T Cells in Chronic Lymphoid Leukemia", N. Eng. J. Med. Aug. 25, 2011; 365(8):725-733.

Porter et al., "Induction of graft-versus-host disease as immunotherapy for relapsed chronic myeloid leukemia," N Engl J Med, Jan. 1994, 330(2): 100-6.

Proposed Order in *Trustees of the University of Pennsylvania v. St. Jude Children's Research Hospital* in the U.S. District Court for the Eastern District of Pennsylvania, dated Nov. 15, 2013. (Doc. 25).

Pui et al., "Childhood acute lymphoblastic leukaemia—current status and future perspectives," Lancet Oncol, Oct. 2001, 2(10): 597-607.

Pule et al. "Virus-specific T cells engineered to coexpress tumor-specific receptors: persistence and antitumor activity in individuals with neuroblastoma," Nature Med., 2008, 14(1 1):1264-1270.

Qi L. et al., "Multiple effects of IL-21 on the ex vivo expansion of human primary NK cells," Immunology, Nov. 28, 2014, vol. 143, No. S2, p. 62-176, Poster Abstract 708.

Qian, L. et al., "Construction of a plasmid for co-expression of mouse membrane-bound form of IL-15 and RAE-1 (e) and its biological activity" Plasmid (2011) vol. 65, pp. 239-245.

Rajagopalan et al., Found: a cellular activating ligand for N Kp44, Blood, 122( 17):2921-2922, Oct. 2013.

Ramos and Dotti, "Chimeric antigen receptor (CAR)-engineered lymphocytes for cancer therapy," Expert Opin Biol Ther., 2011, 11(7):855-873.

Ramos, C.A., et al., "CD19-CAR Trials," The Cancer J. 20: 112-118 (2014).

Ren, P.-P et al., Anti-EGFRvIII Chimeric Antigen Receptor-Modified T Cells for Adoptive Cell Therapy of Glioblastoma, Current Pharmaceutical Design, 23(14), 2113-2116 (2017).

Response to Election of Species Requirement of Office Action in U.S. Appl. No. 10/981,352, dated Mar. 27, 2007.

Response to Office Action in U.S. Appl. No. 13/548,148, dated Jan. 11, 2013.

Response to Office Action in U.S. Appl. No. 11/074,525 dated Jun. 25, 2007.

Response to Office Action in U.S. Appl. No. 11/074,525, dated Apr. 1, 2008.

Response to Office Action in U.S. Appl. No. 11/074,525, dated Dec. 7, 2007.

Response to Restriction Requirement of Office Action in U.S. Appl. No. 10/981,352, dated Dec. 27, 2006.

Riddell, S.P., et al., "T-Cell Therapy of Leukemia," Cancer Control 9: 114-122 (2002).

Riley et al., "The CD28 family: a T-cell rheostat for therapeutic control of T-cell activation," Blood, 2005, 105:13-21.

Riley K, Schwager Z, Stern M, Vleugels RA, Femia A. Assessment of Antimalarial Therapy in Patients Who Are Hypersensitive to Hydroxychloroquine. JAMA Dermatol. 2019; 155(4):491-493. doi: 10.1001 /iamadermatol.2018.5212.

Roberts et al., "Antigen-specific cytolysis by neutrophils and NK cells expressing chimeric immune receptors bearing zeta or gamma signaling domains," J Immunol, Jul. 1998, 161(1): 375-84.

Robertson MJ, et al., "Costimulation of human natural killer cell proliferation: role of accessory cytokines and cell contact-dependent signals", Nat Immun. 1996-1997; 15(5):213-226.

Romanski, Annette et al., CD-19-CAR engineered NK-92 cells are sufficient to overcome NK cell resistance in B-cell malignancies, J Cell Mol Med, 2016; 20(7): 1287-1294 (see abstract).

Romee R, Rosario M, Berrien-Elliott MM, et al. Cytokine-induced memory-like natural killer cells exhibit enhanced responses against myeloid leukemia. Sci Transl Med. 2016;8(357):357ra123. doi: 10.1126/scitranslmed.aaf2341.

Romee R. et al., "Cytokine activation induces human memory-like NK cells", Blood, Jan. 1, 2012, pp. 4751-4760.

Rooney et al., "Use of gene-modified virus-specific T lymphocytes to control Epstein-Barr-virus-related lymphoproliferation," Lancet, Jan. 1995, 345(8941): 9-13.

Rosenberg et al, "Special Report: Use of tumor-infiltrating lymphocytes and interleukin-2 in the immunotherapy of patients with metastatic melanoma," N. Engl. J. Med., 1988, 319: 1676-1680.

Rosenberg, S.A., and Dudley, M.E., "Adoptive cell therapy for the treatment of patients with metastatic melanoma," Curr. Opin. Immunol. 21: 233-240 (2009).

Rosenfeld et al., "Phenotypic characterization of a unique non-T, non-B acute lymphoblastic leukaemia cell line," Nature, Jun. 1977, 267(5614): 841-843.

Rosenstein, M. et al., "Extravasation Of Intravascular Fluid Mediated By The Systemic Administration Of Recombinant Interleukin 2" The Journal of Immunology (1986) vol. 137, No. 5, pp. 1735-1742.

Ross et al., "Classification of pediatric acute lymphoblastic leukemia by gene expression profiling," Blood, Oct. 2003, 102(8): 2951-2959.

Rossi, J.M., et al., "Phase 1 Biomarker Analysis of ZUMA-1 (KTEC19-101) Study: A Phase 1-2 Multi-Center Study Evaluating the Safety and Efficacy of Anti-CD19 CART cells (KTE-C19) in Subjects with Refractory Aggressive Non-Hodgkin Lymphoma (NHL)," Abstract presented at the American Society of Hematology Annual Meeting, Orlando, Florida, available at https://ash.confex.com/ash/2015/webprogramscheduler/Paper80339.html.

Rossig C, et al., "Epstein-Barr virus-specific human T lymphocytes expressing antitumor chimeric T-cell receptors: potential for improved immunotherapy," Blood, 2002, 99:2009-2016.

(56) References Cited

OTHER PUBLICATIONS

Rossig et al., "Targeting of G(D2)-positive tumor cells by human T lymphocytes engineered to express chimeric T-cell receptor genes," Int J Cancer, Oct. 2001, 94(2): 228-236.

Roszak, A. et al., "Prevalence of the NKG2D Thr72Ala Polymorphism in Patients with Cervical Carcinoma", Genetic Testing and Molecular Biomarkers (2012) vol. 16, No. 08, pp. 841-845.

Rowley, J. et al., "Expression of IL-15RA or an IL-15/IL-15RA fusion on CD8+ T cells modifies adoptively transferred T-cell function in cis," European Journal of Immunology, 39: 491-506 (2009).

Rubnitz et al., 2010, NKAML: A Pilot Study to Determine the Safety and Feasibility of Haploidentical Natural Killer Cell Transplantation in Childhood Acute Myeloid Leukemia, J Clin Oncol. 28:955-959.

Rudikoff, et al. "Single amino acid substitution altering antigen-binding specificity", Nov. 23, 1981, 79, 1979-1983.

Ruggeri L, et al., "Effectiveness of donor natural killer cell alloreactivity in mismatched hematopoietic transplants," Science, 2002, 295 :2097-2100.

Sadelain et al., "Targeting tumours with genetically enhanced T lymphocytes," Nat Rev Cancer. Jan. 2003;3(1): 35-45.

Alvarez-Vallina, L. and Hawkins, R.E., "Antigen-specific targeting of CD28-mediated T cell co-stimulation using chimeric single-chain antibody variable fragment-CD28 receptors," Eur. J. Immunol. 26: 2304-2309 (1996).

Batlcvi, C.L., ct al. "Novel immunothcrapics in lymphoid malignancies," Nature Rev. Clin. Oncol. 13:25-40 (2016).

ClinicalTrials.gov, "Administration of Anti-CD19-chimeric-antigen-receptor-transduced T Cells From the Original Transplant Donor to Patients With Recurrent or Persistent B-cell Malignancies After Allogeneic Stem Cell Transplantation," available at https://clinicaltrials.gov/show/NCTO1087294, NCTO1087294 (Retrieved from the Internet on Jun. 21, 2016).

Crow et al., "Type I Interferon in the Pathogenesis of Lupus" J. Immunol. (2014), vol. 192, No. 12, pp. 5459-5468.

Finney et al., "Activation of resting human primary T cells with chimeric receptors: costimulation from CD28, inducible costimulator, CD134, and CD137 in series with signals from the TCR s chain", J Immunol. Jan. 2004 I; 172(1):104-113.

Gilfillan et al. "NKG2D recruits two distinct adapters to trigger NK cell activation and costimulation" Nature Immunnology (2002), vol. 3, No. 12, pp. 1150-1155.

Granzin et al., "Shaping of Natural Killer Cell Antitumor Activity by Ex Vivo Cultivation", Front. Immunol., 2017, pp. 1-18.

Haynes NM, et al., "Rejection of syngeneic colon carcinoma by CTLs expressing single-chain antibody receptors codelivering CD28 costimulation", J Immunol. Nov. 15, 2002; 169(10):5780-5786.

Hu et al., "Chimeric antigen receptor (CAR)-transduced natural killer cells in tumor immunotherapy", Acta Pharmacologica Sinica, vol. 39, 2018, pp. 167-176.

Huang Q. S. et al., Expansion of human natural killer cells ex vivo. Chine J Cell Mol Immunol, Dec. 31, 2008, vol. 24, No. 12, pp. 1167-1170.

Hurtado et al., "Signals through 4-1 BB are costimulatory to previously activated splenic T cells and inhibit activation-induced cell death", J Immunol., Mar. 1997, 158(6):2600-2609.

International Preliminary Report on Patentability, re PCT Application No. PCT/US2024/013779, dated Aug. 14, 2025.

Khammari, A., et al., "Long-term follow-up of patients treated by adoptive transfer of melanoma tumor-infiltrating lymphocytes as adjuvant therapy for stage III melanoma," Cancer Immunol. Immunother. 56: 1853-1860 (2007).

Kim Y J, et al., "Human 4-1 BB regulates CD28 co-stimulation to promote Th1 cell responses. Eur J Immunol", Mar. 1998; 28(3):881-890.

Le Blanc et al., "Mesenchymal stem cells inhibit and stimulate mixed lymphocyte cultures and mitogenic responses independently of the major histocompatability complex," Scand J Immunol, Jan. 2003, 57(1): 11-20.

Li et al., "Expansion of NK cells from PBMCs using immobilized 4-1BBL and interleukin-21", International Journal of Oncology, 2015, 8 pages.

Lusty et al., "IL-18/IL-15/IL-12 synergy induces elevated and prolonged IFN-? production by ex vivo expanded NK cells which is not due to enhanced STAT4 activation", Molecular Immunology, vol. 88, Aug. 2017, pp. 138-147.

Martinez et al. "Cutting Edge: NKG2D-Dependent Cytotoxicity Is Controlled by Ligand Distribution in the Target Cell Membrane", 2011, J. Immunol. 186:5538-5542.

Melero I, et al., "Amplification of tumor immunity by gene transfer of the co-stimulatory 4-1 BB ligand: synergy with the CD28 co-stimulatory pathway," Eur J Immunol., 1998, 28(3):1116-1121.

Melero I, et al., "NK1 . 1 cells express 4-1BB(CDw137) costimulatory molecule and are required for tumor immunity elicited by anti-4-1 BB monoclonal antibodies," Cell Immunol., 1998, 190(2): 167-172.

Michen et al., "Artificial feeder cells expressing ligands for killer cell immunoglobulin-like receptors and CD94/NKG2A for expansion of functional primary natural killer cells with tolerance to self", Cytotherapy, vol. 22, No. 7, Jul. 2020, pp. 354-368.

Naume et al., "A comparative study of IL-12 (cytotoxic lymphocyte maturation factor)-, IL-2-, and IL-7-induced effects on immunomagnetically purified CD56+ NK cells," J Immunol, Apr. 1992, 148(8): 2429-36.

Nicholson et al., "Construction and characterisation of a functional CD19 specific single chain Fv fragment for immunotherapy of B lineage leukaemia and lymphoma," Mol Immunol., 34(16-17): 1157-1165, Nov.-Dec. 1997.

Pan et al., "Regulation of dendritic cell function by NK cells: mechanisms underlying the synergism in the combination therapy of IL-12 and 4-1BB activation," J Immunol, Apr. 2004, 172(8): 4779-89.

Rückert et al., "Clonal expansion and epigenetic inheritance of long-lasting NK cell memory", nature immunology, vol. 23, Oct. 26, 2022, pp. 1551-1563.

Streltsova et al., "Recurrent Stimulation of Natural Killer Cell Clones with K562 Expressing Membrane-Bound Interleukin-21 Affects Their Phenotype, Interferon-? Production, and Lifespan", Int. J. Mol. Sci., vol. 20, No. 2, 2019, 18 pages.

Takahashi C, et al., "Cutting edge: 4-1 BB is a bona fide CDS T cell survival signal", J Immunol. May 1, 1999; 162(9):5037-5040.

Watzl, C. et al., "Signal Transduction During Activation and Inhibition of Natural Killer Cells" Curr. Protec. Immunol (2010), doi:10.1002/0471142735.im1109bs90, 19 pages total.

Whang et al., "Large-Scale Expansion and Engineering of Human NK Cells Sourced from Peripheral Blood Versus Umbilical Cord Blood", nkarta, 2022, 1 page.

Whang et al., "Potentiating the Large-Scale Expansion and Engineering of Peripheral Blood-Derived CAR NK Cells for Off-the-Shelf Application", nkarta, 2021, 1 page.

Zah E. et al., T Cells Expressing CD19/CD20 Bispecific Chimeric Antigen Receptors Prevent Antigen Escape by Malignant B Cells. Cancer Immunol Res., Apr. 8, 2016, vol. 4, No. 6, pp. 498-508.

Spolski, Rosanne et al., "The Yc family of cytokines fine-tuning signals from IL-2 and IL-21 in the regulation of the immune response [version 1, referees 3 approved]" F1000Research, 2017, pp. 1-12, vol. 6, No. 1872.

* cited by examiner

Figures 1A-1D
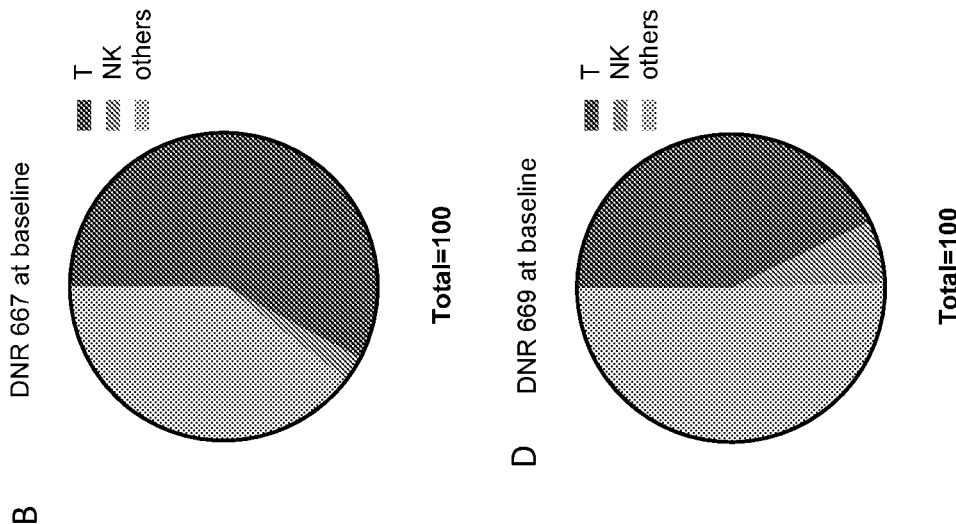
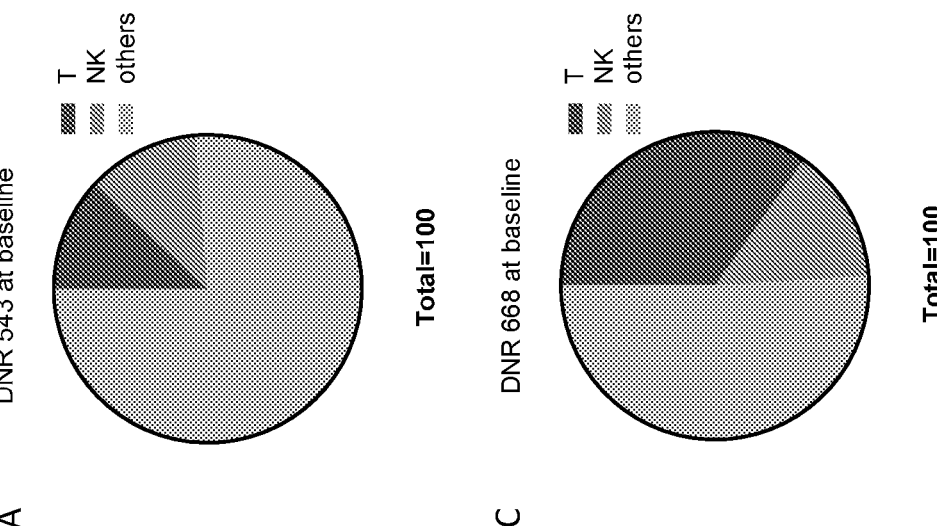

VersaGel 96-well format setup with HL60.NucRed.eCD19.ffluc spheroid single cell

Figure 11:
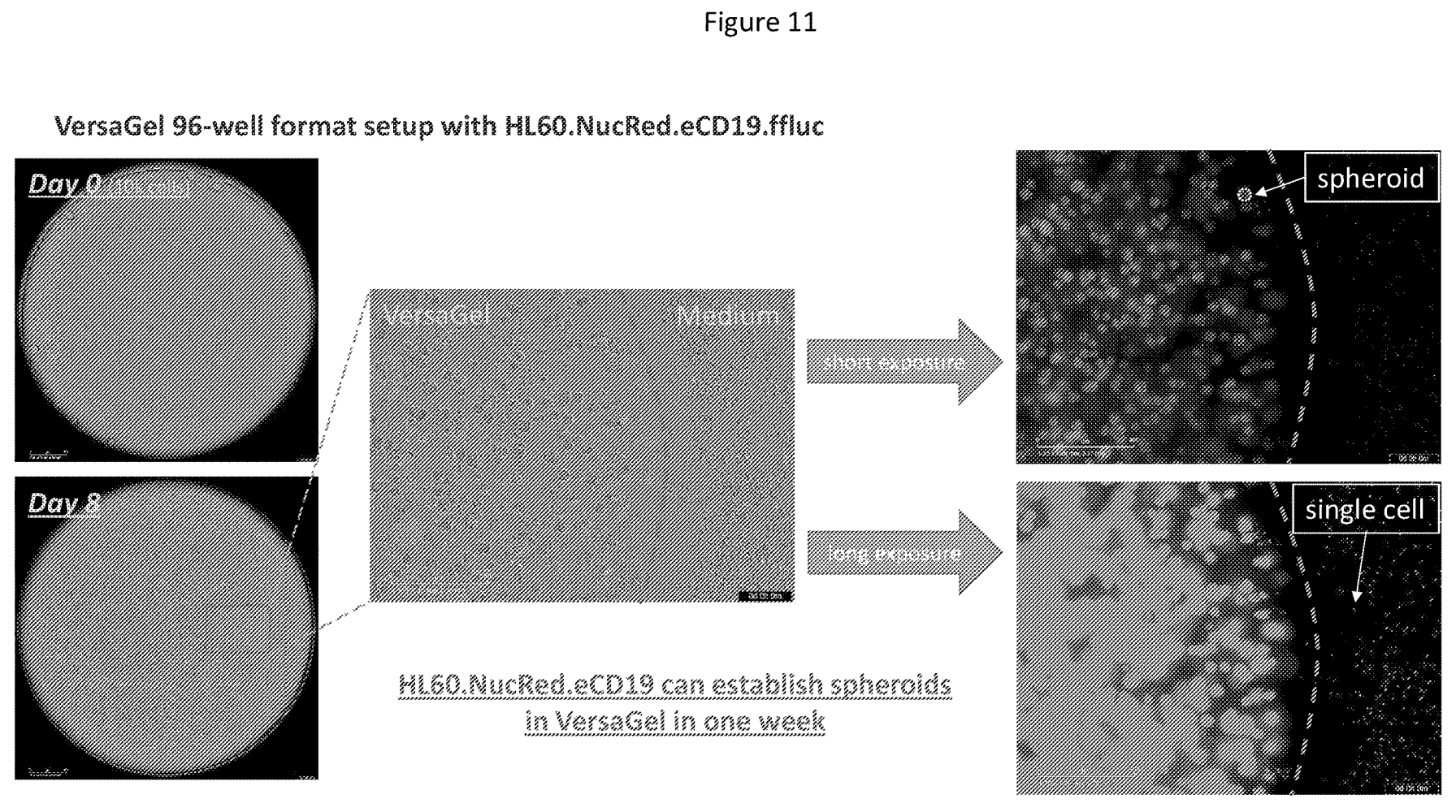

HL60.NucRed.eCD19 can establish spheroids in VersaGel in one week

Figure 12B

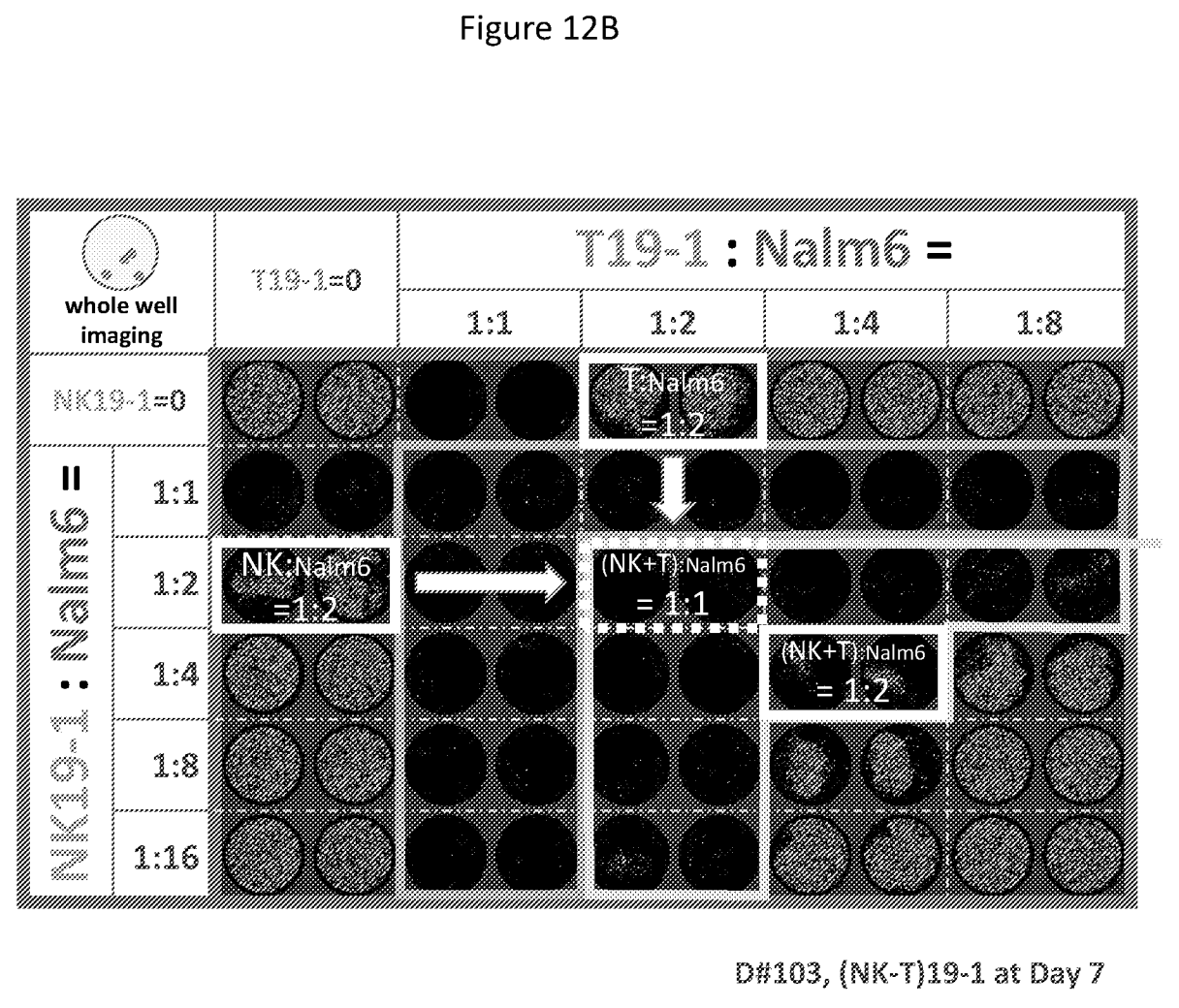

T19-1 : Nalm6 =

T19-1=0    1:1    1:2    1:4    1:8

T:Nalm6 = 1:2

(NK+T):Nalm6 = 1:1

(NK+T):Nalm6 = 1:2

NK:Nalm6 = 1:1 whole well imaging

NK19-1=0    1:1    1:2    1:4    1:8    1:16

NK19-1 : Nalm6 =

D#103, (NK-T)19-1 at Day 7

NK19-1:Nalm6=1:1

F

Figures 16A-16C
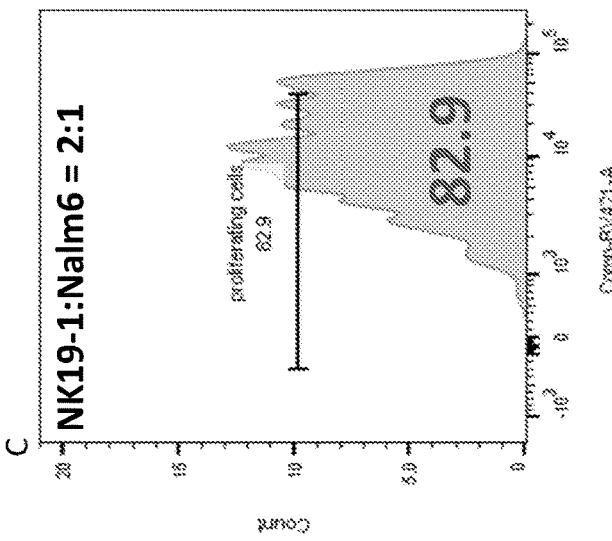
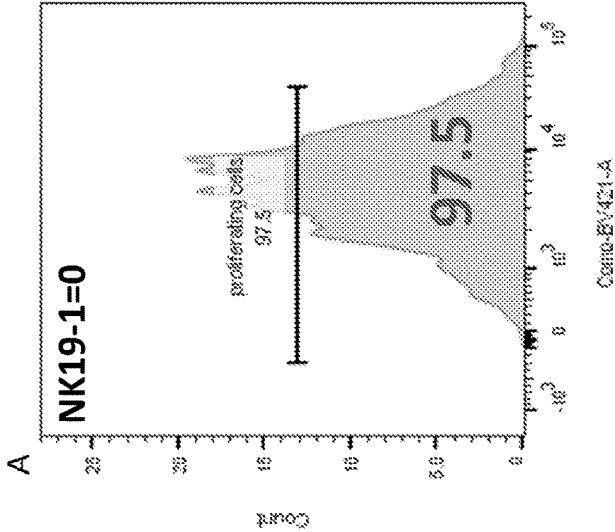

D

Figures 18A-18D
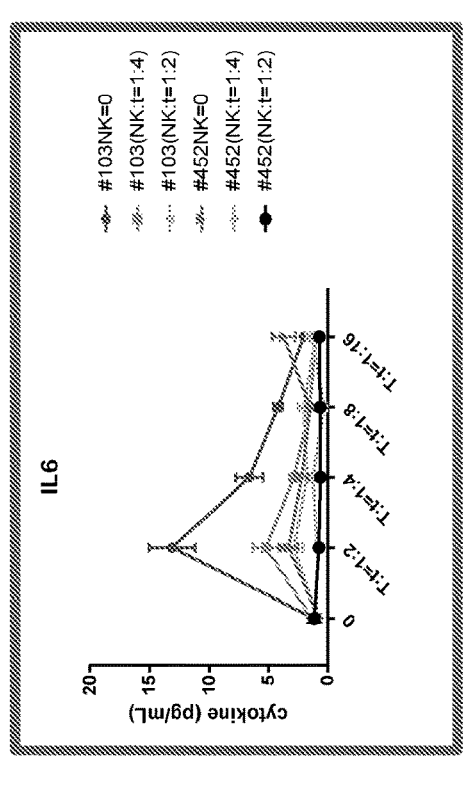
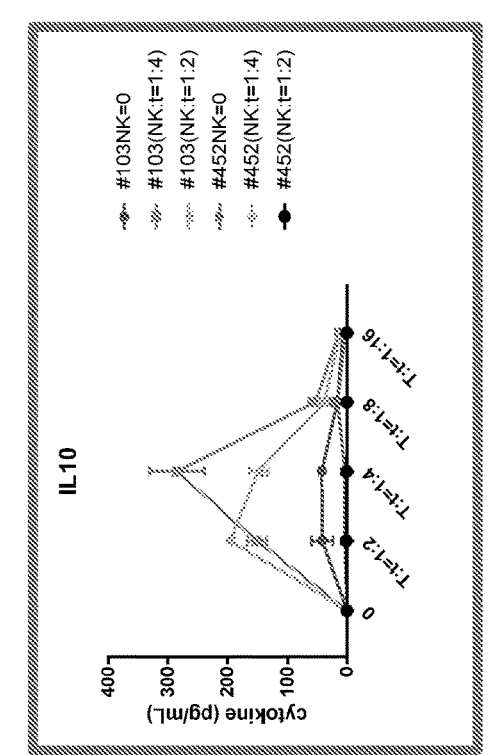
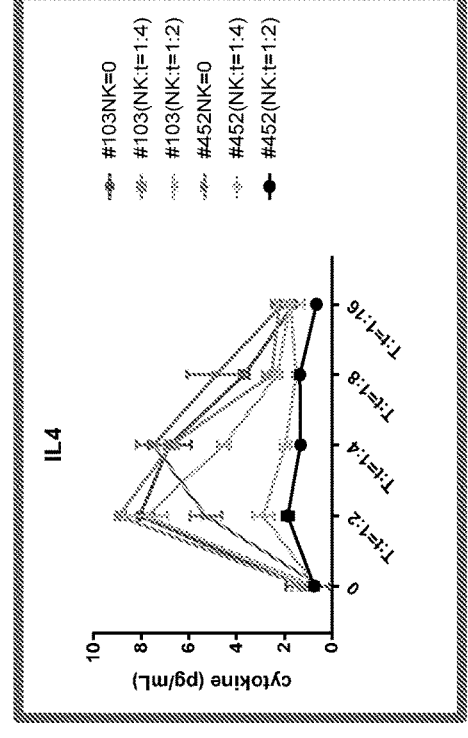

| NSG™ mice | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|---|---|---|---|---|---|---|---|---|---|---|---|---|---|---|---|---|---|
| cell injection (i.v.) | ⇑ | ⇑ | | ⇑ | ⇑ | | | | | | | | | | | | | | | | | | | | | | | | | | | | | | | |
| imaging ○ | | ○ | ○ | | | | | ○ | | | ○ | | | | ○ | | | ○ | | | | ○ | | | ○ | | | | ○ | | | ○ | | | | ○ |
| blood collection<br>∇: serum<br>∆: whole blood | | | | | | | | | | | | ∆ | | | | | | | ∆ | | | | | | | | | | | | | | ∆ | | | |

Injections comprise combinations of NK and T cells bearing anti-CD19 CAR

NK AND T ON DAY 3

<u>NK ON DAY 3, T ON DAY 4</u>

NK19-1 (2.5x10$^6$)
+ T19-1 (2.5x10$^6$)

<u>T ON DAY 3, NK ON DAY 4</u>

NK19-1 (2.5x10$^6$)
+ T19-1 (2.5x10$^6$)

DAY 43

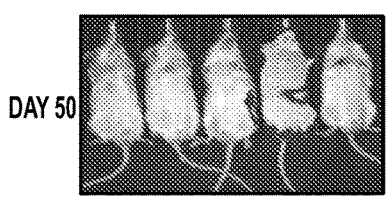
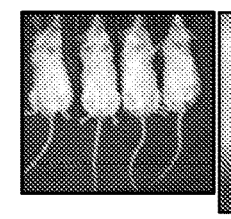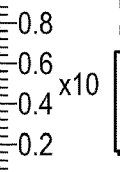

RADIANCE
(p/sec/cm$^2$/sr)

COLOR SCALE
MIN = 5.00e5
MAX = 1.00e7

DAY 50

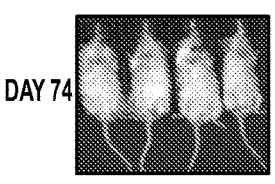
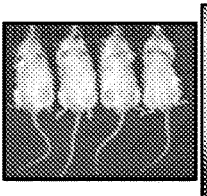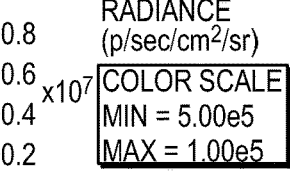

RADIANCE
(p/sec/cm$^2$/sr)

COLOR SCALE
MIN = 5.00e5
MAX = 1.00e5

DAY 74

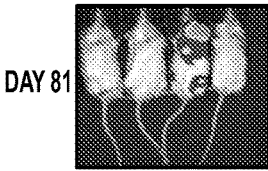
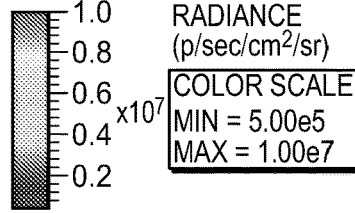

RADIANCE
(p/sec/cm$^2$/sr)

COLOR SCALE
MIN = 5.00e5
MAX = 1.00e7

DAY 81

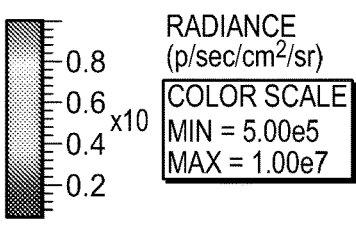

RADIANCE
(p/sec/cm$^2$/sr)

COLOR SCALE
MIN = 5.00e5
MAX = 1.00e7

DAY 88

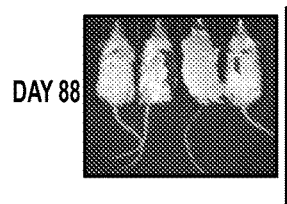
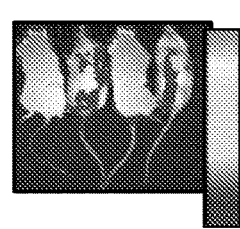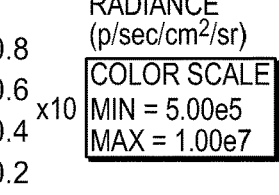

RADIANCE
(p/sec/cm$^2$/sr)

COLOR SCALE
MIN = 5.00e5
MAX = 1.00e7

RADIANCE
(p/sec/cm$^2$/sr)

COLOR SCALE
MIN = 5.00e5
MAX = 1.00e7

DAY 121

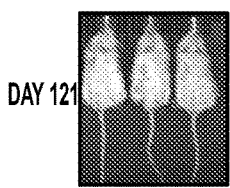
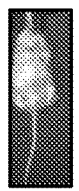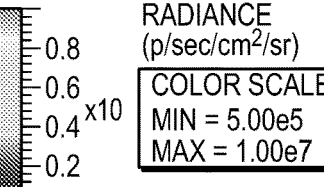

RADIANCE
(p/sec/cm$^2$/sr)

COLOR SCALE
MIN = 5.00e5
MAX = 1.00e7

SEQUENCE LISTING

<160> NUMBER OF SEQ ID NOS: 2

<210> SEQ ID NO 1
<211> LENGTH: 2210
<212> TYPE: DNA
<213> ORGANISM: Homo sapiens
<220> FEATURE:
<221> NAME/KEY: misc_feature
<223> OTHER INFORMATION: NK19-1 DNA

<400> SEQUENCE: 1

```
ggatccgaat tcgccgccac catggcctta ccagtgaccg ccttgctcct gccgctggcc        60
ttgctgctcc acgccgccag gccggactac aaagacgatg acgataaagg cggtggtggc       120
tctggtggtg gcggcagcga catccagatg acacagacta catcctccct gtctgcctct       180
ctgggagaca gagtcaccat cagttgcagg gcaagtcagg acattagtaa atatttaaat       240
tggtatcagc agaaaccaga tggaactgtt aaactcctga tctaccatac atcaagatta       300
cactcaggag tcccatcaag gttcagtggc agtgggtctg gaacagatta ttctctcacc       360
attagcaacc tggagcaaga agatattgcc acttactttt gccaacaggg taatacgctt       420
ccgtacacgt tcggaggggg gaccaagctg gagatcacag gtggcggtgg ctcgggcggt       480
ggtgggtcgg gtggcggcgg atctgaggtg aaactgcagg agtcaggacc tggcctggtg       540
gcgccctcac agagcctgtc cgtcacatgc actgtctcag gggtctcatt acccgactat       600
ggtgtaagct ggattcgcca gcctccacga aagggtctgg agtggctggg agtaatatgg       660
ggtagtgaaa ccacatacta taattcagct ctcaaatcca gactgaccat catcaaggac       720
aactccaaga gccaagtttt cttaaaaatg aacagtctgc aaactgatga cacagccatt       780
tactactgtg ccaaacatta ttactacggt ggtagctatg ctatggacta ctggggccaa       840
ggaacctcag tcaccgtctc ctcaaccacg acgccagcgc cgcgaccacc aacaccggcg       900
cccaccatcg cgtcgcagcc cctgtccctg cgcccagagg cgtgccggcc agcggcgggg       960
ggcgcagtgc acacgagggg gctggacttc gcctgtgata tctacatctg ggcgcccttg      1020
gccgggactt gtggggtcct tctcctgtca ctggttatca cccttactg ccggagggac      1080 cagaggctgc cccccgatgc ccacaagccc cctgggggag gcagtttccg gacccccatc      1140
caagaggagc aggccgacgc ccactccacc ctggccaaga tcagagtgaa gttcagcagg      1200
agcgcagacg cccccgcgta ccagcagggc cagaaccagc tctataacga gctcaatcta      1260
ggacgaagag aggagtacga tgttttggac aagagacgtg gccgggaccc tgagatgggg      1320
ggaaagccga aaggaagaa ccctcaggaa ggcctgtaca tgaactgca gaaagataag      1380 atggcggagg cctacagtga gattgggatg aaaggcgagc gccggagggg caaggggcac      1440
```

-continued

```
gatggccttt accagggtct cagtacagcc accaaggaca cctacgacgc ccttcacatg    1500
caggccctgc cccctcgcgg ctctggcgag ggaaggggtt ccctgcttac ttgcggcgac    1560
gtcgaagaga atcccggtcc gatggccctc ccagtaactg ccctcctttt gcccctcgca    1620
ctccttcttc atgccgctcg ccccaactgg gtcaacgtga ttagcgattt gaagaaaatc    1680
gaggacctta tacagtctat gcatattgac gctacactgt atactgagag tgatgtacac    1740
ccgtcctgta aggtaacggc catgaaatgc tttcttctgg agctccaggt catcagcttg    1800
gagtctgggg acgcaagcat ccacgatacg gttgaaaacc tcatcatcct tgcgaacaac    1860
tctctctcat ctaatggaaa cgttacagag agtgggtgta aggagtgcga agagttggaa    1920
gaaaaaaaca tcaaagaatt tcttcaatcc ttcgttcaca tagtgcaaat gttcattaac    1980
acgtccacta ccacacccgc cccgaggcca cctacgccgg caccgactat cgccagtcaa    2040
cccctctctc tgcgccccga ggcttgccgg cctgcggctg gtggggcggt ccacacccgg    2100
ggcctggatt ttgcgtgcga tatatacatc tgggcacctc ttgccggcac ctgcggagtg    2160
ctgcttctct cactcgttat tacgctgtac tgctaagcgg ccgcgtcgac    2210
```

<210> SEQ ID NO 2
<211> LENGTH: 724
<212> TYPE: PRT
<213> ORGANISM: Homo sapiens
<220> FEATURE:
<221> NAME/KEY: MISC_FEATURE
<223> OTHER INFORMATION: NK19-1 AA

<400> SEQUENCE: 2

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220
```

```
Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
            275                 280                 285

Pro Pro Thr Pro Ala Pro Thr Ile Ala Ser Gln Pro Leu Ser Leu Arg
        290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
            355                 360                 365

Phe Arg Thr Pro Ile Gln Glu Glu Gln Ala Asp Ala His Ser Thr Leu
        370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
            435                 440                 445

Leu Gln Lys Asp Lys Met Ala Glu Ala Tyr Ser Glu Ile Gly Met Lys
        450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
            515                 520                 525

Leu Leu Pro Leu Ala Leu Leu Leu His Ala Ala Arg Pro Asn Trp Val
        530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
            595                 600                 605

Ile Leu Ala Asn Asn Ser Leu Ser Ser Asn Gly Asn Val Thr Glu Ser
        610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
```

-continued

```
              645              650              655

Thr Thr Pro Ala Pro Arg Pro Pro Thr Pro Ala Pro Thr Ile Ala Ser
            660              665              670

Gln Pro Leu Ser Leu Arg Pro Glu Ala Cys Arg Pro Ala Ala Gly Gly
        675              680              685

Ala Val His Thr Arg Gly Leu Asp Phe Ala Cys Asp Ile Tyr Ile Trp
    690              695              700

Ala Pro Leu Ala Gly Thr Cys Gly Val Leu Leu Leu Ser Leu Val Ile
705              710              715              720

Thr Leu Tyr Cys
```

METHODS FOR THE SIMULTANEOUS EXPANSION OF MULTIPLE IMMUNE CELL TYPES, RELATED COMPOSITIONS AND USES OF SAME IN CANCER IMMUNOTHERAPY

CROSS-REFERENCE TO RELATED APPLICATIONS

This application is the United States National Phase pursuant to 35 U.S.C. § 371 of International Patent Application No: PCT/US2019/062851, filed Nov. 22, 2019, which claims the benefit of priority to U.S. Provisional Patent Application No: 62/771,482, Filed Nov. 26, 2018, the entire contents of each of which is incorporated by reference herein.

INCORPORATION BY REFERENCE OF MATERIAL IN ASCII TEXT FILE

This application incorporates by reference the Sequence Listing contained in the following ASCII text file being submitted concurrently herewith: File Name: NKT0028WO_ST25.txt; created Nov. 22, 2019, 9.4 KB in size.

BACKGROUND

Malignancies are the result of uncontrolled growth of cells in the body. Similarly, many diseases or infections result from the dysregulation of normal tissue growth and death. While surgical methods or pharmaceutical therapies have long been the front-line treatment modality, immunotherapy is an emerging option for treating cancerous or diseased tissues.

SUMMARY

Traditional anti-cancer therapies relied on a surgical approach, radiation therapy, chemotherapy, or combinations of these methods. Similarly, many disease or infections are treated with a traditional pharmaceutical approach, though new developments in biologics has recently led to changes in therapeutic approaches. As research led to a greater understanding of some of the mechanisms of certain cancers, this knowledge was leveraged to develop targeted cancer therapies. Targeted therapy is a cancer treatment that employs certain drugs that target specific genes or proteins found in cancer cells or cells supporting cancer growth, (like blood vessel cells) to reduce or arrest cancer cell growth. More recently, genetic engineering has enabled approaches to be developed that harness certain aspects of the immune system to fight cancers. In some cases, a patient's own immune cells are modified to specifically eradicate that patient's type of cancer. Various types of immune cells can be used, such as T cells or Natural Killer (NK cells), as described in more detail below.

In several embodiments, co-expansion of multiple populations of immune cells are provided. In one embodiment, two, three, four or more different cell types are (i) co-expanded together or (ii) co-expanded in parallel and then combined. In several embodiments, NK cells and T cells are expanded together or separately and combined in a ratio of NK cells:T cells of about 5:1, about 10:1, about 20:1, e.g., 5:1, 7:1, 10:1, 12:1, 15:1, 17:1, 20:1 or any ratios therebetween. In another embodiment, there at least 2× more NK cells than T cells. These ratios (where there are more NK cells than T cells) are particularly advantageous in some embodiments because allow for a robust, acute anti-tumor response (due to the more prolific NK cells and their cytotoxic activity), in conjunction with a longer term cytotoxicity from the T cells. In several embodiments, due not only to the less prolific T cells, but the inhibitory effects of NK cells on the T cells, there are coordinate reductions in T-cell cytokine release as compared to a T cell only approach. In a T-cell only therapy, the release of various cytokines by T-cells act in an autocrine-like manner, and upregulate T-cell proliferation and activity. Unchecked, that increased proliferation and activity can lead to various adverse effects, such as neurologic toxicity, "on target/off tumor" recognition, anaphylaxis, or even cytokine release syndrome ("CRS", a potentially life-threatening, systemic inflammatory response observed following administration of antibodies, and adoptive T cell therapy). While the T cells do still release certain cytokines according to several embodiments, rather than causing T-cell stimulation (and further cytokine release, which could cause CRS), those cytokines act to positively stimulate the NK cells. Accordingly, in several embodiments, the NK cells, by virtue of being induced to proliferate (and be more cytotoxic) dampen the ability for T cells to self-stimulate. Therefore, the presence of the NK cells reduces the proliferative and cytokine release activity of the T cells. Thus, in several embodiments, the combination of NK cells and T cells provides for a more efficacious and safer cancer immunotherapy product. In some embodiments, the T cells comprise one, two, three or more of the following subtypes: cytotoxic T cells, helper T cells, NKT cells, or gamma delta T cells. In one embodiment, the collective total of the subtypes is calculated for the ratios described herein (including but not limited to 5-10:1, 10-15:1, 15-20:1). In another embodiment, the total of one of the subtypes is calculated for the ratios described herein (including but not limited to 5:1).

In some embodiments, a first cell type is combined with a second cell type in a ratio of about 5-10:1, e.g., 5:1, 6:1, 7:1, 8:1, 9:1 and 10:1. In some embodiments, a first cell type is combined with a second cell type in a ratio of about 11-15:1, e.g., 11:1, 12:1, 13:1, 14:1, and 15:1. In some embodiments, a first cell type is combined with a second cell type in a ratio of about 16-20:1, e.g., 16:1, 17:1, 18:1, 19:1 and 20:1. In another embodiment, there at least 2×, 3×, 4×, 5×, 6×, 7×, 8×, 9×, 10× or more of cell type one than cell type two. In another embodiment, a third cell type is also included. In one embodiment, cell type one includes NK cells and cell type two includes T-cells. Other cell types are used in other embodiments.

Accordingly, provided for herein are methods of generating a mixed population of immune cells (e.g., engineered immune cells) having particular relative proportions of the sub-populations of the mixed population. In several embodiments, these methods allow the production of a cell population that provides a robust cytotoxic effect against target cells, such as tumor cells, while exhibiting reduced potential for adverse immune effects that could result if larger numbers of a particular sub-population of the engineered immune cells were present. In several embodiments, there is provided a method for the generation of a mixed population of immune cells comprising at least two subpopulations of engineered immune cells, comprising isolating a population of mononuclear cells from a blood sample, wherein the isolated population of mononuclear cells comprises at least a first and a second subpopulation of immune cells, isolating the first subpopulation of immune cells from the isolated mononuclear cells, culturing the first subpopulation of isolated immune cells with a population of feeder cells in a culture vessel, wherein the feeder cells are configured to express at least one molecule for the stimulation of expansion of natural killer (NK) cells within the first subpopulation of immune cells to generate an expanded population of NK cells, isolating the second subpopulation of immune cells from the isolated mononuclear cells, culturing the second subpopulation of immune cells in a culture vessel with at least one molecule for the stimulation of expansion of T cells within the second subpopulation of immune cells, thereby generating an expanded population of T cells, engineering the NK cells and/or T cells to express a protein or agent that improves cytotoxicity and/or reduces side effects, and combining a portion of the engineered cytotoxic NK cells with a portion of the engineered cytotoxic T cells thereby generating a mixed population of engineered immune cells. In several embodiments, the combination of the two (or more) expanded engineered immune cells is done in vitro, while in other embodiments, combination is in vivo (e.g., due to concomitant or sequential administration of the expanded cell types).

In several embodiments, the at least one molecule for stimulating NK cells is selected from 4-1BB ligand (4-1BBL), interleukin 15 (IL-15), and combinations thereof. In several embodiments, the molecule for stimulation of expansion of NK cells comprises a combination of 4-1 BBL and IL15. In several embodiments, the interleukin 15 (IL-15) is membrane bound on the feeder cells. In several embodiments, culturing of the first subpopulation of isolated immune cells further comprises addition of one or more of soluble interleukin 2, soluble interleukin 12, soluble interleukin 18, or combinations thereof, to the culture. In several embodiments, the at least one molecule for stimulation of expansion of T cells comprises one or more of an antibody directed against CD3 or against CD28. In several embodiments, the at least one molecule for the stimulation of expansion of T cells comprises an anti-CD3 antibody. In additional embodiments, a mixture of an anti CD3 and an anti-CD28 antibody is used. In several embodiments, the at least one molecule for the stimulation of expansion of T cells comprises an anti-CD28 antibody. Depending on the embodiment, the antibody directed against CD3 optionally comprises an OKT3 antibody. In several embodiments, the OKT3 antibody, other anti-CD3 antibody, or anti-CD28 antibody is expressed by feeder cells which are co-cultured with the second subpopulation of immune cells. In additional embodiments, the antibodies or other stimulatory molecules are bound to a solid support. The solid support comprises, depending on the embodiment a culture vessel, a biocompatible bead comprising a label, or a superparamagnetic bead. Thus, in several embodiments, the stimulatory molecules are provided by virtue of being expressed by feeder cells, while in some embodiments, cell-free expansion is used (e.g., stimulatory molecules added to culture media or otherwise coupled to a solid support that isn't a feeder cell).

In several embodiments, the methods comprise transducing the expanded NK cell population with a nucleic acid encoding an engineered receptor configured to bind a target expressed by a cancer cell and trigger cytotoxic activity against the cancer cell upon binding to generate engineered cytotoxic NK cells. Likewise, in several embodiments the methods further comprise transducing the expanded T cell population with a nucleic acid encoding an engineered receptor configured to bind a target expressed by a cancer cell and trigger cytotoxic activity against the cancer cell upon binding to generate engineered cytotoxic cells. In several embodiments, the NK cells and the T cells are transduced with the same engineered receptor, while in other embodiments the NK cells and the T cells are transduced with different engineered receptors. In several embodiments, wherein additional subtypes of cells are employed in the mixed population, they may be engineered to express the same engineered receptor as the NK and/or T cells, or a distinct receptor type. In several embodiments, the nucleic acid transduced into the expanded cells encodes a chimeric antigen receptor (CAR). The CAR can be directed against a variety of targets expressed by a tumor cell, including those that are uniquely expressed by the tumor cells as well as those that are overexpressed by the tumor cell (thereby limiting the targeting of native cells with the marker). In several embodiments, the CAR is directed against CD19, CD123, BCMA, galactin, Ral-B, FLT3, CD70, DLL3, CD5, GUCY2C, EGFR, KREMEN2, PSMA, ALPPL2, CLDN6, CLDN18, GPR143, GRM8, LPAR3, GD2, ADAM12, LECT1, or TMEM186. In several embodiments, the CAR is directed against one or more NKG2D ligands, including but not limited to MICA, MICB, ULBP1, ULBP2, ULBP3, ULBP4, ULBP5 and/or ULBP6. In several embodiments, the engineered cells are configured to express CARs directed against different targets, including in come embodiments, a mixture of NK cells and T cells collectively directed against two, three, four or more different tumor targets. In several embodiments, the CAR is directed against CD19. In several embodiments, each sub-population of the mixed population expresses an anti-CD19 CAR. In several embodiments, the anti-CD19 CAR comprises an OX40 co-stimulatory domain and a CD3zeta signaling domain, operatively coupled to an anti-CD19 scFv. In several embodiments, the anti-CD19 CAR is encoded by a nucleic acid having at least 85%, at least 90%, at least 92%, at least 95%, at least 96%, at least 97%, at least 98%, or at least 99% sequence identity to SEQ ID NO: 1. In several embodiments, the anti-CD19 CAR comprises an amino acid sequence having at least 85%, at least 90%, at least 92%, at least 95%, at least 96%, at least 97%, at least 98%, or at least 99% sequence identity to SEQ ID NO: 2.

In several embodiments, the engineered cytotoxic NK cells and the engineered cytotoxic T cells are combined in a ratio wherein (i) the engineered NK cells exhibit enhanced cytotoxicity against the cancer cell as compared to an engineered NK cell alone, (ii) the engineered cytotoxic T cells are capable of increasing the number of proliferating engineered NK cells, and/or (iii) the engineered T cells exhibit reduced cytokine release as compared to an engineered T cell alone. The ratio employed can be tailored to a given patient, tumor type, severity or stage of tumor progression or can be based on other diagnostic or prognostic factors. In several embodiments, the ratio of engineered NK cells to engineered T cells is about 5:1. Other ratios are used in other embodiments. For example, in several embodiments the ratio of the first cell type to the second cell type is about 2:1, about 4:1, about 6:1, about 8:1, about 10:1, about 12:1, about 14:1, about 16:1, about 18:1, about 20:1 or more (or any ratio in between those listed).

In several embodiments, the blood sample from which the immune cells are isolated is a peripheral blood sample. In additional embodiments, the blood sample is a cord blood sample. In several embodiments, the mixed population of engineered immune cells comprises between about $1 \times 10^7$ and about $1 \times 10^{10}$ engineered cytotoxic NK cells and between about $1 \times 10^5$ to about $1 \times 10^8$ engineered cytotoxic T cells. As discussed herein, various embodiments involve the combination of two or more immune cell types, at ratios that allow for the effective cytotoxicity against target tumor cells with a reduced or eliminated risk of adverse immune effects, including CRS. In several embodiments, the mixed population of engineered immune cells exhibits rapid cytotoxic effects against tumor cells, followed by enhanced persistent cytotoxic effects against tumor cells. In several embodiments, an NK portion of the mixed population of engineered immune cells exhibits a longer duration of persistent cytotoxic effects against tumor cells as compared to NK cells or T cells alone.

In several embodiments, there is provided a mixed population of engineered cytotoxic immune cells, comprising a first subpopulation of immune cells comprising NK cells, wherein the NK cells are engineered to express an engineered receptor configured to bind a target expressed by cancer cells and trigger cytotoxic activity against the cancer cell upon binding, wherein the first subpopulation comprises between about $1\times10^8$ and about $1\times10^{10}$ NK cells, a second subpopulation of immune cells comprising T cells, wherein the T cells are engineered to express an engineered receptor configured to bind a target expressed by cancer cells and trigger cytotoxic activity against the cancer cell upon binding, and wherein the second subpopulation comprises between about $1\times10^4$ and about $1\times10^6$ T cells, and wherein the mixed population of engineered NK cells and engineered T cells exhibit greater cytotoxicity against the cancer cells at a given effector to target cell ratio than either the NK cells individually or T cells individually at an equivalent effector to target ratio.

As discussed above, in several embodiments, the engineered receptor comprises a chimeric antigen receptor that can be directed against various targets, such as, for example, against CD19, CD123, galactin, Ral-B, FLT3, CD70, DLL3, CD5, GUCY2C, EGFR, KREMEN2, PSMA, ALPPL2, CLDN6, CLDN18, GPR143, GRM8, LPAR3, GD2, ADAM12, LECT1, or TMEM186. In several embodiments, each sub-population of the mixed population expresses an anti-CD19 CAR. In several embodiments, the anti-CD19 CAR comprises an OX40 co-stimulatory domain and a CD3zeta signaling domain, operatively coupled to an anti-CD19 scFv. In several embodiments, the anti-CD19 CAR is encoded by a nucleic acid having at least 85%, at least 90%, at least 92%, at least 95%, at least 96%, at least 97%, at least 98%, or at least 99% sequence identity to SEQ ID NO: 1. In several embodiments, the anti-CD19 CAR comprises an amino acid sequence having at least 85%, at least 90%, at least 92%, at least 95%, at least 96%, at least 97%, at least 98%, or at least 99% sequence identity to SEQ ID NO: 2.

Additionally, provided for herein is a method for the expansion of a mixed population of immune cells comprising at least two subpopulations of immune cells, the method comprising isolating a population of mononuclear cells from a blood sample, wherein the isolated population of mononuclear cells comprise at least two different types of immune cells, dividing the isolated population of mononuclear cells into at least a first sub-part and a second subpart, culturing the first sub-part of isolated mononuclear cells with a first population of feeder cells in a culture vessel containing a first culture media, wherein the first population of feeder cells express, and/or the first culture media contains, at least one molecule for the stimulation of expansion of natural killer (NK) cells within the first sub-part of isolated mononuclear cells, wherein the at least one molecule is selected from 4-1BB ligand (4-1BBL), interleukin 15 (IL-15), and combinations thereof, thereby generating an expanded population of NK cells, culturing the second sub-part of isolated mononuclear cells with a second population of feeder cells in a culture vessel containing a second culture media, wherein the second population of feeder cells express, and/or the second culture media contains, at least one molecule for the stimulation of expansion of one or more subpopulation of T cells within the second sub-part of isolated mononuclear cells, thereby generating an expanded population of one or more subpopulations of T cells, and combining at least a portion of the expanded population of NK cells with at least a portion of the expanded population of one or more subpopulations of T cells to generate a mixed population of immune cells comprising at least two subpopulations of immune cells.

In several embodiments, the mixed population comprises a greater percentage of NK cells as compared to the percentage of the total of the one or more subpopulations of T cells. In some embodiments, the one or more subpopulations of T cells comprises gamma-delta T cells.

Provided for herein are mixed populations of immune cells produced by the method disclosed herein. In several embodiments, the mixed population of immune cells is configured for use in treating a tumor, whether the tumor is a solid tumor or suspension tumor. Also provided for herein is the use of the mixed populations of immune cells disclosed herein, for the treatment of cancer. In several embodiments, there is provided a use of the mixed population of immune cells in the manufacture of a medicament for the treatment of cancer.

Also provided for in several embodiments is a combination of engineered NK cells and engineered T cells, wherein the ratio of NK cells to T cells is at least 5:1. In several embodiments, there is provided for a combination of engineered NK cells and engineered T cells, wherein the ratio of NK cells to T cells is at least 10:1. In several embodiments, there is provided for a combination of engineered NK cells and engineered T cells, wherein the ratio of NK cells to T cells is at least 12:1. In several embodiments, there is provided for a combination of engineered NK cells and engineered T cells, wherein the ratio of NK cells to T cells is at least 15:1. In several embodiments, there is provided for a combination of engineered NK cells and engineered T cells, wherein the ratio of NK cells to T cells is at least 20:1.

In several embodiments, the combination of cells at or about the indicated ratios induce enhanced cytotoxic activity of the engineered NK cells against a target tumor. In several embodiments, the combination of cells at or about the indicated ratios induces the enhanced persistence of cytotoxic activity of the engineered NK cells against a target tumor as compared to engineered NK cells alone. In several embodiments, the combination of cells at or about the indicated ratios induces a reduction in cytokine release by the engineered T cells as compared to engineered T cells alone. In several embodiments, the combination of cells at or about the indicated ratios induces a reduction in the proliferation of the engineered T cells as compared to engineered T cells alone.

In several embodiments, methods for the treatment of cancer using the mixed populations of cells disclosed herein are provided. As discussed herein, in several embodiments the combination of cells are achieved by mixing the cell types in the desired ratio post-expansion and prior to delivery to a patient. In several embodiments, the combination is made through administration (e.g., the requisite number of cells from each type is administered such that the desired ratio is achieved in vivo). In several embodiments, the treatment methods further comprise administration of IL2. Depending on the embodiment that employs generating the resulting combination in vivo, that may be achieved by administering the first cell type first, or second. In several embodiments, the administration of a first type of engineered immune cell can provide an improved microenvironment for the second type (or third, etc.) of immune cell.

In several embodiments, there are provided methods for co-expansion of multiple populations of immune cells, for example expansion of NK cells and T cells together. There also provided for populations of immune cells comprising a mixture of two or more subpopulations of immune cells, as well as methods and uses of such compositions for the treatment of cancers as well as other diseases or causes of damage tissue. In several embodiments, a mixed cellular population of NK and T cells advantageously provides a dual effect on target cells, for example a rapid phase of cytotoxic effects induced by the NK cells coupled with a longer duration of tumor control as a result of T cell activity. Advantageously, in several embodiments, the two cell types are manufactured together in a single process and can be administered in combination with one another. In some embodiments, NK cells are produced in a first portion of the expansion process, followed by production of T cells and a second portion of the expansion process and the resultant NK and T cell populations are combined to achieve the desired ratio of NK: T cells. In additional embodiments, NK cells and T cells are cultured together and the methodology is adjusted to control the expansion rate of one cell type vis-à-vis the other cell type (as well as with respect to an optional third, fourth or more cell type included in the mixture) such that the desired ratio is achieved after combined expansion culturing process.

In several embodiments, there are provided methods to allow the expansion and transduction of both NK and T cells (and optionally additional immune cell types) within defined parameters, and using optimized constructs, with the resultant combined cell population advantageously exhibiting a synergistic effect on target cells that represents optimized activity of each of the constituent immune cell subpopulations.

According to several embodiments, there are provided methods for the expansion of a mixed population of immune cells comprising at least two subpopulations of immune cells, the method comprising isolating a population of mononuclear cells from a blood sample, culturing the isolated mononuclear cells with a population of feeder cells in a culture vessel, the feeder cells configured to express at least one molecule for the stimulation of expansion of NK cells, exposing the mononuclear cells co-cultured with the feeder cells to at least one molecule for the stimulation of expansion of T cells within the isolated mononuclear cells, and culturing the mononuclear cells co-cultured with the feeder cells and exposed to the at least one molecule for the stimulation of expansion of T cells for a period of time sufficient to allow the expansion of both the NK cell and T cell subpopulations, thereby generating a mixed population of immune cells comprising at least two subpopulations of immune cells. In several embodiments, the wherein the isolated population of mononuclear cells comprise at least two different types of immune cells, such as, for example, NK cells and one or more subtype of T cells (e.g., cytotoxic T cells, NKT cells, gamma delta T cells, etc.).

In several embodiments, the methods provided for herein optionally further comprise enriching the isolated mononuclear cells to increase the relative percentage of NK cells as compared to the isolated population of mononuclear cells. In several embodiments, the methods provided for herein optionally further comprise depleting the isolated mononuclear cells to decrease the relative percentage of T cells as compared to the isolated population of mononuclear cells.

In several embodiments, the at least one molecule for the stimulation of expansion of natural killer (NK) cells within the isolated mononuclear cells is 4-1 BB ligand (4-1 BBL), interleukin 15 (IL-15), or combinations thereof. In several embodiments, other stimulatory molecules may be used, including other interleukins. In some embodiments, the culture media is supplemented with such stimulatory molecules in addition to, or in place of expression of the stimulatory molecules by the feeder cells. In several embodiments, the at least one molecule for the stimulation of expansion of NK cells comprises a combination of 4-1 BBL and IL15. In some embodiments, the interleukin 15 (IL-15) is membrane bound on the feeder cells.

In several embodiments, the at least one molecule for the stimulation of expansion of T cells comprises an antibody that interacts with a portion of a T cell receptor on a T cell. In some embodiments, the antibody used is an antibody directed against CD3 or against CD28. In several embodiments, a bispecific antibody (e.g., targeting both CD3 and CD28) is used. In several embodiments, the antibody comprises an OKT3 antibody. In some embodiments, the CD3, CD28, and/or OKT3 antibody is expressed by the feeder cells. In additional embodiments, the CD3, CD28, and/or OKT3 antibody is provided for in the culture media.

In several embodiments, the at least one molecule for the stimulation of expansion of T cells comprises an anti-CD3 antibody. In several embodiments, the at least one molecule for the stimulation of expansion of T cells comprises an anti-CD28 antibody. In several embodiments, the at least one molecule for the stimulation of expansion of T cells comprises a mixture of an anti CD3 and an anti-CD28 antibody. In some embodiments, the antibodies are bound to a solid support. In several embodiments, the solid support comprises a culture vessel, a biocompatible bead comprising a label, or a superparamagnetic bead.

In several embodiments, the exposing of the mononuclear cells co-cultured with the feeder cells to the at least one molecule for the stimulation of expansion of T cells within the isolated mononuclear cells occurs at the same time that the mononuclear cells are co-cultured with the feeder cells. However, in several embodiments, the exposure is serial (e.g., performed before or after the co-culture). For example, in several embodiments, the exposing of the mononuclear cells co-cultured with the feeder cells to the at least one molecule for the stimulation of expansion of T cells within the isolated mononuclear cells occurs at a time later than the mononuclear cells being co-cultured with the feeder cells. Depending on the embodiment, the later the time at which the mononuclear cells co-cultured with the feeder cells are exposed to the at least one molecule for the stimulation of expansion of T cells is inversely correlated with the degree of expansion of the T cells from the population of mononuclear cells. Thus, in several embodiments the timing of the exposure is used to tailor the degree of expansion of the T cells (or subtypes of T cells) in the resulting mixed cell population.

In several embodiments, the ratio of feeder cells to mononuclear cells ranges from about 10:1 to 1:10. In some embodiments, the ratio of feeder cells to mononuclear cells is about 1:1. Other ratios are used in some embodiments, such as ratios of feeder:mononuclear cells of 1000:1, 500:1, 250:1, 100:1, 50:1, or any other ratio between and including those listed.

In several embodiments, the blood sample is a peripheral blood sample. In several embodiments, the blood sample is a cord blood sample. In several embodiments, the blood sample is from a feta-maternal tissue source, such as placenta. In several embodiments, the source is used to generate a mixed immune cell population that is allogeneic to the recipient. In some embodiments, the recipient is the donor. In some embodiments, the blood sample and/or expanded mixed population is stored (e.g., frozen) until it is ready for delivery to a recipient.

In several embodiments, the mixed population of immune cells has a ratio of NK cells to T cells (including various T cell subpopulations) ranging from about 100:1 to about 1:100. In some embodiments, approximately equal parts NK cells and T cells is used, resulting in the mixed population of immune cells having a ratio of NK cells to T cells of approximately 1:1.

In several embodiments, the mixed population of immune cells having a ratio of NK cells to T cells between approximately 1:1 and approximately 100:1 exhibits rapid cytotoxic effects against tumor cells, followed by persistent cytotoxic effects against tumor cells as compared to NK cells or T cells alone. In some such embodiments, the mixed population of immune cells having a ratio of NK cells to T cells between approximately 1:1 and approximately 1:100 exhibits a longer duration persistent cytotoxic effects against tumor cells as compared to NK cells or T cells alone.

Also provided for herein, in several embodiments, is a population of feeder cells configured to stimulate the expansion of at least two subpopulations of immune cells from a mononuclear cell population, wherein the feeder cells express at least one signal for the stimulation of expansion of NK cells and at least one signal for the stimulation of expansion of T cells (or a subpopulation of T cells), wherein the at least one signal for the expansion of NK cells is selected from 4-1 BB ligand (4-1 BBL), interleukin 15 (IL-15), and combinations thereof, wherein the at least one signal for the expansion of NK cells is selected from a molecule that interacts with CD3 in the T cell receptor and optionally a molecule that interacts with CD28 on the T cell.

There is also provided for herein the use of such populations of feeder cells to generate a mixed cell population comprising NK cells and T cells. In some embodiments, the percentage of NK cells in the mixed cell population is greater than about 10% of the total and wherein the percentage of T cells in the mixed cell population is greater than about 30% of the total. In some embodiments, the percentage of NK cells in the mixed cell population and the percentage of T cells in the mixed cell population are each between about 40% and 60% of the total.

Several embodiments also provide for a mixed population of NK cells and T cells (including subpopulations of T cells), wherein the percentage of NK cells in the mixed cell population is greater than about 10% of the total and wherein the percentage of T cells in the mixed cell population is greater than about 30% of the total. In several embodiments, the percentage of NK cells in the mixed cell population and the percentage of T cells in the mixed cell population are each between about 40% and 60% of the total. In several embodiments, the mixed population exhibits bi-phasic cytotoxic kinetics against target cells. In several such embodiments, the bi-phasic cytotoxic kinetics comprises a rapid and intense early cytotoxic phase followed by an extended lower intensity cytotoxic phase. In several embodiments, the target cells comprise tumor tissue. In several embodiments, the tumor tissue is a solid tumor while in additional embodiments, the tumor tissue is a suspension tumor (e.g., a blood tumor).

Also provided for herein is the use of a mixed population of NK cells and T cells for the treatment of cancer and/or in the manufacture of a medicament for the treatment of cancer.

Several additional embodiments provided for herein relate to methods for the expansion of a mixed population of immune cells comprising at least two subpopulations of immune cells, the method comprising isolating a population of mononuclear cells from a blood sample, wherein the isolated population of mononuclear cells comprise at least two different types of immune cells, culturing the isolated mononuclear cells with a population of feeder cells in a culture vessel containing a culture media, and wherein the culturing is for a period of time sufficient to allow the expansion of both the NK cell and T cell subpopulations, thereby generating a mixed population of immune cells comprising at least two subpopulations of immune cells.

In several embodiments, the feeder cells express, and/or the culture media contains, at least one molecule for the stimulation of expansion of natural killer (NK) cells within the isolated mononuclear cells. In several embodiments, the at least one molecule is selected from 4-1 BB ligand (4-1 BBL), interleukin 15 (IL-15), and combinations thereof. In several embodiments, the feeder cells express, and/or the culture media contains, at least one molecule for the stimulation of expansion of T cells or one or more subpopulation of T cells within the isolated mononuclear cells. In several embodiments, the one or more subpopulation of T cells is one or more of cytotoxic T cells, natural killer T cells (NKT cells), effector T cells, helper T cells, memory T cells, regulatory T cells, gamma delta T cells, mucosal associated invariant T cells. In several embodiments, the blood sample is a cord blood sample.

Also provided for herein are methods for the expansion of a mixed population of immune cells comprising at least two subpopulations of immune cells, the methods comprising isolating a population of mononuclear cells from a blood sample, wherein the isolated population of mononuclear cells comprise at least two different types of immune cells, dividing the isolated population of mononuclear cells into at least a first sub-part and a second subpart; culturing the first sub-part of isolated mononuclear cells with a first population of feeder cells in a culture vessel containing a first culture media, culturing the second sub-part of isolated mononuclear cells with a second population of feeder cells in a culture vessel containing a second culture media, and combining at least a portion of the expanded population of NK cells with at least a portion of the expanded population of one or more subpopulations of T cells to generate a mixed population of immune cells comprising at least two subpopulations of immune cells.

In several embodiments, the first population of feeder cells expresses, and/or the first culture media contains, at least one molecule for the stimulation of expansion of natural killer (NK) cells within the first sub-part of isolated mononuclear cells. In some embodiments, the at least one molecule is selected from 4-1 BB ligand (4-1 BBL), interleukin 15 (IL-15), and combinations thereof wherein the second population of feeder cells express, and/or the second culture media contains, at least one molecule for the stimulation of expansion of one or more subpopulation of T cells within the second sub-part of isolated mononuclear cells.

In several embodiments, the mixed population comprises a greater percentage of NK cells as compared to the percentage of the total of the one or more subpopulations of T cells. In several embodiments, the one or more subpopulations of T cells comprises gamma-delta T cells.

Also provided for in several embodiments, is a composition or use thereof in treating cancerous tumors according to any one of the embodiments described herein.

BRIEF DESCRIPTION OF THE DRAWINGS

The descriptions of the figures below are related to experiments and results that represent non-limiting embodiments of the inventions disclosed herein.

FIGS. 1A-1D depict summary schematics of donor cell composition from four healthy donors. FIG. 1A shows a breakdown of the rough percentage of T cells, NK cells, and other cells in a blood sample collected from a first donor. FIGS. 1B, 1C, and 1D depict the corresponding data from three additional donors.

FIG. 3A demonstrates that certain K562 clones showed expansion efficiency similar to that using the native engineered K562 stimulatory feeder cell line (e.g., a mixed population of engineered K562 cells rather than a population made up of a single replicated clone). FIG. 3B shows that each clone tested at the capacity to robustly stimulate T cell proliferation.

FIG. 4A depict data related to the percentage of NK cells present in the expanded population of cells, after seven days of culture, obtained from each of four donors, when expanded with each of 24 individual clonal K562 populations used as feeder cells. FIG. 4B depicts corresponding data for the percentage of T cells presents after seven days in culture. These data show that generally, the resultant composition of cells after seven days in culture is generally reflective of the incoming (e.g. starting) NK: T cell ratio. As discussed in more detail below, in several embodiments, the methods provided for herein allow manipulation of either the incoming ratio of NK to T cells or, through methodological changes, allow differential expansion of NK and/or T cells to achieve a desired ultimate NK to T cell ratio.

FIG. 5 depicts a timeline for three stages of an expansion protocol. Again at the zero, the culture is supplemented with a low dose of IL-2, which is repeated on day four and then again on day six (at a higher dose of IL-2). The schematic of FIG. 5 shows a matrix that accounts for the addition of a supplemental stimulation source for T cell expansion (e.g. CD3/CD28 beads) at any of the first six days of culture, or not at all ("no beads", a control). FACS analysis is performed at several steps during co-culture over time to assess the relative expansion of NK and T cells as well as the transduction efficiency.

FIG. 6A shows the fold change in NK cells after seven days in culture with an assessment of the presence or absence of beads, as well as the day on which CD3/CD28 beads (a supplemental stimulus for T cells) is added to the co-culture. FIG. 6B shows the corresponding data for T cell expansion.

FIGS. 7A and 7B shows transduction efficiency of each cell type in 4 donors 3 days after transduction, as measured by flow cytometry. FIGS. 7C and 7D show the maintenance of expression at 7 days after transduction.

FIGS. 9A-9C depict schematics of various engineered cell types for in vitro and/or in vivo assessment of mixed NK/T-cell populations.

FIG. 11 depicts data related to the evaluation of immune cell populations according to embodiments disclosed herein in an in vitro 3-D culture environment.

FIG. 12B depicts cytotoxicity as measured by an IncuCyte assay (loss of signal indicates cytotoxic effect against the target cell). Boxes are added to identify the E:T and NK:T ratios demonstrating the greatest cytotoxicity against Nalm6 target cells.

FIG. 14A shows results of assessing NK cell numbers when NK CAR cells are present at 3 different NK:Nalm6 ratios and with T cells present at the indicated ratios (X axis). FIG. 14B shows results of assessing T cell numbers when T CAR cells are present at 6 different T:Nalm6 ratios and with NK cells present at the indicated ratios (X axis). Experiments were conducted after 7 days of co-culturing the NK cells and the T cells (expressing a non-limiting example of an anti-CD19 CAR (labeled as 19-1)) with the Nalm6 cells.

FIG. 15A shows the proliferation of NK cells (bearing an anti-CD19 CAR and present at a 1:1: ratio with target Nalm6 cells) in the absence of any T cells. FIG. 15B shows the proliferation of NK19-1 cells when T cells bearing the same non-limiting example of a CAR are present at a 1:16 T:Nalm6 ratio. FIG. 15C shows the proliferation of NK19-1 cells when T cells bearing the same non-limiting example of a CAR are present at a 1:8 T:Nalm6 ratio. FIG. 15D shows the proliferation of NK19-1 cells when T cells bearing the same non-limiting example of a CAR are present at a 1:4 T:Nalm6 ratio. FIG. 15E shows the proliferation of NK19-1 cells when T cells bearing the same non-limiting example of a CAR are present at a 1:2 T:Nalm6 ratio. FIG. 15E shows additional NK cell proliferation data (with variable T cell numbers) at two different E:T ratios for the NK cells.

FIGS. 16A-16D show data for T cell proliferation in the presence of NK cells bearing an anti-CD19 CAR. FIG. 16A shows the proliferation of T cells (bearing an anti-CD19 CAR and present at a 1:2: ratio with target Nalm6 cells) in the absence of any NK cells. FIG. 16B shows the proliferation of T19-1 cells when NK cells bearing the same non-limiting example of a CAR are present at a 1:1 NK:Nalm6 ratio. FIG. 16C shows the proliferation of T19-1 cells when NK cells bearing the same non-limiting example of a CAR are present at a 2:1 NK:Nalm6 ratio. FIG. 16D shows additional T cell proliferation data (with variable NK cell numbers) at various different E:T ratios for the NK cells.

FIG. 17A shows a schematic of NK cell proliferation when present only with tumor cells. FIG. 17B shows a schematic of T cell proliferation when present only with tumor cells. FIG. 17C shows a schematic of NK cell and T cell proliferation when both NK and T cells are present with tumor cells.

FIGS. 18A-18L show data related to cytokine release by mixed populations of NK and T cells. Shown are concentrations of GM-CSF (18A), IL6 (18B), IL4 (18C), IL10 (18D), IFNg (18E), IL2 (18F), TNFa (18G), IL21 (18H), IL5 (18I), IL13 (18J), IL9 (18K), and IL22 (18L).

FIG. 19 shows a schematic depiction of an in vivo tumor xenograft model used to assess the cytotoxicity of NK cells expanded according to embodiments disclosed herein.

FIG. 20A shows animals receiving PBS (control), NK19-1 (anti-CD19 CAR expressed by NK cells), T19-1 (anti-CD19 CAR expressed by T cells) at either a high or low dose, a combination of NK and T cells (at the indicated doses). All the groups of FIG. 20A received the indicated treatment at day 3. FIG. 20B shows mice receiving combinations of NK cells and T cells at the indicated doses, with the groups on the left columns receiving NK cells on day 3 and T cells on day 4, and the groups on the right columns receiving T cells on day 3 followed by NK cells on day 4. FIGS. 20A-20B show data collected through day 31 post-transplant of tumor cells. FIG. 20C shows data for selected groups (those with surviving mice) from days 43 to 121 post-transplant of tumor cells using the indicated timing and cell doses. FIG. 20D shows survival data for each of the experimental groups. FIG. 20E shows survival data for selected experimental groups (of those shown in 20D).

DETAILED DESCRIPTION

Figure 2:
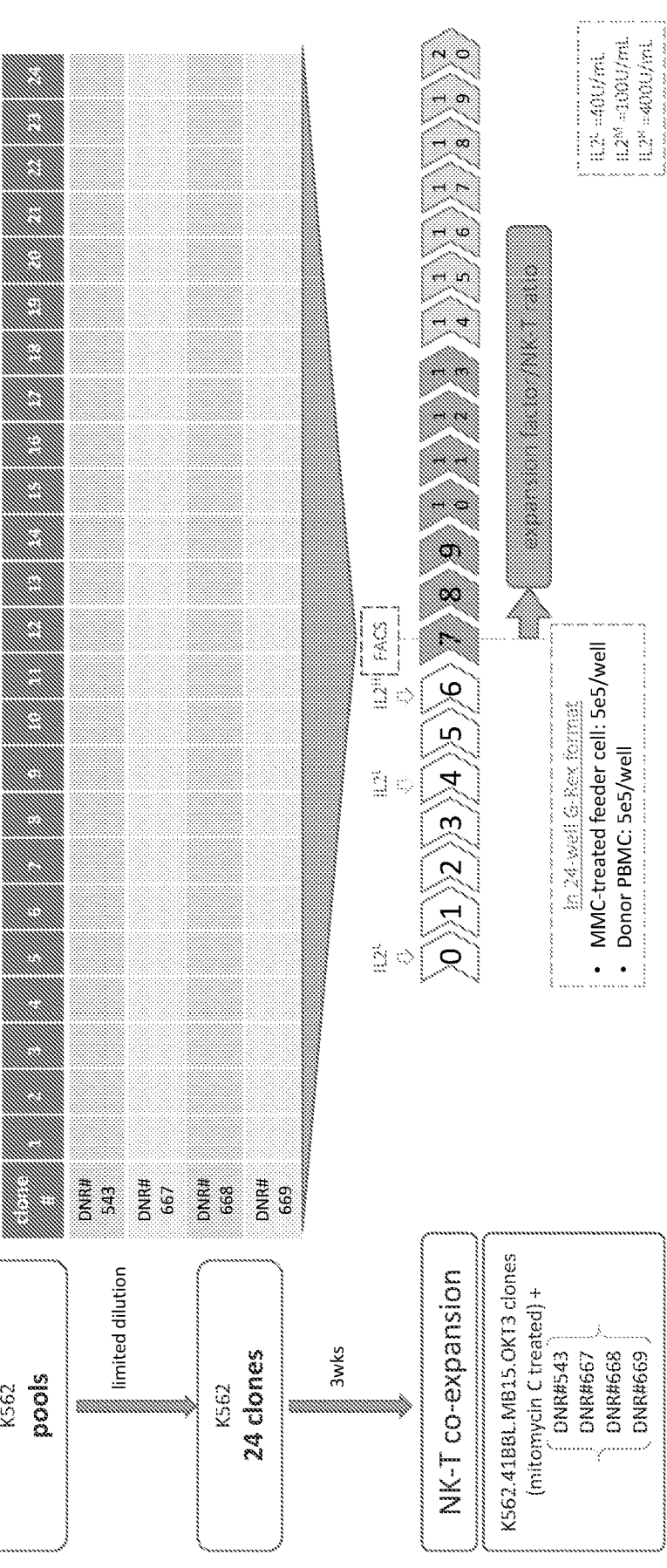
FIG. 2 depicts a schematic process flow diagram by which various K562 clones that are effective at simultaneous NK and T cell expansion can be identified, according to certain embodiments disclosed herein. In brief, a pooled population of K562 undergo limited dilution and testing of a select number of individual clones for their ability to expand both NK and T cells in culture. Blood samples from the four donors depicted in FIG. 1A-1D are used. The feeder cell line (and clones) employed in the simultaneous expansion of the NK and T cells is a modified K562 cell engineered to express 41BBL, membrane-bound IL-15, and a membrane-bound form of the anti-CD3 scFv OKT3. The feeder clones are treated with mitomycin C and are seeded in a culture vessel at $5 \times 10^5$ cells per well. At day zero of culture, donor peripheral blood mononuclear cells are seeded into the same wells as the feeder clones, also at a density of $5 \times 10^5$ cells per well. The co-cultures are supplemented at day zero with 40 units per mL of interleukin 2 (IL-2), which is repeated at day four of the co-culture, and then again at day six with a dose of 400 units per mL of IL-2. Cells are expanded from day 7 to day 13 of co-culture and the ratio of NK to T cells is evaluated during this period. Day 14 through 20 of co-culture are used to determine the ultimate resulting population of cells in the ratio of NK to T cells based on variables that are adjusted earlier in the co-culturing process, for example introduction of a secondary stimulus that supplements the stimulation provided by the modified K562 cells.

Cancer is an abnormal growth of cells. Numerous types of cancer exist and can present as a solid tumor or as suspension cells (e.g., tumors of the blood). Up until recently, cancer treatment has included chemotherapy, radiation, and/or surgery. More recent discoveries relate to certain unique features of cancers that makes them more readily identifiable, not only in a diagnostic setting, but also in connection with the growing field of cancer immunotherapy. Cancer immunotherapy leverages the defense mechanism of various cells of the immune system to interact with cancer cells and reduce or eliminate cancerous cells. Not only can this approach be used to target and treat cancers, but it can also be used to treat other indications, where cells may be infected, for example bacterially or virally infected cells. In several embodiments, the immune cells are engineered for even further heightened efficacy against damaged or diseases tissues/cells. In several embodiments, such as those described in more detail herein, expansion of immune cells, whether for administration to a patient in their native form, as a mixture of cells in their native form, or for subsequent engineering of the cells, is undertaken to achieve greater numbers of immune cells for use in therapy.

Immune Cells for Expansion and Use in Immunotherapy

In several embodiments, cells of the immune system are collected and expanded according to methods disclosed herein, the cells to be leveraged for their ability to exert cytotoxic effects against certain target cells. In several embodiments, the collected/expanded cells are engineered to have enhanced cytotoxic effects against target cells, such as tumor cells. In several embodiments, white blood cells or leukocytes, are used, since their native function is to defend the body against growth of abnormal cells and infectious disease. There are a variety of types of white bloods cells that serve specific roles in the human immune system, and are therefore a preferred starting point for the engineering of cells disclosed herein. White blood cells include granulocytes and agranulocytes (presence or absence of granules in the cytoplasm, respectively). Granulocytes include basophils, eosinophils, neutrophils, and mast cells. Agranulocytes include lymphocytes and monocytes.

Monocytes for Immunotherapy

Monocytes are a subtype of leukocyte. Monocytes can differentiate into macrophages and myeloid lineage dendritic cells. Monocytes are associated with the adaptive immune system and serve the main functions of phagocytosis, antigen presentation, and cytokine production. Phagocytosis is the process of uptake cellular material, or entire cells, followed by digestion and destruction of the engulfed cellular material. In several embodiments, monocytes are used in connection with one or more additional engineered cells as disclosed herein.

Lymphocytes for Immunotherapy

Lymphocytes, the other primary sub-type of leukocyte include T cells (cell-mediated, cytotoxic adaptive immunity), natural killer cells (cell-mediated, cytotoxic innate immunity), and B cells (humoral, antibody-driven adaptive immunity). While B cells are engineered according to several embodiments, disclosed herein, several embodiments also relate to engineered T cells or engineered NK cells (mixtures of T cells and NK cells are used in some embodiments).

T Cells for Immunotherapy

T cells are distinguishable from other lymphocytes subtypes (e.g., B cells or NK cells) based on the presence of a T-cell receptor on the cell surface. T cells can be divided into various different subtypes, including effector T cells, helper T cells, cytotoxic T cells, memory T cells, regulatory T cells, natural killer T cell, mucosal associated invariant T cells and gamma delta T cells. In some embodiments, a specific subtype of T cell is engineered. In some embodiments, a mixed pool of T cell subtypes is engineered. In some embodiments, there is no specific selection of a type of T cells to be engineered to express the cytotoxic receptor complexes disclosed herein. In several embodiments, specific techniques, such as use of cytokine stimulation are used to enhance expansion/collection of T cells with a specific marker profile. For example, in several embodiments, activation of certain human T cells, e.g. CD4+T cells, CD8+T cells is achieved through use of CD3 and/or CD28 as stimulatory molecules. In several embodiments, there is provided a method of treating or preventing cancer or an infectious disease, comprising administering a therapeutically effective amount of T cells either alone, or in combination with NK cells and/or other immune cells as described herein. In several embodiments, the T cells are engineered to have enhanced cytotoxic effects against target cells. In several embodiments, the T cells are autologous cells, while in some embodiments, the T cells are allogeneic cells.

NK Cells for Immunotherapy

In several embodiments, there is provided a method of treating or preventing cancer or an infectious disease, comprising administering a therapeutically effective amount of NK cells alone, or in conjunction with T cells and/or other immune cells as described herein. In several embodiments, NK cells are engineered to have enhanced cytotoxic effects against target cells. In several embodiments, the NK cells are autologous cells, while in some embodiments, the NK cells are allogeneic cells. In several embodiments, NK cells are preferred because the natural cytotoxic potential of NK cells is relatively high. In several embodiments, it is unexpectedly beneficial that combinations of cells disclosed herein (e.g., NK cells and T cells) interact synergistically to yield an even more effective activity against target cells (e.g., tumor or other diseased cells) as compared to either NK cells alone or T cells alone.

Hematopoietic Stem Cells for Cancer Immunotherapy

In some embodiments, hematopoietic stem cells (HSCs) are used in the methods of immunotherapy disclosed herein. In several embodiments, the cells are engineered to express a homing moiety and/or a cytotoxic receptor complex. HSCs are used, in several embodiments, to leverage their ability to engraft for long-term blood cell production, which could result in a sustained source of targeted anti-cancer effector cells, for example to combat cancer remissions. In several embodiments, this ongoing production helps to offset anergy or exhaustion of other cell types, for example due to the tumor microenvironment. In several embodiments allogeneic HSCs are used, while in some embodiments, autologous HSCs are used. In several embodiments, HSCs are used in combination with one or more additional immune cell type disclosed herein.

Feeder Cells for Immune Cell Expansion

In several embodiments, there is provided the use of a feeder cell population (either a clonal population or mixed population) that functions to expand both NK cells and T cells from a blood sample of a donor (who may, in several embodiments, also be the patient).

In several embodiments, cell lines are used in a co-culture with a population of immune cells that are to be expanded. Such cell lines are referred to herein as "stimulatory cells," or referred to as "feeder cells". In several embodiments, the entire population of immune cells is to be expanded, while in several embodiments, a selected immune cell subpopulation, or subpopulations, is preferentially expanded. For example, in several embodiments, NK cells are preferentially expanded relative to other immune cell subpopulations. In some embodiments, two or more subpopulations are expanded together, in some embodiments, simultaneously. Depending on the embodiment, as described in more detail below, the two or more subpopulations need not be expanded to the same degree as one another. Rather, in several embodiments, one subpopulation can be expanded more or less than the other, such that a desired ratio of population 1 to population 2 results at the end of the expansion period.

While in some embodiments, feeder cells are wild type cells, in several embodiments, the feeder cells are genetically modified to render them particularly suitable for expanding and/or activating immune cells, particularly in the presence of one or more additional stimulating signals. As discussed in more detail below, various cell lines are amenable to genetic modification that can result in surface expression of certain molecules that stimulate NK activation. Certain cell types, such as those with low, limited, or otherwise lacking expression of major histocompatibility complex (MHC) I molecules are particularly useful for simultaneous expansion of NK and T cells (and/or other mononuclear cells that may be desired, depending on the embodiment), as MHC I molecules have an inhibitory effect on NK cells. In some embodiments, K562 cells are used, while in some embodiments, one or more of K562 cells, Wilms tumor cell line HFWT, endometrial tumor cell line HHUA, melanoma cell line HMV-II, hepatoblastoma cell line HuH-6, lung small cell carcinoma cell lines Lu-130 or Lu-134-A, neuroblastoma cell lines NB19 or NB69, embryonal carcinoma testis cell line NEC14, cervical carcinoma cell line TCO-2, and neuroblastoma cell line TNB1 are used In some embodiments, the cells need not entirely lack MHC I expression, however they may express MHC I molecules at a lower level than a wild type cell. For example, in several embodiments, if a wild type cell expresses an MHC at a level of X, the cell lines used may express MHC at a level less than 95% of X, less than 90% of X, less than 85% of X, less than 80% of X, less than 70% of X, less than 50% of X, less than 25% of X, and any expression level between (and including) those listed. In several embodiments, the stimulatory cells are immortalized, e.g., a cancer cell line. However, in several embodiments, the stimulatory cells are primary cells. In several embodiments, the feeder cells also have reduced (or lack) MHC II expression. In some embodiments, other cell lines (or clonal lines) that may express MHC class I molecules can be used, in conjunction with genetic modification of those cells to reduce or knock out MHC I expression. Such genetic modification can be accomplished through the use of various gene editing techniques (e.g. the crispr/cas-9 system), inhibitory RNA (e.g., siRNA), or other molecular methods to disrupt and/or reduce the expression of MHC I molecules in addition to blocking antibodies, interfering ligands (e.g., competitive inhibitors, non-competitive inhibitors, etc.).

As discussed in more detail below, certain stimulatory molecules are optionally engineered to be expressed by the feeder cells, such stimulatory molecules acting to promote immune cell expansion and/or activation. The stimulatory molecules may, in several embodiments, be expressed by the feeder cells, but can also be provided separately. In several embodiments, they may be added directly to the culture medium, which provides an advantage in that their concentration can be readily assessed and replenished. In some embodiments, the molecules are provided anchored or otherwise bound to an additive material, for example metal, glass, plastic, polymeric materials, particles (e.g., beads or microspheres), and/or lipids (either natural or synthetic), or some other material to which a stimulatory molecule could be coupled.

Certain molecules promote the expansion, survival, and/or activation of immune cells, and in some embodiments, specific sub-populations of immune cells. Depending on the embodiment, the stimulatory molecule, or molecules, can be expressed on the surface of the feeder cells used to expand the immune population (or populations). In still additional embodiments, one or more stimulatory molecules are used to supplement the cell culture media, either directly or attached to some additive material (e.g., beads). In some embodiments, the immune cell population is expanded relatively uniformly (e.g., no particular subpopulation is preferentially expanded). However, in several embodiments, two or more subpopulations are expanded. Depending on the embodiment, the two subpopulations may or may not be expanded to the same degree as one another. They may, in some embodiments, be expanded to the same, or similar, relative extent, but in terms of absolute number of cells in the resultant expanded immune cell population, the numbers vary based, at least in part, on a different starting number of cells of each of the two subpopulations. In some such embodiments, optionally before or following expansion of all immune cell populations, desired subpopulations are selectively separated (e.g., NK cells are separated from T cells, or vice versa) for further use.

In some embodiments interleukin 15 (IL15) is used to facilitate expansion of immune cells, such as NK cells. In some embodiments, the IL15 is membrane bound on the feeder cells (referred to herein as "mbIL15"). In some embodiments, IL15 is membrane bound by virtue of being coupled or conjugated to a transmembrane molecule or integral membrane protein. In several embodiments, a transmembrane domain of CD8a is used. In several embodiments, wild type (e.g., a full-length) IL15 is expressed on, or by, the feeder cells. In some embodiments, the IL15 is at least 70%, at least 75%, at least 80%, at least 85%, at least 90%, at least 95% homologous with full-length IL15. In some embodiments, truncated forms of IL15 are used. Further details about this, and other constructs relevant to expansion of immune cells, can be found in PCT Application No. PCT/SG2018/050138, filed Mar. 27, 2018, the entire contents of which are incorporated by reference herein.

In some embodiments 4-1BB ligand (4-1BBL) is used to facilitate expansion of immune cells. 4-1BBL has an extracellular domain that interacts with its receptor on T cells, 4-1BB, thereby providing the T cells co-stimulatory signals for survival, proliferation, and differentiation. In some embodiments, 4-1 BBL is membrane bound on the feeder cell by virtue of being coupled or conjugated to a transmembrane molecule or an integral membrane protein. In several embodiments, wild type (e.g., a full-length) 4-1 BBL is expressed on, or by, the feeder cells. In some embodiments, the 4-1 BBL is at least 70%, at least 75%, at least 80%, at least 85%, at least 90%, at least 95% homologous with full-length 4-1 BBL. In some embodiments, truncated forms of 4-1 BBL are used. In several embodiments, 4-1 BBL is expressed or provided to the culture in a manner other than by expression on the feeder cells. In several embodiments, 4-1 BBL is expressed on the surface of the feeder cells (including by a clonal population of feeder cells) in conjunction with mbIL-15. In several embodiments, this combination of stimulatory signals provides stimuli to induce expansion of NK cells in a starting sample of immune cells, or peripheral blood mononuclear cells.

As discussed herein, in several embodiments, there is also provided a supplemental expansion stimulus that functions to further enhance the expansion of one or more subpopulations of immune cell. For example, in several embodiments, a supplemental stimulus is provided that augments NK cell expansion. In several embodiments, a supplemental stimulus functions to enhance expansion of T cells (while another stimulatory molecule, or molecules, induces expansion of NK cells). In several embodiments, the supplemental stimulus may be accomplished by a single additional stimulatory molecule. However, in some embodiments, the supplemental stimulus is delivered by two or more stimulatory molecules acting in concert with one another.

For example, in several embodiments one or more cytokines is added to the media in which the NK and T cells are cultured. In several embodiments, IL12, IL18, or IL21 (or combinations thereof) is added. In several embodiments, the cytokine(s) is added by way of engineering a feeder cell to express the cytokine(s). Some embodiments employ membrane bound cytokines, while others involve engineered feeder cells that express soluble cytokines. In several embodiments, one or more soluble cytokines is added to the culture media at the inception or, or various time points during, NK and T cell expansion.

In some embodiments, an anti-CD3 antibody is used to facilitate expansion of immune cells. In some embodiments, the anti-CD3 antibody is membrane bound on the feeder cells. In several embodiments, a full-length anti-CD3 antibody is expressed on the feeder cells. However, in some embodiments, the anti-CD3 antibody comprises a single chain fragment variable region (scFv) fragment. Depending on the embodiment, the antibody can be monoclonal or polyclonal. In some embodiments, the anti-CD3 antibody comprises a variety of antigenic fragments and/or fusions selected from a Fab', a F(ab')2, a single domain antibody (e.g., a diabody, a nanobody). In some embodiments, the antibody is selected from the group consisting of muromonab-CD3, otelixizumab, teplizumab and visilizumab or from the group consisting of antibodies (or fragments) that are at least 70%, at least 75%, at least 80%, at least 85%, at least 90%, at least 95% homologous (or functionally equivalent) with one or more of muromonab-CD3, otelixizumab, teplizumab and visilizumab. In several embodiments, the anti-CD3 antibody is provided attached to an additional material that is added to the culture medium when the feeder cells are co-cultured with the immune cells to be expanded. In several embodiments, this additional material is in addition to expression of anti-CD3 antibody by the feeder cells, either on their surface or via secretion.

In some embodiments, an anti-CD28 antibody is used to facilitate expansion of immune cells. In some embodiments, the anti-CD28 antibody is membrane bound on the feeder cells. In several embodiments, a full-length anti-CD28 antibody is expressed on the feeder cells. However, in some embodiments, the anti-CD28 antibody comprises a single chain fragment variable region (scFv) fragment. Depending on the embodiment, the antibody can be monoclonal or polyclonal. In some embodiments, the anti-CD28 antibody comprises a variety of antigenic fragments and/or fusions selected from a Fab', a F(ab')2, a single domain antibody (e.g., a diabody, a nanobody). In some embodiments, the antibody is selected from the group consisting of Therali-zumab and antibodies (or fragments) that are at least 70%, at least 75%, at least 80%, at least 85%, at least 90%, at least 95% homologous (or functionally equivalent) with one or more of Theralizumab. In several embodiments, the anti-CD28 antibody is provided attached to an additional mate-rial that is added to the culture medium when the feeder cells are co-cultured with the immune cells to be expanded. In several embodiments, this additional material is in addition to expression of anti-CD28 antibody by the feeder cells, either on their surface or via secretion.

In several embodiments, anti-CD3 and anti-CD28 anti-bodies are provided together, in order to synergistically enhance the expansion of T cells. In several embodiments, the anti-CD3 antibody and the anti-CD28 antibodies are provided coupled to a solid support or other additional material, such as a bead or other geometric shape. In several embodiments, population of beads has a portion that is coupled to anti-CD3 and another portion coupled to anti-CD28 antibodies, whereas in several embodiments, the antibodies are both present on the beads (or other material).

Depending on the embodiment, and on the stimulatory molecule (or molecules) in question, the stimulatory mol-ecules may be introduced (e.g., added to the culture or expressed by the feeder cells) at particular times during the process of co-culturing with an immune cell population, or a plurality of immune cell subpopulations. For example, rather than being constitutively expressed throughout co-culture, one or more of the stimulatory molecules may be under the control of an inducible, or otherwise regulatable promoter. As such, a triggering molecule or stimulus can be added to the co-culture at a desired time, resulting in the expression of the desired stimulatory molecule(s) at a par-ticular point during the expansion and activation protocol. For example, in several embodiments, it may be desirable to initially expand NK cells preferentially, followed by T cells. As such, stimulatory molecules for NK cells could be "turned on" in the initial phases of expansion and at a later time, stimulatory molecules for T cells could be "turned on". As mentioned above, "turning on" could either be a result of regulated expression of the stimulatory molecule, or simply addition of the stimulatory molecule to the culture. As used herein, the terms "inducible promotor" and "regulatable promotor" shall be given their ordinary meaning and shall also refer to promotors whose transcriptional activity is modulated (e.g., stimulated or inhibited) by the presence of certain biotic or abiotic factors. As used herein, the terms "triggering molecule" or "triggering stimulus" shall be given their ordinary meaning and shall refer to chemical or physi-cal substances or conditions that act on an inducible or regulatable promotor, including but not limited to alcohol, tetracycline, steroids, metal and other compounds, as well as high or low culture temperatures. Additionally, regulatable expression of the stimulatory molecules can also be used to reduce and/or eliminate expression of a particular stimula-tory molecule during the culturing process. Such embodi-ments can facilitate the preferential expansion of certain subpopulations of immune cells, such as NK cells, by for example providing a particular stimulatory signal at a point in time during the activation and expansion process when the NK cells are particularly sensitive to such a signal. In several embodiments, such an approach can lead to an unexpectedly robust activation and expansion of NK cells. In still additional embodiments, the duration of proliferation of the NK cells is extended, ultimately leading to a larger population of activated NK cells for use in, for example, cancer immunotherapy. Likewise, in several embodiments, alternative signals can be provided to expand a second (or further) desired sub-population of immune cells, such as T cells. As a result, in several embodiments, the resultant expanded population of cells can comprise a mixture of NK cells and T cells, expanded to a degree that is distinct from the relative amounts of NK:T cells present in a donor.

In several embodiments, within a given population of feeder cells, certain individual cells within the population are particularly suited for expanding more than one type of desired immune cell, such as simultaneous expansion of both NK and T cells. Identification of such individuals (e.g. clones) is described in more detail below. In several embodi-ments, an identified clone is replicated such that there is provided a clonal population of feeder cells, each individual sharing the beneficial characteristics of the original parent cell with respect to the ability to simultaneously expand more than one type of immune cell, such as NK cells and T cells. Thus, in several embodiments, a clonal population of feeder cells is used to expand one or more subpopulations of immune cells together, optionally simultaneously (for example NK cells and T cells).

Donor Material and Processing

In several embodiments, the methods for expanding mul-tiple populations of immune cells are particularly advanta-geous as they provide sufficient flexibility to account for variations in donor cell populations. As shown in FIG. 1A-1D, the relative distribution of NK cells and T cells to other cells in a baseline blood sample can vary to a large degree. In normal peripheral blood, the relative frequency of T cells ranges from about 10 to about 25%, while the normal frequency of T cells ranges from about 2 to about 5% (see, e.g., https://www.bio-rad-antibodies.com/static/2017/flow/flow-cytometry-cell-frequency.pdf). FIG. 1A shows those percentages from a first donor, who exhibits ~12.5% T cells, ~12.5% NK cells, with the remaining ~75% made up of other cell types. A second Donor, shown in FIG. 1B exhib-ited ~35% T cells, with only ~5% NK cells. Donor 3, shown in FIG. 10 had about 20% T cells and about 10% NK cells. Similarly, Donor 4, shown in FIG. 1D had about 25% T cells and about 5% NK cells. These sample data show that donor to donor variability can be fairly large, and sometimes may lie outside the "normal" expected ranges of NK and T cells.

As can be seen from the data above, adjustment of culture methodology or processing, according to several embodi-ments can account for this variability in starting material. For example, in some embodiments the methods and pro-cesses herein allow for achieving a desired NK: T cell ratio even when starting with substantially different initial NK in T-cell populations. In several embodiments, the percentage of NK cells provided as a starting material can range from about 0.5% to about 35% of the peripheral blood mononu-clear cells of a blood sample, including about 0.5% to about 1%, about 1% to about 2%, about 2% to about 4%, about 3% to about 5%, about 2% to about 5%, about 5% to about 10%, about 10% to about 15%, about 15% to about 20%, about 20% to about 25%, about 25% to about 30%, about 30% to about 35%, and any percentage of NK cells in a starting sample in between those expressly listed (including end-points). In several embodiments, the percentage of NK cells in a starting sample ranges from about 2% to about 5%. Likewise, the percentage of T cells present in a blood sample can vary as well. For example, in several embodiments, the percentage of T cells provided in a starting sample can range from about 5% to about 30%, including about 5% to about 10%, about 10% to about 15%, about 15% to about 20%, about 20% to about 25%, about 25% to about 30%, and any percentage of T cells in a starting sample in between those expressly listed (including endpoints).

In several embodiments, the variation in starting material has a minimal impact on the ultimate mixed cell population due to the substantial degree of expansion that occurs during the performance of the methods and processes disclosed herein. In other words, in several embodiments, the cell populations are expanded to such a significant degree that the resultant number of NK cells, T cells, and/or other desired immune cell subpopulations are clinically relevant, despite potential differences in absolute number of cells as compared to one another.

As will be discussed in more detail below, advantageously, despite potentially substantial differences in the relative percentage of NK cells versus T cells in a starting blood sample, the methods and processes disclosed herein allow for a tailored expansion of both cell types (optionally including additional immune cell subpopulations that can be tailored) to achieve a desired ratio in the ultimate mixed population of NK and T cells. For example, in several embodiments the ratio of NK cells to T cells in the ultimate mixed population of cells can range from about 100 to 1 to about 1 to 100, depending on the embodiment.

Combined Expansion of Immune Cells

As mentioned above, in several embodiments multiple subpopulations of immune cells are expanded in culture together with one another. Depending on the embodiment, a single expansion protocol may be used to expand multiple cell populations in series (e.g., an initial expansion of NK cells, followed by an expansion of T cells) or in parallel (e.g., simultaneous co-culturing of NK cells and T cells). A single expansion protocol, according to several embodiments, may comprise multiple phases that are directed to preferentially expand one cell type over another, even when, for example both NK cells and T cells are present in the culture at the same time.

As discussed above, various types of feeder cells may be used to induce the expansion of multiple types of desired immune cells. The feeder cells used may, in some embodiments, comprise a mixed population the feeder cells comprising a population of feeder cells having an overall stimulatory in pro-expansion effect, but with each individual cell within the population potentially having varied characteristics as compared to the other members of the population of feeder cells. In some embodiments however, feeder cells having desirable characteristics to stimulate expansion of multiple immune cell subpopulations are identified and clonally expanded, and the resultant clonal population of feeder cells is used for the combined expansion of multiple types of immune cells. Depending on the embodiment, two, three, four (or more) types of immune cells can be co-expanded. In several embodiments, the co-expanded immune cells are two or more of NK cells, cytotoxic T cells, natural killer T cells (NKT cells), effector T cells, helper T cells, memory T cells, regulatory T cells, gamma delta T cells, mucosal associated invariant T cells, and/or NK cell subpopulations of various types (e.g., NK cells with a greater activating receptor signaling as compared to inhibitory receptor signaling or vice versa). A non-limiting embodiment of an approach for co-expansion is schematically depicted in FIG. 2 and described in more detail in the Examples below.

Depending on the embodiment, feeder cells (whether a mixed population or a clonal population) are seeded into culture vessels. Seeding density may vary, depending on the embodiment and can range, for example from about $0.5 \times 10^5$ cells/cm$^2$ to about $5 \times 10^7$ cells/cm$^2$, including about $1.0 \times 10^5$ cells/cm$^2$ to about $1.5 \times 10^5$ cells/cm$^2$, about $1.5 \times 10^5$ cells/cm$^2$ to about $5 \times 10^5$ cells/cm$^2$, about $5 \times 10^5$ cells/cm$^2$ to about $1.0 \times 10^6$ cells/cm$^2$, about $1.0 \times 10^6$ cells/cm$^2$ to about $5 \times 10^6$ cells/cm$^2$, about $5 \times 10^6$ cells/cm$^2$ to about $1 \times 10^7$ cells/cm$^2$, about $1 \times 10^7$ cells/cm$^2$ to about $5 \times 10^7$ cells/cm$^2$, and any population density therebetween, including endpoints. In several embodiments, greater or lesser initial seeding densities may be used, depending on the anticipated number of immune cells to be cultured with the feeder cells. In several embodiments, an initial seeding density of about $1 \times 10^6$ cells per cm$^2$ is used.

In several embodiments, the feeder cells are optionally pretreated with one or more agents to reduce the expansion rate of the feeder cells themselves. For example, in several embodiments, the feeder cells are irradiated prior to culturing with the immune cell populations to be expanded. In several embodiments, as an alternative or a supplement to irradiation, the feeder cells are treated with an anti-proliferative agents such as for example mitomycin C.

As mentioned above, in several embodiments certain individual cells within a larger population of feeder cells have characteristics that are desirable for the expansion of more than one subtype of immune cell. In several embodiments, the feeder cell that is used to expand the immune cell populations is a clonally derived population of feeder cells. In other words, an individual clone that has been identified as having desirable characteristics for expansion of one or more types of immune cells is itself clonally expanded such that the resulting population all share those beneficial characteristics. In several embodiments, the exposure of immune cells to be expanded to a clonal population of feeder cells advantageously reduces variability in the ultimate expanded immune cell population. Consequently, in several embodiments greater product consistency is achieved.

Also as mentioned above, in several embodiments the expansion culture media can be supplemented with one or more stimulatory molecules. In several embodiments, such molecules function to promote the general health of the feeder cell layer, stimulate the immune cell populations to be expanded, enhance the health of the immune cell populations prior to, during, or after expansion, or some combination of the above. In several embodiments, interleukin-2 (IL2) is used to supplement the culture media. Depending on the embodiment, interleukin two concentrations may vary across the time period during which immune cell expansion occurs. I'll two concentrations can range from about 10 units per mL to about 1000 units per mL including about 10 to about 20 units per mL, about 20 to about 40 units per mL, about 40 to about 60 units per mL, about 60 to about 80 units per mL, about 80 to about 100 units per mL, about 100 to about 150 units per mL, about 150 to about 200 units per mL, about 200 units per mL to about 300 units per mL, about 300 units per mL to about 400 units per mL, about 400 units per mL to about 500 units per mL, about 500 units per mL to about 750 units per mL, about 750 units per mL to about 1000 units per mL, and any concentration in between those expressly listed, including endpoints. Stimulation with IL-2 can be repeated multiple times per expansion protocol, according to certain embodiments. Additionally, not only canned restimulation be performed, but stimulation at varying concentrations can be performed at different time points during the expansion protocol. Depending on the embodiment, other interleukins or other stimulatory molecules can be employed in the processes disclosed herein.

Depending on the embodiment, the duration of expansion of cells can range anywhere from about 4 to about 20 days. In several embodiments, different immune cell subpopulations expand at different rates depending on the duration in culture with the feeder cells. For example, certain cell types expand more rapidly at early time points, while other cell types expand more rapidly at later time points. Thus, depending on the desired proportion of different immune cells subtypes within the ultimate expanded immune cell population, the timing of expansion can be adjusted accordingly. In some embodiments, expansion conditions are employed for about 4 to 6 days, about 6 to 8 days, about 8 to 10 days, about 10 to 14 days, or about 14 to 21 days. In some embodiments, longer expansion culture times can yield larger overall absolute numbers of expanded cells. However, in some embodiments a preliminary enrichment step can be performed, such that the starting number of each immune cell subtype to be expanded is greater it was in the original collected sample, and thus expansion times can be coordinately reduced.

Depending on the embodiment, the ratio of feeder cells to immune cells to be expanded and be adjusted depending on the ultimate desired outcome and makeup of the expanded immune cell population. For example, in several embodiments a feeder cell: "target" cell ratio of about 5:1 is used. In several embodiments, 1:1 ratios are used, while in additional embodiments, can range from about: 1:10, 1:20, 1:50, 1:100, 1:1,000, 1:10,000, 1:50,000, 1:100,000, 100,000:1, 50,000:1, 10,000:1, 1,000:1, 100:1, 50:1, 20:1, 10:1, and any ratio in between those listed, including endpoints. In some embodiments, combinations of cell types are used (e.g., K562 with one or more additional cell types), with the resultant activation and/or expansion of NK cells being greater than could be achieved with the use of any single cell type alone (e.g., as a result of synergy between the cell types). In some such embodiments, MHC I expression need not necessarily be reduced and/or absent in each of the cell lines used in combination. In some embodiments the relative frequency of one cell type versus the others in combination can be varied in order to maximize the expansion and activation of the desired immune cell population. For example, if two feeder cell populations are used, the relative frequency can range from a ratio of 1:10, 1:20, 1:50, 1:100, 1:1,000, 1:10,000, 1:50,000, 1:100,000, 100,000:1, 50,000: 1, 10,000:1, 1,000:1, 100:1, 50:1, 20:1, 10:1, and any ratio in between those listed, including endpoints.

Likewise, given that multiple immune cell subpopulations are to be expanded in combination according to several embodiments disclosed herein, the initial ratio of the immune cells subtypes with respect to one another can be adjusted in certain embodiments. For example, as discussed above there may be donor to donor variability in the relative abundance of, for example, NK cells to T cells in a given blood sample. Thus, in several embodiments if a particular sample has a relative overabundance of one cell type as compared to the other, enrichment or depletion steps may be performed to achieve a desired input ratio of cell type 1 to cell-type 2. Take, by way of non-limiting example, a blood sample that was collected from a donor wherein T cells made up roughly 25% of the collected cell population and NK cells made up approximately 5% of the collected cell population. In some such embodiments, a preliminary expansion step could be used to increase the number of NK cells such that the absolute number of NK cells was roughly equivalent to the absolute number of T cells from the collected blood sample. Thereafter, with comparable NK and T cell numbers, the NK cells and T cells could be cultured with the feeder cells and induce to expand, resulting in a desired ratio of NK cells to T cells in the ultimate expanded cell population, for example a one-to-one ratio. In an alternative approach, the larger population of T cells could be depleted to reduce the number of T cells to an amount approximately equivalent to the number of NK cells, followed by co-culture with similar numbers of NK cells and T cells with the feeder cells as disclosed herein.

Similar to the adjustment in the ratio of feeder cells to immune cells to be expanded, relative adjustments can be made in the ratio of the various types of immune cells to be expanded within a given culture. For example, the ratio of NK cells to T cells at the initial stage of a given culture can range from about 10,000:1 to about 1:10,000 cells, including about 10,000:1, about 7500:1, about 5000:1, about 2500:1, about 2000:1, about 1500:1, about 1000:1, about 750:1, about 500:1, about 250:1, about 100:1, about 75:10, about 50:1, about 25:1, about 15:1, about 10:1, about 5:1, about 1:1, about 1:5, about 1:10, about 1:25, about 1:50, about 1:75, about 1:100, about 1:250, about 1:500, about 1:750, about 1:1000, about 1:1500, about 1:2000, about 1:2500, about 1:5000, about 1:7500, about 1:10,000, and any ratio in between those listed, including endpoints.

As disclosed in more detail below, several embodiments employ a supplemental stimulus that is intended to induce the preferential expansion of one of the multiple types of immune cells that is being cultured in combination with other types of immune cells as well as the feeder cells. In several embodiments, the supplemental stimulus is added at the outset of the expansion phase and can essentially be considered part of the original stimulation milieu. In additional embodiments, introduction of the supplemental stimulus is delayed to allow for, for example, a first phase of expansion of a particular cell type followed by a second phase of expansion of a different cell type, the latter being induced by the introduction of the supplemental stimulus. Depending on the embodiments the supplemental stimulus may be administered after about three days since the inception of co-culture, after about four days, after about five days, after about seven days, after about 10 days, after about 14 days or at any time point after inception of co-culture between those listed. Put another way, the supplemental stimulus can be added when approximately 0% of the expansion protocol has been completed, after about 10% of the expansion protocol has been completed, after about 25% of the expansion protocol has been completed, after about 50% of the expansion protocol has been completed, or after about 75% of the expansion protocol has been completed.

Depending on the embodiment, as described in more detail below, the two or more subpopulations need not be expanded to the same degree as one another. Rather, in several embodiments, one subpopulation can be expanded more or less than the other, such that a desired ratio of population 1 to population 2 results at the end of the expansion period. A desired ratio post-expansion can be, for example, a ratio of NK cells to T cells ranging from about 10:000:1 to about 1:10,000 cells, including about 10,000:1, about 7500:1, about 5000:1, about 2500:1, about 2000:1, about 1500:1, about 1000:1, about 750:1, about 500:1, about 250:1, about 100:1, about 75:10, about 50:1, about 25:1, about 15:1, about 10:1, about 5:1, about 1:1, about 1:5, about 1:10, about 1:25, about 1:50, about 1:75, about 1:100, about 1:250, about 1:500, about 1:750, about 1:1000, about 1:1500, about 1:2000, about 1:2500, about 1:5000, about 1:7500, about 1:10,000, and any ratio in between those listed, including endpoints.

Engineering of Expanded Cells

Depending on the embodiment, the immune cells post-expansion can be administered to a subject in need of immunotherapy without further modification. In some embodiments the expanded immune cell populations are mixed with the pharmaceutically acceptable carrier and then administered. As discussed in more detail below, administration can be by any of a variety of routes and can be in an autologous or an allogeneic context. In several embodiments the expanded cells are engineered to enhance their cytotoxic effects against target tumor cells. For example, NK cells and/or T cells, can be engineered to express chimeric receptors that enhance the ability of the NK cells and/or T cells to recognize and/or exert cytotoxic effects against for example a tumor cell. Cells may be engineered in a variety of different ways, including those described in detail in PCT Patent Application No. PCT/US2018/024650, filed Mar. 27, 2018, the entire contents of which is incorporated by reference herein.

Cytotoxic Receptor Complexes

Various cytotoxic receptors can be expressed by the NK/T cells disclosed herein. In several embodiments, the receptor comprises a Chimeric Antigen Receptor. In several embodiments, the CAR is directed against one or more of the target tumor markers disclosed herein. In several embodiments, the CAR is encoded by a specific polynucleotide which encodes an amino acid sequence. In several embodiments, there is provided a polynucleotide encoding an anti-CD19moiety/CD8hinge/CD8TM/OX40/CD3zeta chimeric antigen receptor complex. The polynucleotide comprises or is composed of an anti-CD19 scFv, a CD8a hinge, a CD8a transmembrane domain, an OX40 domain, and a CD3zeta domain. In several embodiments, the chimeric antigen receptor further comprises mbIL15. In such embodiments, the polynucleotide comprises or is composed of an anti-CD19 scFv, a CD8a hinge, a CD8a transmembrane domain, an OX40 domain, a CD3zeta domain, a 2A cleavage site, and an mbIL-15 domain as described herein. In several embodiments, this receptor complex is encoded by a nucleic acid molecule having the sequence of SEQ ID NO: 1. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 1. In several embodiments, the chimeric receptor comprises the amino acid sequence of SEQ ID NO: 2. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 2. In several embodiments, the CD19 scFv does not comprise a Flag tag. In several embodiments, a humanized and/or codon-optimized CAR is used. Additional examples of tumor binding constructs that can be used according to embodiments disclosed herein can be found in PCT Patent Application No. PCT/US2018/024650, filed Mar. 27, 2018, U.S. Provisional Patent Application No. 62/814,180, filed Mar. 5, 2019, U.S. Provisional Patent Application No. 62/895,910, filed Sep. 4, 2019, U.S. Provisional Patent Application No. 62/932,165, filed Nov. 7, 2019, and U.S. Provisional Patent Application No. 62/924,967, filed Oct. 23, 2019, the entire contents of each of which is incorporated by reference herein in its entirety.

Administration and Dosing

Further provided herein are methods of treating a subject having cancer, comprising administering to the subject a composition comprising a mixed population of expanded immune cells (e.g., a mixture of NK cells and T cells). In several embodiments, the expanded cells are engineered to express a cytotoxic receptor complex (e.g., a chimeric receptor or chimeric antigen receptor). Uses of such engineered immune cells for treating cancer are also provided. In certain embodiments, treatment of a subject with the expanded, mixed cell populations disclosed herein achieves one, two, three, four, or more of the following effects, including, for example: (i) reduction or amelioration of the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy, (xii) a dual-phase (e.g., rapid and prolonged) cytotoxic effect on target cells. Each of these comparisons are versus, for example, a different therapy for a disease, which includes a cell-based immunotherapy for a disease using cells that do not express the constructs disclosed herein.

Administration can be by a variety of routes, including, without limitation, intravenous, intra-arterial, subcutaneous, intramuscular, intrahepatic, intraperitoneal and/or local delivery to an affected tissue. Doses of expanded, mixed populations of immune cells can be readily determined for a given subject based on their body mass, disease type and state, and desired aggressiveness of treatment, but range, depending on the embodiments, from about $10^5$ cells per kg to about $10^{12}$ cells per kg (e.g., $10^5$-$10^7$, $10^7$-$10^{10}$, $10^{10}$-$10^{12}$ and overlapping ranges therein). In several embodiments, the mixed population of immune cells have engineered ratios of the various cell types. For example, in a mixed population with, for example NK cells and T cells, ratios of NK:T cells can range from about 1000:1, about 750:1, about 500:1, about 250:1, about 100:1, about 75:1, about 50:1, about 25:1, about 10:1, about 5:1, about 2:1, about 1:1, about 1:2, about 1:5, about 1:10, about 1:25, about 1:50, about 1:75, about 1:100, about 1:250, about 1:500, about 1:750, or about 1:1000 (or any ratio between those listed. In several embodiments, the ratio of NK to T cells is expressed in terms of the target cell number. For example, in several embodiments, the NK:target cell ratio is about 1:1, 1:2, 1:4, 1:8, or 1:10 and the T cell:target ratio is about 1:2, 1:4, 1:8, or 1:10. In several embodiments, combinations of these ratios is used, for example NK:target of 1:4 with T cell:target of 1:8.

Likewise, in some embodiments, three (or more) different types or subtypes of cells may be used in a mixed population. Ratios there can range from about 1:1:1 where the three subtypes of cells are roughly equivalent to one another to about 1000:1:1 or about 1:1:1000, where one cell type is more prevalent that the others. Likewise, intermediate ratios can be used as well, depending on the embodiment, such as, for example a ratio of about 10:5:1, or about 1:5:10, or about 5:1:10. Additionally, subpopulations can be combined in a fixed ratiometric range with respect to one another. For example, if a population is to be made up of two cell types, a given parameter can be used to determine the population size of a first cell type, which is then used to determine the population size of the second (or third, fourth etc. cell type). By way of non-limiting example, the cytotoxicity of NK cells against a target cell population can be calculated to determine the number of NK cells to be added to the population, which is then used as an input value in a subsequent calculation to calculate how many T cells are added to the population. If a highly effective population of NK cells is used, then they may comprise, for example 25% of a mixed population with gamma-delta T cells making up the remainder (or less than the remainder if a third or fourth cell type is to be added).

Dose escalation regimens are also provided, in several embodiments. In several embodiments, a range of immune cells (e.g., NK cells and T cells) is administered, for example between about $1 \times 10^6$ cells/kg to about $1 \times 10^8$ cells/kg. Depending on the embodiment, various types of cancer can be treated. In several embodiments, hepatocellular carcinoma is treated. Additional embodiments provided for herein include treatment or prevention of the following non-limiting examples of cancers including, but not limited to, acute lymphoblastic leukemia (ALL), acute myeloid leukemia (AML), adrenocortical carcinoma, Kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, glioblastoma, craniopharyngioma, ependymoblastoma, ependymoma, medulloblastoma, medulloepithelioma), breast cancer, bronchial tumors, Burkitt lymphoma, cervical cancer, colon cancer, chronic lymphocytic leukemia (CLL), chronic myelogenous leukemia (CML), chronic myeloproliferative disorders, ductal carcinoma, endometrial cancer, esophageal cancer, gastric cancer, Hodgkin lymphoma, non-Hodgkin lymphoma, hairy cell leukemia, renal cell cancer, leukemia, oral cancer, nasopharyngeal cancer, liver cancer, lung cancer (including but not limited to, non-small cell lung cancer, (NSCLC) and small cell lung cancer), pancreatic cancer, bowel cancer, lymphoma, melanoma, ocular cancer, ovarian cancer, pancreatic cancer, prostate cancer, pituitary cancer, uterine cancer, and vaginal cancer.

As discussed in more detail herein, a variety of engineered cells can be used to target numerous different tumor types. Solid tumors or suspension tumors can be targeted, depending on the embodiment. In several embodiments, blood tumors are treated using engineered cells as disclosed herein. For example, acute myeloid leukemia (AML) cells are targeted in several embodiments. AML results from the clonal expansion of blasts in bone marrow, blood or other tissues. AML accounts for approximately 3% of all cancers, and the incidence of AML increases with age. In patients under 65 years of age, complete remission can occur in roughly 70-80% of patients with overall survival rates of ~35%. For patients over 65, the numbers are reduced, with remission in 40-60% of cases and overall survival reduced to ~5%. Shown in the immunohistochemistry panel of FIG. 2 is a bone marrow aspirate with positive stained leukemic blasts.

A variety of markers can be targeted using the engineered cells disclosed herein. CD19, CD123, NY-ESO, BCMA and others are expressed in many cancers. In several embodiments, particularly with AML, CD123 and NKG2D ligands are upregulated. In certain patients (e.g., AML patients), surface expression of NKG2D ligands (including, but not limited to MICA, MICB, ULPB1, ULPB2, ULPB3) is upregulated. Likewise, in some of those patients, significant percentages (e.g., greater than about 80%) of blast cells, leukemic stem cells and endothelial cells are CD123 positive. Therefore, in several embodiments, immune cells are engineered to target an NKG2D ligand and/or CD123.

The following list comprises a non-limiting set of examples of antigens which can be bound by the binder/activation moieties disclosed herein: Her2, prostate stem cell antigen (PSCA), alpha-fetoprotein (AFP), carcinoembryonic antigen (CEA), CD123, CD19, claudin 6, NY-ESO, GD-2, GD-3, dectin-1, cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, high molecular weight melanoma-associated antigen (HMW-MAA), protein melan-A (melanoma antigen recognized by T lymphocytes; MART-1), myo-DI, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, an abnormal p53 protein, fuc-GMI, GM2 (oncofetal antigen-immunogenic-1; OFA-I-1); GD2 (OFA-I-2), GM3, GD3, alpha-actinin-4, Bage-1, BCR-ABL, Bcr-Abl fusion protein, beta-catenin, CA 15-3 (CA 27.29\BCAA), CA 195, CA 242, CA-50, CAM43, Casp-8, cdc27, cdk4, cdkn2a, coa-1, dek-can fusion protein, EBNA, EF2, Epstein Banvirus antigens, ETV6-AML1 fusion protein, HLA-A2, HLA-A11, hsp70-2, KIAAO205, Mart2, Mum-1, 2, and 3, neo-PAP, myosin class I, OS-9, pml-RARa fusion protein, PTPRK, triosephosphate isomerase, Gage 3,4,5,6,7, GnTV, Herv-K-mel, Lage-1, NA-88, NY-Eso-I/Lage-2, SP17, SSX-2, TRP2-Int2, gplOO (Pmel 17), tyrosinase, TRP-1, TRP-2, MAGE-1, MAGE-3, RAGE, GAGE-1, GAGE-2, p15(58), RAGE, SCP-1, Hom/Me1-40, PRAME, HER-2/neu, E2A-PRL, H4-RET, IGH-IGK, MYL-RAR, human papillomavirus (HPV) antigens E6 and E7, TSP-180, p185erbB2, p180erbB-3, c-met, nm-23H1, PSA, TAG-72-4, CA 19-9, CA 72-4, CAM 17.1, NuMa, 13-Catenin, Mum-1, pi 6, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90, TAAL6, TAG72, TLP, TPS, CD19, CD22, CD27, CD30, CD70, EGFRvIll (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), integrin av63 (CD61), galactin, Rat-B, FLT3, CD70, DLL#, CD5, GUCY2C, EGFR, KREMEN2, PSMA, ALPPL2, CLDN6, CLDN18, GPR143, GRM8, LPAR3, GD2, ADAM12, LECT1, TMEM186, among others.

EXAMPLES

The following are non-limiting descriptions of experimental methods and materials that were used in examples disclosed below.

Example 1—K562 Clone Screening

As discussed above, in several embodiments a feeder cell line is used to expand both NK cells and T cells from a blood sample of a donor. The present example was performed to identify, from a population of modified K562 in view of the above, in several embodiments preliminary steps are undertaken to adjust the relative ratio of certain cell types within the population of immune cells that are isolated from a donor. For example, in several embodiments a portion of T cells may be selectively removed from an initial sample, in order to prevent the T cells from overwhelming NK cells during the expansion process. Depending on the embodiment any given ratio of NK to T cells can be achieved through such a preliminary step. For example in several embodiments a 1:1 NK:T cell ratio is used at the outset of expansion. In additional embodiments, NK cells can be enriched in the starting pool of material vis-à-vis T cells, if so desired. For example in several embodiments a starting ratio of about 1000:1 to about 10:1 NK:T cells is used, including about 1000:1, about 750:1, about 500:1, about 250:1, about 100:1, about 75:1, about 50:1, about 25:1, about 10:1 or any ratio in between those expressly listed.

As shown in FIG. 2, limiting dilution was applied to a population of K562 cells to generate a smaller number of individual K562 clones for screening. The starting K562 cells were engineered to express 4-1 BBL as well as membrane bound IL15. Depending on the embodiment, the K562 cells can be further modified to express one or more additional stimulatory molecules, such as, for example IL12 and/or IL18. In additional embodiments, the K562 cells need not be modified, but are optionally modified, and the culture media is supplemented with one or more of such additional stimulatory molecules. More information about such K562 cells can be found in PCT Application No. PCT/SG2018/050138, filed Mar. 27, 2018, the entire contents of which is incorporated by reference herein. In this particular example, which is applied in other embodiments as well, the K562-41BBL-mbIL15 clones were also engineered to express a single chain fragment variable (scFv) of the OKT3 antibody, which is a murine monoclonal antibody of the immunoglobulin IgG2a isotype. This antibody targets CD3, which is part of a multimolecular complex found only on mature T cells. Interaction between T cells and OKT3 causes T-cell activation. The murine OKT3 antibody is reactive with an epitope on the epsilon-subunit within the human CD3 complex and therefore can serve to endow the NK-cell stimulating K562 cells with an augmented ability to stimulate T cells. Cloning with limited dilution allows for identification of different subclones that may express different amounts of the transduced genes (here mbIL15, 4-1BBL and scFv OKT3). In particular, variability in expression of genes transduced into the feeder cells can lead to different characteristics with respect to expansion of immune cells. In other words, a given clone may expand NK cells more robustly (e.g., efficiently) than it does T cells. In some embodiments, a given clone may expand T cells more robustly (e.g., efficiently) than it does NK cells. In still additional embodiments, a given clone may result in an expanded population of immune cells that is generally healthier, able to survive longer, more effective against target cells, etc. The identification of clones with specific expansion characteristics can be useful in tailoring the ultimate make-up of a mixed cell population. For example, if a given clone is identified as expanding NK cells at twice the rate as it expands T cells, and a mixed cell population is desired with an approximate 2:1 ratio, such a clone could be used to expand a starting population to that desired ratio. In some embodiments, two or more clones can be used to independently expand immune cells, with the ultimate mixed cell population being a combination of the independently expanded immune cell populations. In such an approach, a given clone can be selected based on its ability to preferentially expand a specific immune cell type. For example, for a mixed population of NK cells, cytotoxic T cells and gamma-delta T cells, three clones could be utilized to expand one of those three populations, the selected clones being chosen because of the beneficial characteristics they exhibit for expanding one of the cell types.

While 24 clones were identified and clonally expanded (each clone was clonally expanded for 3 week) in this example, larger numbers can readily be prepared. After clonal expansion, the K562 cells (which were pretreated with mitomycin C) were plated at $5\times10^5$ cells per well (24 well plate). In this experiment, a gas permeable membrane culture vessel was used (G-Rex, Wilson Wolf, ST Paul Minnesota). In other embodiments, standard culture vessels can also be employed. $5\times10^5$ immune cells (NK cells and T cells) from each of 4 donors were plated at Day 0, each sample plated with a clonally expanded K562 population. Cultures were supplemented with 40 U/mL of IL-2 at day 0, day 4 and an elevated concentration of 400 U/mL at day 6 of co-culture. Co-culture was carried out for a total of 20 days.

Figures 3A, 3B:
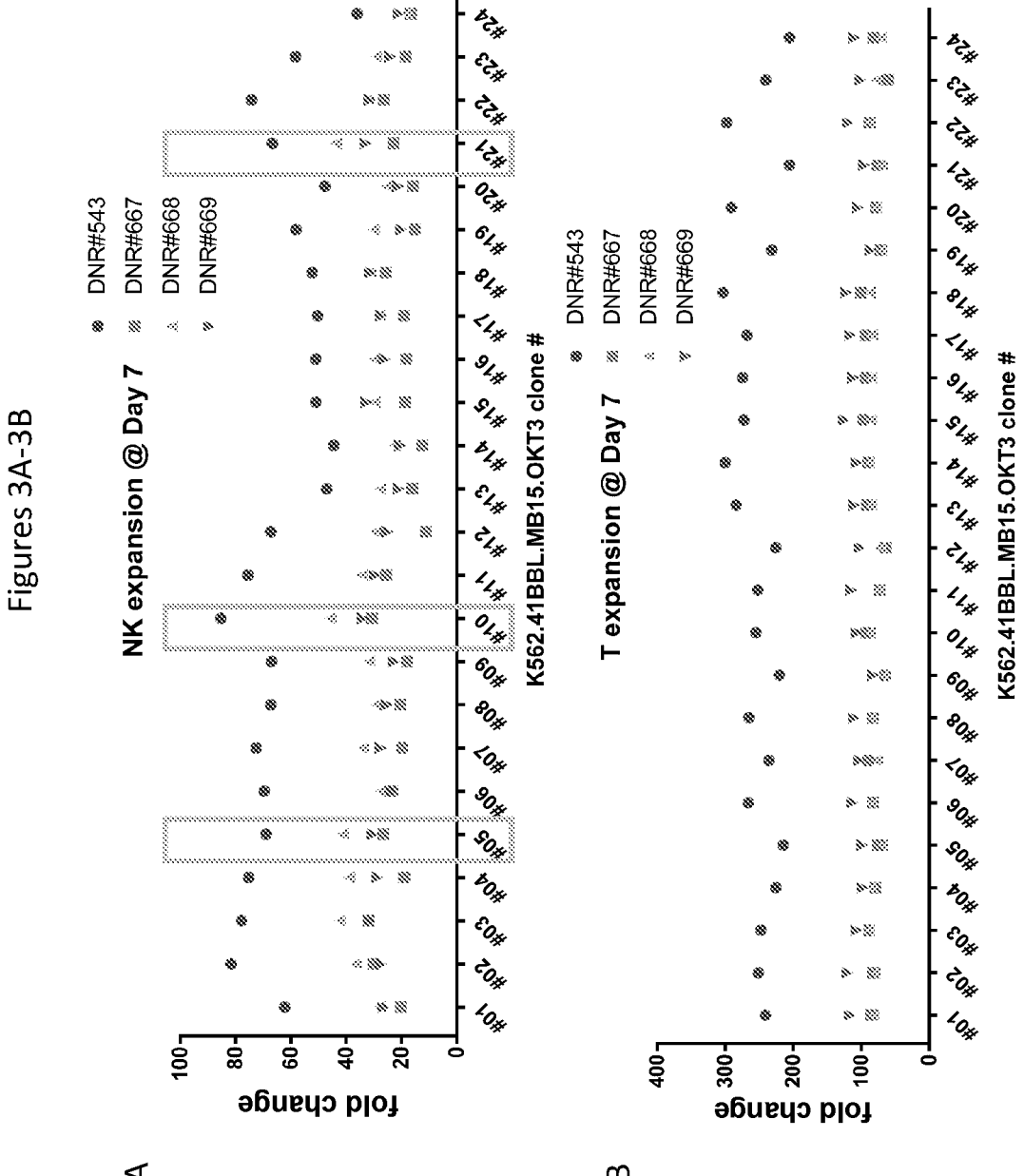
FIGS. 3A-3B depict data related to the fold change increase in NK cell or T cell expansion from four donors after seven days in culture and using 24 different K562 clones.

FIGS. 3A-3B depict data related to the expansion of the NK cells (FIG. 3A) and T Cells (FIG. 3B). Together, these data demonstrate that both NK cells and T cells can be expanded using clonally derived K562 cell populations as the feeder cells. As indicated in FIG. 3A, certain clones demonstrated particularly effective NK cell expansion. Notably, FIG. 3A indicates that clonal K562 feeder cells induce NK cell expansion ranging from approximately 15-fold to about 90-fold, depending on the clone and the donor used. FIG. 3B indicates that T cell expansion was robustly stimulated by all K562 clones tested, with expansion ranging from about 50 fold to about 350 fold, depending on the clone and the donor tested. Doubling time for T cells was less than about 24 hours across all donors. These data indicate that the expansion of both NK cells and T cells in the same culture is not only feasible but robust expansion of each individual cell type can occur.

Figures 4A, 4B:
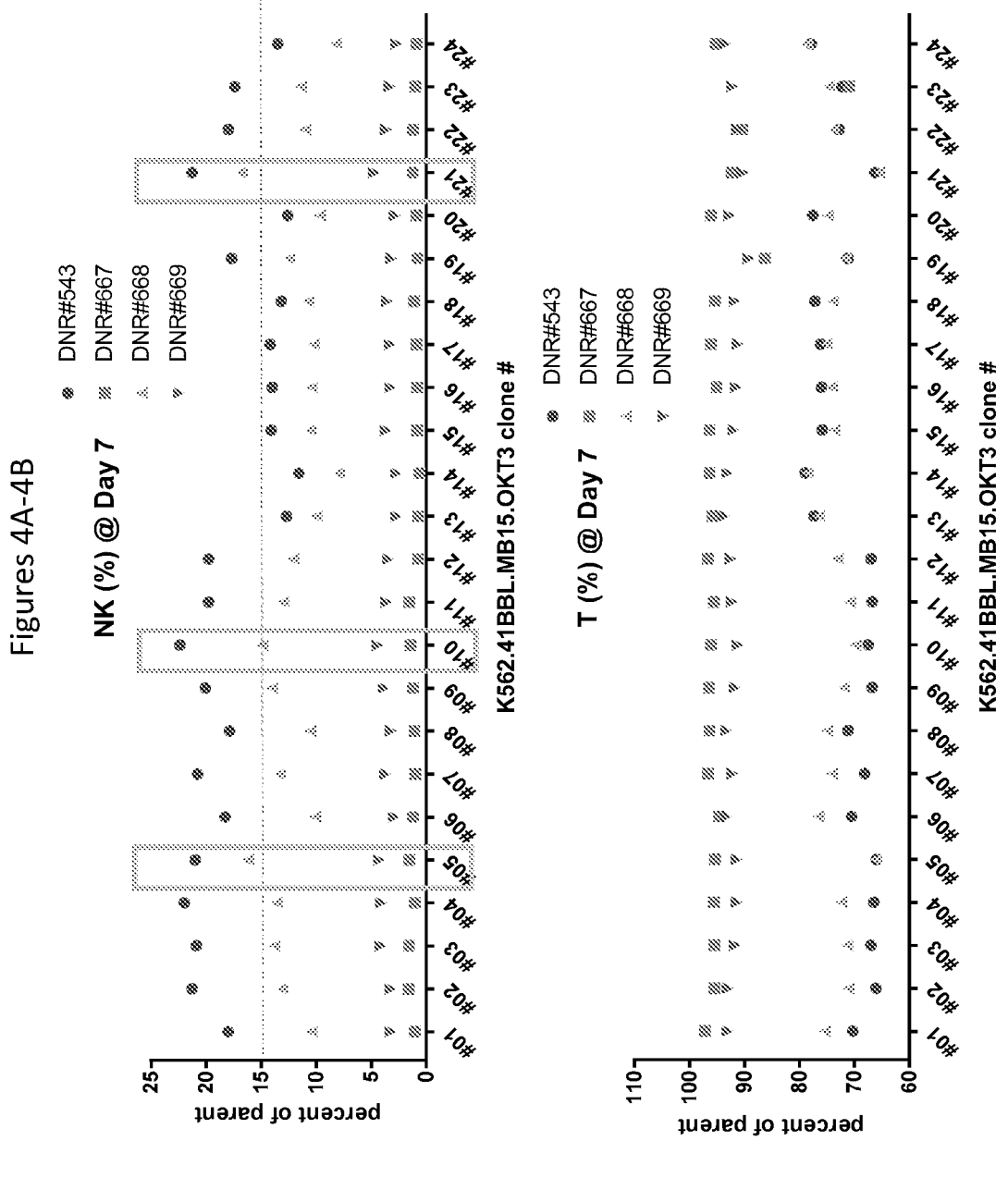
FIGS. 4A-4B depict data related to the resultant cell composition for four different donors after seven days in expansion culture utilizing 24 different K562 clones for expansion.

FIGS. 4A-4B depict data when a mixed population of NK cells and T cells from each of the four donors was expanded using each of the 24 K562 clones as a feeder cell for a period of seven days. Broadly speaking, the composition of the expanded cell population is largely reflective of the incoming ratios of NK cells to T cells. As shown in FIG. 4A, the NK cells post-expansion ranged from about 2% to about 23% of the cells of the parent sample (e.g., a rough comparison of how many cells out of a total population are present post expansion, as compared to the same percentage from the original donor sample shown in FIGS. 1A-1D). FIG. 4B shows similar data for T cells, with the percentage ranging from about 65% to about 95% of the parent population. In general the respective NK:T cell ratios post expansion are reflective of the relative ratios from the original samples (e.g., those of FIGS. 1A-1D). Therefore, in several embodiments the starting NK cell to T cell ratio can be used as a guideline for the ultimate NK cell to T cell ratio that will result post-expansion. As discussed above, in certain embodiments initial adjustments to the cell ratio prior to initiating expansion can be used to direct the ultimate ratio of the different cell types to one another after expansion is complete. Additionally, as discussed in more detail below methodological changes during expansion can be implemented to further fine-tune the ratio of cells that result post-expansion.

Example 2—Dual Modality Expansion of Mixed
Cell populations

As discussed above, NK cells and T cells can be co-expanded together in culture and yield cell-type ratios that are largely reflective of the starting ratios of the cells from the initial blood sample. The present example was per-formed in order to implement a dual-modality expansion protocol that allows for tailoring of the relative expansion rates of the NK cell and T cell subpopulations.

Figure 5:
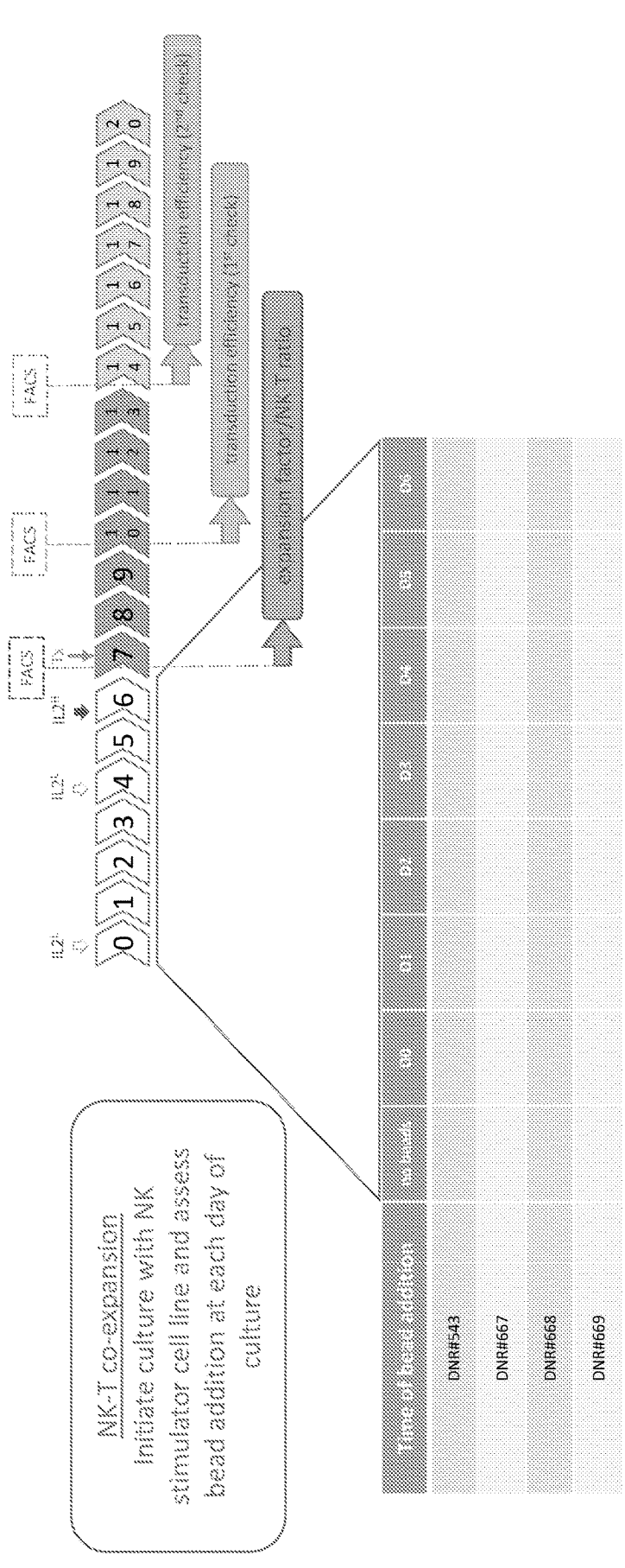
FIG. 5 depicts a schematic of expansion protocols according to several embodiments provided for herein wherein a supplemental stimulation source is added to the culture at a variable timepoint. Similar to FIG. 2.

FIG. 5 depicts a schematic for the experimental design implemented. The expansion timeline and initial seeding of cells is substantially similar to those discussed above, how-ever, the cultures are either exposed to a supplemental expansion stimulus at various time points post-co-culture initiation or maintained as above (as a control). The sche-matic of FIG. 5 shows this addition of the supplemental expansion stimulus in a matrix covering the first six days of co-culture. In this example, as discussed above, the supple-mental expansion stimulus comprises the addition of CD3/CD28 dyna beads to the culture medium in order to stimulate T cell expansion. In additional embodiments, these (or other) supplemental expansion stimuli can be added —for example direct addition of one or more antibodies to stimu-late T cell expansion. As indicated in the schematic, the culture is supplemented with IL-2 at various time points and FACS analysis is used to evaluate the expansion factor and NK:T cell ratio, as well as during and post-expansion transduction efficiencies.

Figure 6A:
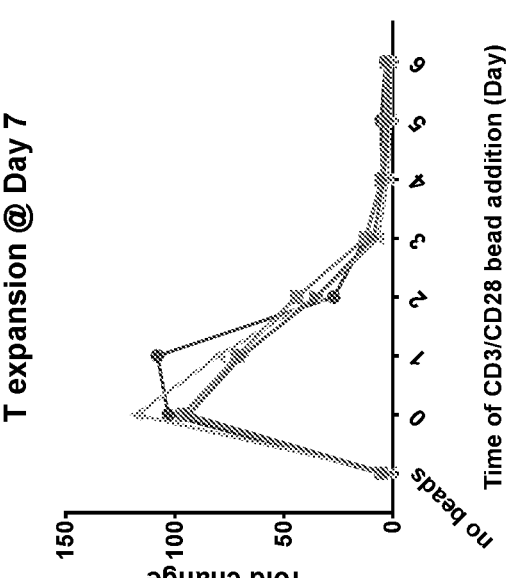
FIGS. 6A-6B depict data related to the expansion of NK cells and T cells upon the addition of a supplemental expansion stimulus.
Figure 6B:
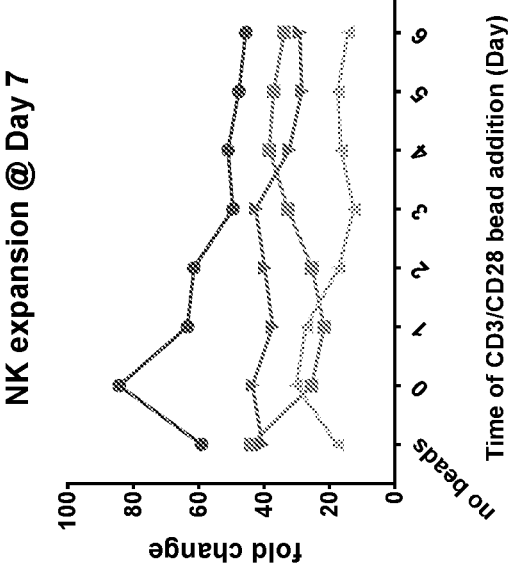

FIGS. 6A-6B depict data related to the NK cell (FIG. 6A) and T cell (FIG. 6B) expansion measured after 7 days of culture, with the time of CD3/CD28 polystyrene beads (beads coated with anti-CD3 and anti-CD28 antibodies as the supplemental expansion stimuli for T cells) added at various time points post-expansion initiation. In other words, the column at Day 2 is the relative expansion of NK or T cells when CD3/CD28 polystyrene beads were added at day 2 and expansion was measured at day 7 (an incubation of 5 days with the beads). FIG. 6A indicates, at the outset, that NK cell expansion was not adversely impacted by the addition of the CD3/CD28 polystyrene beads. As shown in the "no beads" data points, the fold change expansion was on par with that shown in the data of FIG. 3A. The addition of CD3/CD28 polystyrene beads between days 0 (at co-culture inception) and day 6 did not appear to significantly alter the NK cell expansion across any of the 4 donors, each population still exhibiting between about 15-fold to about 85-90-fold at a peak. Furthermore, the expansion of the NK cells was relatively consistent over time within a given donor. For example, Donor 669 consistently exhibited about 40-fold increase in NK cells, whether there were no beads, or if beads were added at any time within the first 6 days of culture. In several embodiments, the addition of the CD3/CD28 polystyrene beads may actually enhance the NK cell expansion, rather than simply fail to inhibit the process.

FIG. 6B shows the related data for T cell expansion with the addition of the CD3/CD28 polystyrene beads as a supplemental expansion stimulus. In contrast to the NK cells, the T cell expansion varies significantly depending on the presence/absence of the CD3/CD28 polystyrene beads and on the timing of the addition of the CD3/CD28 poly-styrene beads. As shown in the "no beads" portion, the absence of CD3/CD28 polystyrene beads induced little to no T cell expansion when measured at day 7. As can be seen from the general shape of the curve in FIG. 6B, T cells were more robustly expanded when the CD3/CD28 polystyrene beads were added earlier in the culture process. For example, the addition of CD3/CD28 polystyrene beads at the inception of co-culture with NK cells and K562 feeder cells led to nearly a 100-fold increase in T cells across all donors. This induction dropped to about 75-fold increase when the beads were added after one day of culture. The relative expansion continued to drop as the beads were added later and later in the process. Thus, in several embodi-ments, maximal T cell expansion occurs when the supple-mental expansion stimulus is present at early time points, e.g., at the inception of co-culture, within about six hours of co-culture, within about 12 hours of co-culture within about 18 hours of co-culture, or within about 24 hours co-culture. In several embodiments, the relative expansion of the T cells can be fine-tuned based on when the supplemental expan-sion stimulus is provided in order to achieve a desired NK:T cell ratio in the final expanded population. In other words, should the desired final population have a larger percentage of T cells as compared to NK cells, the supplemental T cell expansion stimulus can be provided relatively early in the co-cultures process. Alternatively, should the desired final cell population be more evenly distributed between NK cells and T cells the addition of a supplemental T cell expansion stimulus can be delayed until later in the co-culture process. Thus, depending on the embodiment, the culture conditions and relative timing of the inclusion of (or exclusion of) a supplemental stimulus to expand T cells can be fine-tuned to control the ultimate ratio of cells in the final expanded immune cell population.

As indicated above, in several embodiments, the expanded population of immune cells (e.g., NK cells and T cells) can be administered to a subject in need of treatment on an "as-is" basis and/or after incorporation into a phar-maceutically acceptable carrier. In several embodiments, however, the cells are genetically engineered with chimeric constructs to enhance their cytotoxicity against target cells (see, e.g., PCT Patent Application No. PCT/US2018/024650, filed Mar. 27, 2018, the entire contents of which is incorporated by reference herein). In order to assess the capacity of the expanded population of NK cells and T cells, experiments to determine the ability to transduce the cells were performed.

Figures 7A, 7B, 7C, 7D:
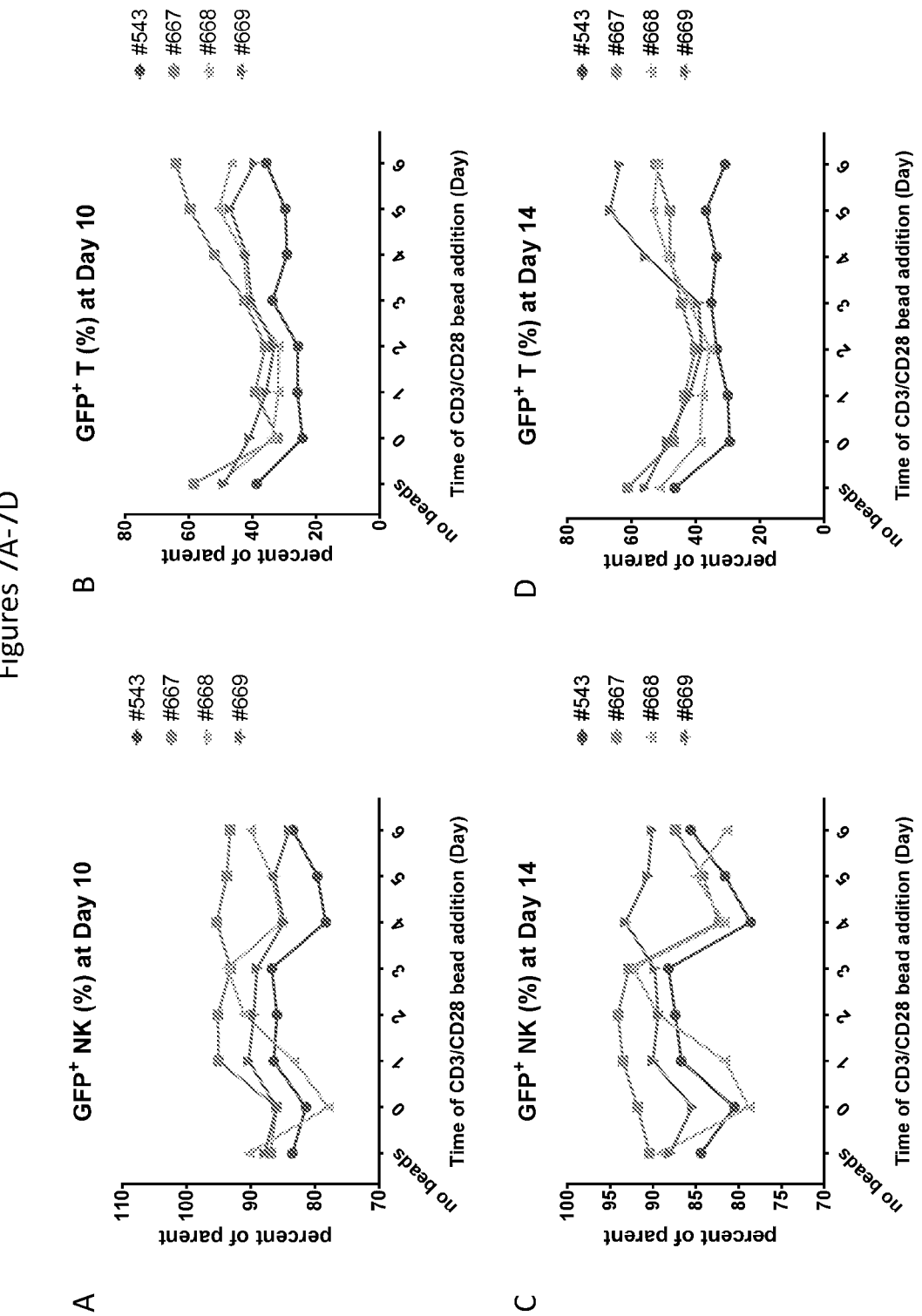
FIGS. 7A-7D depict data relating to the ability to simultaneously transduce both NK and T cells with a vector carrying an exogenous gene for expression relative to the time of addition of CD3/CD28 beads to the culture, and the ability of both cell types to maintain expression of the transduced gene.

NK cells and T cells that were co-expanded were trans-duced with a γ-retrovirus encoding green fluorescent protein (GFP). Cells were transduced at Day 7 and transduction efficiencies were measured by FACS at day 10 and day 14. Data are shown in FIGS. 7A-7D. FIG. 7A shows the percentage of GFP positive NK cells relative to the total NK cells present in the culture on day 10 on a donor by donor basis relative to the presence or absence of CD3/CD28 polystyrene beads ("no bead" control) or depending on the time of the addition of the beads relative to the inception of co-culture with the T cells and K562 feeder cells. As shown, neither the presence or absence of the beads nor the time of the addition of the beads appeared to substantially impact the transduction efficiency of NK cells a day 10. Overall, across all four donors, transduction efficiencies ranged from about 80% to about 95% (relative to the starting population of NK cells in the original blood sample collected). Simi-larly, T cells were also readily transduced at 10 days, as shown in FIG. 7B. While transduction efficiencies appeared slightly lower than as compared to NK cells at 10 days, across all four donors, efficiencies ranged from about 25% to about 65% (relative to the starting population of NK cells in the original blood sample collected).

Carrying the analysis of transduction efficiency out to 14 days post inception of co-culture demonstrated the stability of transgene expression in both NK cells and T cells after transduction is maintained at least into the second week of culture independent of initial donor variability and the presence/absence of CD3/CD28 beads or the timing of the addition of the CD3/CD28 beads. These data are shown in FIG. 7C (for NK cells) and FIG. 7D (for T cells). FIG. 7C shows that transduction efficiency across all donors and irrespective of the addition, or timing of addition, of CD3/CD28 beads to expand T cells remained between about 78% and 95%. As with the T cells at 10 days of co-culture, after 14 days, across all four donors, transduction percentage of T cells ranged from about 30% to about 70%. Taken together, these data indicate that not only are both NK and T cells readily expanded in each other's presence, but that each cell type is amenable to transduction, which indicates that the cells can be engineered to have enhanced cytotoxic effects on target cells.

Figures 8A, 8B, 8C, 8D:
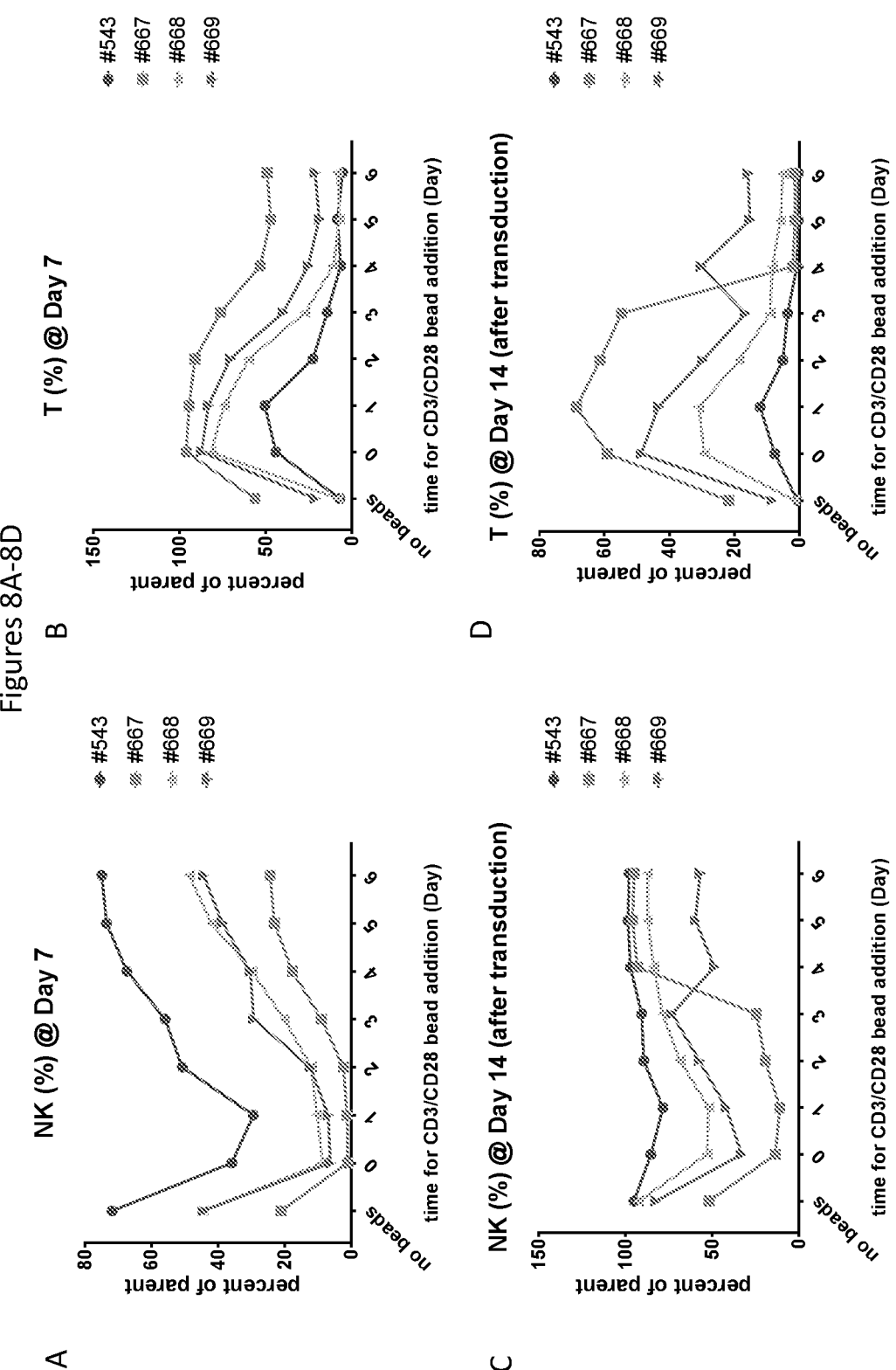
FIGS. 8A-8D depict data related to the changes in the ratio of NK to T cells as co-culture expansion times are lengthened.

As discussed above, the ratio of NK:T cells can be tailored based on the conditions employed during the expansion period (as well as with specific steps taken to adjust the ratios of starting cell populations or adjustment post-expansion). To determine how the ratio of NK to T cells changes depending on the time of addition of the CD3/CD28 beads, the proportion of each cell type in the final culture was measured at days 7 and 14, with the results being shown in FIGS. 8A-8D. FIG. 8A shows the data for NK cell numbers at day 7 (either for "no bead control" or cell populations from each donor co-cultured with K562-41 BB-mbIL15 cells and CD3/CD28 bead added at various time points). Consistent with the relative expansion of each cell type, FIG. 8A shows an interesting trend that NK cells exhibit an increase as a proportion of the final culture as CD3/CD28 beads are added progressively later in the expansion period. Interestingly, as shown in FIG. 8C, at 14 days the NK cells had continued to increase as a proportion of the final culture, with several donors having NK cells at nearly 100% of the cells present in the initial sample. This is notable also in that the day 14 evaluation is post-transduction, which indicates that the NK cells do not lose their ability to expand as a result of transduction with an exogenous vector, while T cells may require earlier stimulation, or may become exhausted during the culture period.

In contrast to NK cells, the percentage of T cells decrease when CD3/CD28 beads are added during the culture period. The T cell populations that were exposed to beads later in the co-culture period show a reduced overall T cell percentage. This is perhaps of the reduced duration of time that those T cell populations were exposed to the stimulatory effects of the CD3/CD28 beads. The data in FIG. 8D also show that T cell percentages drop in the second week of culture, as represented by data at Day 14. These data show that T cell percentages at 14 days peaked at about 70% of the parent cell number, but went as low as 1-2% (e.g., for those samples where CD3/CD28 beads were added at 4, 5, or 6 days of co-culture). This may again reflect a reduced period of stimulus of T cells and/or an effect of the removal of a large number of the stimulatory beads during the transduction protocol. This may also be reflective of T cell exhaustion. Together, however, these data show that a trend is for NK cells to increase over a two-week co-culture time frame, while T cells tend to decrease. Knowing this general behavior allows one to tailor the culture conditions to optimize the rate of increase of NK cells vis-à-vis the rate of the decrease in T cells in order to arrive at a post-expansion mixed cell population with the desired characteristics.

Taken together the data from this experiment (as well as Example 1) demonstrate that, in accordance with several embodiments disclosed herein, NK cell and T cells can successfully be co-expanded. According to several embodiments, NK and T can be co-expanded simultaneously through the co-culture of the two immune cell populations with K562 cells, which in some embodiments, are modified to express 4-1BBL and/or mbIL15. In still additional embodiments, the K562 cells are further modified to present a specific T cell stimulating signal, such as for example an antibody or other molecule that interacts with T cells to stimulate their expansion. In several embodiments, the K562 cells are modified to express an OKT3 antibody. Alternatively or according to some embodiments in addition to, a separate T cell stimulus is provided. For example, according to several embodiments, anti-CD3 and/or anti-CD28 antibodies are provided in order to stimulate T cell expansion. Thus, these data indicate that there are multiple different methods by which NK cells and T cells can be co-expanded. Advantageously, the choice of the method to be used can be tailored depending on the desired ratio of NK cells to T cells in the final post expansion immune cell population. For example, the data presented herein indicate that K562.41BBL.mbIL15.scFv-OKT3 clones can expand NK cells while also robustly expanding T cells. Thus, such an approach may be desirable when they high T: NK ratio is preferred. Additionally, certain K562 clones have been identified that yield a higher NK percentage following expansion. Thus, in some embodiments, such clones could be used when a more balanced NK to T cell ratio is desired. In addition, should a more fine-tuned control over the ultimate NK to T cell ratio be desired, rather than engineering the T cell stimulus into the feeder cell line, the feeder cell line engineered to preferentially expand NK cells can be coupled with a separate, supplemental T cell expansion stimulus. According to several embodiments this can be achieved by combining feeder cells, such as K562.41BBL.mbIL15 feeder cells, with, for example CD3/CD28 T-cell stimulating beads. The timing of introduction of the separate T cell stimulus can also be used to fine tune the ultimate ratio of NK cells to T cells. For example, a higher NK:T ratio can be achieved by introduction of the T cell stimulus later in the co-culturing process, whereas in contrast, a higher T:NK ratio can be achieved through introduction of the separate T cell stimulus earlier in the co-culturing process. Thus, the expansion methods disclosed herein are advantageously flexible with respect to varied starting materials and adjustment of the procedures to ultimately result in a combined immune cell population with the desired ratio between the various cell types in the resulting expanded population.

Example 3—Model Systems to Evaluate Mixed Immune Cell Populations

As can be appreciated, development of novel mixed cell populations such as those described herein, made by various embodiments of the methods disclosed herein, may require an innovative evaluation panel. In several embodiments, there are therefore provided certain model systems for evaluation of one or more of the survival, proliferation, persistence, intravasation, and/or efficacy (e.g., cytotoxicity) of mixed immune cell populations.

Figures 9A, 9B, 9C:
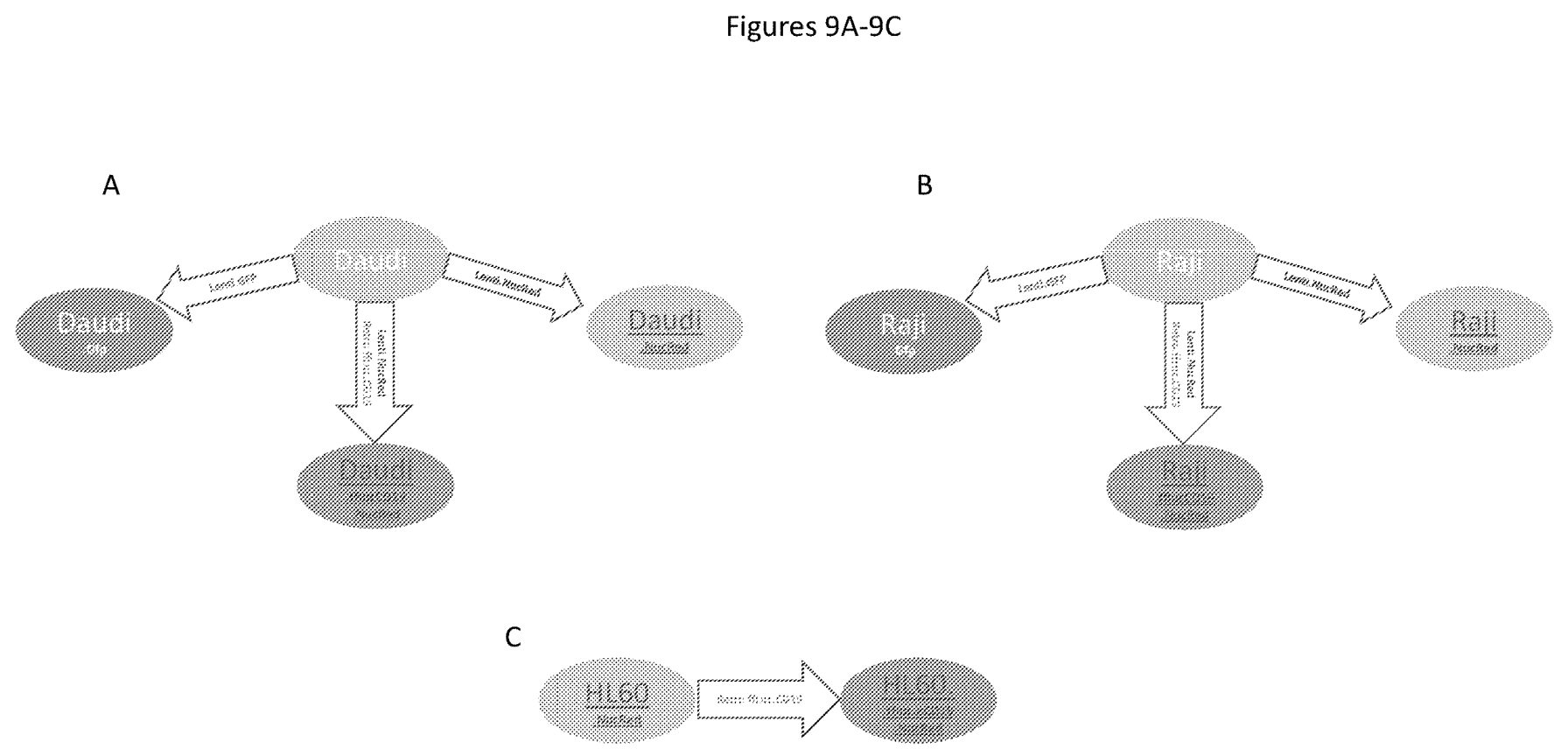

FIGS. 9A-9C schematically depicts the generation of various custom cell types for evaluation of the efficacy of combined immune cell populations. Daudi cells are B lymphoblastic suspension cells derived from the patient with Burkitt's lymphoma. As shown in FIG. 9A, Lentiviral constructs will be used to transfect Daudi cells with various reporters, such as Green Fluorescent Protein (GFP), Nuclear Red (NucRed) or CD19 (lacking the intracellular domain) coupled to firefly luciferase (fflucCD19). Raji cells, which are another human B lymphocyte suspension cell line are engineered in similar fashion, as shown in FIG. 9B. FIG. 9B shows the schematics for introducing CD19 (lacking the intracellular domain) and luciferase into HL60 cells, which is a human myeloblastic suspension cell line. These NucRed and GFP constructs were used for in vitro studies, which the firefly-luciferase constructs were used for in vivo studies. Each CD19 construct (lacking the intracellular domain) was engineered so that tumor cells that don't normally express CD19 would in fact express CD19, which could then be targeted by NK and T cells engineered to induce cytotoxic effects against CD19-expressing target cells. Functional evaluation was also performed using a kinetic analysis killing assay in order to determine the timeframe in which NK cells and T cells for inducing cytotoxic effects against target cells, respectively.

Figure 10:
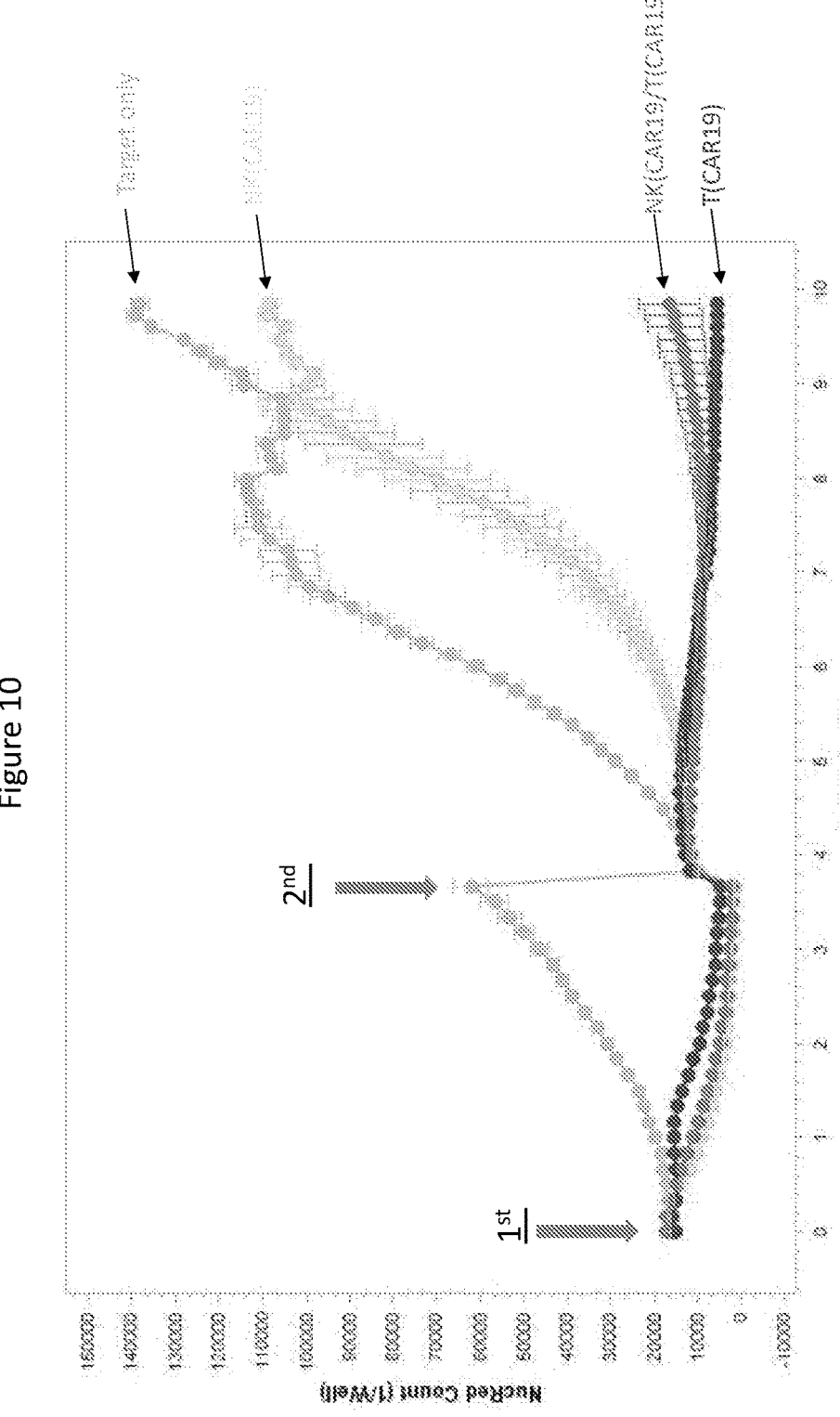
FIG. 10 depicts data related to the cytotoxic effects of NK cells, T cells and a mixed population of NK+T cells in a re-challenge assay.

CD19-expressing HL60 target cells were used in a re-challenge assay to assess the cytotoxic effects of NK cells alone, T cells alone, or a combination of NK+T cells. At Day 0, populations of NK cells, T cells, NK+T cells were challenged by exposure to 20,000 CD19-expresing HL60 cells. At Day 4, these cell populations were re-challenged with an additional 10,000 CD19-expresing HL60 cells. Target only cells were cultured under the same conditions, but were washed with PBS prior to adding a second round of target cells (as a control). The resultant data are shown in FIG. 10, where the NucRed count is representative of the number of live CD19-expressing HL60 cells counted per well.

As can be seen from the NK(CAR19) curve, NK cells targeting CD19 shows a rapid initial kill of target cells. However, after re-challenge on Day 4, the number of surviving HL60 cells steadily increased. In contrast, the T cell curve (T(CAR19)) reveals a slower initial killing kinetics. The T cells eliminated most targets, but in contrast to the rapid effects with NK cells, it took T cells nearly until Day 4 to eliminate the original bolus of CD19-expressing HL60 cells. After challenge with additional HL60 cells on day 4, the T cells retained a steady cytotoxic effect on the CD19-expressing HL60 cells.

The NK+T cell population was generated by replacing 50% of a population of NK(CAR19) cells with T(CAR19) cells. When initially challenged with CD19-expressing HL60 cells, the NK cell portion of the population retained the ability to induce a rapid kill of target cells. In contrast to the NK-only population, however, after re-challenge on day 4 with additional CD19-expressing HL60 cells, the longer-term cytotoxic effects of the T cells kicked in, resulting in a similar overall cytotoxic effect post-re-challenge as compared to T cells alone. As shown in this experiment, when the total number of effectors cells (NK, T, or NK+T) are held constant, NK+T (in 1:1 ratio) showed more rapid killing than T(CAR19) alone, with greater sustained killing activity than NK(CAR19) by itself.

Thus, the NK+T cell population advantageously retained the rapid killing and sustained killing effect. This "mixed" cytotoxicity presents several advantages in the context of cancer immunotherapies. Many cancers are known to be adaptive and implement "camouflage" mechanisms to avoid detection by the immune system. The rapid killing effect of the NK cells in the NK+T mixed population can aid in eliminating cancer cells prior to such camouflaging actions taking effect. Additionally, even when cancer cells are rapidly killed, the persistence of a small number of cells can lead to a recurrence of a tumor. To that end, the T cell portion of the NK+T cell population can help induce a long-term cytotoxic effect to reduce the risk of relapse. While this experiment demonstrated a 1:1 effector cell ratio (NK:T), as discussed above, in several embodiments, other ratios can be achieved with the methods disclosed herein. In some embodiments, the ultimate ratio can be tailored to a specific therapeutic context. For example, a slower growing tumor may be optimally treated with a lower NK:T ratio, which would also bias the cytotoxic kinetics to a slower, but longer duration anti-cancer effect. In contrast, for an aggressive tumor, a higher NK:T ratio may be desired, as the fast initial cytotoxic kinetics could achieve rapid destruction of tumor cells and/or tumor debulking, with the longer kinetics of the T cells to "clean up" the remainder of the tumor. Likewise, in several embodiments NK+T cell populations of varied ratios may be administered at different points over the treatment of a patient. For example, rapidly cytotoxic high ratio NK:T populations may be administered early in a dosing regimen to control initial tumor expansion, then shifted to lower ratio NK:T cell populations to maintain and reduce growth over the long term (akin to a loading dose followed by a maintenance dose of a pharmaceutical)

Example 4—Functional Evaluation in Three-Dimensional Culture

To more readily replicate the native environment of some tumors, particularly solid tumors, a 3-D culture system was developed to model tumor intravasation and study how mixed immune cell populations react and perform in a modeled tumor microenvironment.

FIG. 11 shows a schematic of one such model environment. VersaGel® (Cypre, Inc. San Francisco, Calif.) is a hydrogel that can be used to encapsulate cells and that has optical characteristics that are amenable to downstream optical imaging for analysis of the cells. VersaGel® was placed in central portion of a well of a 96-well culture dish and 10,000 CD19-expressing HL60 cells were seeded into the gel. The upper left portion of FIG. 11 shows the seeded cells at Day 0, note the circular shape of the region with cells representing the margins of the gel in the central region of the well, with normal culture well at the exterior portion. The lower left panel shows a representative culture well at Day 8, with the central inset showing the generation of spheroids. The left hand portion of the inset shows the generation of spheroids being limited to the region of VersaGel®, the dotted line shows the division between the gel and normal culture media, with the right hand portion showing normal cell culture growth of the HL60 cells. The upper right portion of FIG. 11 shows a short exposure visualization of the NucRed expressing HL60 spheroids (label/arrow). A longer exposure (lower left) shows a single NucRed expressing HL60 cell that is outside the VersaGel® boundary and thus not forming a spheroid.

In several embodiments, the spheroids recapitulate a 3D tumor microenvironment and allow for studies of how immune cells, such as mixed NK+T cell populations function in a replicated tumor microenvironment. For instance, this approach can be used to study the ability of NK+T cell populations to infiltrate a tumor and exert cytotoxic effects within the depths of a tumor, rather than just acting on surface cells.

In several embodiments, 3D tumor spheroids are exposed to various ratios of NK+T cell populations and tumor cell viability is evaluated, for example by detection of red channel fluorescent signal in the case of CD19-expression NucRed expressing HL60 (or other) tumor cells. In several embodiments, the mixed population of NK+T cells will exhibit enhanced cytotoxic activity as compared to either NK cells or T cells alone. Likewise, in several embodiments, a mixed population of NK+T cells will exhibit enhanced tumor infiltration as compared to either NK cells or T cells alone. In several embodiments, the ratio of NK:T cells is varied to alter the kinetics of cytotoxicity to achieve, as described above, an initial rapid onset of cytotoxic effects followed by a long term cytotoxic effects or alternatively a ratio can be implemented for a slower initial phase and longer duration cytotoxic phased (based on the T cells).

Example 5—Evaluation of Combination NK and T Cell Therapies

Further experiments were conducted, both in vitro and in vivo, in order to further assess the beneficial interaction between NK cells and T cells in a combination therapeutic. As discussed above, and further elaborated on based on experimental data below, in several embodiments, NK and T cells interact with one another in a synergistic fashion, including in terms of expansion of the cells and their cytotoxic impact on target tumor cells. As a brief overview of the experiments discussed below, the interaction of NK and T cells was evaluated in terms of cytotoxicity (using a matrix assay) and also in terms of cytotoxic persistence (using a tumor re-challenge assay). Additionally, experiments were conducted to attempt to elucidate the cellular mechanisms underlying synergy between NK cell and T cells. The cytokine profiles of NK and T cells were also evaluated as was the in vivo anti-tumor efficiency in a xenograft mouse model.

The goals of the present experiments were to determine whether the combination of NK and T cells could achieve efficient tumor killing activity, enhanced persistence of activity, and improved cytokine release, in terms of improved patient safety (e.g., cytokine release profile that reduces risk of cytokine release syndrome).

Figure 12A:
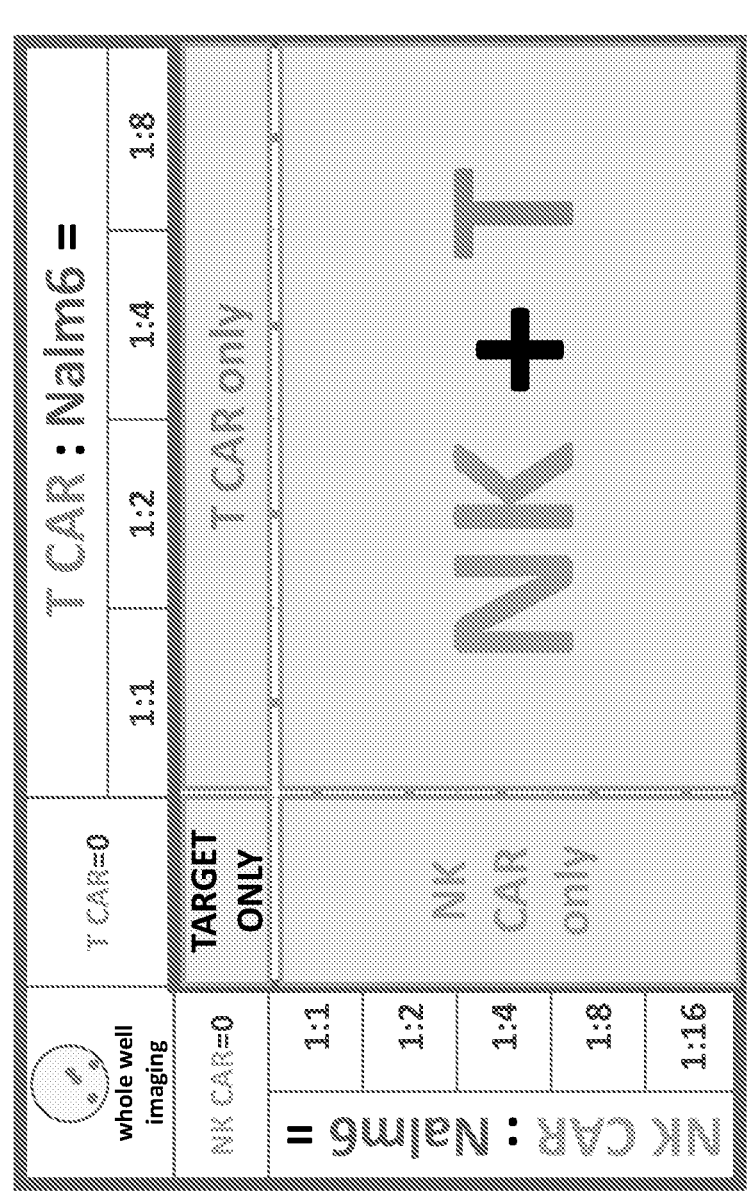
FIG. 12A depicts an experimental setup designed to identify effective ratios of NK cells bearing a chimeric antigen receptor and T cells bearing a chimeric antigen receptor as a combination therapy against target tumor cells.

FIG. 12A depicts a schematic matrix setup to evaluate various concentrations of NK cells and T cells expressing an anti-CD19 CAR (as a non-limiting example of an chimeric antigen receptor) and the resultant cytotoxic effects against Nalm6 tumor cells (as an example of a target cancer type). In terms of the CAR construct used in this experiment, which is a non-limiting example of a CAR that can be used in the NK and T cells used in embodiments disclosed herein, the anti-CD19 binder is an FMC63 scFv. In several embodiments, the binder is humanized. In the experiments discussed herein, the CAR has a Flag tag, but it shall be appreciated that, according to several embodiments, no tag is used —for example, with clinical constructs. In several embodiments, the CAR comprises an OX40 co-stimulatory domain and a CD3zeta stimulatory domain. In several embodiments, the nucleic acid encoding the CAR further encodes an IL15 domain. In several embodiments, the IL15 is expressed separately by the NK and/or T cells as a membrane bound polypeptide. As shown in the Figures, T cells expressing this construct are shown as T19-1 and NK cells expressing this construct are shown as NK19-1. Returning to the Figure, 12A shows the various T19-1 to Nalm6 ratios on the X-axis of the matrix (shown as T19–1=0, or 1:1, 1:2, 1:4, or 1:8). The Y-axis shows the various NK19-1 to Nalm6 ratios (shown as NK19–1=0, or 1:1, 1:2, 1:4, 1:8, or 1:16). By tracing to the intersection of the X and Y axes, one can identify what ratio of NK and T cells were present against the Nalm6 target cells. Nalm6 target cells are a B cell precursor leukemia cell line that is CD19 positive and also stably express NucRed, which can be used as an indicator of Nalm6 cell survival (which thus correlates with NK/T cell cytotoxicity).

FIG. 12B shows the results of the experiment with reductions in red fluorescent signal correlating with greater degrees of cytotoxicity against the Nalm6 tumor cells. As can be seen from the data, when the E:T ratio decreases (for either NK cells or T cells), the survival of the Nalm6 cells increases. See for example, the T19-1:Nalm6 of 1:8 and NK19–1=0 (upper right pair of circular images). At this E:T, the T cells were unable to produce significant cytotoxic effects against the Nalm6 target cells. Likewise, even if both NK and T cells were present, if at low concentrations, the Nalm6 cells continued to grow (see lower most right pair of circular images for T19-1 at 1:8 and NK19-1 at 1:16). However, at many of the other E:T ratios, combinations of NK and T cells worked together to produce robust anti-tumor effects. As can be seen from the results, when either the NK19-1 or the T19-1 cells were present at 1:1 E:T ratio, regardless of the ratio of the other effector cell type to tumor cells, Nalm6 growth was nearly completely eliminated. Similar results were seen when either NK cells or T cells were present at 1:2. These 1:1 E:T ratios were titrated down (using each individual effector cell type alone). Notably, there was some Nalm6 cell growth at an E:T of 1:2 when NK19-1 cells were used alone, and also when T19-1 cells were used alone. However, when T cells and NK cells were used in combination at an E:T of 1:2 for each cell type to yield an overall effector:target ratio of 1:1, Nalm6 growth was eliminated. These results show that NK and T cells act synergistically with one another, since neither cell type alone could control Nalm6 growth at 1:2, but when combined at an "ineffective" individual concentration, the combination of NK+T cells resulted in enhanced cytotoxic effects (see images in dashed box labeled "(NK+T):Nalm6=1:1"). The synergy between NK cells and T cells is more evident when the two cell types were combined, each at a 1:4 effector: target ratio. Both NK and T cells allowed for significant Nalm6 growth when used alone at 1:4. However, when used in combination at 1:4 E:T for both NK and T cells, for an overall ratio of 1:2, Nalm6 growth was substantially reduced, indicating enhanced cytotoxicity, as compared to either cell type alone at that E:T ratio. Again, these data demonstrate that a combination therapy using both NK and T cells allows the two immune cell types to operate synergistically with one another and yield enhanced cytotoxic effects against the target cell.

Figure 13:
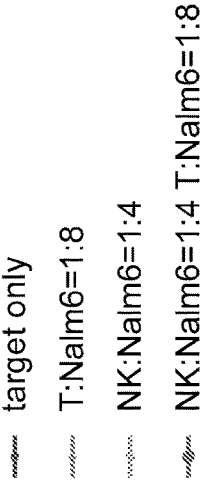
FIG. 13 shows data related to the cytotoxicity of the indicated control NK-only, T-only, or NK+T constructs on target tumor cells, in a first phase, and with a second re-challenge of tumor cells.
Figure 13:
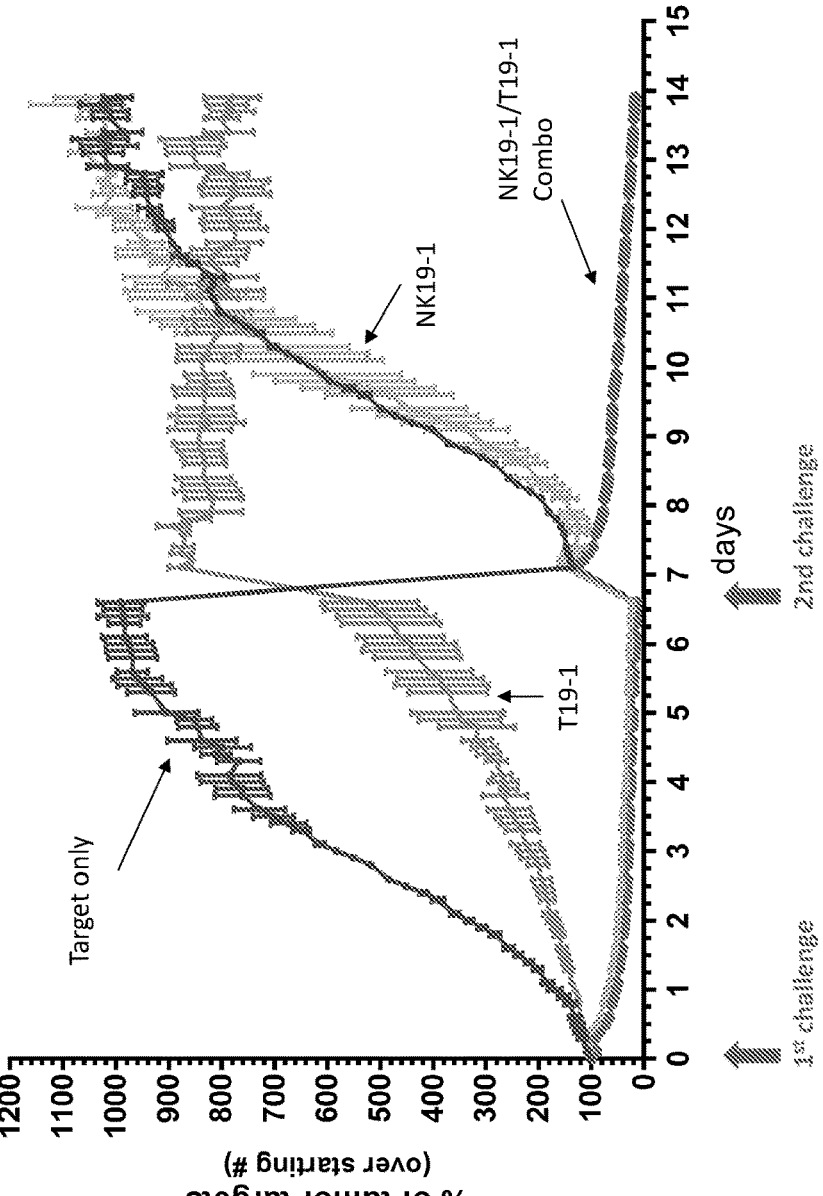

FIG. 13 shows additional data related to the enhanced ability of mixed populations of NK and T cells to act cytotoxic way on target tumor cells. The data presented in FIG. 13 shows the growth of Nalm6 tumor cells in a rechallenge model using either T cells or NK cells alone as well as a combination of NK cells and T cells. The first challenge with the tumor cells occurs at time zero of the experiment with the second challenge after seven days. As can be seen, there is significant growth of target tumor cells alone over the first seven days and again during the second rechallenge. Using T cells alone (in this nonlimiting experiment, the T cells are expressing an anti-CD 19 CAR), there was continual growth of Nalm6 cells over the first seven days. Growth of the target cells spiked at the second challenge and levels were maintained fairly consistently throughout the experiment. NK cells expressing an anti-CD 19 CAR, in accordance with several embodiments disclosed herein, effectively controlled growth over the first challenge period. There was a slight delay in target cell growth immediately after the second challenge, however thereafter, target tumor cells experience significant growth. Notably, however, the combination of NK and T cells controlled target cell growth during the first challenge period, as well as throughout the second challenge period, effectively eliminating target cell growth for the entire duration of the experiment. These data demonstrate that the combination of NK and T cells not only have enhanced cytotoxicity (as shown by way of the results discussed above), but also show enhanced cytotoxic persistence. According to several embodiments, this enhanced persistence is advantageous because it not only allows for a longer duration of cytotoxicity against the target cell, but can also allow for reduced frequency between doses which can be advantageous in limiting potential side effects.

Figure 14A:
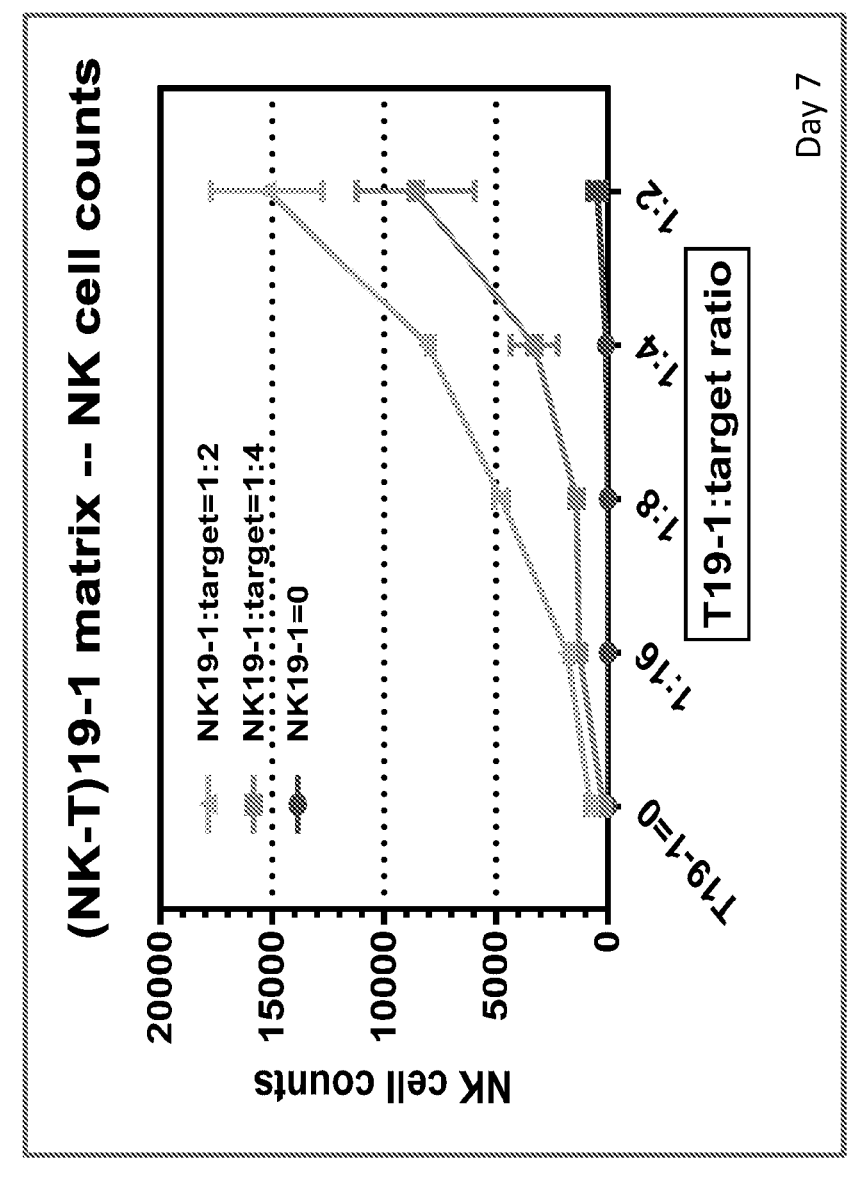
FIGS. 14A-14B relate to experiments to determine the impact of each of NK cells and T cells on the cell number of the other cell type.
Figure 14B:
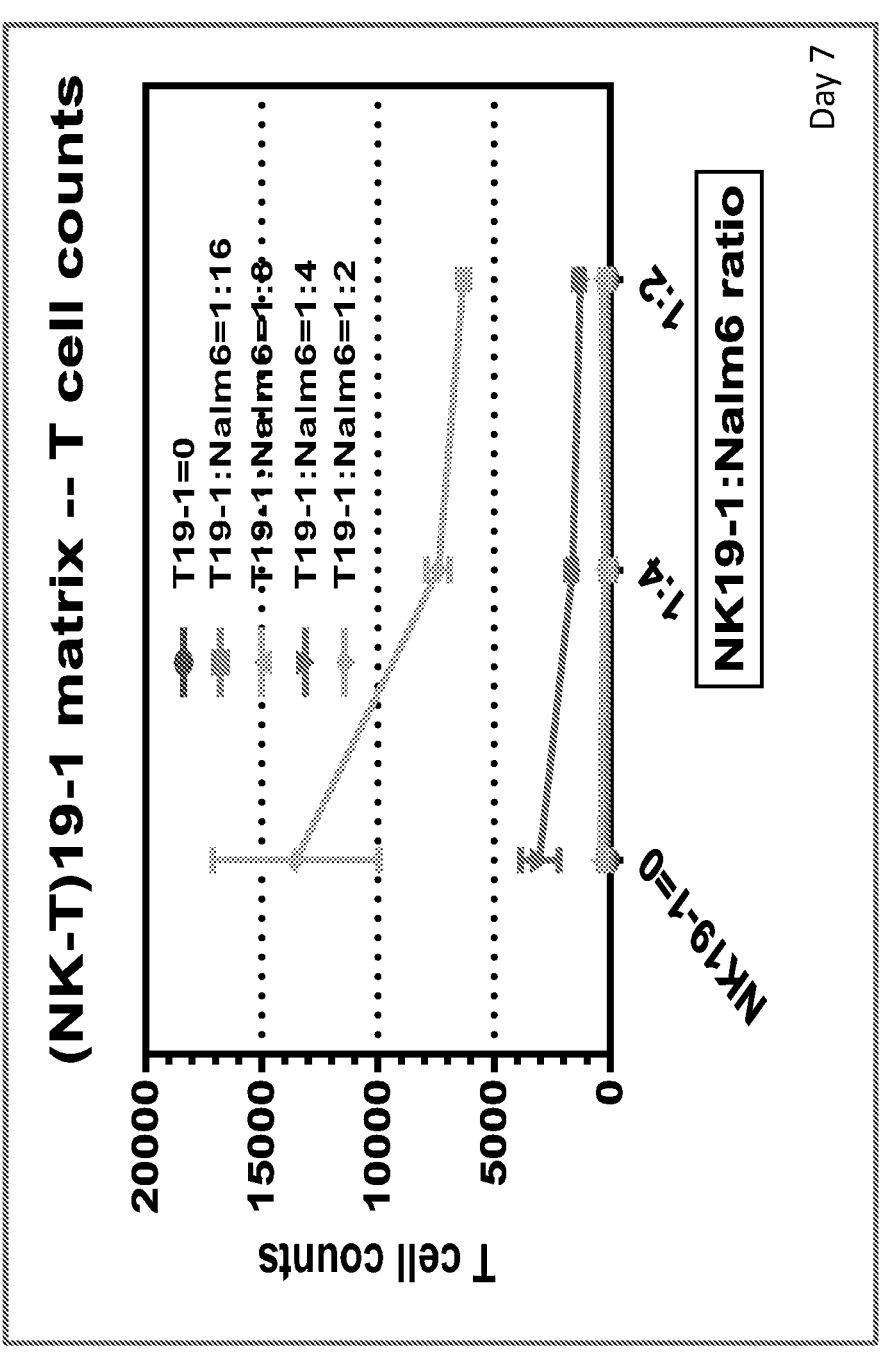

Further experiments were undertaken in order to determine some of the mechanisms that play when combinations of NK cells and T cells are used. It was noted that the combination of NK cells plus T cells resulted in at least a qualitative increase in immune cell number, leading to the inquiry of whether the increased cell number is a mediator of the observed increased persistence. In addition, a goal was to determine whether the increased cell number resulted from an increase in NK cells, T cells, or a combination thereof. FIGS. 14A-14B show cell count data that was gathered using a combination of a fluorescence cytotoxicity assay (as used/described in experiments above) in conjunction with FACS phenotyping of the cells. These data were collected at Day 7 after the immune and target cell populations were mixed. FIG. 14A shows NK cell counts when the indicated NK:target (Nalm6) ratios (traces) were used with the indicated T:target ratio (X-axis). Again, as a nonlimiting embodiment both the NK cells and T cells in this experiment were engineered to express an anti-CD 19 CAR (19-1). As shown in the lowest trace (filled circles) there were no NK cells detected at any T cell: target ratio when the input number of NK cells was zero. In contrast, when the NK cell:Nalm6 ratio was 1:4, the number of NK cells detected (filled squares) increased as the T cell:Nalm6 ratio decreased (e.g., more T cells present). NK cell number increased in a nonlinear fashion as the T cell:Nalm6 ratio went from 1:8 to 1:4, than to 1:2. This general pattern was also detected with a lower NK cell:Nalm6 ratio (1:2, filled triangles). It is notable that when no T cells were present, there was limited NK cell growth, regardless of the starting number of NK cells (see T19–1=0). When T cells were present at a 1:16 ratio, NK cell numbers (indicative of NK cell growth) changed very little, whether starting with a 1:2 or 1:4 NK:Nalm6 ratio. However, at higher relative concentrations of T cells, a greater degree of NK cell growth was induced in the NK:Nalm6 1:2 samples. FIG. 14B show the corresponding data related to the measurement of T-cell counts in the presence of varying concentrations of NK cells. Each of the traces relate to one of the indicated ratios of T cells to Nalm6 target tumor cells, and the X-axis indicates the various concentrations of NK cells:Nalm6 target tumor cells. With the exception of the two traces related to T cell:Nalm6 ratios of 1:4 or 1:2, NK cells had limited impact on T cell numbers. In the presence of NK cells at a 1:4 or 1:2 NK cell:Nalm6 ratio, however, final T cell numbers markedly declined (see closed inverted triangle and closed diamond traces).

Figures 15A, 15B, 15C:
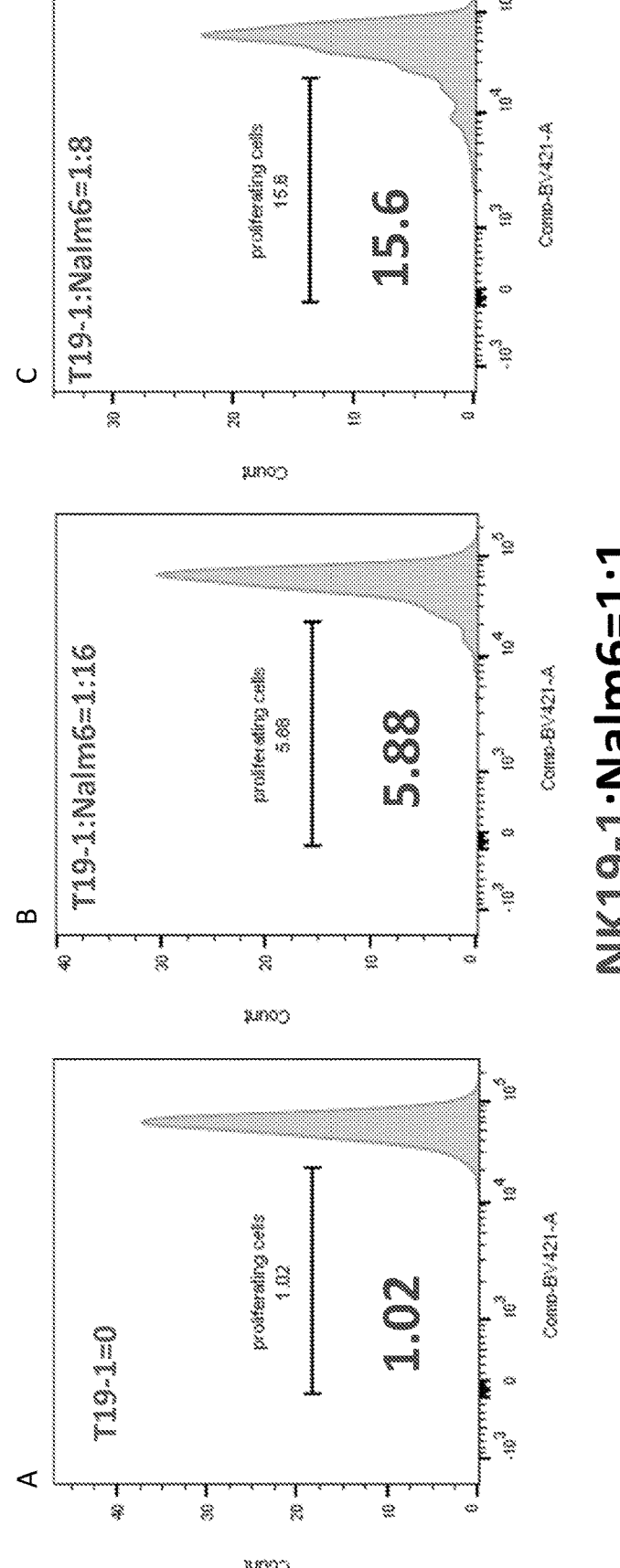
FIGS. 15A-15F show data for NK cell proliferation in the presence of T cells bearing a chimeric antigen receptor.
Figure 15D:
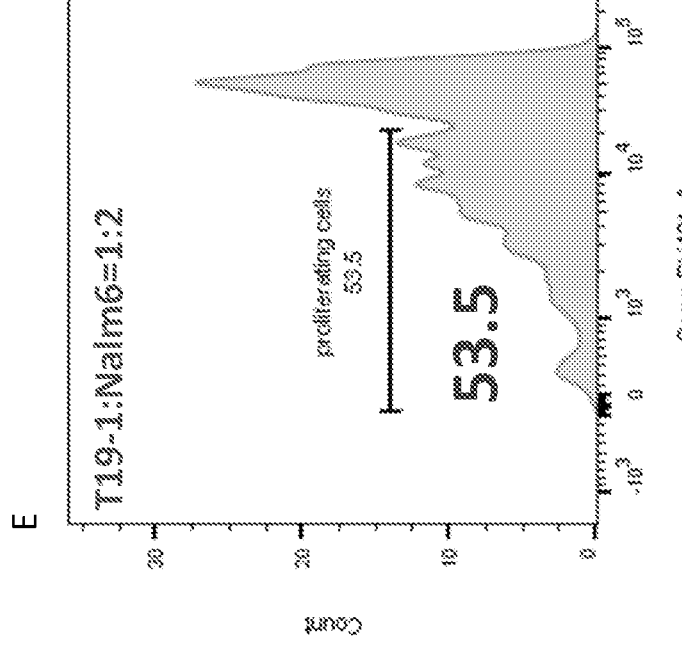
Figure 15E:
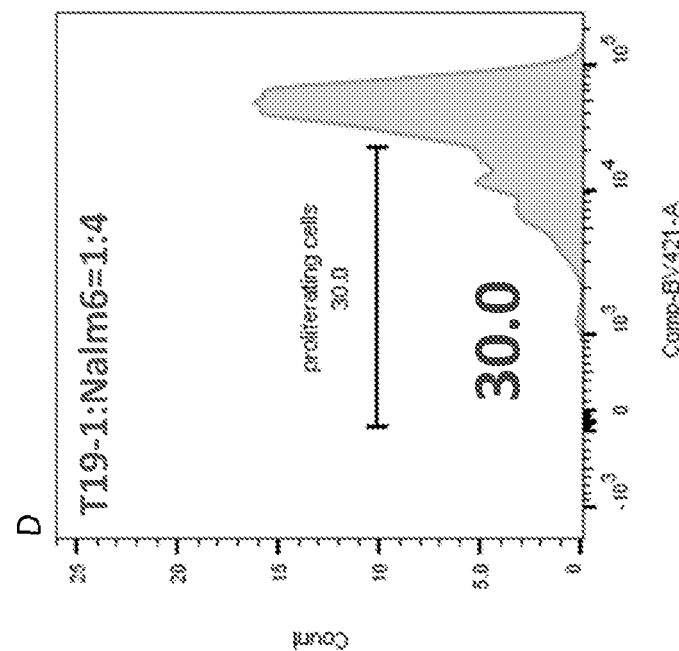
Figure 15F:
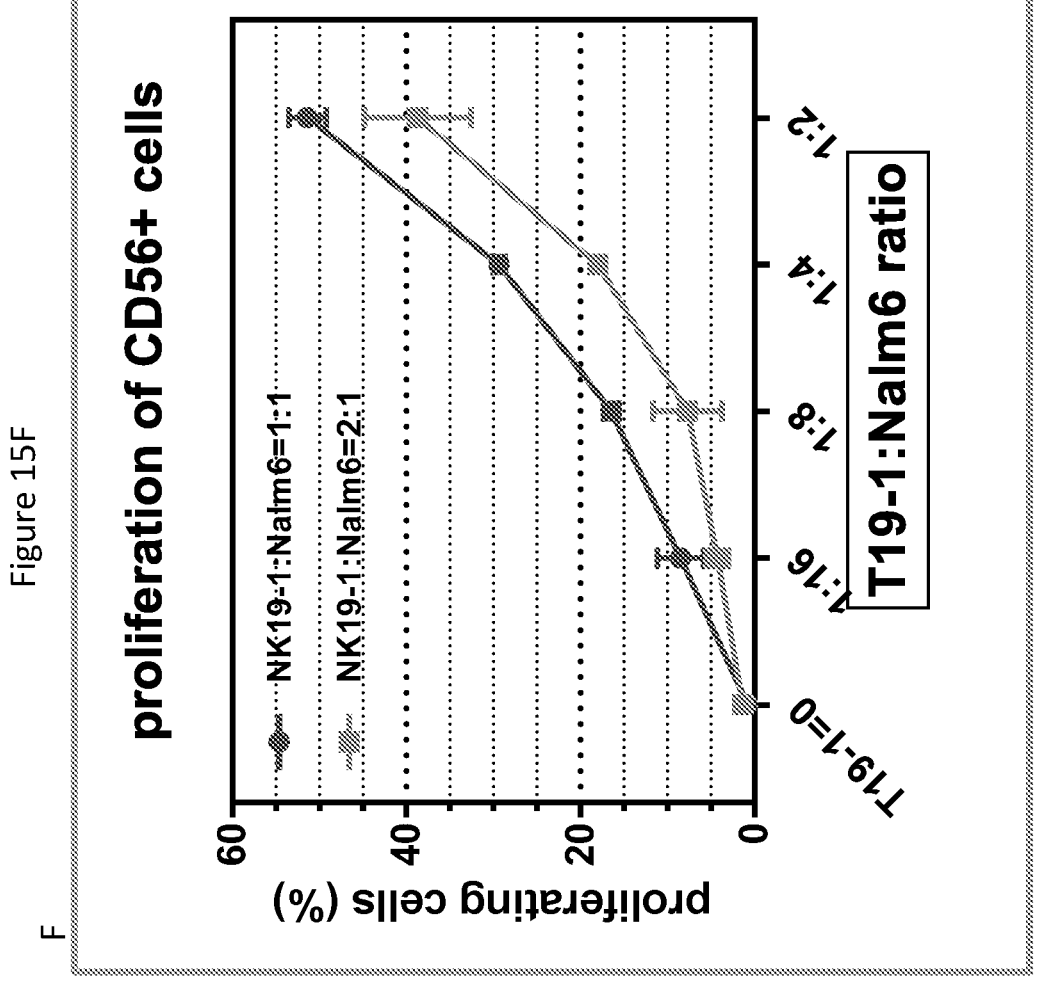

Additional investigation was undertaken to monitor whether the changes in cell numbers were attributable to changes in cell proliferation. An approach was used in which the change in fluorescence with increasing cell count was monitored. In this approach, cells at time zero are loaded with a fluorescent dye (the CellTrace™ Violet Cell Proliferation Kit Violet from ThermoFisher was used). With each mitotic division of that parent cell, the fluorescent signal is coordinately reduced, as it is now split between two cells. Likewise upon the second mitotic division each of the two first-generation daughter cells will give rise to two granddaughter cells and the relative fluorescent signal will decrease accordingly. Thus, in this assay a decrease in fluorescent signal corresponds to proliferation of the labelled cells. For these experiments, as above, both NK cells and T cells were engineered to express a non-limiting embodiment of an anti-CD 19 car to allow them to exert cytotoxic effects againstNalm6 target cells. Post-transduction, NK cells and T cells were co-cultured and subject to the cell proliferation fluorescent analysis. The NK/T cells were challenged with Nalm6 cells and incubated for 6 days. Thereafter the cells were stained with CD56-PE and CD3-APC dyes in order to detect NK or T cells (respectively) by FACS analysis using gates for $CD56^+CD3^-$ or $CD56^-CD3^+$ cells (NK cells or T cells, respectively). The resultant data from the FACS analysis is shown in FIGS. 15A-15E. Each of FIGS. 15A to 15E show the NK cell count with an increasing number of T cells (reduced T cell:Nalm6 ratio) and the NK19-1:Nalm6 ratio at 1:1. As can be seen, with each successive increase in the number of T cells the shoulder on the curve gated for $CD56^+CD3^-$ gets wider, indicating an increased number of proliferating NK cells. Data are summarized in FIG. 15F, which shows two curves, one for the NK19-1:Nalm6 ratio of 1:1 (raw data in FIGS. 15A-15E), and one for growth of NK cells when the starting NK cell:Nalm6 ratio is 2:1. This summary data indicates that NK cells respond to the presence of an increasing number of T cells with a coordinate increase in NK cell proliferation.

Figure 16D:
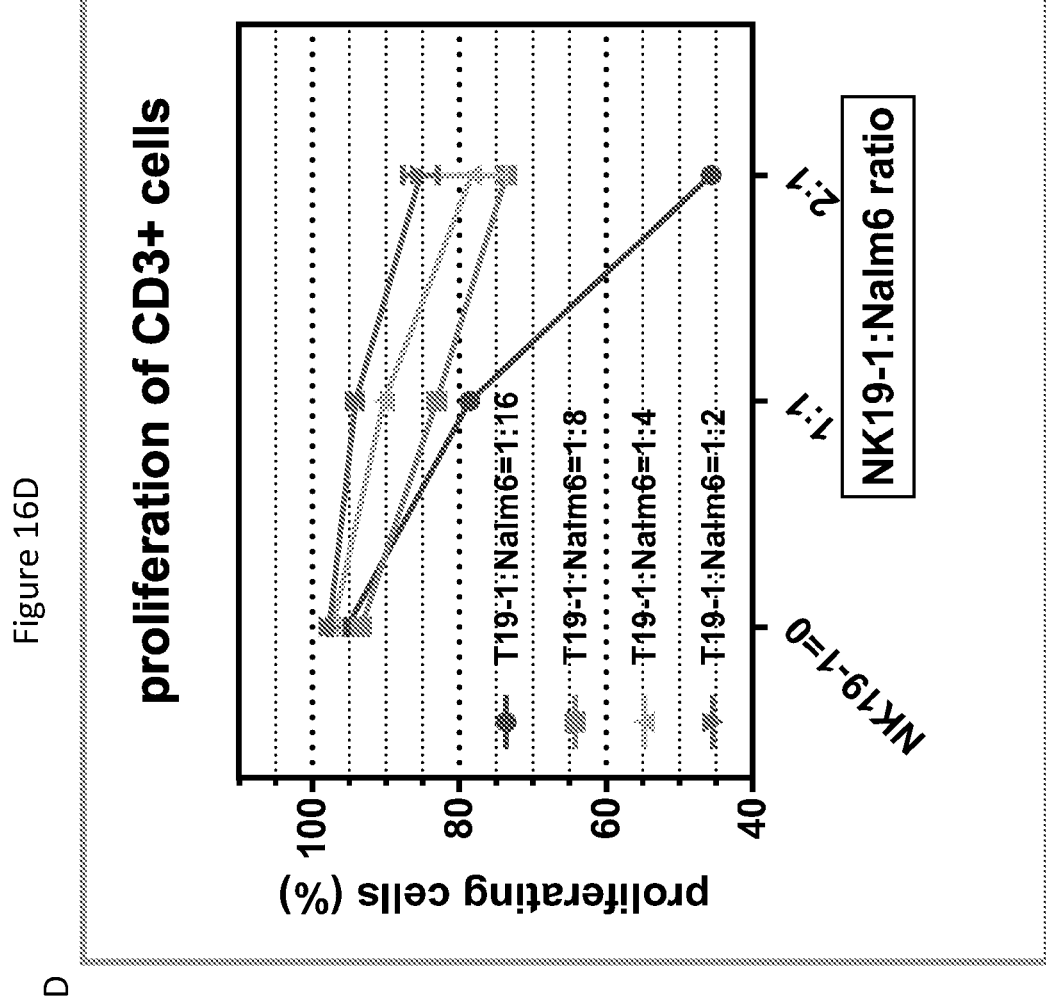

Corresponding data are shown for T cells in FIGS. 16A-16D. FIGS. 16A-16C measures the T cell count in the presence of successively increased NK cell numbers (NK=0 in A, NK:Nalm6=1:1 in B, and NK:Nalm6=2:1 in C). The T cell:Nalm6 ratio was 1:2. In contrast to the curve shown in FIG. 15, the signal related to proliferating T cells successively decreases with an increase in the number of NK cells. These data are summarized in FIG. 16D, which shows a consistent decrease in the percentage of T cells that are proliferating when the ratio of NK cells to target cells is increased. Most notable is the substantial decrease detected with use of the most dilute T cell concentration (T19-1: Nalm6 of 1:16).

Figures 17A, 17B, 17C:
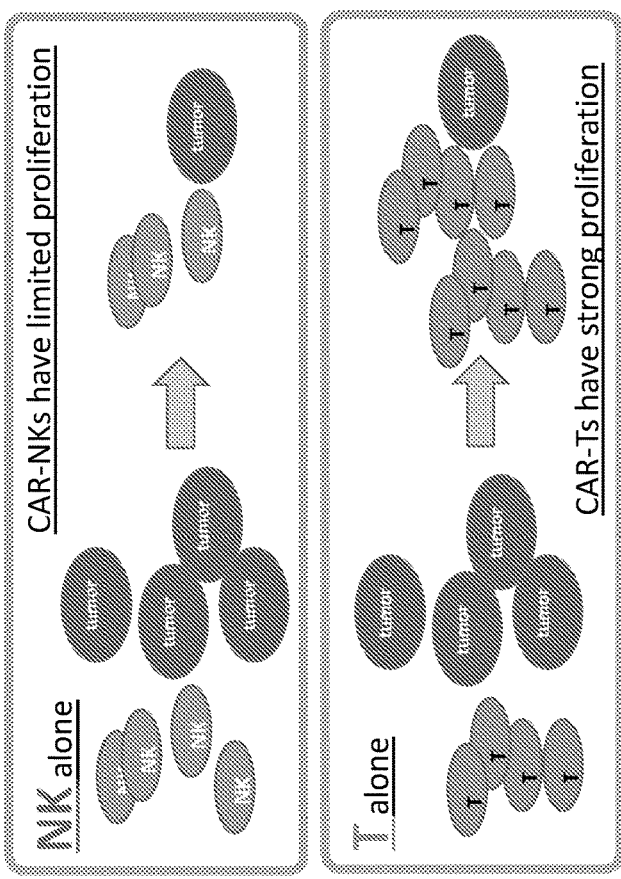
FIGS. 17A-17C are a collective schematic of the interaction between NK cells and T cells with respect to proliferation.

Without being bound by theory, the data related to increasing number of T cells promoting increasing numbers of proliferating NK cells and the data showing that increasing numbers of NK cells leads to decreases in the number of proliferating T cells, a schematic model was developed in the shown in FIGS. 17A-17C. FIG. 17A depicts the growth of NK cells alone in the presence of target tumor cells, with the resultant limited proliferation of NK cells expressing CARs. FIG. 17B shows the corresponding schematic model when T cells are alone in the presence of target tumor cells, when the T cells exhibit strong proliferation. FIG. 17C schematically depicts proliferation of NK cells when also in the presence of T cells as well as target tumor cells. As schematically depicted, at least a portion of the proliferative signaling that would otherwise cause T cell expansion positively impacts NK cells. As a result, the NK cells (which would have experienced limited proliferation on their own) now exhibit proliferation. This is in contrast to the T cells, which when cultured alone with target tumor cells exhibit robust expansion, but in the presence of NK cells show a more limited degree of proliferation. Taking these data together, the positive impact that T cells have on NK cell growth appear to be initiated when a threshold population or concentration of NK cells are present. Accordingly, in several embodiments when a mixed population of NK and T cells are used, the ratio of the NK cells to the T cells is tuned such that the beneficial impacts on NK cell expansion are realized. Thus, as discussed above and in accordance with several embodiments disclosed herein, mixed populations of NK cells and T cells can be generated such that the overall population exhibits enhanced cytotoxicity against target tumor cells, as well as enhanced persistence, one or both of which is due, at least in part, to the T cell-based enhancement of NK cell proliferation.

Figure 18E:
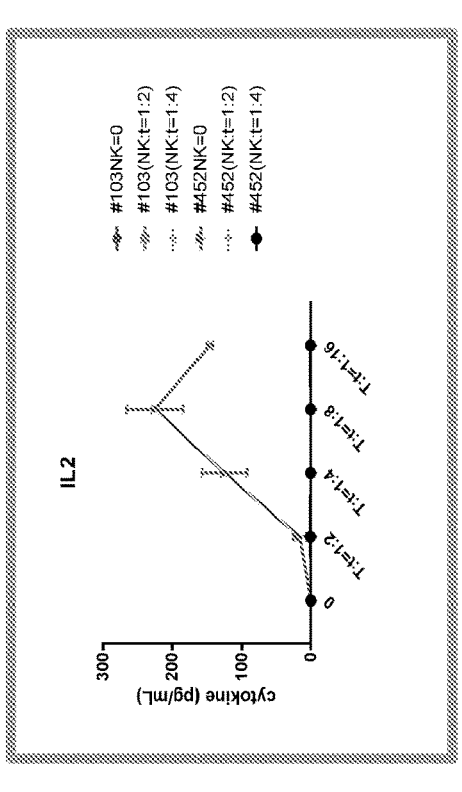
Figure 18F:
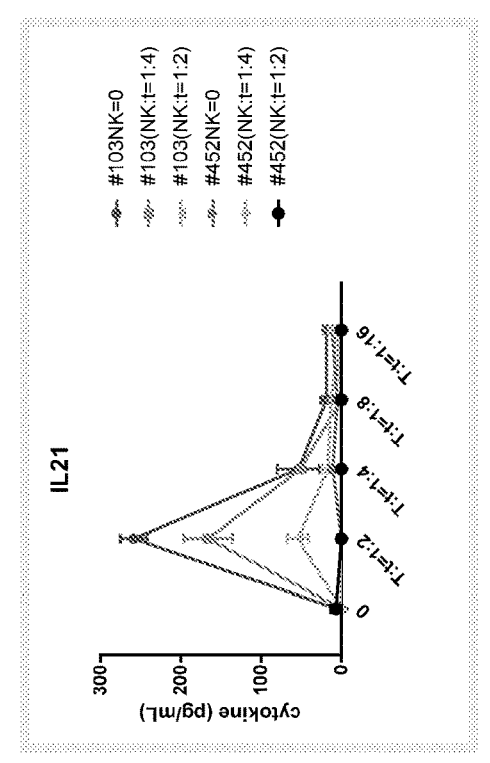
Figure 18G:
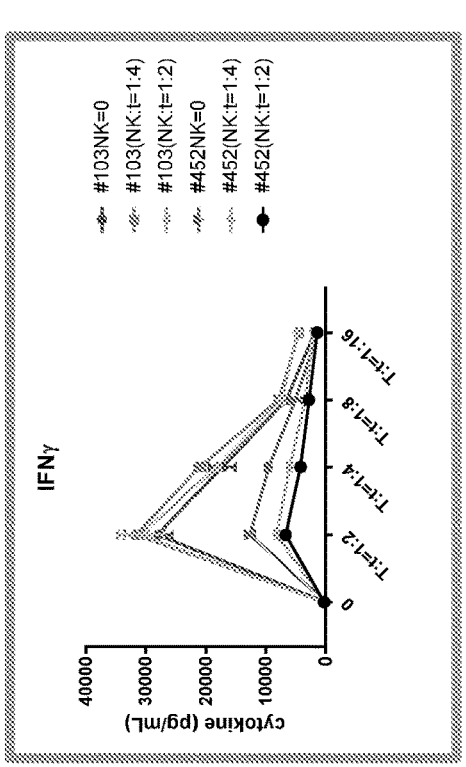
Figure 18H:
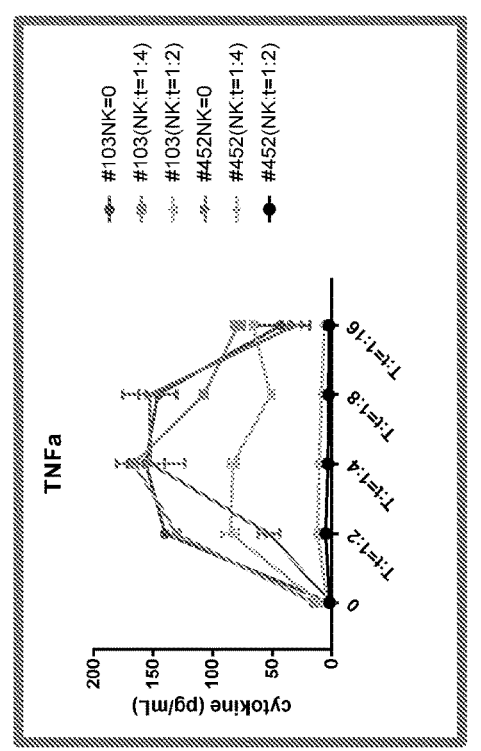
Figure 18I:
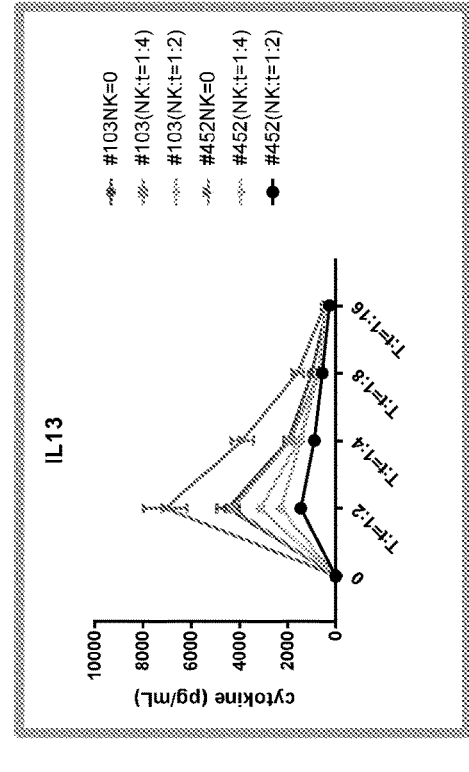
Figure 18J:
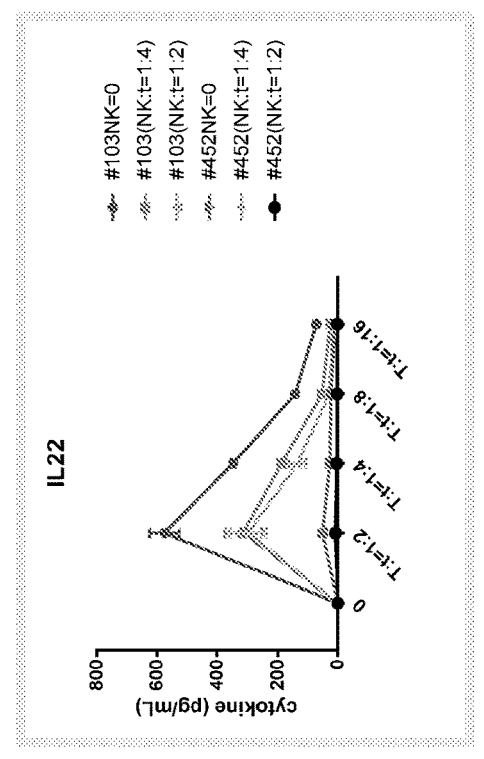
Figure 18K:
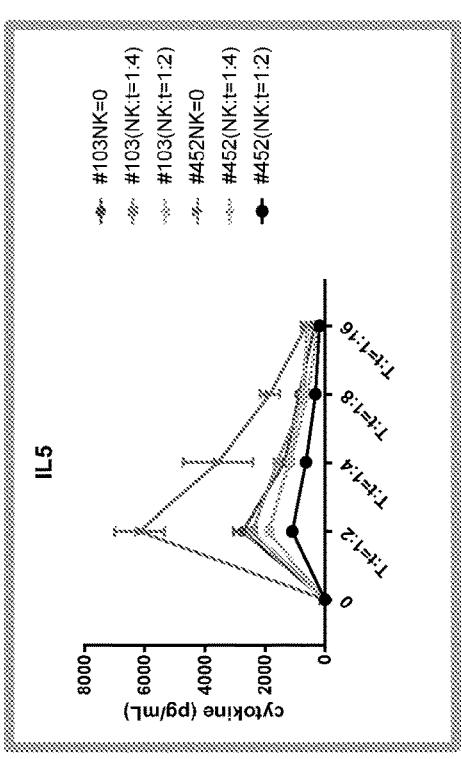
Figure 18L:
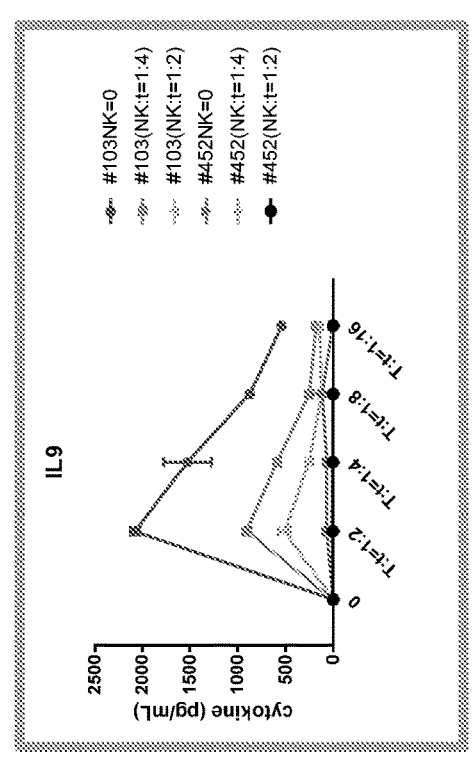

To further elucidate the mechanisms that play a role in the enhanced cytotoxicity and persistence of mixed NK and T cell populations, a cytokine profile analysis was created, the results of which are shown in FIGS. 18A-18L. Data were collected using cells from two different donors. For each donor, analysis of cytokine production by NK and T cells was measured when a mixed population of NK cells (at either NK=0, NK:Nalm6=1:4, or NK:Nalm6=1:2) were used to target Nalm6 cells alone (T=0), or in the presence of T cells, at T:Nalm6 ratio of 1:2, 1:4, 1:8, or 1:16. Evaluation was performed at day 5 after the start of immune cell-target co-culture. Generally, the data in FIGS. 18A-18L show a decrease in the production of the selected cytokines that correspond with a decreasing amount of T cells, importantly those like GM-CSF and IL6 that are associated with potential side effects from T cell therapy, like Cytokine Release Syndrome. For example, FIG. 18A shows the concentration of GM-CSF released from T cells from two different donors. These data demonstrate that with a lower T cell to target ratio, less GM-CSF is produced by the cells, thereby lessening the potential for CRS. While this trend holds in the presence of NK cells, FIG. 18A shows that increasing the number of NK cells in the co-culture decreases the levels of GM-CSF accumulating in the system, regardless of the starting T cell concentration. Another notable trend is shown in FIG. 18E. This figure shows that the addition of increasing numbers of NK cells does not decrease IFNg production, a cytokine important to the induction of cytotoxicity against target cells. In other words, the combinations of cells used in several embodiments disclosed herein are not self-limiting in that the presence of NK cells with T cells causes disruption of the activity of one of the cells. Rather, as discussed herein, these two cell types work in tandem with one another, leading to synergistic cytotoxic effects on target cells. FIG. 18F shows production of IL2. In the first donor, very little IL-2 was produced by the T cells, regardless of the number of NK cells present. In the second donor IL-2 production was only detected by T cells when NK cells were absent, however production was not correlated with a dose dependency. The presence of NK cells may either alter the degree of secretion by a given T cell, alter the overall levels of T cells contributing to cytokine accumulation, or the NK cells may act a s a sink for binding of the secreted cytokines (with consequent effects on NK cell proliferation or activity). It is also possible that, in addition to those cytokines tested here, other cytokines produced by T cells may contribute directly, or indirectly, to NK cell proliferation and/or persistence. Advantageously, in several embodiments, the reduction of cytokine production when NK cells and T cells are used in combination coordinately recues the risk of Cytokine Release Syndrome, while also inducing the enhanced cytotoxicity and persistence of NK cells.

Figure 20A:
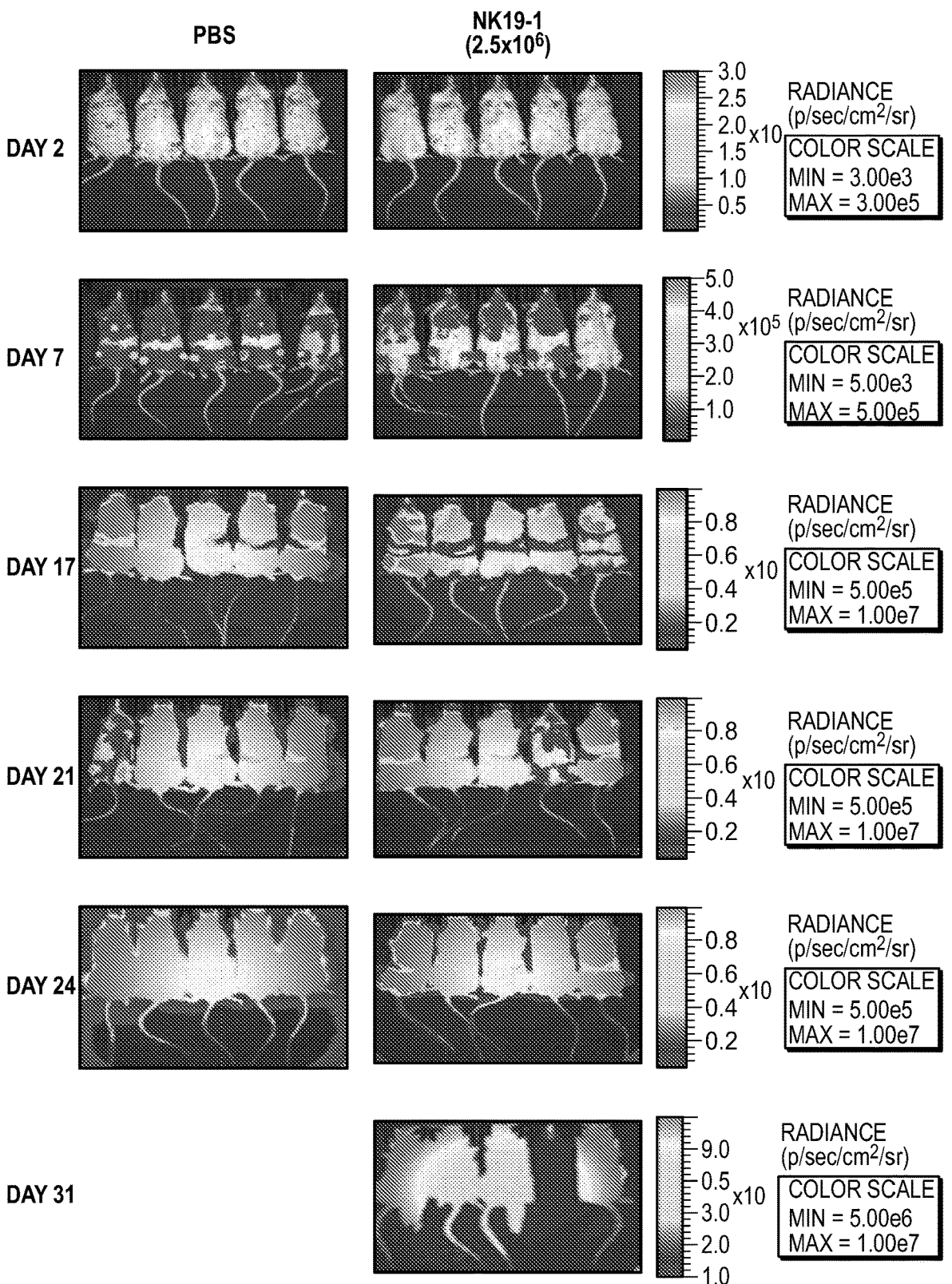
FIGS. 20A-20E show bioluminescence and survival data reflecting the tumor burden in mice receiving the indicated treatments.
Figure 20A:
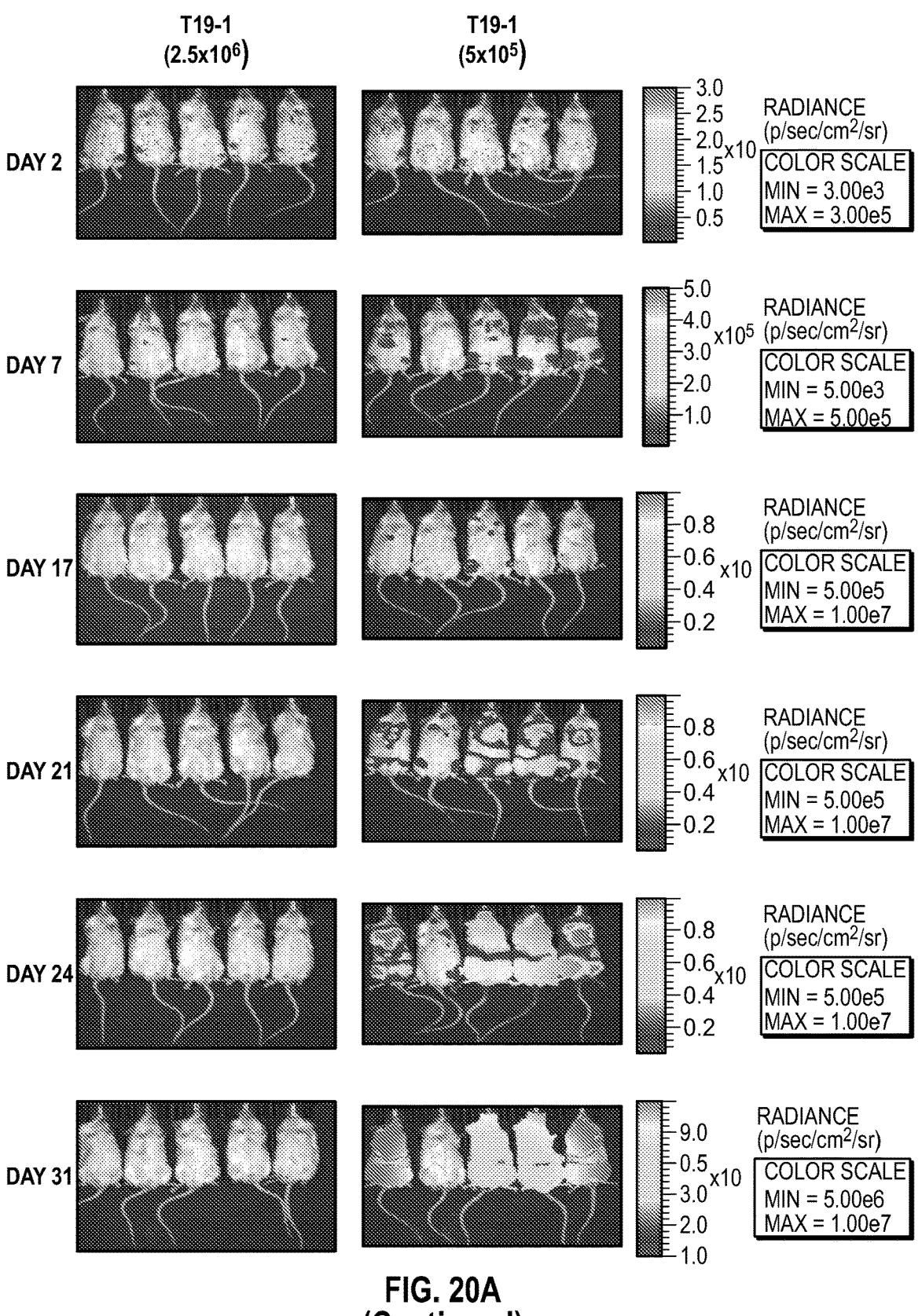
Figure 20A:
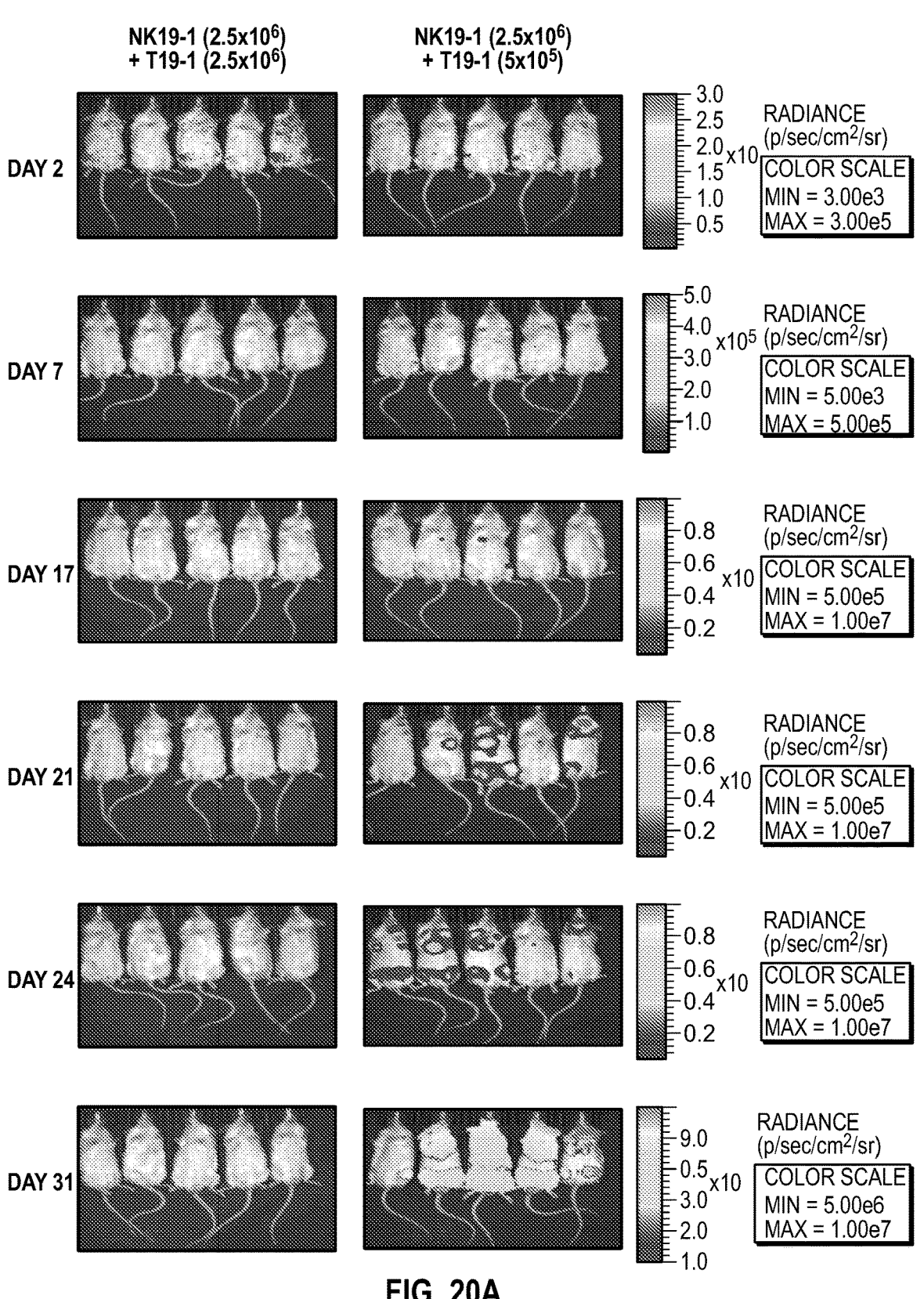
Figure 20B:
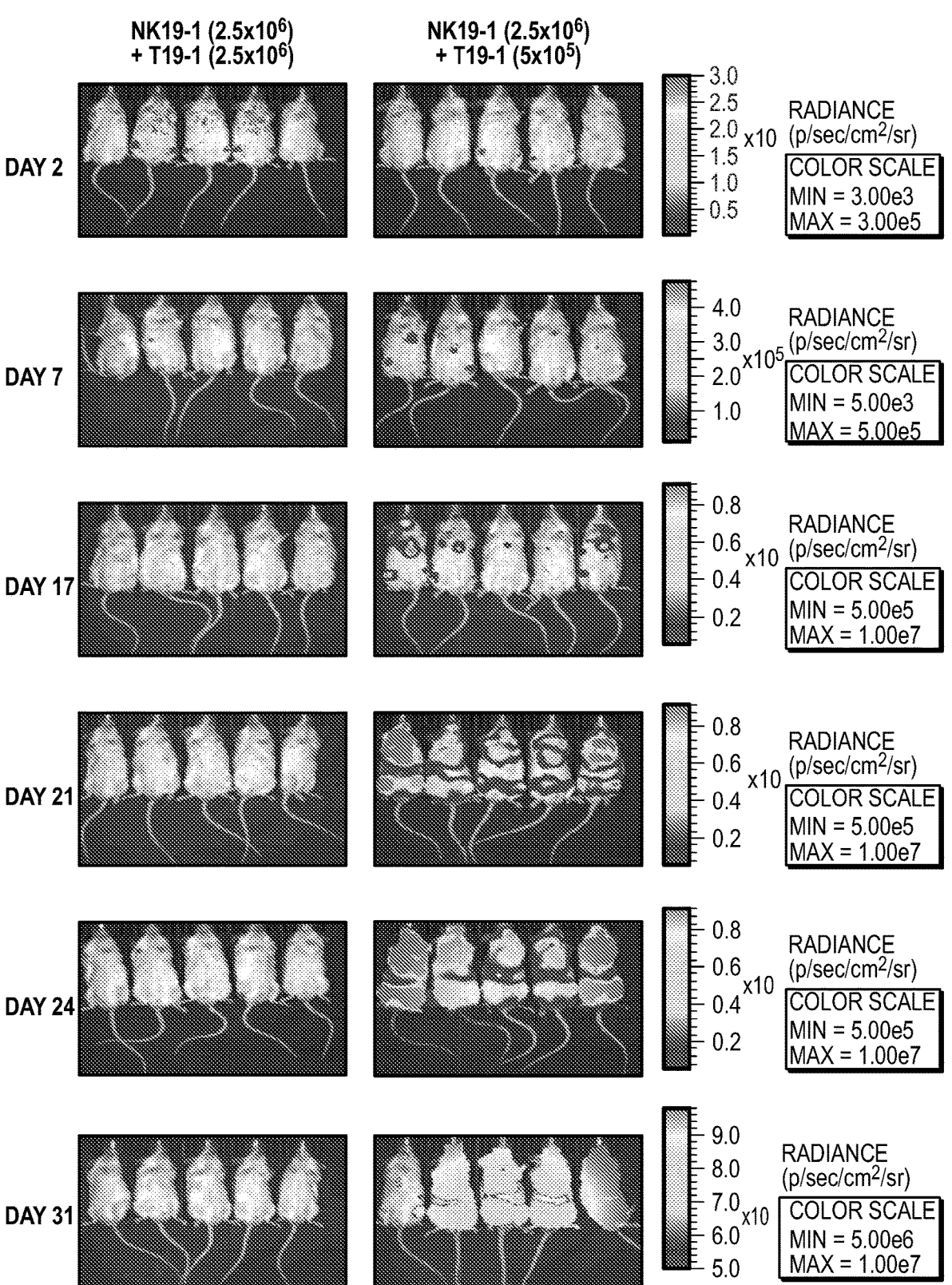
Figure 20B:
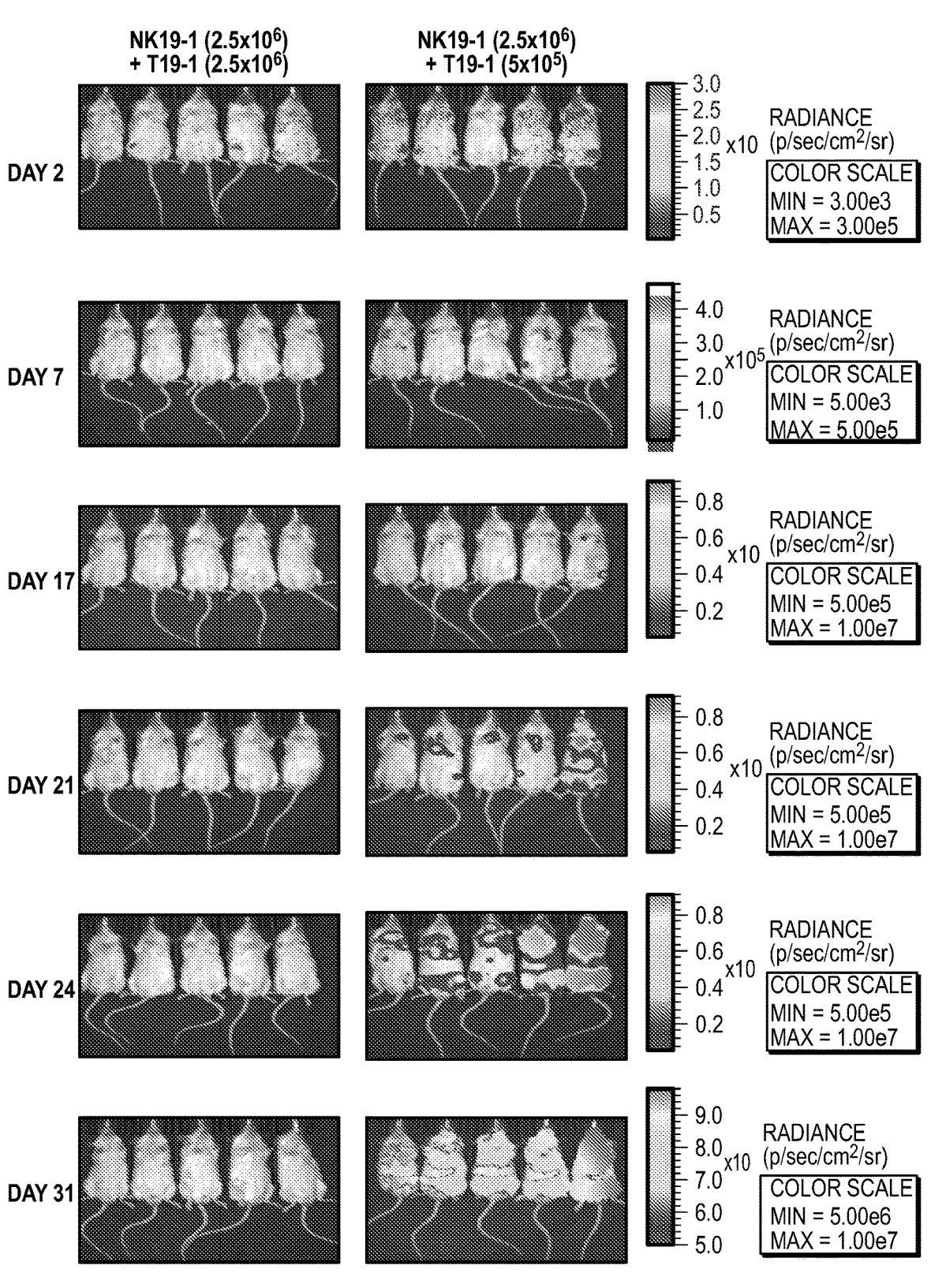
Figure 20C:
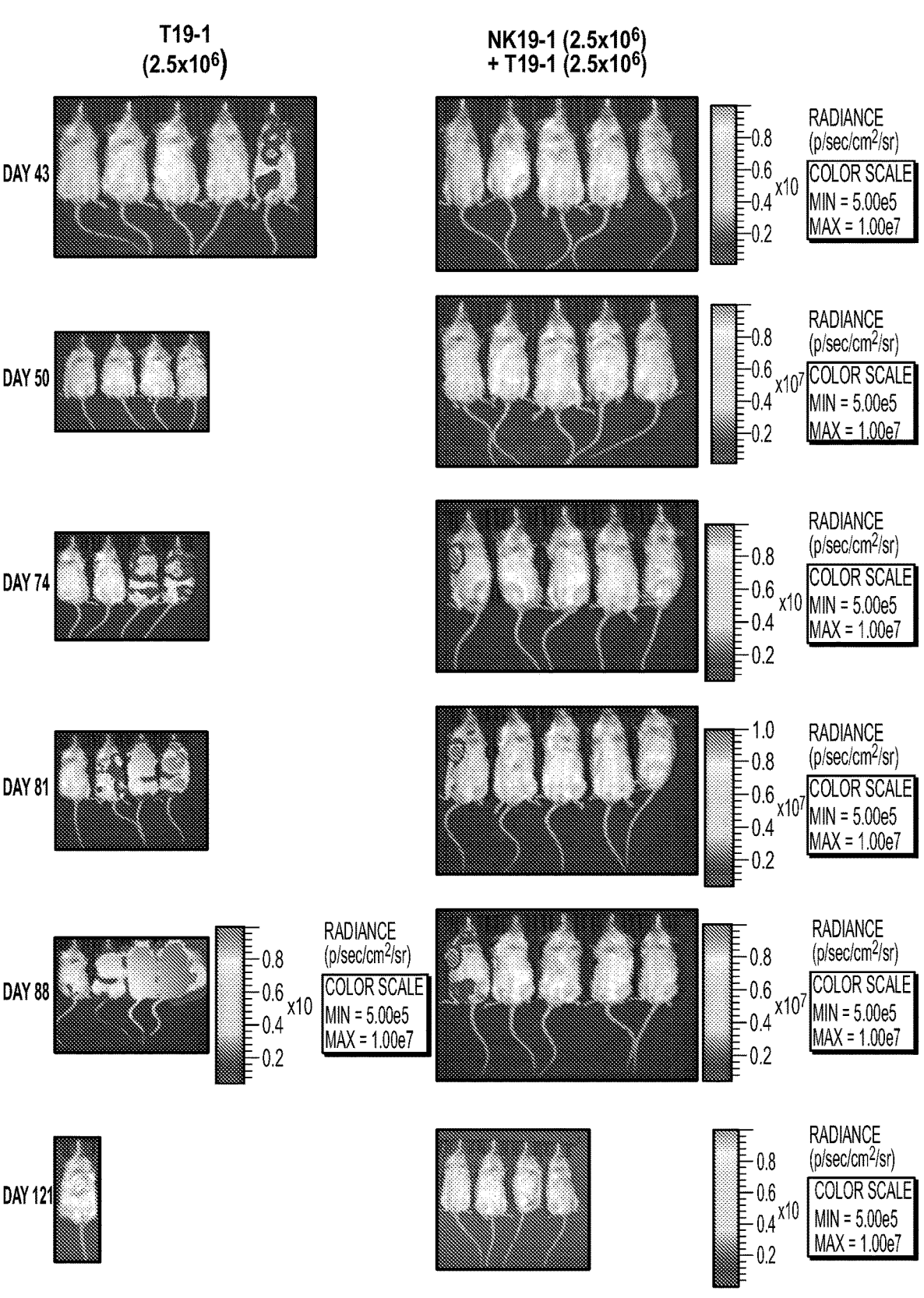

To further evaluate the enhanced cytotoxicity and persistence of mixed populations of NK cells and T cells, a xenograft model was used in which Nalm6 target tumor cells were transplanted into NSG mice. The Nalm6 cells were engineered to express GFP as well as firefly luciferase, the latter enabling detection of tumor burden in transplant recipient mice by measurement of bioluminescence. FIG. 19 shows the schematic study plan for the xenograft model. Mice received injections of combinations of NK cells and T cells engineered to express a non-limiting example of an anti-CD19 CAR (19-1). Tumor cells were injected at day zero; NK and T cells were injected alone, or in combination on day three (FIG. 20A). In some groups, NK cells were administered at day 3 followed by T cells at day four, or T cells were administered at day three followed by NK cells at day 4 (FIG. 20B). Bioluminescent imaging was performed at the intervals indicated in FIG. 19. The bioluminescent results are shown in FIGS. 20A-20C, which show the data separated by day posts transplant, as well as by cell dose and delivery order of the indicated cells. FIG. 20A shows bioluminescent data for days two through 31 of the experiment for experimental groups receiving PBS, NK cells expressing the anti-CD19 CAR 19-1 construct at a dose of $2.5 \times 10^6$ cells, T cells expressing the anti-CD19 CAR 19-1 construct at a dose of either $2.5 \times 10^6$ or $5 \times 10^5$ cells, a combination of NK cells and T cells (both at $2.5 \times 10^6$ cells), or a combination of NK and T cells (with the NK cells at $2.5 \times 10^6$ cells and the T cells at $5 \times 10^5$ cells). FIG. 20B shows data for the same timeframe wherein the experimental groups shown received staggered doses of NK and T cells on days 3 and 4. The left two columns show experimental groups receiving NK cells on day 3 followed by T cells on day 4, while the right to columns show experimental results for groups receiving T cells on day 3 followed by NK cells on day 4. Each group was broken into two subgroups, one receiving both NK cells and T cells at a dose of $2.5 \times 10^6$ (high dose), and a second group receiving NK cells at $2.5 \times 10^6$ and T cells at $5 \times 10^5$ cells (low dose).

Across the first 30 days of the experiment, when combinations of cells were delivered together, it is noted that NK cells alone inhibited tumor growth more effectively as compared to the PBS control. The combination of NK cells at a high dose and T cells at a low dose (right-most column in 20A), which is in accordance with several embodiments disclosed herein, shows significantly improved tumor control as compared to NK cells alone (when the NK cells are at the same dose). This treatment group also shows improved tumor control as compared to the T cells alone (when the T cells are at the same dose). In several embodiments, the NK:T cell ratio not only allows for tumor control, but achieves the same in conjunction with reduced cytokine release and lessened risk of CRS. T cells alone at the high dose, and NWT cells at the high doses both showed control of tumor through 30 days.

In terms of preventing increase in tumor burden, the next most efficacious treatment was the early dose of NK cells followed by the low dose of T cells the following day (see second column FIG. 20B). The next most efficacious treatment was T cells alone at the lower dose, which prevented significant tumor growth for almost 3 weeks. The next most efficacious treatment was the combination of T cells and NK cells, with the T cells being delivered first, at the lower dose, followed by the NK cells one day later. Next, NK cells and a low dose of T cells administered at the same day showed the next most effective treatment. Again this hierarchy were for those treatment groups that exhibited some degree of tumor progression across the first 30 days of the experiment. However, the data over the first 30 days confirms that, in accordance with several embodiments, a ratio of a greater number of NK cells as compared to T cells, for example about 5:1, about 10:1, or about 20:1, depending on the embodiment, yields robust acute and mid-long term cytotoxicity. As discussed above, the lower number of T cells is still able to provide sufficient NK-cytotoxicity and NK-proliferation stimulus, while not being so populous that the NK cells are unable to provide some suppression of T cell proliferation, which in turn results in reduced T cell induced cytokine release (and thus reduced adverse inflammatory effects).

Figure 20D:
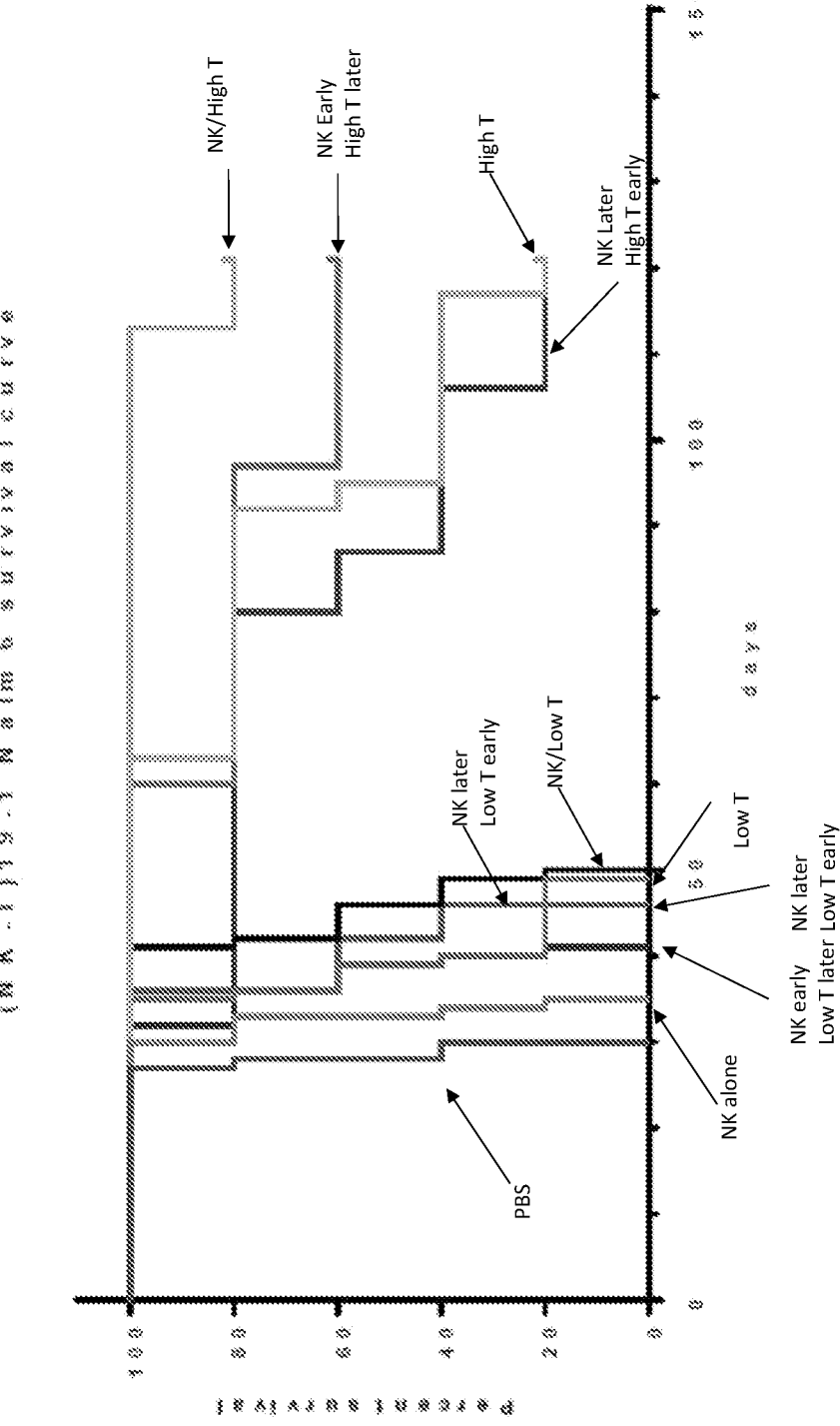
Figure 20E:
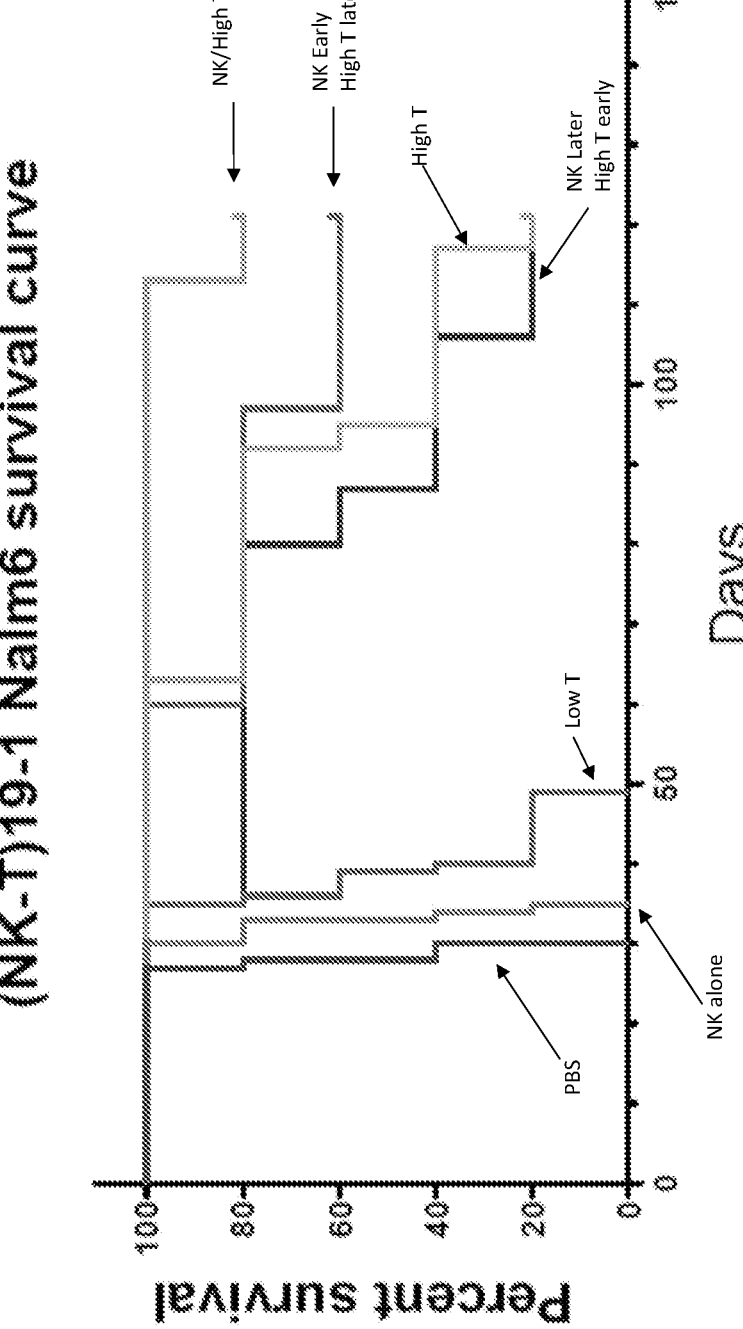

The other groups tested prohibited tumor growth until after that time point, and are presented in FIG. 20C. Without being bound by theory, these data suggest that there is perhaps a more robust initial response in these groups, which facilitates long-term control, and/or there is some early-stage inhibition or other restraint on T cell proliferation that may impart a longer lasting active lifespan prior to exhaustion. Over the first 74 days, the administration of T cells and NK cells at the higher dose, with T cells being delivered on day 3 followed by NK cells on day 4 inhibited tumor growth for nearly 65 days, with significant tumor burden only being identified at 74 days post tumor transplant. The administration of T cells alone at a higher dose also resulted in significant delay in tumor advancement, with only modest tumor growth detected at day 74. The two most efficacious treatments overall involved combinations of NK cells and T cells. Administration of NK cells on day 3 followed by the high dose of T cells on day 4 saw 80% of the mice in the treatment group survive, with little to no detectable tumor burden at 74 days. Similarly, but with even further enhanced efficacy, the administration of a high dose of both NK cells and T cells at day 3 yielded survival of 100% of the mice in the treatment group with tumor detection in only one of those mice, and only to a modest extent, at 74 days post tumor transplant. Moving beyond that timepoint to days 81-121 post-tumor transplant, these trends continue, with the administration of T cells (high dose) followed by NK cells and the high dose of T cells similarly controlling tumor growth. Notably, the combination of NK cells followed by T cells showed enhanced control of tumor growth, and the most effective control was seen with the combination of NK cells and T cells (high dose) delivered on the same day. FIG. 20D shows the survival curves for all groups together, which reflects the bioluminescence data discussed above. FIG. 20E shows only selected groups to show a clearer picture of the enhanced tumor control over four months that is seen when NK and T cells are combined. In particular, the administration of NK cells followed by T cells and the combination of NK and T cells administered together show markedly enhanced tumor control. Taken together, these data indicate that combinations of NK cells with T cells are highly efficacious cancer therapies. According to some embodiments, the NK cell to T cell concentration can be altered to fine-tune not only the cytotoxicity of the combined product, but also the persistence, such that long-term control of tumor growth can be achieved. Likewise, according to some embodiments, the combinations of NK cells and T cells need not necessarily be administered simultaneously to be highly effective. According to some embodiments, one of the two cell types can be delivered at an early time point, while the other cell type can be delivered at a later time point. In some embodiments, this allows one of the cell types, such as the NK cells, to exert its effects at a primary time point, with those effects later synergistically supplemented by the cytotoxic effects and/or growth promoting effects of the second cell type, such as T cells. Depending on, for example, the tumor type to be treated the order of administration may be varied such that the administration of the first cell type creates a beneficial environment (e.g., an artificial tumor microenvironment) that enhances and/or maximizes one or more characteristics of the second cell type. In other words, in several embodiments, the sequential administration of the first cell type and the second cell type results in the first cell type priming the tumor microenvironment for optimal cytotoxic performance by the second cell type. Additionally, as provided for in several embodiments disclosed herein, a mixed population of NK cells and T cells can be co-administered to achieve highly effective antitumor effects.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a population of expanded NK cells" includes "instructing the administration of a population of expanded NK cells." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "90%" includes "90%." In some embodiments, at least 95% homologous includes 96%, 97%, 98%, 99%, and 100% homologous to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence.

Articles such as "a", "an", "the" and the like, may mean one or more than one unless indicated to the contrary or otherwise evident from the context. The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, 5 optionally, additional unlisted elements. Only terms clearly indicative to the contrary, such as "only one of" or "exactly one of" will refer to the inclusion of exactly one element of a number or list of elements. Thus claims that include "or" between one or more members of a group are considered 10 satisfied if one, more than one, or all of the group members are present, employed in, or otherwise relevant to a given product or process unless indicated to the contrary. Embodiments are provided in which exactly one member of the group is present, employed in, or otherwise relevant to a given product or process. Embodiments are provided in which more than one, or all of the group members are present, employed in, or otherwise relevant to a given product or process. Any one or more claims may be amended to explicitly exclude any embodiment, aspect, feature, element, or characteristic, or any combination thereof. Any one or more claims may be amended to exclude any agent, composition, amount, dose, administration route, cell type, target, cellular marker, antigen, targeting moiety, or combination thereof.

Any titles or subheadings used herein are for organization purposes and should not be used to limit the scope of embodiments disclosed herein.

---

What is claimed is:

1. A method for the generation of a mixed population of engineered immune cells comprising at least two subpopulations of engineered immune cells, the method comprising:

(a) isolating a population of mononuclear cells from a blood sample, wherein the isolated population of mononuclear cells comprises at least a first and a second subpopulation of immune cells;

(b) isolating the first subpopulation of immune cells from the isolated mononuclear cells, wherein the first subpopulation of immune cells comprises natural killer (NK) cells;

(c) culturing the first subpopulation of isolated immune cells with a population of feeder cells in a culture vessel, wherein the feeder cells express at least one molecule selected from 4-1BB ligand (4-1BBL), interleukin 15 (IL15), and combinations thereof, thereby generating an expanded population of NK cells;

(d) isolating the second subpopulation of immune cells from the isolated mononuclear cells, wherein the second subpopulation of immune cells comprises T cells;

(e) culturing the second subpopulation of immune cells in a culture vessel with at least one molecule comprising one or more of an antibody directed against CD3 or against CD28, thereby generating an expanded population of T cells;

(f) transducing the expanded NK cell population with a nucleic acid encoding an engineered receptor that binds a target expressed by a cancer cell, thereby generating engineered NK cells;

(g) transducing the expanded T cell population with a nucleic acid encoding an engineered receptor that binds a target expressed by a cancer cell, thereby generating engineered T cells; and (h) combining a portion of the engineered NK cells with a portion of the engineered T cells, wherein the ratio of engineered NK cells to engineered T cells is between about 5:1 and about 20:1.

2. The method of claim 1, wherein the at least one molecule for the stimulation of expansion of NK cells comprises 4-1BBL and interleukin 15 (IL15).

3. The method of claim 1, wherein the culturing the first subpopulation of isolated immune cells further comprises addition of one or more of soluble interleukin 2 (IL2), soluble interleukin 12 (IL12), soluble interleukin 18 (IL18), or combinations thereof, to the culture.

4. The method of claim 1, wherein the NK cells and the T cells are both transduced with the same nucleic acid encoding an engineered receptor.

5. The method of claim 4 wherein the engineered receptor is a chimeric antigen receptor (CAR) directed against CD19.

6. The method of claim 5, wherein the CAR comprises an OX40 co-stimulatory domain and a CD3zeta signaling domain.

7. The method of claim 1, wherein the at least one molecule for the stimulation of expansion of T cells comprises an anti-CD3 antibody.

8. The method according to claim 1, wherein the blood sample is a peripheral blood sample.

9. The method according to claim 1, wherein the mixed population of engineered immune cells comprises between about $1\times10^8$ and about $1\times10^{10}$ engineered NK cells and between about $1\times10^6$ to about $1\times10^8$ engineered T cells.

10. The method according to claim 1, wherein the blood sample is a cord blood sample.

11. The method of claim 1, wherein the NK cells and the T cells are transduced with a different nucleic acid encoding an engineered receptor.

12. The method of claim 2, wherein the IL15 is membrane bound on the feeder cells.

13. The method of claim 1, wherein the at least one molecule for the stimulation of expansion of T cells comprises an anti-CD28 antibody.

14. The method of claim 1, wherein the at least one molecule for the stimulation of expansion of T cells comprises an anti-CD3 antibody and an anti-CD28 antibody.

15. The method of claim 1, wherein the ratio of engineered NK cells to engineered T cells is between about 5:1 and about 10:1.

16. The method of claim 1, wherein the ratio of engineered NK cells to engineered T cells is about 5:1.

17. A method for the generation of a mixed population of engineered immune cells comprising at least two subpopulations of engineered immune cells, the method comprising:

(a) isolating a population of mononuclear cells from a blood sample, wherein the isolated population of mononuclear cells comprises at least a first and a second subpopulation of immune cells;

(b) isolating the first subpopulation of immune cells from the isolated mononuclear cells, wherein the first subpopulation of immune cells comprises natural killer (NK) cells;

(c) culturing the first subpopulation of isolated immune cells with a population of feeder cells in a culture vessel, wherein the feeder cells express 4-1BB ligand (4-1BBL) and interleukin 15 (IL15), thereby generating an expanded population of NK cells;

(d) isolating the second subpopulation of immune cells from the isolated mononuclear cells, wherein the second subpopulation of immune cells comprises T cells;

(e) culturing the second subpopulation of immune cells in a culture vessel with an anti-CD3 antibody and an anti-CD28 antibody, thereby generating an expanded population of T cells;

(f) transducing the expanded NK cell population with a nucleic acid encoding a chimeric antigen receptor (CAR) that binds to CD19, thereby generating engineered NK cells;

(g) transducing the expanded T cell population with a nucleic acid encoding a CAR that binds to CD19, thereby generating engineered T cells; and (h) combining a portion of the engineered NK cells with a portion of the engineered cells, wherein the ratio of engineered NK cells to engineered T cells is betweenat least about 5:1 and about 20:1.

18. The method of claim 17, wherein the ratio of engineered NK cells to engineered T cells is between about 5:1 and about 10:1.

19. The method of claim 17, wherein the ratio of engineered NK cells to engineered T cells is about 5:1.

20. The method according to claim 17, wherein the blood sample is a peripheral blood sample.

21. The method according to claim 17, wherein the blood sample is a cord blood sample.

22. The method according to claim 17, wherein the mixed population of engineered immune cells comprises between about $1\times10^8$ and about $1\times10^{10}$ engineered NK cells and between about $1\times10^6$ to about $1\times10^8$ engineered cells.

\*   \*   \*   \*   \*